(12) United States Patent
Bauer et al.

(10) Patent No.: US 11,981,900 B2
(45) Date of Patent: May 14, 2024

(54) INCREASING GENE EDITING AND SITE-DIRECTED INTEGRATION EVENTS UTILIZING MEIOTIC AND GERMLINE PROMOTERS

(71) Applicant: MONSANTO TECHNOLOGY LLC, St. Louis, MO (US)

(72) Inventors: Matthew J. Bauer, Manchester, MO (US); Lisa Kanizay, Chesterfield, MO (US); Jonathan Lamb, Wildwood, MO (US); Matthew S. Marengo, Wildwood, MO (US); Brent O'Brien, St. Charles, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 17/470,784

(22) Filed: Sep. 9, 2021

(65) Prior Publication Data
US 2022/0073937 A1    Mar. 10, 2022

Related U.S. Application Data
(60) Provisional application No. 63/076,705, filed on Sep. 10, 2020.

(51) Int. Cl.
| | | |
|---|---|---|
| *C12N 15/82* | (2006.01) | |
| *C12N 9/22* | (2006.01) | |
| *C12N 15/11* | (2006.01) | |

(52) U.S. Cl.
CPC ........... *C12N 15/8213* (2013.01); *C12N 9/22* (2013.01); *C12N 15/11* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 4,897,355 | A | 1/1990 | Eppstein et al. |
| 4,946,787 | A | 8/1990 | Eppstein et al. |
| 5,049,386 | A | 9/1991 | Eppstein et al. |
| 5,106,739 | A | 4/1992 | Comai et al. |
| 5,159,135 | A | 10/1992 | Umbeck |
| 5,188,958 | A | 2/1993 | Moloney et al. |
| 5,322,938 | A | 6/1994 | McPherson et al. |
| 5,352,605 | A | 10/1994 | Fraley et al. |

(Continued)

FOREIGN PATENT DOCUMENTS

| | | |
|---|---|---|
| CA | 2401858 A1 | 9/2001 |
| CA | 3036234 A1 | 3/2018 |

(Continued)

OTHER PUBLICATIONS

Feng et al. "High-efficiency genome editing using a dmc1 promoter-controlled CRISPR/Cas9 system in maize" 2018 Plant Biotech. J. 16:1848-1857 (Year: 2018).*

(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

This disclosure provides methods and compositions for increasing genome editing and site-directed integration events utilizing guided endonucleases and meiotic cell-preferred, egg cell-preferred or embryo tissue-preferred promoters.

7 Claims, 5 Drawing Sheets

Specification includes a Sequence Listing.

(56) References Cited

U.S. PATENT DOCUMENTS

| | | | |
|---|---|---|---|
| 5,359,142 | A | 10/1994 | McPherson et al. |
| 5,378,619 | A | 1/1995 | Rogers |
| 5,463,174 | A | 10/1995 | Moloney et al. |
| 5,530,196 | A | 6/1996 | Fraley et al. |
| 5,538,880 | A | 7/1996 | Lundquist et al. |
| 5,550,318 | A | 8/1996 | Adams et al. |
| 5,591,616 | A | 1/1997 | Hiei et al. |
| 5,641,876 | A | 6/1997 | McElroy et al. |
| 5,750,871 | A | 5/1998 | Moloney et al. |
| 5,824,877 | A | 10/1998 | Hinchee et al. |
| 5,837,848 | A | 11/1998 | Ely et al. |
| 5,850,019 | A | 12/1998 | Maiti et al. |
| 6,051,753 | A | 4/2000 | Comai et al. |
| 6,096,950 | A | 8/2000 | John |
| 6,140,078 | A | 10/2000 | Sanders et al. |
| 6,153,812 | A | 11/2000 | Fry et al. |
| 6,160,208 | A | 12/2000 | Lundquist et al. |
| 6,175,060 | B1 | 1/2001 | Lefebvre et al. |
| 6,177,611 | B1 | 1/2001 | Rice |
| 6,194,636 | B1 | 2/2001 | McElroy et al. |
| 6,232,526 | B1 | 5/2001 | McElroy et al. |
| 6,252,138 | B1 | 6/2001 | Karimi et al. |
| 6,294,714 | B1 | 9/2001 | Matsunaga et al. |
| 6,384,301 | B1 | 5/2002 | Martinell et al. |
| 6,399,861 | B1 | 6/2002 | Anderson et al. |
| 6,426,446 | B1 | 7/2002 | McElroy et al. |
| 6,429,357 | B1 | 8/2002 | McElroy et al. |
| 6,429,362 | B1 | 8/2002 | Crane |
| 6,433,252 | B1 | 8/2002 | Kriz et al. |
| 6,437,217 | B1 | 8/2002 | McElroy et al. |
| 6,635,806 | B1 | 10/2003 | Kriz et al. |
| 7,151,204 | B2 | 12/2006 | Houmard et al. |
| 10,995,327 | B2 | 5/2021 | Chittoor et al. |
| 11,447,786 | B2 | 9/2022 | Fox |
| 2004/0216189 | A1 | 10/2004 | Houmard et al. |
| 2007/0050869 | A1 | 3/2007 | Dresselhaus et al. |
| 2007/0130645 | A1* | 6/2007 | Wu et al. ........... C12N 15/8234 800/278 |
| 2018/0092316 | A1 | 4/2018 | Chintamanani |
| 2019/0136250 | A1 | 5/2019 | Que |
| 2019/0169596 | A1 | 6/2019 | Armstrong et al. |
| 2019/0376074 | A1 | 12/2019 | Li et al. |
| 2020/0080096 | A1 | 3/2020 | Flasinski et al. |

FOREIGN PATENT DOCUMENTS

| | | | | |
|---|---|---|---|---|
| CA | 3043774 | A1 | 5/2018 | |
| CN | 105916989 | A | 8/2016 | |
| CN | 108738326 | A | 11/2018 | |
| CN | 109982560 | A | 7/2019 | |
| CN | 111465321 | A | 7/2020 | |
| WO | 199116024 | A1 | 10/1991 | |
| WO | WO 91/16024 | A1 | 10/1991 | |
| WO | 199117424 | A1 | 11/1991 | |
| WO | WO 91/17424 | A1 | 11/1991 | |
| WO | 0011200 | A2 | 3/2000 | |
| WO | WO-0164924 | A1 * | 9/2001 | ........... C07K 14/415 |
| WO | WO-2006128707 | A1 * | 12/2006 | ............... A01H 1/08 |
| WO | 2014093622 | A2 | 6/2014 | |
| WO | WO 2014/093622 | A2 | 6/2014 | |
| WO | WO-2018052919 | A1 * | 3/2018 | ............... A01H 1/08 |
| WO | 2018102816 | A1 | 6/2018 | |
| WO | 2019084148 | A1 | 5/2019 | |
| WO | WO 2019/084148 | A1 | 5/2019 | |
| WO | WO 2019/113000 | A1 | 6/2019 | |
| WO | WO 2020/131788 | A1 | 6/2020 | |

OTHER PUBLICATIONS

Cordts et al. "ZmES genes encode peptides with structural homology to defensins and are specifically expressed in the female gametophyte of maize" (2001 Plant J. 25(1):103-114) (Year: 2001).*

Streatfield et al. "Analysis of the maize polyubiquitin-1 promoter heat shock elements and generation of promoter variants with modified expression characteristics" (2004 Transgenic Res. 13:299-312) (Year: 2004).*
Altschul et al., "Basic local alignment search tool." *Journal of Molecular Biology*, 215(3):403-410 (1990).
Bevan et al.,, Structure and transcription of the nopaline synthase gene region of T-DNA, *Nucleic Acids Research*, 11(2): 369-385 (1983).
Campbell and Gowri, "Codon Usage in Higher Plants, Green Algae, and Cyanobacteria," *Plant Physiology*, 92(1): 1-11 (1990).
Chandler et al., "Two regulatory genes of the maize anthocyanin pathway are homologous: isolation of B utilizing R genomic sequences," *Plant Cell*, 1(12): 1175-1183 (1989).
Chenna et al., "Multiple sequence alignment with the Clustal series of programs," *Nucleic Acids Research*, 31(13): 3497-3500 (2003).
Depicker et al., "Nopaline synthase: transcript mapping and DNA sequence," *Journal of Molecular and Applied Genetics*, 1(6): 561-573 (1982).
Ebert et al., "Identification of an essential upstream element in the nopaline synthase promoter by stable and transient assays," *Proceedings of the National Academy of Sciences*, USA, 84: 5745-5749 (1987).
Fraley, et al., "Expression of bacterial genes in plant cells," *Proceedings of the National Academy of Sciences, USA*, 80(15): 4803-4807 (1983).
GenBank Accession V00087.1, "Agrobacterium tumefaciens gene encoding nopaline synthetase. (Resident in plasmid pTiT37)," *National Library of Medicine: NCBI*, retrieved May 13, 2019 <https://www.ncbi.nlm.nih.g0V/nuccore/V00087>.
Gilles et al., "Haploid induction in plants," *Current Biology*, 27(20):R1095-R1097 (2017).
Kam et al., "Nanotube molecular transporters: internalization of carbon nanotube-protein conjugates into mammalian cells," *Journal of American Chemical Society*, 126 (22):6850-6851 (2004).
Khodakovskaya et al., "Carbon Nanotubes Are Able To Penetrate Plant Seed Coat and Dramatically Affect Seed Germination and Plant Growth," *ACS Nano* 3(10):3221-3227 (2009).
Larkin et al., "Clustal W and Clustal X version 2.0," *Bioinformatics*, 23 (21): 2947-48 (2007).
Lawton et al., "Expression of a soybean β-conclycinin gene under the control of the Cauliflower Mosaic Virus 35S and 19S promoters in transformed petunia tissues," *Plant Molecular Biology*, 9:315-324 (1987).
Liu et al., "Carbon Nanotubes as Molecular Transpprters for Walled Plant Cells," *Nano Letters*, 9(3): 1007-1010 (2009).
Murray et al., "Codon usage in plant genes," *Nucleic Acids Research*, 17(2):477-498 (1989).
Nakamura et al., "Codon usage tabulated from international DNA sequence databases: status for the year 2000,", *Nucleic Acids Research* 28(1):292 (2000).
Odell et al., "Identification of DNA sequences required for activity of the cauliflower mosaic Virus 35S promoter," *Nature*, 313: 810-812 (1985).
Thompson et al., "Clustal W: Improving the sensitivity of progressive multiple sequence alignment through sequence weighting, position-specific gap penalties and weight matrix choice," *Nucleic Acids Research*, 22(22): 4673-4680 (1994).
Wang et al., "Multiplex gene editing in rice with simplified CRISPR-Cpf1 and CRISPR-Cas9 systems," *Journal of Integrative Plant Biology*, 60(8):626-631 (2018).
Yang et al., "Maize sucrose synthase-1 promoter directs phloem cell-specific expression of Gus gene in transgenic tobacco plants," *Proceedings of the National Academy of Sciences, USA* 87(11): 4144-4148 (1990).
Zhang et al., "PowerBlast: A network application for automated analysis of large genomic sequences," *Genome Research*, 7: 649-656 (1997).
Altschul, S.F. et al. (Oct. 5, 1990). "Basic Local Alignment Search Tool," J. Mol. Biol. 215(3):403-410.
Bevan, M. e al. (1983). "Structure and Transcription of the Nopaline Synthase Gene Region of T-DNA," Nucleic Acids Research 11(2):369-385.

(56) References Cited

OTHER PUBLICATIONS

Campbell, W. H. et al. (1990). "Codon Usage in Higher Plants, Green Algae, and Cyanobacteria," Plant Physiol. 92:1-11.
Chandler, V. L. et al. (Dec. 1989). "Two Regulatory Genes of the Maize Anthocyanin Pathway Are Homologous: Isolation of B Utilizing R Genomic Sequences," The Plant Cell 1:1175-1183.
Chenna, R. et al. (Jul. 1, 2003). "Multiple Sequence Alignment with the Clustal Series of Programs," Nucleic Acids Research 31(13):3497-3500.
Depicker, A. et al. (1982). "Nopaline Synthase: Transcript Mapping and DNA Sequence," Journal of Molecular and Applied Genetics 1(6):561-573.
Ebert, P. R. et al. (Aug. 1987). "Identification of an Essential Upstream Element in the Nopaline Synthase Promoter by Stable and Transient Assays," Proc. Natl. Acad. Sci. USA 84:5745-5749.
Fraley, R. T. et al. (Aug. 1983). "Expression of Bacterial Genes in Plant Cells," Proc. Natl. Acad. Sci. USA 80:4803-4807.
GenBank Accession No. V00087, created on Mar. 18, 1996, located at <https://www.ncbi.nlm.nih.gov/nuccore/V00087.1/>, last visited on Jun. 20, 2022, two pages.
Larkin, M. A. et al. (e-pub Sep. 10, 2007, Nov. 1, 2007). "Clustal W and Clustal X Version 2.0," Bioinformatics 23(21): 2947-2948.
Lawton, M. A. et al. (1987). "Expression of a Soybean Beta-Conclycinin Gene Under the Control of the Cauliflower Mosaic Virus 35S and 19S promoters in Transformed Petunia Tissues," Plant Molecular Biology 9:315-324.
Murray, E. E. et al. (1989). "Codon Usage in Plant Genes," Nucleic Acids Res. 17(2):477-498.
Nakamura, Y. et al. (2000). "Codon Usage Tabulated From The International DNA Sequence Databases: Status For The Year 2000," Nucl. Acids Res. 28(1):292, 1 page.
Odell, J. T. et al. (Feb. 28, 1985). "Identification of DNA Sequences Required for Activity of the Cauliflower Mosaic Virus 35S Promoter," Nature 313:810-812.
Smith, T. F. et al. (1981). "Comparison of Biosequences," Advances in Applied Mathematics 2:482-489.
Thompson, J.D. (Nov. 11, 1994). "Clustal W: Improving the Sensitivity of Progressive Multiple Sequence Alignment Through Sequence Weighting, Position-Specific Gap Penalties and Weight Matrix Choice," Nucleic Acids Res. 22(22):4673-4680.
Yang, N. S. et al. (Jun. 1990). "Maize sucrose Synthase-1 Promoter Directs Phloem Cell-Specific Expression of Gus Gene in Transgenic Tobacco Plants," Proc. Natl. Acad. Sci. USA 87:4144-4148.
Zhang, J. et al. (1997). "PowerBLAST: A New Network BLAST Application for Interactive or Automated Sequence Analysis and Annotation," Genome Methods 7:649-656.
International Search Report and Written Opinion issued in International Application No. PCT/US2021/49680 dated Feb. 9, 2022.
GenBank Submission AC232233, *Zea mays* cultivar B73 chromosome 9 clone ZMMBBb-315G18, Sep. 13, 2014 [online], Retrieved on Jan. 11, 2022, <URL:https://www.ncbi.nlm.nih.gov/nuccore/AC232233>.
GenBank Submission JN185196, *Zea mays* EA1-like protein 1 mRNA, complete cds, Aug. 1, 2011 [online], Retrieved on Jan. 11, 2022, <URL:https://www.ncbi.nlm.nih.gov/nuccore/JN185196>.
Schmidt et al., "Efficient induction of hefitable inversions in plant genomes using the CRISPR/Cas system", *The Plant Journal*, 98:577-589 (2019).
Mao et al., "Development of germ-line-specific CRISPR-Cas9 systems to improve the production of heritable gene modifications in *Arabidopsis*", *Plant Biotechnology Journal*, 14:519-532 (2016).

\* cited by examiner

```
                              SEQUENCE LISTING

<160> NUMBER OF SEQ ID NOS: 102

<210> SEQ ID NO 1
<211> LENGTH: 1568
<212> TYPE: DNA
<213> ORGANISM: Zea mays
<220> FEATURE:
<221> NAME/KEY: promoter
<222> LOCATION: (1)..(1568)
<223> OTHER INFORMATION: Promoter from ZmDSUL1

<400> SEQUENCE: 1
tttgctcaca ggtgactcag tagatgacga tcatgatgcg ctttaggtca tatatttgaa      60
gttcatcact gacctcatca aggaacatgt ttctagtgac cttggtgtta gggtgttctt     120
atggggtcgt aggtcatgct accatcactg tcgatcgagg cattgtagga atcgttcagt     180
caagtcattg accgcccttc actcaatcag tcattgaccg cccatcactc aaccaggtca     240
cgagtacctg acttatgcat gggacaatac ttcctttact aggtgcgata aggcactata     300
tggcaatggt tgtcttcatg ggggtaggct cgatgtcact ctgaagtcac aaccctaggc     360
gtgataccat acttttttg tgcaatagat agagcaactc gtaggtcatg gatcttagag      420
ttccaagggc ccttaagggg ggtctaggcg atcaagagga ctcaaggaga atgagagcgt     480
cttggagtgt cctaggggcc ttgagtgccc tctgtttcac ttgttctaac aaatggttgt     540
ggctgggata gtcttacatg tctacggagg cccgagacca gatcctctga tatgttaggc     600
ttgtatctta gctagagtcg aggttagtcg cggatcagac aattccttct atcgaggttc     660
tttgaaaggc atcctatcaa ctcattaggg tatgatctac tcccgttgtt aataaacgta     720
ttttataaca caacactcac atcatgaatt gtatttaaac tcaaccagaa cttcagcatc     780
tcctcaccag tatgaatcat cacatattca tcaacgatgt tttcagagtc catgcctcta     840
aataaattta ttataaaaaa tattctataa ctaatctaat aatacttatt ttatattaaa     900
aaattagtac ttatataact ttagtcaaag ttcaaactgt ttgaggaagc caacattata     960 cttttttatgg atggttgaag tatacagttt tctataaact ttgtcaaatt atgtatggta    1020
acttaactta gaaaataaca agaaataatg gagagatatc acatttggaa acggcgtagt    1080
attccacttg gaacactttt attttaagat gcaaaaaaaa atggctggtg gagctaaaat    1140 atttttatt tgagccgaga cattcttttt ttgtgaacta cttcatctgc gcagcggcag     1200
acttcgcgtg cgtattaatg tttatactgt gttgaacttt agatacataa accgataaac    1260
gcatgcaaat taaagttgt tcttgctgcc acgcctatcg gttgagttgc atgactttca     1320
ggccaacaca ctgcaagcaa aatggaattg gagatttact acgagagcga gtggtcaagt    1380
attcatgact agccggctgc ctcgtcttct tctcgaatgg aatggctccc acttgctgca    1440
aacggcccgc cggagacgct tcgttacccc actaatccct ggaaaggagt ttacatggac    1500
agtgggagcc tatataagca cgttcatggc gagacactac atccgagaag gacgatcagg    1560
cttcaggc                                                             1568

<210> SEQ ID NO 2
<211> LENGTH: 2000
<212> TYPE: DNA
<213> ORGANISM: Zea mays
```

```
<220> FEATURE:
<221> NAME/KEY: promoter
<222> LOCATION: (1)..(2000)
<223> OTHER INFORMATION: Promoter from ZmEA1

<400> SEQUENCE: 2
cacgtccacg tgcaccaagg aggagaggac actactgtcg ccactttat tttactagta      60 gtcttccaga gaccgcccag gcgcgcgccc aaccatgcgc cccttcgact gcgaccctac     120
cctagagcta gccagcaaac atacgaacag cagctaatcc gccgtctttg tggaggactg     180
caaagtaaag ctgcgggttc gcaaggaacg ccgcgcggga tataacctgc ccggcgacgc     240
cgggtgcaac cattgtcacc aagggacaaa cagatgacac agctggaccc accacgaagg     300
acactatggc cgccgccacc gccaccgccg ccaccgccag tagtgagaac actgctccca     360
tgatcttgaa ggagagtgat gaatcaaaca agtcgtcaag cgcgctcgct ctctggtata     420
gggttggtac tattgataga caccgcgtgg aatttctgcg acagagaagt catctatttg     480
taggtcggcc agaggcggct gctggccttc tatgggggtg cgttgcatgc gtgcgtaatt     540
gctgccgtct cacgtacggc gaagtgcgcg tgctggggaa aacgaatcgg cctgggaact     600
ccaagaggcg ttgctccgcc tccgactctg agtgcatagc caagtactgc agctactgcc     660
cgctccgccc gatgcgccga tcaacaccca tttcgcaaag tgtagccggc cccatcaaat     720
gcagaagtcg actcgtcgat tcggagtgag aacgatcatt ttccgacaat actaatccaa     780
aggcaggctc atggtggtac atgtccaagt ccaatcttct aatgggtata gttaggttat     840
ttaaaataat accctgagtt ctgtcacttt cttcattttt aatactaatc caagctgcca     900
cgacggattg gtgggtagtg gacgagtagt atcggcaaaa aaaaaatac tactttttgcc     960 ggtgaaattt aattactact ctacataatt agcaaatgaa attaatcacc tcttatgcac    1020
gtatgtgttt taatttccat cagttcactt ttagggctga tttggtggtc agtgatcccg    1080
agaggatcca tgagaggaat cccccttgata ttcaaaattg aattgtaagg ggatttctct    1140
cccatgaatc atcttggaat ctctgatcac caaatcagcc cttaaaatga aaagaaatt     1200 tatattatcc ggaagctttg gaaaatatac tcataatttc gtatataaac caaaagcatt    1260 attaaaccctt gagtcaaatg catgtaacct tgaggggtta cctaatccta gtgtgccaaa    1320
gcatgtaacc ttgagggggtc ggttccttag gaaggcgccg taaggcaagg gtaaaaccaa    1380
cgttctaccc gaggtaaaac cacacgcccct tgtgagcccc agattcacct ggatgtcttg    1440
tatttacggc accgggctgc gggggccaat gcaccatcat ttaagctatg tcgaccgctg    1500
gcctttatag catggcctcg aggtgactcg tagttaatga aattaattta attactactc    1560
tacataatta gcagatgaaa ttaattacct cttatgcacg ttctcactac taccaagcaa    1620
caattcagct tctgcatttc gctaccgttc tcttcaactt caatgcgctc gactgatcgc    1680
gcacattgcg aagctgtctc ttcgtcgtcg cctcccatcg tgatttgaga ctggggagca    1740
aatgcgcacg gcatgcatcg caatgcacgc gatgaagctg agcagccgcc tggccaacct    1800
cgatccggcg ctgcagccta ctacaaatag atgttcaatt aacacaacac gcagcgaccg    1860
ctgtccagtg tccattcatt ccaaacccag ccgatcgctc tcctccaatt aagcagcaag    1920
ggcagaagca acaccggcgt gccacccgga cgacgctgaa tcctgcatgt caacctgccc    1980
ggccatcgtc attcgtcaac                                                2000

<210> SEQ ID NO 3
<211> LENGTH: 2000
<212> TYPE: DNA
```

<213> ORGANISM: Zea mays
<220> FEATURE:
<221> NAME/KEY: promoter
<222> LOCATION: (1)..(2000)
<223> OTHER INFORMATION: Promoter from ZmES4

<400> SEQUENCE: 3

```
tttccttaat ctcctgggtc acttagaccc cgcaaggacc accacacact taggtgtctc      60
ttgcttcgat tacaaatcac ttgagaaaag aaatgggaaa ggaagaaggc aatccaagag     120
gcaagagctc aaaagaacac aaaatctctc tctcacaagt cactaagtgc ttgagttgaa     180
tttgggactt ggagaggctt tgatcttttg aattgtgtct acgagtgaat gctagagctc     240
ttgtaatgaa tgtgatactc agaaatcttg gatgcttgga gtggtggtgg ttgggggta      300
tttatagccc tcaaccacca aacaaccgtt ggggagggcc gctgtcgatg ggcgcaccgg     360
acagtctggt acgccaccgg acactgtccg gtgcgccagc cacgtcacgc aaccgttagg     420
gtttgggagc tgtcgaccgt tggaggcttt gtcctctagt ggcaccggac agtccggtgc     480
cgcaccggat agccactgtt cagtgtccgg tatgctctaa ctctaggctc tgactcagcc     540
gcgtattgtt gtgcgctgta gcgctcgtca ggagccgttg cagtcgacca ttgcgctgga     600
ttgtcgttac tccgctggtg caccggacag tccggtggca caccggatag tccggtgaat     660
tgtagcggag agcgccagaa gaaacccgag agtggccgtt tggactctgt acggtcctgg     720
tgcaccgac actgtccggt ggcacaccgg aaagtccggt gcgtgaaaga gaaatatggt      780
ttaactttt cctataaatg attttggtgg ttgaatgccc aacacaaata attgtactaa      840
ctagtttgct ccagattata tattctatag gtgcataaaa ggttcaacac aaaccaataa     900
aagatcaaag ttagggttta aaaagaaagg aacaaagaaa ccaaagtgtg ccctggtctg     960
gcacaccgga ctgttcggtg tgccacgtcg atgtttgcac agctcgcccg aggccactct    1020
tgggcgggag accccagggt agcctcgcgt gagccatgac tgtgcctccc gtccgagtgt    1080
ggcctcagac gacagacata gaaccatgat gtactgtaga tatatatcta tgtttatagt    1140
acatcaacag attctgaagt ctatttcagg ttgaattagg tttgtactcg gacgagtgat    1200
atttatcgtt ccatatctat gtttatata aattttttac tctcgtcgta acatataggc     1260
acatacctgt tcaaatatat gtgcgattgt gctcatatgg gtagaagaag gaactggatg    1320
tgaagacatg tatatataga ccaaaaatgt atcttagccg atttcaaact gcctagcgaa    1380
aagatgaagc tgctccgtgt ttgggtgact gcagcattat gtatcttatt aatcgatttc    1440
acagaagact tgtctctcat ggaacaaacg aacctattag cagtctgtat ataaagaagt    1500
gacttccaga ctgccaagtt tagtgattag ggctgctgtg actgaccatt taccttgcaa    1560
acaatctttc gatctactgc tctgtcatgc atggttttg catcgtccat tatgtttatt     1620
tcccattgtt gcagcttacg atatcgtgta tacctggcac ctatgtttat gacaatgaaa    1680
ctcaccatct ttattctatt ggcattcatt ttcattcaaa ttacataacg tatgctagaa    1740
cgaccgaata caaattactg ctaataaaca tcctgcgtac gcgcaatggt gcaccattta    1800
ccaattaata gctgtaacgg tactgcaagt aatggtcgaa gcgttatgtt ttctctcctc    1860
tcttcccacc gtacaggatc atatattcat atatatatac acatgcctct ggaacggcta    1920
attcgatagt tccaccacgt tacttccata tatttcccctt ggattggatc gtcggcgccc    1980
aaacgaatac taatccggca                                                2000
```

<210> SEQ ID NO 4
<211> LENGTH: 2999

```
<212> TYPE: DNA
<213> ORGANISM: Zea mays
<220> FEATURE:
<221> NAME/KEY: promoter
<222> LOCATION: (1)..(2999)
<223> OTHER INFORMATION: Promoter from ZmDMC1

<400> SEQUENCE: 4
```

| | | | | | |
|---|---|---|---|---|---|
| acctaacctg | gctgagccaa | cacctgaggc | cctcccctaa | accagggagt | ccctgatgat | 60 |
| ccctactcaa | aggtgataag | ggtgaaaacc | cttcattata | cacattttga | aaagcatttt | 120 |
| cttttgatcc | cggctgggtg | gccataataa | cttgtctcaa | aatcatatca | tgcataaaat | 180 |
| aacaggctga | gggttgtggt | tgaaaaatca | taggtaattt | atgcatcaaa | gggatccagt | 240 |
| gagtttgtcg | tgcttatccg | acgaaggggg | aagaggagct | cgcggaactg | tcttctagct | 300 |
| ccactgcctg | gcgtagactt | gcagatctgg | cctccacgag | acgacatgaa | cgctccgata | 360 |
| actatgcaac | atgaataagc | aaacatacaa | accaacaagt | ataccaacaa | atatttagta | 420 |
| tagtggtcag | aatagcgata | tatggatggg | tagagtcgtg | agtagaatct | gtgtcatgtg | 480 |
| gtgttgagat | actactagtg | gtggagcgga | ggtgcttacc | aggagggtgg | actggaggcg | 540 |
| aagcgacact | atgcgtgtag | ccggcagagc | ggagtaacta | agtgagtggg | gtgtttgcct | 600 |
| tggctgaggg | tgttgagtgt | gtgtggagag | ggagagggta | gctgggtgta | tttatagctg | 660 |
| ggtgtatgtg | gtgtagcaca | atgaagttca | ttgttggtga | aatagtgac | atatgaatcg | 720 |
| tctgacttag | tatgaacagg | agagttatat | gcagaatatg | ggacaagagt | attttgggag | 780 |
| ttttctggaa | tatgaaccat | acttaagtga | tgacatggtt | ggatagggaa | taatttgata | 840 |
| agaatttaga | aacaagaatt | attggaatcg | gagtttggaa | gcctggttcg | aaggaatctc | 900 |
| aaagttaagc | gtgctcaact | tagagaaacc | tgggatgggt | gaccagatgg | gaagttccct | 960 |
| actggaagga | aaatcacagt | caccggagtt | cgtatgactg | aaatatgggt | ctggctggtc | 1020 |
| ttaggtggac | tggatagcat | gatggatgag | tagttgaaat | ttagggtgat | cggatgatcg | 1080 |
| atgaatagtg | tcttggaatg | agaaggaaga | aagcacgatt | gcaaaagcta | agcgacaaga | 1140 |
| gcgacaaata | acacacagat | cactctctct | ctcaagtcac | taatcactaa | tgatcacttg | 1200 |
| tcttaattgt | ggaacttgga | gagattgaa | gctttgattg | tgtcttggaa | tggattgcta | 1260 |
| gctcttgtat | tgaatgtgaa | ggattggaat | gcttgggtgt | catgaatgga | ggtggttggg | 1320 |
| gttgtattta | tagccctcaa | ccacttccta | gccgttgctc | cttttctacc | gaccgcggac | 1380 |
| ggtccgcgcc | cctggtccgg | acagtccgcc | cctgcacatc | aacggctgaa | atcgcaacga | 1440 |
| tcagcagtaa | cggctatatc | aacggctata | tagcatttaa | tgtgtcgtca | gatgtcagat | 1500 |
| aaaagcagtc | gcagacggtc | cggtcatgca | ccccggacgg | tccgcgagga | tgctataatt | 1560 |
| cattttaccg | aacccgtcac | cttcgggttt | ttcggttctt | caccgacctg | atggtccgcg | 1620 |
| cctgaggccg | gatggtccgc | gcttggtctc | ggacggtgct | tggctttcca | tcggacggtc | 1680 |
| cgtagtgtag | acttgtgttt | ttgtattggt | tctgtcctag | gctcacccta | gtttcgcgga | 1740 |
| cggtccgccg | caagggccca | gacggtccgc | gcttatgtga | ttttccaaaa | agcttctcct | 1800 |
| gtccagaata | atctacggta | ttccggacag | tcgactttag | aatagttgta | gatgaactta | 1860 |
| tgcacctgtg | gaatgatcaa | ttagacaaac | cggttagtcc | acaaggtttg | tgatggtcgt | 1920 |
| caaacaccaa | aaccgattat | agggaatatt | gaaactattt | cccttcaat | tatatttgtt | 1980 |
| tagttgaggt | tctaaatttt | ttatagcaag | gcccgtttgg | ttagagagac | taattttagt | 2040 |
| ccctgacttt | tagtctcatt | tagtctctat | tttgccaaac | ggaaggacta | aagtagggac | 2100 |

```
taattggttt tagggcatgt ttggttcgtt acctcaattg ccacattttg cctaactttt    2160
ctgcctaagg ttagttattc aattcgaata actaaccttα ggcaaagtgg ggcacagtta    2220
gccacaaacc aaacaagccc ttagtctttα gtcccttaca tagatgctaa aagggactaa    2280 agggaatat ttactctaat taccctGgcc tagaaaacta gtgtgaaaca aaaaaaagag    2340
tattttgatc tttatgtatt acatttaatg tatttaaaat ctgtttagcc cctacaacta    2400
aacaatatag agactaaagt ttagtttagg gactaaactt tagtcctaag actaatggag    2460
ccaaacgggg cccaaatctc gtttaaaaat ttgaagcaaa cacatccttα acggaccgtg    2520 ggcaatgagc tgagtctccc ctgactctgg gccgcaaagt cctggtacac ttgatcatgt    2580
tggtccatcc tatggctgac cgcgacttcc ctagactgaa atcaacccat tcctaggctc    2640
ctagcccagc ccaacggccg agcacacgat ccgttcgaga gcgagaaggt cctccggcct    2700
cagcaccctc aagtacacag tacaccctcg caccggtacc gcggtccgcg cacacgaca    2760 cccccactcg tctgtcgact cacgtctgat cgtctctccc caacaatctc tcgagtcttg    2820
ccattcgcct cagcttgccc ctcctccaag cgtccaagcc ccaccggcc attgcctcct    2880 cctcctgccg caggtaagct agctgctcca gcttctcttg ccatcgcgtg tcctgcactc    2940
accgccctcg cgcgtgtaac tcctcctccg tccccgatc gggctactag tgcaggcac    2999

<210> SEQ ID NO 5
<211> LENGTH: 1979
<212> TYPE: DNA
<213> ORGANISM: Zea mays
<220> FEATURE:
<221> NAME/KEY: promoter
<222> LOCATION: (1)..(1979)
<223> OTHER INFORMATION: Promoter from ZmMps1

<400> SEQUENCE: 5
tgatatggtt tggttgcact tgagaaatga ttagtttcct aatttgcacc attctaaatt      60
aatgcctcgt gttgctggtc cttttaaggt gctaacaaag attaatgata atgcttatat     120
ccttgacctg tctgtagaat ttggtgttta cactagtttt aatgttccag atttgaaacc     180
atacatgggc gaggatgacg agttaccgtt gaggatgact tcacttcaag aaggggagga     240
tgatgaggat atcaactgca acacgagtac gatacaccag cagcaccacc acctcaggcg     300
ccacatccct cctcagctag gccaacttca ccttaggcac cacttccttc attagttggg     360
caaatcactc ggaccgtgc aagagatctt aacttcgtca tgctactgaa taatgaggga     420
ccagaagaat agacgaccgg cccaattacg acccaaggtg gaggacctag gatgggccgc     480
ccctagggtt gcgttttttcc accttggccg ccaccagggg ctgtgcccct ctctctattt     540
atctagtagc tgcacctcct tttgttcctt gagttttgtt ttacattagc cttagctatt     600
cccaaacacg cacatattag cgctgtcttc gtgtattcag aactccacca tcgagtaata     660
gactagattg ctcgtatctt tttcttgttc gttcttcgat tgcgtgcagg aaatgatctt     720
tgtgatcagg ctgatcttgc accagcaagg tcggtaacca tagggagttg gttcagcgat     780
tgcattggcg cctcgagctt gctcgtcgta gtcggaccgt gagggtcatc ttcgccagat     840
cgaaattatc tccactcacc gaaagatcgg gcacttcagc cttatcaggg agtggctgcg     900
gcatgggtcc cttcggtcag ctagtgatga ggtcggtgca gtgatttggt ttgggccgag     960
gagaagattc agcccaggtc taggtatgct tctcttcttt atattttgtg ccttctttct    1020
tgaatttaga ttctatattc aactccaaat tatttttgag tttcaaacta taatatacα    1080 aacaataatg caacaatatt ttattattct attatttat tattctagag aagcaattgc    1140
```

```
ttctagctat gtaattcaca cataaatagt ttattttaga gaaataattt ctattgtata    1200
gctatcaaga tatgatttaa ctcaaatttc tttaaagagt tatagatcaa caaagggata    1260
acttaattat cttttcattt gatcttttat tagaaaaagt tattcatttt gtgagaaaat    1320
ccttattaaa aagatatgtt ggttcaaatc cttttggaga agcttttata ggtgctagaa    1380
taggattttg gggttagagt gttgctctag ctaattaaaa tagtagaata gccgtttgta    1440
gtcgcggtcc tagaataggc gggtttatgt taaattcgtt gatcacggat cacggtccac    1500
atattcttgg gtgggcctct cctctcgttt gcctgcgccg ccgcgatcgc caatcggcgc    1560
tcttcccaaa ccccgcccgc caacgccgac ggcgtcagcg gccacgggca cctcctcgtc    1620
gcgaatagac tcgccatcgc taaaggccgc gctcgcaatg gctctcatcc actacaaccg    1680
cctccctggc aaagccaacg ccaccgcggg cacatcaccc ccgtctctcc tccactggaa    1740
gcgcaaggtc ccattcccct agcagcaaca accctcggat caaaccctaa cctccgcctc    1800
tgacattaga tctccttctc ccgcccaggc caaggaccgg aagcgcgaaa tcctccgcct    1860
ccgcgaggag ctcaaggtcc tccaaggtat gtaaggccat gccaatctat ccgcgctatt    1920
gttcgtctgg ccgaattcca ttgcaggcgt cgtggaaatt gagtttgtta tcggagcag     1979

<210> SEQ ID NO 6
<211> LENGTH: 1824
<212> TYPE: DNA
<213> ORGANISM: Zea mays
<220> FEATURE:
<221> NAME/KEY: promoter
<222> LOCATION: (1)..(1824)
<223> OTHER INFORMATION: Promoter from ZmAdf1

<400> SEQUENCE: 6
agaccaacac gagaattttg tgcgtacttt gtcctcactc atacgcacca gagaatactt      60
ttcgatcgat cactcatcct aaggttgctt taggccaaac acgtttaacc taaaggttct     120
ttcgcagcag gcttccgaaa aaaagataca ccttgttgat atggatattc tattaatttt     180
attaagtctt agcgaggatg tcacaatcca accaggctag gatatcacaa tcctccctct     240
tagaagaccg acgtcctcat cggtcaaccc caagccaaaa acctccctct tacccgtgac     300
tgtatgtcta gtgtcgtcat attccatgcc atttgaccac tctgagccta catacgtcgt     360
gcaacatata cccaaaaccc tagcctacac acgtccgtga aaccacgagg gtcgtctctg     420
ataccatttg taacatctca tccactgtcg gaccagtgat acttactcct gacaaccctc     480
tagaaccata aaccatcctt acaaaccaac acgagtcttt tgtgcgcact ttatcctcac     540
tcatacgaac tagggaggat ttgtcggtcg ggcacacatc ctaagattgc tctagaccaa     600
gcacacttaa cctagatggt tcttttaaga catacttcat aatgtagtta tttgttttga     660
tttatttcta ttattccaac aaattatgta acatttacat ccttgcagtg accataacta     720
tagatgcaat acaatgaact atggagttca atgtatctat aggtgttgtt ctgctagtgc     780
taaactctag ggaggttgcg ctgtgtccaa tgtcgctggc catgtcgcgt gacgtgcctc     840
gcgacaggct actggtagtt ctgcgccgaa cattggttga tccacgccta agaccacgca     900
ctaagccggt ctatccgtgt tcaacatcgt agttctgcac ctctgggata cacaaccgcc     960
ttgtccaacg ccatgcccca agccaccgca tacgtcgggg ctatcagtgt ctcctttctc    1020
agcgtgctaa catgatacat gttacaatcg aagacgagct cgcatcgtgg caacaaattt    1080
tggtgctcca aagctttgga aaggttatcc tcaacattgt tgggatccat ggcggtctag    1140
```

| | | | | |
|---|---|---|---|---|
| aatcaaccat | atgaaacact | agcggctagg | gttcggagga | gatcattagg gaggagaagg | 1200 |
| agaggtcaag | tctaagttgg | gctaggtgag | aacgatcatg | ggtagatgga tggcagtacc | 1260 |
| gggtaatttt | catcaactta | cgattaatag | tgggtctttt | attaaaaata agctgatata | 1320 |
| agcatctttt | gagaagctta | tagggttatc | ataatctcaa | gtactagatt atataatttt | 1380 |
| atcacataag | ttgcttcata | cttagtttgt | ctatcactag | cttatttaca tagaatttag | 1440 |
| attatataat | accaaaccct | aaatgacctg | aaccaaagat | acccagattg cttcacatca | 1500 |
| tttgtgtggc | actgtggcta | catgaggacg | tgggaatggg | cgaatggcgc ggaacgaccc | 1560 |
| ccgataggtt | tccgatattg | ccctccccac | gcgcacgatt | taaccgatcc gcccccgttt | 1620 |
| ctttcttttt | ctccacgaga | acgagattac | gagacaagag | acaagtagac aacccagctc | 1680 |
| tccagcggtc | cagcggtcca | gcctctccta | gccgaggcca | aaaccccat accaacacac | 1740 |
| acttcgcttc | tcgctgcctc | cgcggcggcg | cgccgctccg | ctccgagccc tcttcctcct | 1800 |
| cctcctctgc | ccgttcggtc | gaga | | | 1824 |

<210> SEQ ID NO 7
<211> LENGTH: 3681
<212> TYPE: DNA
<213> ORGANISM: Artificial
<220> FEATURE:
<223> OTHER INFORMATION: Synthetic sequence

<400> SEQUENCE: 7

| | | | | |
|---|---|---|---|---|
| tcgaagctcg | agaagttcac | caactgctac | tcgctgagca | agacgctgcg gttcaaggcg | 60 |
| atccccgtcg | ggaagaccca | ggagaacatc | gacaacaagc | ggctcctggt cgaggacgag | 120 |
| aagcgcgccg | aggactacaa | gggcgtcaag | aagctgctgg | accggtacta cctctccttc | 180 |
| atcaacgacg | tcctgcactc | gatcaagctc | aagaacctga | caactacat ctcgctgttc | 240 |
| cgcaagaaga | cacggaccga | gaaggagaac | aaggagctcg | agaacctcga gatcaacctg | 300 |
| cgcaaggaga | tcgcgaaggc | gttcaagggc | aacgaggggt | acaagagcct gttcaagaaa | 360 |
| gacatcatcg | agaccatcct | gccggagttc | ctggacgaca | aggacgagat cgcgctggtg | 420 |
| aactcgttca | acgggttcac | cacggccttc | accgggtttt | tcgacaaccg ggagaacatg | 480 |
| ttcagcgagg | aggccaagtc | gaccagcatc | gccttccggt | gcatcaacga gaacctcacc | 540 |
| cgctacatca | gcaacatgga | catcttcgag | aaggtggacg | ccatcttcga caagcacgag | 600 |
| gtccaggaga | tcaaggaaaa | gatcctgaac | tcggactacg | acgtggaaga cttctttgag | 660 |
| ggcgagttct | tcaacttcgt | cctcacccag | gagggcatcg | acgtctacaa cgccatcatc | 720 |
| ggcggcttcg | tgacggagag | cggcgagaag | atcaagggcc | tcaacgagta catcaacctc | 780 |
| tacaaccaga | agactaagca | gaagctcccg | aagttcaagc | cgctgtacaa gcaagtcctg | 840 |
| agcgaccggg | agtccctctc | gttctacggc | gagggctaca | cgagcgacga ggaggtgctg | 900 |
| gaggtgttcc | gcaacacgct | gaacaagaac | agcgagatct | tcagctcgat caagaaactc | 960 |
| gagaagctgt | tcaagaactt | cgacgagtac | agcagcgccg | gcatcttcgt caagaacggg | 1020 |
| cccgcgatca | gcaccatcag | caaggacatc | ttcgggagt | ggaacgtgat ccgcgacaag | 1080 |
| tggaacgccg | agtacgacga | catccacctc | aagaaaaagg | cggtggtcac ggagaagtac | 1140 |
| gaggacgacc | gccggaagtc | cttcaagaaa | atcgggagct | tcagcctcga gcagctccag | 1200 |
| gagtacgcgc | acgccgacct | gagcgtggtg | gagaagctca | aggagatcat catccagaag | 1260 |
| gtcgacgaga | tctacaaggt | ctacggctcg | agcgagaagc | tgttcgacgc ggacttcgtg | 1320 |
| ctggagaagt | ccctcaagaa | gaacgacgcc | gtggtggcca | tcatgaagga tctgctcgac | 1380 |

```
agcgtgaagt cgttcgagaa ctacatcaag gcattctttg gggagggcaa ggagacgaac    1440
cgggacgagt ccttctacgg ggacttcgtg ctcgcgtacg acatcctcct gaaggtcgac    1500
cacatctacg acgcgatccg gaactacgtc acgcagaagc cctacagcaa ggacaagttc    1560
aagctctact tccagaaccc gcagttcatg ggcgggtggg acaaggacaa ggagaccgac    1620
taccgggcca cgatcctgcg gtacgggtcc aagtactacc tcgccatcat ggacaagaag    1680
tacgccaagt gcctccagaa gattgacaag gacgacgtga acgggaacta cgagaagatc    1740
aactacaagc cctcccgggg cccaacaag atgctgccga aggtgttctt cagcaagaag     1800
tggatggcct actacaaccc ctcggaggac atccagaaga tatacaagaa cggcacgttc    1860
aaaaaggggg acatgttcaa cctgaacgac tgccacaagc tgatcgactt tttcaaggac    1920
agcatcagcc gctacccgaa gtggtcgaac gcctacgact tcaacttctc ggagacggag    1980
aagtacaagg acattgcggg cttctaccgg gaggtggagg agcagggcta caaggtctcc    2040
ttcgagagcg cctccaagaa agaggtggac aagctcgtgg aggagggcaa gctgtacatg    2100
ttccagatct acaacaagga cttctcggac aagtcgcacg gcaccccgaa cctccacacg    2160
atgtacttca gctgctgtt cgacgagaac aaccacgggc agatccgcct cagcggcggg    2220
gcggagctgt tcatgcgccg cgcgtccctc aagaaggagg agctggtcgt gcaccccgcc    2280
aactccccga tcgcgaacaa gaaccccgac aaccccaaga agacaaccac cctctcgtac    2340
gacgtctaca aggacaagcg gttctcggag gaccagtacg agctgcacat cccgatcgcc    2400
atcaacaagt gccccaagaa catcttcaag atcaacaccg aggtgcgggt gctgctcaag    2460
cacgacgaca accccctacgt catcgggatc gaccgcggcg agcggaacct gctctacatc    2520
gtggtcgtgg acgggaaggg gaacatcgtg gagcagtaca gcctgaacga gatcatcaac    2580
aacttcaacg gcatccgcat caagacggac taccacagcc tcctggacaa gaaggagaag    2640
gagcggttcg aggcgcggca gaactggacc tccatcgaga acatcaagga gctgaaggcc    2700
ggctacatca gccaggtcgt gcacaagatc tgcgagctcg tggagaagta cgacgcggtg    2760
atcgcgctgg aggacttgaa cagcgggttc aagaactccc gggtcaaggt cgagaagcag    2820
gtctaccaga gttcgagaa gatgctgatc gacaagctca actacatggt ggacaagaag    2880
tccaacccct cgccaccgg cggcgccctc aagggctacc agatcaccaa caagttcgag     2940
tccttcaagt cgatgtctac gcagaacggg ttcattttct acatcccggc gtggctcacc    3000
agcaagatcg acccgagcac gggcttcgtc aacctcctga gaccaagta caccagcatc    3060 gcggacagca agaagttcat ctcctcgttc gaccgcatca tgtacgtccc cgaggaagac    3120
ctgttcgagt cgccctcga ctacaagaac ttctcccgga cggacgccga ctacatcaaa     3180
aagtggaagc tctacagcta cggcaaccgg atccgcatct ccgcaaccc caagaagaac    3240 aatgtgttcg actgggagga ggtgtgcctg acgagcgcct acaaggagct cttcaacaag    3300
tacggcatca actaccagca aggggacatc cgcgcgctgc tctgcgagca gtccgacaag    3360
gcgttctact cgtcgttcat ggccctgatg agcctcatgc tccagatgcg caacagcatc    3420
accggccgga cggacgtgga cttcctgatc agcccggtca gaacagcga cggcattttc    3480 tacgacagcc ggaactacga ggcccaggag aacgccatcc tccccaagaa cgccgacgcg    3540
aacggcgcct acaacatcgc gcggaaggtg ctgtgggcca tcggccagtt taaaaaggcg    3600
gaggacgaga agctgacaa ggtcaagatc gccatcagca acaaggagtg gctcgagtac     3660
gcgcagacga gcgtgaagca c                                              3681
```

<210> SEQ ID NO 8
<211> LENGTH: 36
<212> TYPE: DNA
<213> ORGANISM: Lycopersicum esculentum
<220> FEATURE:
<221> NAME/KEY: misc_structure
<222> LOCATION: (1)..(36)
<223> OTHER INFORMATION: NLS1-Monopartite Nuclear Localization Signal
      (NLS) from the tomato heat stress transcription factor HSFA1

<400> SEQUENCE: 8
atggcgggat ctaagaagag aagaattaaa caagat                                36

<210> SEQ ID NO 9
<211> LENGTH: 33
<212> TYPE: DNA
<213> ORGANISM: Lycopersicum esculentum
<220> FEATURE:
<221> NAME/KEY: misc_feature
<222> LOCATION: (1)..(33)
<223> OTHER INFORMATION: NLS2-Monopartite Nuclear Localization Signal
      (NLS) from the tomato heat stress transcription factor HSFA1

<400> SEQUENCE: 9
ggatctaaga agagaagaat taaacaagat tga                                   33

<210> SEQ ID NO 10
<211> LENGTH: 200
<212> TYPE: DNA
<213> ORGANISM: Zea mays
<220> FEATURE:
<221> NAME/KEY: promoter
<222> LOCATION: (1)..(200)
<223> OTHER INFORMATION: Promoter from ZmU6

<400> SEQUENCE: 10
cggcgtatgt gccaaaaact tcgtcacaga gagggccata agaaacatgg cccacggccc        60
aatacgaagc accgcgacga agcccaaaca gcagtccgta ggtggagcaa agcgctgggt       120
aatacgcaaa cgttttgtcc caccttgact aatcacaaga gtggagcgta ccttataaac       180
cgagccgcaa gcaccgaatt                                                  200

<210> SEQ ID NO 11
<211> LENGTH: 2008
<212> TYPE: DNA
<213> ORGANISM: Zea mays
<220> FEATURE:
<221> NAME/KEY: promoter
<222> LOCATION: (1)..(2008)
<223> OTHER INFORMATION: Promoter, 5' UTR and intron from ZmUbqM1

<400> SEQUENCE: 11
gtcgtgcccc tctctagaga taaagagcat tgcatgtcta agtataaaaa aattaccaca        60
tatttttttg tcacacttat ttgaagtgta gtttatctat ctctatacat atatttaaac       120
ttcactctac aaataatata gtctataata ctaaataat attagtgttt tagaggatca       180
tataaataaa ctgctagaca tggtctaaag gataattgaa tattttgaca atctacagtt       240
ttatcttttt agtgtgcatg tgatctctct gttttttttg caaatagctt gacctatata       300
atacttcatc cattttatta gtacatccat ttaggattta gggttgatgg tttctataga       360 ctaatttta gtacatccat tttattcttt ttagtctcta aattttttaa aactaaaact       420 ctatttagt tttttattta ataattaga tataaaatga aataaaataa attgactaca       480
aataaaacaa atacccttta agaaataaaa aaactaagca aacattttc ttgtttcgag       540

| | |
|---|---|
| tagataatga caggctgttc aacgccgtcg acgagtctaa cggacaccaa ccagcgaacc | 600 |
| agcagcgtcg cgtcgggcca agcgaagcag acggcacggc atctctgtag ctgcctctgg | 660 |
| accccctctcg agagttccgc tccaccgttg gacttgctcc gctgtcggca tccagaaatt | 720 |
| gcgtggcgga gcggcagacg tgaggcggca cggcaggcgg cctcttcctc ctctcacggc | 780 |
| accggcagct acgggggatt cctttcccac cgctccttcg ctttcccttc ctcgcccgcc | 840 |
| gtaataaata gacacccct ccacaccctc tttccccaac ctcgtgttcg ttcggagcgc | 900 |
| acacacacgc aaccagatct cccccaaatc cagccgtcgg cacctccgct tcaaggtacg | 960 |
| ccgctcatcc tcccccccc cctctctcta ccttctctag atcggcgatc cggtccatgg | 1020 |
| ttagggcccg gtagttctac ttctgttcat gtttgtgtta gagcaaacat gttcatgttc | 1080 |
| atgtttgtga tgatgtggtc tggttgggcg gtcgttctag atcggagtag gatactgttt | 1140 |
| caagctacct ggtggattta ttaattttgt atctgtatgt gtgtgccata catcttcata | 1200 |
| gttacgagtt taagatgatg gatggaaata tcgatctagg ataggtatac atgttgatgc | 1260 |
| gggttttact gatgcatata cagagatgct ttttttctcg cttggttgtg atgatatggt | 1320 |
| ctggttgggc ggtcgttcta gatcggagta gaatactgtt tcaaactacc tggtggattt | 1380 |
| attaaaggat aaagggtcgt tctagatcgg agtagaatac tgtttcaaac tacctggtgg | 1440 |
| atttattaaa ggatctgtat gtatgtgcct acatcttcat agttacgagt ttaagatgat | 1500 |
| ggatggaaat atcgatctag gataggtata catgttgatg cgggttttac tgatgcatat | 1560 |
| acagagatgc ttttttcgc ttggttgtga tgatgtggtc tggttgggcg gtcgttctag | 1620 |
| atcggagtag aatactgttt caaactacct ggtggattta ttaattttgt atctttatgt | 1680 |
| gtgtgccata catcttcata gttacgagtt taagatgatg gatggaaata ttgatctagg | 1740 |
| ataggtatac atgttgatgt gggttttact gatgcatata catgatggca tatgcggcat | 1800 |
| ctattcatat gctctaacct tgagtaccta tctattataa taaacaagta tgttttataa | 1860 |
| ttattttgat cttgatatac ttggatgatg gcatatgcag cagctatatg tggattttt | 1920 |
| agccctgcct tcatacgcta tttatttgct tggtactgtt tcttttgtcc gatgctcacc | 1980 |
| ctgttgtttg gtgatacttc tgcaggtc | 2008 |

<210> SEQ ID NO 12
<211> LENGTH: 927
<212> TYPE: DNA
<213> ORGANISM: Artificial
<220> FEATURE:
<223> OTHER INFORMATION: synthetic sequence

<400> SEQUENCE: 12

| | |
|---|---|
| tgcccggtct ccattattcg caagacccctt cctctatata aggaagttca tttcatttgg | 60 |
| agaggacacg ctgaaatcac cagtctctct ctacaaatct atctctctct attttccgga | 120 |
| ccgaccgtct tcggtacgcg ctcactccgc cctctgcctt tgttactgcc acgtttctct | 180 |
| gaatgctctc ttgtgtggtg attgctgaga gtggtttagc tggatctaga attacactct | 240 |
| gaaatcgtgt tctgcctgtg ctgattactt gccgtccttt gtagcagcaa aatataggga | 300 |
| catggtagta cgaaacgaag atagaaccta cacagcaata cgagaaatgt gtaatttggt | 360 |
| gcttagcggt atttatttaa gcacatgttg gtgttatagg gcacttggat tcagaagttt | 420 |
| gctgttaatt taggcacagg cttcatacta catgggtcaa tagtataggg attcatatta | 480 |
| taggcgatac tataataatt tgttcgtctg cagagcttat tatttgccaa aattagatat | 540 |

-continued

```
tcctattctg tttttgtttg tgtgctgtta aattgttaac gcctgaagga ataaatataa      600
atgacgaaat tttgatgttt atctctgctc ctttattgtg accataagtc aagatcagat      660
gcacttgttt taaatattgt tgtctgaaga ataagtact gacagtattt tgatgcattg       720
atctgcttgt ttgttgtaac aaaatttaaa aataaagagt ttcctttttg ttgctctcct      780
tacctcctga tggtatctag tatctaccaa ctgacactat attgcttctc tttacatacg      840
tatcttgctc gatgccttct ccctagtgtt gaccagtgtt actcacatag tctttgctca      900
tttcattgta atgcagatac caagcgg                                          927
```

<210> SEQ ID NO 13
<211> LENGTH: 987
<212> TYPE: DNA
<213> ORGANISM: Artificial
<220> FEATURE:
<223> OTHER INFORMATION: synthetic sequence

<400> SEQUENCE: 13

```
tgcccggtct ccattatttt gcttcttgta tgcccggtct ccattattcc tctcattata       60
tgcccggtct ccattattcg caagacccctt cctctatata aggaagttca tttcatttgg     120
agaggacacg ctgaaatcac cagtctctct ctacaaatct atctctctct attttccgga      180
ccgaccgtct tcggtacgcg ctcactccgc cctctgcctt tgttactgcc acgtttctct      240
gaatgctctc ttgtgtggtg attgctgaga gtggtttagc tggatctaga attcactct       300 gaaatcgtgt tctgcctgtg ctgattactt gccgtccttt gtagcagcaa aatatagga      360 catggtagta cgaaacgaag atagaaccta cacagcaata cgagaaatgt gtaatttggt      420
gcttagcggt atttatttaa gcacatgttg gtgttatagg gcacttggat tcagaagttt      480
gctgttaatt taggcacagg cttcatacta catgggtcaa tagtatagg attcatatta     540 taggcgatac tataataatt tgttcgtctg cagagcttat tatttgccaa aattagatat      600
tcctattctg tttttgtttg tgtgctgtta aattgttaac gcctgaagga ataaatataa      660
atgacgaaat tttgatgttt atctctgctc ctttattgtg accataagtc aagatcagat      720
gcacttgttt taaatattgt tgtctgaaga ataagtact gacagtattt tgatgcattg       780
atctgcttgt ttgttgtaac aaaatttaaa aataaagagt ttcctttttg ttgctctcct      840
tacctcctga tggtatctag tatctaccaa ctgacactat attgcttctc tttacatacg      900
tatcttgctc gatgccttct ccctagtgtt gaccagtgtt actcacatag tctttgctca      960
tttcattgta atgcagatac caagcgg                                          987
```

<210> SEQ ID NO 14
<211> LENGTH: 1077
<212> TYPE: DNA
<213> ORGANISM: Artificial
<220> FEATURE:
<223> OTHER INFORMATION: synthetic sequence

<400> SEQUENCE: 14

```
tgcccggtct ccattattct gacgactata tgcccggtct ccattatttc ctgctaatta       60
tgcccggtct ccattattat cctcaccata tgcccggtct ccattatttt gcttcttgta     120
tgcccggtct ccattattcc tctcattata tgcccggtct ccattattcg caagacccctt    180 cctctatata aggaagttca tttcatttgg agaggacacg ctgaaatcac cagtctctct     240
ctacaaatct atctctctct attttccgga ccgaccgtct tcggtacgcg ctcactccgc      300
cctctgcctt tgttactgcc acgtttctct gaatgctctc ttgtgtggtg attgctgaga      360
```

| | |
|---|---|
| gtggtttagc tggatctaga attacactct gaaatcgtgt tctgcctgtg ctgattactt | 420 |
| gccgtccttt gtagcagcaa aatatagggg catggtagta cgaaacgaag atagaaccta | 480 |
| cacagcaata cgagaaatgt gtaatttggt gcttagcggt atttatttaa gcacatgttg | 540 |
| gtgttatagg gcacttggat tcagaagttt gctgttaatt taggcacagg cttcatacta | 600 |
| catgggtcaa tagtataggg attcatatta taggcgatac tataataatt tgttcgtctg | 660 |
| cagagcttat tatttgccaa aattagatat tcctattctg tttttgtttg tgtgctgtta | 720 |
| aattgttaac gcctgaagga ataaatataa atgacgaaat tttgatgttt atctctgctc | 780 |
| ctttattgtg accataagtc aagatcagat gcacttgttt taaatattgt tgtctgaaga | 840 |
| aataagtact gacagtattt tgatgcattg atctgcttgt ttgttgtaac aaaatttaaa | 900 |
| aataaagagt ttccttttg ttgctctcct tacctcctga tggtatctag tatctaccaa | 960 |
| ctgacactat attgcttctc tttacatacg tatcttgctc gatgccttct ccctagtgtt | 1020 |
| gaccagtgtt actcacatag tctttgctca tttcattgta atgcagatac caagcgg | 1077 |

<210> SEQ ID NO 15
<211> LENGTH: 18
<212> TYPE: DNA
<213> ORGANISM: Artificial
<220> FEATURE:
<223> OTHER INFORMATION: synthetic sequence

<400> SEQUENCE: 15

| | |
|---|---|
| tgcccggtct ccattatt | 18 |

<210> SEQ ID NO 16
<211> LENGTH: 2973
<212> TYPE: DNA
<213> ORGANISM: Artificial
<220> FEATURE:
<223> OTHER INFORMATION: synthetic sequence

<400> SEQUENCE: 16

| | |
|---|---|
| cctgcagctc aggtggacct ccgcacccTT ggctactctc agcaacagca agagaagatc | 60 |
| aagccaaagg tgcggtcaac agtcgcacag caccatgagg cactggtggg ccacgggttc | 120 |
| acccacgctc atattgtcgc actcagccag catcctgcag cacttggcac cgttgcagtg | 180 |
| acgtaccagc acatcattac agccctccca gaggcgaccc atgaggacat cgtcggcgtt | 240 |
| gggaagcagt ggagcggcgc aagagctctc gaggctctgc tcaccgatgc aggcgagctt | 300 |
| aggggggcctc ctctgcagct cgacacaggc caactggtga agatcgcaaa agagaggcggg | 360 |
| gtcaccgcga tggaggctgt tcacgcaagc cggaacgctc tcaccggtgc accgcttaat | 420 |
| ctcactccag tcaggtcgt ggctatcgcg tccaacaatg gcggcaagca ggcgctcgag | 480 |
| actgtccaga ggctcctccc cgttctgtgc caggaccacg ggctcacccc agatcaggtg | 540 |
| gtcgctatcg cgtcccatga cggcgggaag caggccctgg agaccgtgca gcgcctcctg | 600 |
| ccggtcctct gccaggacca cggcctgacg ccagatcagg ttgtggctat tgccagccac | 660 |
| gatggcggga agcaggcgct cgagacagtt cagaggctcc tgccagtgct gtgccaggat | 720 |
| cacggcctga ctcctgatca ggtcgttgcg atcgcttcgc acgatggggg gaagcaggct | 780 |
| ctggagaccg tccagcggct cctgccggtt ctgtgccagg atcatgggct cacgccagat | 840 |
| caggtggtcg ccattgcgtc taacaatggg gggaagcagg cgctcgaaac agtgcagcgc | 900 |
| ctcctgccag tcctctgcca ggaccatggg ctcactcctg atcaggttgt ggctatcgcc | 960 |

```
tcaaacaatg cgggaagca ggccctggaa accgttcaga ggctcctgcc ggtgctgtgc    1020
caggaccatg ggctgacccc agatcaggtc gttgcgattg cttccaatgg cgggggcaag    1080
caggcgctcg aaaccgtgca gcggctcctg ccagttctgt gccaggatca cgggctgact    1140
cctgaccagg tcgtcgctat cgcgagccat gacgggggca agcaggccct ggagactgtc    1200
cagcgcctcc tgccggtctt atgccaggat catgggctga ctccggacca ggtcgtggct    1260
attgcctcga acggggggg gaagcaggcg ctcgaaactg tgcagaggct cctgccagtc    1320
ctgtgccagg accatggcct cacccccggac caggtggttg cgatcgcttc tcacgacggc    1380
gggaagcagg ccctggaaac agtgcagcgg ctcctgccgg tcctgtgcca ggaccacggg    1440
ctgaccccgg accaggtcgt ggccattgcg tcacatgacg gggggaagca ggcgctcgaa    1500
acggtccagc gcctcctgcc agtcttatgc caggaccatg gcctgacccc ggaccaggtg    1560
gtggctatcg cctccaacat cgggggggaag caggccctgg aaactgtcca gaggctcctg    1620
ccggtcttgt gtcaggatca tgggctgaca ccggaccagg tcgttgcgat cgcctccaat    1680
ggcggcggca agcaggcgct cgaaacagta cagcggctcc tgccagtctt gtgtcaggac    1740
catgggctga cacctgacca ggttgtcgct atcgcgtcga acggggtgg aagcaggcc    1800 ctggaaacgg ttcagcgcct cctgccggtc ctatgccagg atcatggcct caccccggat    1860
caggtcgtcg ctatcgccag caatataggt gggaagcagg ccctcgagac agtccagagg    1920
ctcctgccag tcttatgtca ggatcatggc ctcactccgg accaggttgt tgcgatcgct    1980
tccaacggcg gcggcaagca ggccctcgag actgtccagc ggctcctgcc ggtgctctgc    2040
caggatcatg gcctcactcc agaccaggtt gtggcgattg cctctaatgg ggggggaag    2100 caggctctcg agtctattgt ggcgcagctc tcaagaaggg accggcgct agcggctctg    2160 actaatgacc atctcgtggc tctggcttgc ctgggggggc ggcctgctct ggacgctgtg    2220 aagaagggc tcccacacgc tccagagttc atccgcaggg tgaacaggag gattgctgag    2280
cggacaagcc acagggtcgc tgactacgct catgtggtcc gcgttctgga gttcttccag    2340
tgccactcgc atccggctca cgccttcgat gaggccatga cccagttcgg catgtctcgg    2400
catgggctga tccagctctt caggcgggtt ggcgtgactg agttcgaggc tcgctacggg    2460
accctgccac cagcgtccca gcgctgggac aggatcctcc aggcgagcgg catgaagagg    2520
gctaagccaa gccctacctc ggctcagacg ccagaccaga catctctcca cgcgttcgct    2580
gattcactgg agagggacct cgatgctcca tccccaatgc atgagggcga ccagaccagg    2640
gcgtccagcc gcaagaggtc acggtccgat agggctgtga cggggccatc ggctcagcag    2700
gctgtcgagg ttagggtgcc tgagcagagg gacgctctcc acctgccact ctcctggagg    2760
gtcaagcgcc ctaggacgag gatctgggc gggctgccag accctggcac accgattgcc    2820
gcggatctcg ctgcctcgtc tactgttatg tgggagcagg acgctgctcc attcgctggc    2880
gctgctgacg atttcccagc cttcaatgag gaggagctgg cttggctgat ggagctgctg    2940
cctcagtcgg ggtcggttgg cgggacaatc tga                                2973
```

<210> SEQ ID NO 17
<211> LENGTH: 990
<212> TYPE: PRT
<213> ORGANISM: Artificial
<220> FEATURE:
<223> OTHER INFORMATION: synthetic sequence

<400> SEQUENCE: 17

Pro Ala Ala Gln Val Asp Leu Arg Thr Leu Gly Tyr Ser Gln Gln Gln

-continued

```
1               5                   10                  15
Gln Glu Lys Ile Lys Pro Lys Val Arg Ser Thr Val Ala Gln His His
            20                  25                  30
Glu Ala Leu Val Gly His Gly Phe Thr His Ala His Ile Val Ala Leu
            35                  40                  45
Ser Gln His Pro Ala Ala Leu Gly Thr Val Ala Val Thr Tyr Gln His
            50                  55                  60
Ile Ile Thr Ala Leu Pro Glu Ala Thr His Glu Asp Ile Val Gly Val
65                  70                  75                  80
Gly Lys Gln Trp Ser Gly Ala Arg Ala Leu Glu Ala Leu Leu Thr Asp
                85                  90                  95
Ala Gly Glu Leu Arg Gly Pro Pro Leu Gln Leu Asp Thr Gly Gln Leu
            100                 105                 110
Val Lys Ile Ala Lys Arg Gly Gly Val Thr Ala Met Glu Ala Val His
            115                 120                 125
Ala Ser Arg Asn Ala Leu Thr Gly Ala Pro Leu Asn Leu Thr Pro Ala
            130                 135                 140
Gln Val Val Ala Ile Ala Ser Asn Asn Gly Gly Lys Gln Ala Leu Glu
145                 150                 155                 160
Thr Val Gln Arg Leu Leu Pro Val Leu Cys Gln Asp His Gly Leu Thr
                165                 170                 175
Pro Asp Gln Val Val Ala Ile Ala Ser His Asp Gly Gly Lys Gln Ala
            180                 185                 190
Leu Glu Thr Val Gln Arg Leu Leu Pro Val Leu Cys Gln Asp His Gly
            195                 200                 205
Leu Thr Pro Asp Gln Val Val Ala Ile Ala Ser His Asp Gly Gly Lys
210                 215                 220
Gln Ala Leu Glu Thr Val Gln Arg Leu Leu Pro Val Leu Cys Gln Asp
225                 230                 235                 240
His Gly Leu Thr Pro Asp Gln Val Val Ala Ile Ala Ser His Asp Gly
                245                 250                 255
Gly Lys Gln Ala Leu Glu Thr Val Gln Arg Leu Leu Pro Val Leu Cys
            260                 265                 270
Gln Asp His Gly Leu Thr Pro Asp Gln Val Val Ala Ile Ala Ser Asn
            275                 280                 285
Asn Gly Gly Lys Gln Ala Leu Glu Thr Val Gln Arg Leu Leu Pro Val
            290                 295                 300
Leu Cys Gln Asp His Gly Leu Thr Pro Asp Gln Val Val Ala Ile Ala
305                 310                 315                 320
Ser Asn Asn Gly Gly Lys Gln Ala Leu Glu Thr Val Gln Arg Leu Leu
                325                 330                 335
Pro Val Leu Cys Gln Asp His Gly Leu Thr Pro Asp Gln Val Val Ala
            340                 345                 350
Ile Ala Ser Asn Gly Gly Gly Lys Gln Ala Leu Glu Thr Val Gln Arg
            355                 360                 365
Leu Leu Pro Val Leu Cys Gln Asp His Gly Leu Thr Pro Asp Gln Val
            370                 375                 380
Val Ala Ile Ala Ser His Asp Gly Gly Lys Gln Ala Leu Glu Thr Val
385                 390                 395                 400
Gln Arg Leu Leu Pro Val Leu Cys Gln Asp His Gly Leu Thr Pro Asp
                405                 410                 415
Gln Val Val Ala Ile Ala Ser Asn Gly Gly Gly Lys Gln Ala Leu Glu
            420                 425                 430
```

```
Thr Val Gln Arg Leu Leu Pro Val Leu Cys Gln Asp His Gly Leu Thr
        435                 440                 445

Pro Asp Gln Val Val Ala Ile Ala Ser His Asp Gly Lys Gln Ala
450                 455                 460

Leu Glu Thr Val Gln Arg Leu Leu Pro Val Leu Cys Gln Asp His Gly
465                 470                 475                 480

Leu Thr Pro Asp Gln Val Val Ala Ile Ala Ser His Asp Gly Gly Lys
                485                 490                 495

Gln Ala Leu Glu Thr Val Gln Arg Leu Leu Pro Val Leu Cys Gln Asp
            500                 505                 510

His Gly Leu Thr Pro Asp Gln Val Val Ala Ile Ala Ser Asn Ile Gly
                515                 520                 525

Gly Lys Gln Ala Leu Glu Thr Val Gln Arg Leu Leu Pro Val Leu Cys
        530                 535                 540

Gln Asp His Gly Leu Thr Pro Asp Gln Val Val Ala Ile Ala Ser Asn
545                 550                 555                 560

Gly Gly Gly Lys Gln Ala Leu Glu Thr Val Gln Arg Leu Leu Pro Val
                565                 570                 575

Leu Cys Gln Asp His Gly Leu Thr Pro Asp Gln Val Val Ala Ile Ala
            580                 585                 590

Ser Asn Gly Gly Gly Lys Gln Ala Leu Glu Thr Val Gln Arg Leu Leu
                595                 600                 605

Pro Val Leu Cys Gln Asp His Gly Leu Thr Pro Asp Gln Val Val Ala
        610                 615                 620

Ile Ala Ser Asn Ile Gly Gly Lys Gln Ala Leu Glu Thr Val Gln Arg
625                 630                 635                 640

Leu Leu Pro Val Leu Cys Gln Asp His Gly Leu Thr Pro Asp Gln Val
                645                 650                 655

Val Ala Ile Ala Ser Asn Gly Gly Gly Lys Gln Ala Leu Glu Thr Val
            660                 665                 670

Gln Arg Leu Leu Pro Val Leu Cys Gln Asp His Gly Leu Thr Pro Asp
        675                 680                 685

Gln Val Val Ala Ile Ala Ser Asn Gly Gly Gly Lys Gln Ala Leu Glu
    690                 695                 700

Ser Ile Val Ala Gln Leu Ser Arg Arg Asp Pro Ala Leu Ala Ala Leu
705                 710                 715                 720

Thr Asn Asp His Leu Val Ala Leu Ala Cys Leu Gly Gly Arg Pro Ala
                725                 730                 735

Leu Asp Ala Val Lys Lys Gly Leu Pro His Ala Pro Glu Phe Ile Arg
            740                 745                 750

Arg Val Asn Arg Arg Ile Ala Glu Arg Thr Ser His Arg Val Ala Asp
            755                 760                 765

Tyr Ala His Val Val Arg Val Leu Glu Phe Phe Gln Cys His Ser His
        770                 775                 780

Pro Ala His Ala Phe Asp Glu Ala Met Thr Gln Phe Gly Met Ser Arg
785                 790                 795                 800

His Gly Leu Val Gln Leu Phe Arg Arg Val Gly Val Thr Glu Phe Glu
                805                 810                 815

Ala Arg Tyr Gly Thr Leu Pro Pro Ala Ser Gln Arg Trp Asp Arg Ile
            820                 825                 830

Leu Gln Ala Ser Gly Met Lys Arg Ala Lys Pro Ser Pro Thr Ser Ala
        835                 840                 845
```

```
Gln Thr Pro Asp Gln Thr Ser Leu His Ala Phe Ala Asp Ser Leu Glu
    850                 855                 860

Arg Asp Leu Asp Ala Pro Ser Pro Met His Glu Gly Asp Gln Thr Arg
865                 870                 875                 880

Ala Ser Ser Arg Lys Arg Ser Arg Ser Asp Arg Ala Val Thr Gly Pro
                885                 890                 895

Ser Ala Gln Gln Ala Val Glu Val Arg Val Pro Glu Gln Arg Asp Ala
                900                 905                 910

Leu His Leu Pro Leu Ser Trp Arg Val Lys Arg Pro Arg Thr Arg Ile
            915                 920                 925

Trp Gly Gly Leu Pro Asp Pro Gly Thr Pro Ile Ala Ala Asp Leu Ala
930                 935                 940

Ala Ser Ser Thr Val Met Trp Glu Gln Asp Ala Ala Pro Phe Ala Gly
945                 950                 955                 960

Ala Ala Asp Asp Phe Pro Ala Phe Asn Glu Glu Leu Ala Trp Leu
                965                 970                 975

Met Glu Leu Leu Pro Gln Ser Gly Ser Val Gly Gly Thr Ile
            980                 985                 990

<210> SEQ ID NO 18
<211> LENGTH: 612
<212> TYPE: DNA
<213> ORGANISM: Cauliflower mosaic virus
<220> FEATURE:
<221> NAME/KEY: promoter
<222> LOCATION: (1)..(612)
<223> OTHER INFORMATION: 35S promoter

<400> SEQUENCE: 18
ggtccgattg agactttca acaaagggta atatccggaa acctcctcgg attccattgc      60
ccagctatct gtcactttat tgtgaagata gtggaaaagg aaggtggctc ctacaaatgc     120
catcattgcg ataaaggaaa ggccatcgtt gaagatgcct ctgccgacag tggtcccaaa    180
gatggacccc cacccacgag gagcatcgtg aaaaagaag acgttccaac cacgtcttca     240
aagcaagtgg attgatgtga tggtccgatt gagactttc aacaaagggt aatatccgga     300
aacctcctcg gattccattg cccagctatc tgtcacttta ttgtgaagat agtggaaaag   360
gaaggtggct cctacaaatg ccatcattgc gataaaggaa aggccatcgt tgaagatgcc   420
tctgccgaca gtggtcccaa agatggaccc ccacccacga ggagcatcgt ggaaaaagaa   480
gacgttccaa ccacgtcttc aaagcaagtg gattgatgtg atatctccac tgacgtaagg   540
gatgacgcac aatcccacta tccttcgcaa gacccttcct ctatataagg aagttcattt    600
catttggaga gg                                                        612

<210> SEQ ID NO 19
<211> LENGTH: 501
<212> TYPE: DNA
<213> ORGANISM: Citrus yellow mosaic virus

<400> SEQUENCE: 19
ctggtggccc tccaccagca caaactcgct tacatcagaa gcaaagctac aagggacaac      60
gcatatgccg ataggctacc cacatgcaat cgggaccacg agcaactgtg tgaagtggtc    120
gagctattag aaggaatctc ggaaagaatc agcgatacag ctgtctagga cagctggctt    180
caattatgga gcgtgatgga ccccccgca ataatccaaa gtttggtgtg cttttagtag     240
tgcgtcttta tggaccacta ctttattgta ataatcgatg cttttgtag tgcgctcttc     300
```

```
gtgcgctcta ctttatgctt ttgcttttgt aagtgcgctg taagtgcgcc tgtctttctt    360
cagatgctta tcctttaagc atcttttgct ttttgcgtgg catcctttag ttcacaattt    420
aaagaatgac gatggggccc aagatgtgca cccggttctc taaattgcct atataaggat    480
atcccatagc cttgtttttg c                                              501

<210> SEQ ID NO 20
<211> LENGTH: 560
<212> TYPE: DNA
<213> ORGANISM: Sorghum bicolor

<400> SEQUENCE: 20
agaagtaaaa aaaagttcg tttcagaatc ataaaggtaa gttaaaaaaa gaccatacaa     60
aaaagaggta tttaatgata aactataatc cagaatttgt taggatagta tataagaata    120
agaccttgtt tagtttcaaa aaaatttgca aaattttcca gattcctcgt cacatcaaat    180
ctttagaggt atgcatggag tattaaatat agacaagacc taaataagaa acatgaaat    240 gttcacgaaa aaaatcaagc caatgcatga tcgaagcaaa cggtatagta acggtgttaa    300
cctgatccat tgatctttgt aatctttaac ggccacctac cgcgggcagc aaacggcgtc    360
cccctcctcg atatctccgc ggcggcctct ggcttttttcc gcggaattgc gcggtgggga    420
cggattccac gagaccgcaa cgcaaccgcc tctcgccgct gggccccaca ccgctcggtg    480
ccgtagcccg tagcctcacg ggattctttc tccctcctcc ccgtgtata aattggcttc    540 atcccctccc tgcctcatcc                                               560

<210> SEQ ID NO 21
<211> LENGTH: 1998
<212> TYPE: DNA
<213> ORGANISM: Zea mays

<400> SEQUENCE: 21
tgcccgggtc ggggccggaa gtcgcgcgtg gggcctgtcc atcgaacaaa agcgagagaa     60
aacgtgcatc ggccggtggt ggcccgtacg gtgggctggg ctcgaatcaa cagcagatga    120
attggtagac aagacagcgc gatgcatgaa tagtgcgtga ttgggcttct cgagatagac    180
gcggttaatt gggccggatt gcacacgcaa aaacaaaaaa aaaaaactgt cggcgtttgc    240
agttgcagtt gggcagtgtg cacacacgtt aacaacagca gaagcagcaa atgcacggc    300 tcggctcatc aattagctgc tgccacaaac aagggtttac ctgtcggctc atcaattagc    360
tactactaat aatcagcagc gctcggcact ctggcagcac aagcgcagga cccaccagta    420
ctgtgtgcgt gacagcgtga gtactgagtt gggaagccac accccacacc acacggcgta    480
ttggctgtca accgacccgg atcgatcgac tagttgcggt tgccgtcggt tgctcggaca    540
ctcagccctg tcaaggtagc agtactcctc ccggccttat cactccggtg cagtgcagtg    600
gaaacaaaag gcagaaatcc ctaccacggc ggcgcattga tgaatccccg ctgctgtgac    660
tcagagcctg acgaggggt gctatgctac ggcctactcc gggctagggt gtggagcgag    720
tgtctgggac tgggagaatc cagcgtcgtg tactgtccac gcgtacgcgg gttctcggca    780
aggccaagtg ggcaacatgg cagggtggca agacggtact gtatgtacct accggcacta    840
cgcttcgacg cctccttttt tccaaaacct tccaagcccc gcgttcaaac tgtgcctagg    900
cgacggatcc tcggtgctag tagatcacac acacacacac acacgggc gaaatgtcgg      960 cgagttaatg acggtggtta aagtgaaacc tggatccagc accagcagca gtctttcagg   1020
tttcaagaac actcaggtcc tgcgttactg tggactgtgg taaaagtgcc ggaagttcag   1080
```

```
ttcgacgggg gaagaaaaga agggccgcac ctgcacacag cacacctact acactagtac    1140
actgctgcaa tgtactacct gggccgtgct ccaaaagtcg taaccactcg agacttccc    1200 tctgtcctat ctccgatcac tgatacatct cacaccctca ccacaccgtg acataatttg    1260
ccagtagggt ttacggtgcg gtatcgataa taaccacact acttgcacaa cagctcactt    1320
cttcgttatt ttttttttgt caagtggggt cgatctggcg ctgcctatga ttcaagtgtg    1380
agaattcagc aacagccagc cagctcctgt ttccgtgtac atacgctttc taaaagctgg    1440
accaggccgg cccaatgctc cagttgcccg tgcgcgctgc ttcgcccccct accccaggcc    1500 tagccgcacg gaaatgaatg cgggcccact gcccggacga cttgcaacta gtctccaccc    1560
tgttcaatta aatccacaga cgctgggaaa acaattcttt ttgaaaggta gaaataaata    1620
aaagattgtg ggctgttgaa gtgcaatcta accccttct cagactatct tctaaataac    1680 tactttcgc agaatcaggc gtgtcatctc tagacgatga gattacacca gtcagctaca    1740
gatgacgaat ctgattaaaa aaaatttggt gctagtatac tctaatcgtt ttacgctaga    1800
tatgttgtca ttaattaatt gataaaaaaa aaacaatatt tgtaactgat gccatgcatg    1860
cagcaggctg cacggcacgg tcgtccggaa ctccggatga tgatataaga ccagcgtcac    1920
ccccgcgcgc gcagcctgct gtgatgcgcc caagtcgatc aatcatcgtc cgctctcatc    1980
atctcatcgc aaagccaa                                                 1998

<210> SEQ ID NO 22
<211> LENGTH: 1992
<212> TYPE: DNA
<213> ORGANISM: Zea mays

<400> SEQUENCE: 22
atctctcctc tcctctcctc tcctcccgtt ggtgtgactg tagtagatcc tttgcccgtg      60
tcagaacaag ctgctcctcg gaccgggtaa tgttaaacat cggaggagcc tttgcctagg     120
atccgtaacg gggaggaaag agaaaaaaaa ctaaggatga ttatggatac cgtgtaataa     180
ctgctaacta cagttagccc atctcagcgg actctctgcc ctatattgta tgtcactttc     240
tattataaac tacactatac aacctatgat gtaaataat gttttgcacg ttcatatata      300
aatcagtcga agaaagggtg cctcactaca gggaatggtt tctattggac accttagcat     360
tcaatcagtc atgtcccccc ccccccccaa aaaaaaatg cacccatcca gtcgattttt     420
gtcatatttg aattcggtgg tgctccatgc acgcgtacct gctttgacca atttatacga     480
tcaatatata acttacgttc ttacggttct tagactttat gagactttgc aagtatgttt     540
ggatacaaat cacactaatg tgcatctttg taaactaaat tcttttgatt aaatttgtaa     600
ttttaaggtt taacctgttt ttgttgtgta gacgacgtta ggcaccgatc gtcgcttcgc     660
tatatatctt tgttgtagac gacgttagac tcctagatta aataagcgaa aaccgatcgt     720
cgcttcgcta tctttgttta tttgtttgtg gctgctctac gctgaagagc ccacaggcca     780
cagccccaca cgacacgtta ggcaccccca cccaccatcc gcgcataata taagctactg     840
caaaatatat gccggcggag cccgagcgag ctttgtactt gctccgccgt ggcctggctc     900
caggatgctt tggatttcgt gcggcgccgt acgtccaggc aaacagacaa gtggagctgc     960
atgtcctaaa agcccggcaa tcaaacacgc tctagcagca gcatggatca cagatatcag    1020
tcatggggtg gcgctggcgc gggtgggtgg ccaggtggag gtgggtgcat gtcgtcgtcg    1080
tcgtcccata cagaaattgg ctcacgtatg tatacgctgc gtacaggcag tagtacacaa    1140
```

-continued

| | |
|---|---|
| ttactagcac caatgcaatc caacggatgg atcttcgcac acccgccacc cggttaaatt | 1200 |
| aagctactcc tacctctccc agtctcccct tggcctgcctc tatattttg ggcagcctcc | 1260 |
| accagccggg cggatggggt tggatcgtcg tatctgaggc ggcgtggtcg tccaaggcga | 1320 |
| aagcaacggc gcagggctgg gaccctagta ggtgcatgag gtcgtgcatg gcgcgcgaga | 1380 |
| tgcatggttt gggttaggcc taggaggttc tctctccatg gcatgggtag ctcgcgccgc | 1440 |
| ttggctgccg ttctcgtgta tgcgcatgca ccaggcattt gcaccgcgcc gtgtatattt | 1500 |
| ctggcgtggg ggccggcgcc gcattggagc tgcagcccg tttcggcacg acacgggac | 1560 |
| acctcccgtt agggtaagcc cggggcagtg ggtaactgcc cagcgccact actccgaatt | 1620 |
| taccctcctt ttattttaa agcttgggag aggggagaat ggatggatgg atggatgtag | 1680 |
| acgcgtgaaa aagatgcgcg agaccggcag cgtgtgctac aggggcagcc aggcacacac | 1740 |
| acacacagtg accctgcccc ttttcccggc cgtctcgctc tccaccgata ttccgctcct | 1800 |
| cctgtccagt cctcctcccc cgagccggct cattatatcg tccgtcgcgc agcacaacgc | 1860 |
| aagtttgcta gcggccggat cagcagccac aaaacgagga gagcaaccac gctgcacaca | 1920 |
| gagacgcccg tgtgtgagat atagagcaag ctcgatcgaa ggaaggaggg aagctagaga | 1980 |
| tcgtacgtcg cc | 1992 |

<210> SEQ ID NO 23
<211> LENGTH: 1998
<212> TYPE: DNA
<213> ORGANISM: Zea mays

<400> SEQUENCE: 23

| | |
|---|---|
| atagaaaatt cctcaaggaa ctgcacgagg aaatgatcca gcaagacata tgcaaaatca | 60 |
| atccagcaca cagaaccatt ccacgtgagg actgcggaac gcagtggaaa ctccaagtta | 120 |
| gaagttagaa cagttgtgtt tttgaaggaa cagagaggcc cttgtctgg aaacgcatga | 180 |
| gcatgcatgc atgtctcatg catctgtgca ggatgtccta attattatcc attaccctgg | 240 |
| agcagcagat caagtttttt ttggtgccct ttagttcaca aaatataacg taaataataa | 300 |
| taataatggt ttacattcga gtactggtgg taataataag tttgaataga ccgatatcaa | 360 |
| tttttagtat gatatctgat tatggttgaa tttaagcaaa cataatttaa cgttatcagt | 420 |
| tacccaatta attacaaata taaaaatcaa acggcaccta gggtacgcag atgtacacag | 480 |
| gagtcaggag gcgctgaacg atctccatgg tcagttctta ataacatcca tgcatgcacc | 540 |
| taagtcaaat catacaataa taccgaccct gcagttgttg gatgaggccc agcattacgt | 600 |
| acacacacga aaatttttt gataatggaa ataagtgttc cggcttttcg catcatcaga | 660 |
| tacgtacaac cattacatgt caattattga ttcaatggac agttatttag ttctttattt | 720 |
| gaaaaatgaa actaactcga caaaaccaaa taacatagct atggaaaata aacactaggc | 780 |
| acacataagt cttgcatttg atcgccatcg atgaatcgca aagatttcca tcaccatcac | 840 |
| ttctaaagct tgtcacatat cgagaatttc ttgttgtact cctccttct gtaggagtct | 900 |
| ctaaaacctg agccagtggg tacctctgaa aatgacctac acaattgatg atattggttt | 960 |
| ttgattaaaa gtcacctcgt ttcgaataag ccaaatagac caaataaag ttgatattac | 1020 |
| agtaagtagt aactttttta tactagacca caattacttg tccaagacct gataaatatga | 1080 |
| ttaatgttga ctgtcgtttc tatttctaga gcaagataaa ttatcatcca aatattttg | 1140 |
| gcaatatagc aatcgaaaaa gagttaagta cacacacga ctgatatagg caaacagtat | 1200 |
| tttggccgct agctagtctt cctcatccct gttgcttcaa ctcgatttta cacggttcca | 1260 |

-continued

```
tgtaaatatg ctgctggtaa aacaagtaac gatgcatgtg tgcgtatgca tgcatatcga   1320
tctgaaagaa gatttcagca tcggtctatc cattattcat gtgagcctgc agtgactgtg   1380
aggtcggtat atcgtcgagt ttcacaggcc tgtttagtgg atgtgggtaa tgccggtgat   1440
gatgagaaac aaaaggttac atgtgtatga tgtctataga tagtctcata gaacatttgg   1500
actgtgtata tgtatgtggg catgcagcag gcacagtgtg aacatgatag accaagcagg   1560
gcctcgcgct tgtgcgaatg gaccaacctt ttcctagcta actctgagga ctgtatgcag   1620
ccttgacagc aagaggagtc cgccgtttga aactcaagac catggaaaac attttcaagg   1680
tccattcggg gtagtagtcc cttaatttcc tttttattaa ttttttttaa aaggaaaagg   1740
accgggctac ttttcaacgc ttagcttgtc gacccagcag ctagctagct ggccgataga   1800
acgagctagc ggggcaagcg ctctctctgg attctataaa tccagcattt tgctcacatt   1860
ctgctctcgc cacctttgaa cgatagcctt tctcactccg acacttgaaa cacgttcatc   1920
aggagctcgt cctcaggctt gctagtagct tatattacct acctagctag ctagctagtc   1980
aagactcaag atccatcc                                                 1998

<210> SEQ ID NO 24
<211> LENGTH: 1898
<212> TYPE: DNA
<213> ORGANISM: Zea mays

<400> SEQUENCE: 24
cgacgagaac tgttttcggt ctgatatcca cggctctgag ccagacctgt gtgcctcctg     60
gaaaaacctc gttacatcca gtaggtttat tttgtccccc taggtctact tttgatatgt    120
ttctatcaca gatgagtggg tgcgctggta ccctttttatt ttgtcgatat gagacaatct    180
ttactgtttt gttatgcaaa taatagaaac ggatcctacc gtcgtaaaaa atgaccaaag    240
tccataatgg atcgatgaat tagttgttgt ttttgccatc aaacatgata tacgttaaaa    300
aaactatatg gacaaaagaa gcaaacatac tgctaagtct tttccttacc gaatcgaagc    360
catgtgtgtc ttgctgaatg tggattccct tgatgggcag ggcattagga aagagtgggg    420
tcaggtgatg tctccagctc agtgtcaggg ctcactggtt cgccaagctc accaactgcc    480
acggacgagt cacatcatcg tgatgagcga tattaggctt gccgggctgg ctggcgttgc    540
gatgacgatg agcggggcgg gcgacatcac atacctagaa cgggcagtgg tggtaatatc    600
gagaacgggg catcgaggtg gactgactag agcagcgtca ggaataatag gattgaatgg    660
atagatgcga ggactaatcc aaaaaaggag gataggagtc aagaggactg gactgatctt    720
acgaggaggc caagataaaa cgattttagc ccactaaaaa actttaattt tttctatact    780
taaccctaaa tgaacactag gtataagagg ttataaaaat taagggccca ctttgcaccc    840
cctgaatcag ccgctagtaa gtgtccactc tccaatctcc atggcggcaa gcgacagacg    900
acaggtctat ttggttgtat aactaagatg cctaaatttg acacatattt tctgccacac    960
ttgactgagg ttaggtattc aaattcttcg tcacatctta gcatactaag acaactttgc   1020
tgtactttta caagtcattg acgagttaga cctctgtata ggagaaaaat tttgtcataa   1080
ctatggctac aaaccaaaca cgtgactaag ctagtcaaat atgtctaacc ttaaacttgg   1140
taacagagac aacaaaccaa acatgccccc catgttttcc tcattttctt tttccacttt   1200
tgtttcaatt tttcttgggt aatatacagt gagtatatta ttttcttctt ctttttctca   1260
tggccaaaat ccacaatgga tcgatgaatt agctgtcgtt gttgccaaca aaagaacaaa   1320
```

| | |
|---|---|
| atcatgtgac gcacgagcac aatgcaagta gccaaactga gcttccgggc accgacgaac | 1380 |
| ggttgcacgc catcggcggg aaggaacagg ccgggctgtc aatggacaaa cgggccgcca | 1440 |
| agctggaggg agtgtcatgg gctttgagaa ccatcgtcag ggcctagttt tttcttttgt | 1500 |
| ttttatcaaa ggcggtaaac tcggggaacg aatatactag gaaaaacact agccagtcag | 1560 |
| agtcagtcaa agtggactga gttaaaattg caacgataca tacacacgca gcagtcaggg | 1620 |
| cgtcgggaat gaacaatgga tgaatttatt atagtctgaa gaaaacgaag ggacacagcc | 1680 |
| acaacgaaca ctggggagtg aatgaatgca tgcattccac tggactgttc cagcgcttcg | 1740 |
| tgtgcatcgc tagatgcgct gaacactcga acgccatgga cctcgctccg ctctctatat | 1800 |
| atagagggaa ggccttcagt ctacttctcg ggatatacca ctgaacgtca ccaagaagag | 1860 |
| tactgatcga tcagcaactc gatcgttctc agagagag | 1898 |

<210> SEQ ID NO 25
<211> LENGTH: 1118
<212> TYPE: DNA
<213> ORGANISM: Zea mays

<400> SEQUENCE: 25

| | |
|---|---|
| agtcacactt gaacatgatt aatacttatt ctgcaaatat gtcaaataac atttgaagta | 60 |
| gtattttttt aatgtacata actaggaaaa ggtataccttt tttgacataa gtatccacgt | 120 |
| gcaactgctt gcaattgagc tatgttatgc ccataatatt tgttcaattt tcttcaaaac | 180 |
| tatagatgtg catacagata gttaaaatgt taaactcatc attgttttcc ttccacatgt | 240 |
| ttccatagaa aaaatctaag gaaaaccatt acaattttcc ttgaatgcct tgtttctaat | 300 |
| aaaaagcggg aacaaaacgg ggcagtttga tctcaattaa gaagggtctc ttccttccat | 360 |
| tctttaattg tcgtgatcct actttcttat acttaagggg atattctatt tcaatatgca | 420 |
| ttttttgagt tgatggtggt cgttaataaa ttcttctaag aaaataatct ttagtgacta | 480 |
| tatgatgttt tcttagtatt aactactaag ttgtgtagtt gttccataat tctacaagat | 540 |
| taggtacaat aatacaagtt gttaccacat tattatattg ttaagatttt gaactgatttt | 600 |
| gatacttgcg atatttggac tttatgtggt caaatattgc tcatattgtt taatatattt | 660 |
| aatttagtaa gctaaggatt ttatgtggtt gtaatatttg gattttatgt ggttcaaata | 720 |
| tatgagttag gctacggctt gttttagtgc cgcactagtt ttgtatactt taggctggca | 780 |
| caatgccatc aaaaaaaaaa ttagttctac ttaactcgaa ctatttttaat acgaagcaaa | 840 |
| gtccggccag cactactgcc tgccacggca cactactggc ctctgtagct cacgacacgg | 900 |
| tctccaagaa gaagctgttt cccaatgtta tcatggagtc catggatcag taaattagtt | 960 |
| cggggacagc gtggaatacg aaggcatttt gcataaatca agggacttat catacaggta | 1020 |
| atataaatac ccctctgat cgctagtagt agttcactat cacactaacc ttgcatcaaa | 1080 |
| taaaccatta ctacttcacc ttgccaggcc gcctgggc | 1118 |

<210> SEQ ID NO 26
<211> LENGTH: 1898
<212> TYPE: DNA
<213> ORGANISM: Zea mays

<400> SEQUENCE: 26

| | |
|---|---|
| ccgaaggttc tcaaagaaaa tgagcgaact cctagatgtc accgccgttg acgtggtgag | 60 |
| tgcattcacc tacgacacca ccaacgagtc gtccacgagc ttggacaggg gtgacaaaag | 120 |
| atggccaccg acctcttcga catagcggtc gctgacgagg aagacgtggt gggggcaatt | 180 |

```
ttccgcaaga gaaaaaactc gcgtgatgcc gacgagccca gcggcgaaac gagggatcaa      240
cgagagcacc ctggtagacg tcagataaac cactgcccca cacgaaccga ggaaggagaa      300
gacactgtcg cggaccggtc gctaggggtg ggcgttcggg ttacccgaaa ttttcgggtc      360
gggtaattcg ggttttaaa atttcgggtt ttgagaattg atacccgaaa ttacaatggg       420
ttttgcaata cccgaaaatt cgggtacccg gaatttcggg ttcgggttcg ggtattcccg      480
aactacccga actattatgt tggcttcata aaaacacata taccctatta aattagtata      540
aaaacatagt ttgaataatg atatacatgg acatataaaa cataagctat ctacaatcac      600
aagttatgca cacttacaca taattataga tgtacaaatt aataattaat catgacatga      660
gtatatgaca catgaaagtt cgggtaattc gggtacccga attttccgaa ataaattcgg      720
gttttgtaag ttgctacccg aaattctcga acaaaattcg ggtatttcga gttcaggttc      780
gggtattccg gattcgggtt tcggttacg ggttttttgc tcagccttac cggccgccca       840
cacaactggc gaagaacgac aacgaccact tatagagtgg aaataccat agagtggaaa       900 tttttgacac gaggcggtgg ctgtatggac aggaccggag gaggatgcgc ggtacgtagg      960
ccgattgtgc cagcctatta gggcatgtac agtgggtgtt ttaagttgtg tcttacaacg     1020
tgtctagagg ggtgaatgta aaaaaactta agacacgtat cttgacgaag acacagtgtc     1080
ttagctctat gttcgagaca gaagactagc tgattggtca ttttaattta ttgaatgctc     1140
tgattggtac aatgaatatc gtaagacaca tgttttagat atgaccactg tattatgttg     1200
tgttttagtt gtatcttgta cttggagtac cgtgcagcag tatctgggtt gtacgtgccc     1260
ttatgtaggg gaagggagta gaaatacgat caatgcgaac gcacgttgat gacggtgaaa     1320
acggtagaaa ccggtggaag tagagattac agcaaacatg gagggacggc tttcgtccac     1380
ccaccggtcc ttggcgcgcg cgcggcgagc ctacgatcca aaagccgcga ccgcttggtg     1440
ttttggctga cgcttgggaa cctgccgcag ctgcatttct tgctttggga gccatgtacg     1500
gcgaactcat acttttgacg tcggttcttt ttcgaaaaaa cttttgacgg tcagttttcc     1560
ccactcccgc tatatttaaa accccccacc actccccccaa tatttatgac ttgacaacaa     1620
ttcccacatc gattcattgt cacttgccag aagtcgggcg ccatcgatc ccactccac       1680 cgcttacagc cggcccagtc ctcgtcggcg ccggacgggg cgaaggtaac ccccaagctt     1740
ccagattctc tgtcaacttc agttatgcgt ttttctttta agatgaacct gaaacatttt     1800
agctttagat caccggagtc attttttttt ttcattaggc gattggagtt aaaacaggcc     1860
gagtgggaga atttcctgga tcttatctgt tctccatc                             1898
```

<210> SEQ ID NO 27
<211> LENGTH: 2000
<212> TYPE: DNA
<213> ORGANISM: Zea mays

<400> SEQUENCE: 27

```
ccgacaacat cggcatacgg cggaaatact ggcagatgct gctcgtctcg tcgctcgcta       60
tcttttattt acgacgatca cttgctcaca gtcacagcta gcgctagcta gcgatcgaac      120
aggcagcgaa cgtggcagcg gcagctgccg cgccggccgt gcggaggatg gtaaaataca      180
actgcgggtt ggcctcgaac accgcgcggc agatgaccca acctgcggcg ccgggcgcct      240
tcatcatcat ccccgccgaa gcggggccca ccacgggcca caggaaatag atgccgaaga      300
cgcccatggc ggcaaacgcc accgccgctc ccatagcgcc tatgcccctcg tcgtccttca     360
```

```
tgttgacgaa tgacgatggc cgggcaggtt gacatgcagg attcagcgtc gtccgggtgg      420
cacgccggtg ttgcttctgc ccttgctgct taattggagg agagcgatcg gctgggtttg      480
gaatgaatgg acactggaca gcggtcgctg cgtgttgtgt taattgaaca tctatttgta      540
gtaggctgca gcgccggatc gaggttggcc aggcggctgc tcagcttcat cgcgtgcatt      600
gcgatgcatg ccgtgcgcat tgctccccca gtctcaaatc acgatgggag gcgacgacga      660
agagacagct tcgcaatgtg cgcgatcagt cgagcgcatt gaagttgaag agaacggtag      720
cgaaatgcag aagctgaatt gttgcttggt agtagtgaga acgtgcataa gaggtaatta      780
atttcatctg ctaattatgt agagtagtaa ttaaattaat tcattaact acgagtcacc       840 tcgaggccat gctataaagg ccagcggtcg acatagctta aatgatggtg cattggcccc      900
cgcagcccgg tgccgtaaat acaagacatc caggtgaatc tggggctcac aagggcgtgt      960
ggttttacct cgggtagaac gttggtttta cccttgcctt acggcgcctt cctaaggaac     1020
cgacccctca aggttacatg ctttggcaca ctaggattag gtaaccccctc aaggttacat     1080 gcatttgact caaggtttaa taatgctttt ggtttatata cgaaattatg agtatatttt     1140
ccaaagcttc cggataatat aaatttcttt tcatttttaa gggctgattt ggtgatcaga     1200
gattccaaga tgattcatgg gagagaaatc cccttacaat tcaattttga atatcaaggg     1260
gattcctctc atggatcctc tcgggatcac tgaccaccaa atcagccctca aaagtgaact     1320 gatggaaatt aaaacacata cgtgcataag aggtgattaa tttcatttgc taattatgta     1380
gagtagtaat taaatttcac cggcaaaagt agtatttttt tttttgccga tactactcgt     1440
ccactaccca ccaatccgtc gtggcagctt ggattagtat taaaaatgaa gaaagtgaca     1500
gaactcaggg tattatttta ataacctaa ctataccccat tagaagattg gacttggaca     1560
tgtaccacca tgagcctgcc tttgattag tattgtcgga aaatgatcgt tctcactccg     1620
aatcgacgag tcgacttctg catttgatgg ggccggctac actttgcgaa atgggtgttg     1680
atcggcgcat cgggcggagc gggcagtagc tgcagtactt ggctatgcac tcagagtcgg     1740
aggcggagca acgcctcttg gagttcccag gccgattcgt tttccccagc acgcgcactt     1800
cgccgtacgt gagacggcag caattacgca cgcatgcaac gcaccccccat agaaggccag     1860 cagccgcctc tggccgacct acaaatagat gacttctctg tcgcagaaat tccacgcggt     1920
gtctatcaat agtaccaacc ctataccaga gagcgagcgc gcttgacgac ttgtttgatt     1980
catcactctc cttcaagatc                                                  2000

<210> SEQ ID NO 28
<211> LENGTH: 2000
<212> TYPE: DNA
<213> ORGANISM: Zea mays

<400> SEQUENCE: 28
tttccttaat ctcctgggtc acttagaccc cgcaaggacc accacacact taggtgtctc       60
ttgcttcgat tacaaatcac ttgagaaaag aaatgggaaa ggaagaaggc aatccaagag      120
gcaagagctc aaaagaacac aaaatctctc tctcacaagt cactaagtgc ttgagttgaa      180
tttgggactt ggagaggctt tgatcttttg aattgtgtct acgagtgaat gctagagctc      240
ttgtaatgaa tgtgatactc agaaatcttg gatgcttgga gtggtggtgg ttgggggta       300 tttatagccc tcaaccacca aacaaccgtt ggggagggcc gctgtcgatg ggcgcaccgg      360
acagtctggt acgccaccgg acactgtccg gtgcgccagc cacgtcacgc aaccgttagg      420
gtttgggagc tgtcgaccgt tggaggcttt gtcctctagt ggcaccggac agtccggtgc      480
```

```
cgcaccggat agccactgtt cagtgtccgg tatgctctaa ctctaggctc tgactcagcc    540
gcgtattgtt gtgcgctgta gcgctcgtca ggagccgttg cagtcgacca ttgcgctgga    600
ttgtcgttac tccgctggtg caccggacag tccggtggca caccggatag tccggtgaat    660
tgtagcggag agcgccagaa gaaacccgag agtggccgtt tggactctgt acggtcctgg    720
tgcaccagac actgtccggt ggcacaccgg aaagtccggt gcgtgaaaga gaaatatggt    780 ttaactttt cctataaatg attttggtgg ttgaatgccc aacacaaata attgtactaa     840
ctagtttgct ccagattata tattctatag gtgcataaaa ggttcaacac aaaccaataa    900
aagatcaaag ttagggttta aaagaaagg aacaaagaaa ccaaagtgtg ccctggtctg     960
gcacaccgga ctgttcggtg tgccacgtcg atgtttgcac agctcgcccg aggccactct   1020
tgggcgggaa accccagggt agcctcgcgt gagccatgac tgtgcctccc gtccgagtgt   1080
ggcctcagac gacagacata gaaccatgat gtactgtaga tatatatcta tgtttatagt   1140
acatcaacag attctgaagt ctatttcagg ttgaattagg tttgtactcg gacgagtgat   1200
atttatcgtt ccatatctat gttttatata aattttttac tctcgtcgta acatataggc   1260
acatacctgt tcaaatatat gtgcgattgt gctcatatgg gtagaagaag gaactggatg   1320
tgaagacatg tatatataga ccaaaaatgt atcttagccg atttcaaact gcctagcgaa   1380
aagatgaagc tgctccgtgt ttgggtgact gcagcattat gtatcttatt aatcgatttc   1440
acagaagact tgtctctcat ggaacaaacg aacctattag cagtctgtat ataaagaagt   1500
gacttccaga ctgccaagtt tagtgattag ggctgctgtg actgaccatt taccttgcaa   1560
acaatctttc gatctactgc tctgtcatgc atggttttg catcgtccat tatgtttatt    1620
tcccattgtt gcagcttacg atatcgtgta tacctggcac ctatgtttat gacaatgaaa   1680
ctcaccatct ttattctatt ggcattcatt ttcattcaaa ttacataacg tatgctagaa   1740
cgaccgaata caaattactg ctaataaaca tcctgcgtac gcgcaatggt gcaccattta   1800
ccaattaata gctgtaacgg tactgcaagt aatggtcgaa gcgttatgtt ttctctcctc   1860
tcttcccacc gtacaggatc atatattcat atatatatac acatgcctct ggaacggcta   1920
attcgatagt tccaccacgt tacttccata tatttccctt ggattggatc gtcggcgccc   1980
aaacgaatac taatccggca                                              2000
```

<210> SEQ ID NO 29
<211> LENGTH: 2000
<212> TYPE: DNA
<213> ORGANISM: Zea mays

<400> SEQUENCE: 29

```
ccttaccggc gatgtgtgcg catgccggag agcaaggagg agtgcaaggc ctcacgacgc     60
ggcgccaggt gagggctact catgtgcgtc acccattgct ggtaagtcct cattgctcct    120
cccttctcaa gtctctgcta cgcgtgtgca ttagttgtag gaatacatg atgttaagta    180 tgtactgatt ttctgatgca acctcaatag atttgtaagt tttggctatc ttctaagagg    240
tacatagaat tagtgacagg atggactact tcctatctga tgtctcatgt aagctgggac    300
ctgggagcat gaaaatgttg gtgcatgata ccagcaatgt cttttttttt tgcttatgtc    360
atcttgtttg aaccaaaaca aaatacatta ggtaacacga tcctatgatg tcgggtcatg    420
ctcaagagaa tggtgctgtc gctgaaattt tgcattaatt tatcatgttc agctccttgt    480
gcctagatac gagagatggt taactgaaac tagatatttt accatgttca tctcctgatg    540
```

```
tctggataca aggtggttaa ctgaaacaag atggaatgtg tttgcaaggg acaccaacaa    600
ggttactgtc atgtacatac atattgatta acgagcatga cacgaacctc tttgttgaat    660
gtgattttga cgtaagaact tttagttcat gtggtttcaa acctatttat atgatatata    720
acaattgtag caaaacacgg acaactagct agtatatatt tataacattt gacactttaa    780
tatccccttc ctgtcacttc tatagcattt gtctagtgtt gctcattcaa aacttctcgg    840
tcgacttcat ggtcttattt tttgttctgg taaaattccg ataaaaatca gtaaattccg    900
attaaaatcg gtaaccgaac aaaacgatcg taaaaatgat acactgattt cgatactgat    960
ttcgtttcct aataatattg ttacccgtga atccgatcga gaaaaatcga aaacggtttt   1020
cgaaattcta agaaattccg aaactgtttt catcatacct ttgcctgtct ctccaatgga   1080
ttctggagtg gcggcatcgc ctatcagagt agaatttctt ccccaagaac aaccaaccgc   1140
tgaaccaaca gcagaatgag ggcttttccc ttccaaaggt gaacatgttt cggagttacc   1200
ctagctgtcg cagagaagat ggagtacgaa accagagatg atgacttggg ggacttccag   1260
gctgctcaat tgatataccg tgtatcttgt acataccgaa tgttactgag acgacatttt   1320
cattttggt ctatcttcta gcggctctca ggtactatga ttttttagat caaatggtgt   1380
ttgagaacac atacaagatc gaactctgaa ttttaaacta ttgttttgcc aataccacgg   1440
tattttgggg ttaaaaaatc tttggtctag accaaagttt ttttgtttgc gcgcagctat   1500
atcatgatat acattaaact gcggtattat aagatgttgt tttaagaaat aaagttccta   1560
aataggccct cagtgttcct gtaagcctcc tcttctcata ttctatatac agtacgtact   1620
agtactacaa cacactagct agctagtcag tcaaagtcga ttgcacggat gcacacgcag   1680
tcacggtcac gggcttgaga atgaacgatg gatgaccta gcaggcagca gctgttactc   1740
tcatgttatt aattatctgt gtgaggaaaa cgaagggaca cagccaccca ccgcaacaca   1800
ggggaatgaa tggatgcatt ccacttgacc gttcgttcca atccagcgct tgacagtttg   1860
acactaggta gaacgccatc gaccacgctc cgcactctat aaatagaggg aaggcctcca   1920
ctctcctctg cgggagatac cagtaaacgg cgacgaagac aattctctac caagaagagg   1980
actgatcgag tgggagagat                                              2000
```

<210> SEQ ID NO 30
<211> LENGTH: 2000
<212> TYPE: DNA
<213> ORGANISM: Zea mays

<400> SEQUENCE: 30

```
cctgccgacc ccaagacgac ccaaggatct taccccctccc gaggggcaag atgacttcgt     60
ctacttcact taagatttct tcctcgaatt gatctcttaa ttcctaggcg actctacgtc    120
gtctggggac gccctaggtg acttgctgac ccggagcacc ctaaggtctc ttccctaggg    180
ggcgagatct aggtcctatg aggagaagaa gacgaccatg cgccatccca gaccgtccag    240
cccagagcgc agatcgtccg tacagcgtgc agggaagaag ccgcttctgt cgccaggtcg    300
cggaccatcc aacctagagc cacgggcagt ccgcgcaatc gcagcaagca ccgccaggca    360
acccagcgac gcgtcgcgga ccgccgcgcc atccacctcg cacaaccgaa cccaaggtat    420
tgctcatcac gagaagaccc tagggttcgt tactgtttgg tcccacatag gtggtggcca    480
tcatagaggt ggtattacac cttcatgata accatcttag gtacatcaag tgataatccc    540
cttgtctata aggattcctt tgaagaccac attcaagata atgttatttg tcttacatct    600
tatttgttat ctccctcccc atggtctcga cccaccgtgg gcaaaaccta gggatcatcc    660
```

```
ccaaggtccg aactcactac gaggacgacc taggaatcat gtcactttrg tagcatttgt    720
ctagcgttgc tcattcaaaa cttccccgtc ggattcatgg gttttttatt ctggtaaaat    780
ttcgataaaa acgagaaatt tcaattaaaa tcggtaactg aacaaaacag tcgtaaaaat    840
ggtacaccga ttttgatacc gattatgttt cctaataata ttgttaccgg tgaatctgat    900
cgagaaaaac taaatgatt  ttcaaaattc taaaaaattc tgaaatcgtt ttcatcccta    960
ccttcacctg tctctccaac ggattctgga atggcagcgt cgcctatcag agtataattt   1020
cttccccaag agcaactggc cactgaaccc aacagcagaa cgagggcttt cccttccaaa   1080
ggtgaacctg tttcggagca actagctacc gcaaagaagt tggagcaaaa aaacggggat   1140
gacgacttag gggacttcca ggctgcttag gtgatatacc gtgtatcatg tacatacaga   1200
atgttactta gaccacattt tcattttrtgg tctatcttct tgcgacactc agggtctgta   1260
tgggaacaca atattttctt agttataata ccgtagcatt tgcgcatact atagtatttt   1320
agatcaaatg tagtttgata ggacatacag aactttgtat ttttaaacta ttgtttgcta   1380
ataccacact attttrtgggg ggttaaaaaa tctttggtct tgaccaaagt ttttgtttg    1440
catgcagcta cagttttctt ttctcttaca ttacaactaa aatactatgt ctctaaacag   1500
gtgttgaatt ggactgacgt aaaatataca tagttatatc acgatataca ttaaactgcg   1560
cggtattata agctgcggtt ttaagaaaca aagttactaa ataggcccac agtgttcctg   1620
taagcttcct tttcatgacc tacaacacac tatctagcta gtcagtcaaa gtcgattgca   1680
cagattcaca cgatcacggg cttgggaatg aacaatggat gaatttagcc gccgctgtta   1740
ctctcgtgtt attaattatc tgtgtgaaga aaacgaaggg acacagccac caaccgtggc   1800
aacacagggg aatcaatgaa tgcatgcact ccactggacc gttcgttcca ttccagcgct   1860
tgacactggc tagaacgcca tcgaccacgc tccgcactct atatatagag ggaaggcctc   1920
cactctcctt tgcgggagat accagtaaac ggcgacgaag gcaatcctct attaagaaga   1980
ggactgatcg agtgagagag                                               2000

<210> SEQ ID NO 31
<211> LENGTH: 2000
<212> TYPE: DNA
<213> ORGANISM: Zea mays

<400> SEQUENCE: 31
ttcactgctc ctcactcgca accttgccgg cgaccttacc ggcgaagtgt gcgcgtgccg     60
gagagcaagg aggagtgcaa ggcctcacga cgcgccgcca ggtgagggct actcatgtgc    120
gtcacccatt gctggtaagt cctcattgct cctcccttct caagtctctg ctacgcgtgt    180
gcattagttg tagggaatac atgatgttaa gtatgtactg attttctgat gcaacctcga    240
tagatttgta agttttggct atcttctaag aggtacatag aattagtgac aggatggact    300
acttcctatc tgatgtctca tgtaagctgg gacctgggag catgaaaatg ttggtgcatg    360
ataccagcaa tgtctttttt tgcttatgtc gtcttgtttg aaccaaaaca aaatacatta    420
ggtaacacga tcctatgatg tcaggtcatg ctcaagagaa tggtggtgtc gctgaaattt    480
tgcattaatt tatcctgttc agctccttgt gcctagatac gagagatggt taactgaaac    540
tagatatttt atcatgttca tctcctgatg tctggataca aggtggttaa ctgaaacaag    600
atggaatgtg tttgcaaggg acgccaacaa agttactgtc atgtacatac atattgatta    660
acgagcatga cccgaacctc tttgttgaat gtgattttga ggtaagaact tttagttcat    720
```

```
gtagttttcaa acctatttat atgatatata acaattgtag caaaacacgg acaactagct    780
agtatatatt tataacattt gacactttaa tatcccttc ctgtcacttc tatagcattt     840
gtctagtgtt gctcattcaa aacttctcgg tcgacttcat ggtcttattt tttgttctgg    900
taaaattccg ataaaaaatc agtaaattcc gattaaaatc ggtaaccgaa caaaacggtc    960
gtaaaaatga tacactgatt tcgatactga ttctgtttcc taataatatt gttactcatg   1020
aatccgatcg agaaaaatcg aaaacggttt tcgaaattct aagaaattcc gaaactgttt   1080
tcatcctacc tttgcatgtc tctccaatgg attctggagt gacggcgtcg cctatcagag   1140
tagaatttct tccccaagaa caaccaaccg ctgaaaccaa cagcagaatg agggcttttc   1200
ccttccaaag gtgaacatgt tttggagtta ccctagctgt cgcagagaag atggagtagg   1260
aaaccagaga tgatgacttg ggggacttcc aggctcctca attgatatac cgtgtatctt   1320
gtacataccg aatgttactg agaagacatt ttcattttt gtctatcttc tagcggctct    1380
caggtactat gatatttag atcaaatggt gtttgagaac acatacaaga tcgaactctg   1440
aattttaaac tattgttttg ccaataccac ggtatttggg ggttaaaaaa tctttggtct   1500
agaccaaagt ttttgtttg cgcgcagcta tatcatgaca tacattaaac tgtggtatta    1560
taagatgtgg ttttaagaaa taaagttcct aaataggccc ttcctgtaag cttcctcttc   1620
tcataaccta tatacgtact acaacacact agctagctaa tcagtcaaag tcgattgcac   1680
ggatgcacac acagtcacgg tcacgggctt gggaatgaac aatggatgaa tttagccgct   1740
gttactctcg tgttattaat tatctgtgtg aggaaaacga aggggcacag ccacccacaa   1800
ccacagcaca ggggaatgaa tgcatgcact ccactggacc gttcgttcca tttcagcgct   1860
tgacactagc tagaacgcca tcgaccacgc tccgcactct atatatagag ggaaggcctc   1920
cactctccac tgcgggagat accagcaaac ggcgacgaag acaatcctct accaagaaga   1980
ggactgatcg attgagacag                                                2000

<210> SEQ ID NO 32
<211> LENGTH: 2000
<212> TYPE: DNA
<213> ORGANISM: Zea mays

<400> SEQUENCE: 32
gtagcaaaat ggttcgtgcc agatgcacga gggacagtgg acaatgttta caggttcggg     60
ccgcttagag atgcgtaaca ccctacgtcc tggtgagtat gcttggtgaa tgaggttaca    120
agagagctct ctgaattgag aatgcagaga attgaggtgg gtggctgagt aatagggtcg    180
atcgttctga agggtgccc cctaggcctt atatactcga ccgtggggca atacacgtgg    240
atatgataac aatgtgtaag aaaaagatag tgaactgttt gagtttatct ccctatagtt    300
ttgccgacct atcctcgcat ggctccgttg cttgggggct ccagcgcggg aaagtcggat    360
ctctgttgtg gtcgctcgct cgatgttgtg ggccgtccgg gcttgcacca atccggcctc    420
atgtcaatct gctttgctga ttgtccctcc caggcccacg aaagaatgac cttacgattt    480
attggaccct tgggcctttc gtgaggtctt ttacttcttc tagtggaccc aagggatatc    540
tgtcccccac accaccatac tagttcctaa ggtaagcatt aatatatgtc atgaacctcc    600
atgttgtaga catgttgtcc acacatgata ggctagcggt gttgttcacc ctacttcatt    660
gcacctccta gtacattgtg cacacattac aaggatccca agatgctata tgtctgtctt    720
agagccccca gagtgctttg tagactaggt tgtgcgttca tgcacacttt gtaatgccat    780
ttatcttgca ttaaatgtgt tgtatcgtat aattatatac taagctattg ttttatacca    840
```

```
ctcttcgaga tttcactcgg acgaggccca catattggtt gtatacgccc ctaacaagcc      900
cctagtgttc gtatggtcct tgctgggcct gagctatttg ttaaacatat ggccgagaca      960
cgtgtgagtc taaggaaata tcacgcgagg gatgccgggg cgaggggccc tgggacttga     1020
gggactttaa ggtctcatct attatgcatc gcgaggtgcg agacgaccta ggccttagt     1080
caataggtgc cttagggcac gaggcatctc gaggtcttga tcattaagcg ccctagggca     1140
tgatggacct caagtctta ttcaataggt gcctcaaggc acgagggacc taggggcttt     1200
atttgttaag tgtcctaaca tgtgatgggt cccatggtcc tatatgttag gtgttcaggg     1260
tgcgaggtgt tctgtggttt tatttatttg gtgtctcgat gcgtgagggg tccgaggcct     1320
tatccattag acatcttgag ataagaagag ctctaaaggc ttatttagtg aatgttccaa     1380
gacatacgaa gcctcgatcc agctcgataa ttgaccagag atgtgtgagt ccttgtgtta     1440
aggatccttg agcacgttac aatactatcg aggagggcta tgtgctttcc tagatactaa     1500
catatggtgg agggctatgt cctttctcag atgctaacat atgatgcgca agaaaagtg     1560
ttgtgtactt tgtacctaaa cttaggggct gtttggtttg tgcctaacta tgccacattt     1620
tgtttaaggt tagtcgttcg aattgaaaaa ctaatcttaa acagaaaagt tagacaaaat     1680
atgacaagtt agggagagaa ccaaacatac ccttaatgta gggcattggt tacggtatag     1740
cggtcaattt aattggcctg tttgttacgc tgtagaaaac cttaagtaat aacgaccgtt     1800
gggggtacat aatgcgtttt ttttgcatgt tatacgcatc gttttccaat aaatgatgtc     1860
cataactcca tcagttagca cctctggacg taacagtgca aaagaagagt cactgcatat     1920
ttatatggag agagaggtag aagacgtgaa gttggggatt cacagccttc tccttctccc     1980
tcgctcgcgt gttagaaata                                                 2000

<210> SEQ ID NO 33
<211> LENGTH: 1595
<212> TYPE: DNA
<213> ORGANISM: Zea mays

<400> SEQUENCE: 33
tgagtacttc gatgaatcag cttgattcgt atattcatgt cttgcactcc acatttattc       60
cagcacattg ctagagcatt gcaagcacca aaagcctagt gaggagatta gagaatcata      120
atccgcgttt gttcctcatt agcgctagcg agagccacct agagcacaca ccacttgcat      180
taggcttctc ttggtcaagc gaaagtctac gacttgttac tcttggtgat cggcatcacc      240
tagacggctt ggtggcgttg ggagctcggt gatcaccgtg aagatcttgt tggtgacccg      300
actcaagttt gtaagcggtc tcgagggatc caccgcgccg gagtggcaaa ggatcatctc      360
gtagtgagca cttggttctt gcgaggacca agggggagcg ataccttgc gcgggtgctc      420
caacgaggac taatggagag tgccgactct tcggtacctc gggaaaaatt ggaggagtct      480
tctaaacttt gctttacatt ccgcacttaa ttcaagcact ttacattgtg tatttgttta      540
gcaagtatt gaagtattgt cttagcattg ttgcatttct agtattatat tcttagtgct       600
agttgttggg gtgaagttgg gctcttgctt agtctttaat tagtgttgat ttttagaaaa      660
gcccaattca ccccccctat tgggcatcgt gatccttttca aggttctttg caatgccaga      720
taaaaatttt cccagcacac aaattcctta gtagatgatc tgggaaggat ttgcggccta      780
ttttagagag ggcaataaaa ttgagaccat gttttttggt cagatccgaa acgtatctaa      840
gttttttaaa tccttgaact cattgttgtt ctaaagatt cctttttattg ggaaacagtt      900
```

| | | |
|---|---|---|
| aattaataat caagcccggc ctcttttag aacacaacga accgtaatcc gtaactatat | 960 | |
| ggttttgtac atactgactt aatcagtcca tcaatgccat ctgtctcttc atgtataata | 1020 | |
| tccgcacaca aatgatttaa aataaaataa tcaaactctt cgtcctctag tactccctt | 1080 | |
| cccataaaat cagataaatc agccttgttc ttacctatat taatctctaa tttttttaac | 1140 | |
| tggccaatag aggaagcaac tgaactagga ttagaacccg ctaaaatatc aatattttta | 1200 | |
| aaagaatcaa aaatataatt atcaggtaaa ccaataaaaa acattattac ctttagtcgg | 1260 | |
| ctgaactagt atgaattggc atcggtagga aatgcagttc acacgactag aaggataaaa | 1320 | |
| atcgcagccc taaactgtaa attctctttg tgtaaactgg aaaacgagaa gtttctgaag | 1380 | |
| taaattagct tcaatgcccg actcttcgtg cgaactggaa agacgctttt gtcgtttcgt | 1440 | |
| tttctgatct gtgacctgtc agactccagg gcgattcagc gcatgctgca cgcaccagcc | 1500 | |
| accaggtatt ttaaggggtc acacttgctt gtttcatgta ctagcacaag aagaaaccgt | 1560 | |
| accacttcat caggccaaat cgccagcaat ccacc | 1595 | |

<210> SEQ ID NO 34
<211> LENGTH: 970
<212> TYPE: DNA
<213> ORGANISM: Zea mays

<400> SEQUENCE: 34

| | | |
|---|---|---|
| agtgtacaaa gtctaatcca cagctgtgac cctgtgagct gggggttggg cctgcctcgg | 60 | |
| aggggatcgt gtcttttctg tttgtgcaat tatcagtgcc taaagaacat gtgttataac | 120 | |
| agttatacac ggtcaattat tcaatccatc ttttaacgtg tgtttggttg tacgtataag | 180 | |
| aagggatcaa agagggcggc cacattttct ataacatttg gatgagagtc acacgagaac | 240 | |
| gagatgaaca ccgaagtaat ttttatgac agcatgatcc aaaaaaatcg agagaacggt | 300 | |
| gttatccccg tctcatccta ttttgatctc aaaccaaaca cataattagt caatgagcac | 360 | |
| tgacttgatg tagaagaact tggtacatat accaggaaat gactctgact tgctgagatg | 420 | |
| ccttgtagtc cctcggtccc gtaaattata cagtagtatt taaacttcct cgcacaaagg | 480 | |
| aaaactattt gttttgcat gccttgtaaa ttagctatca agtttttttt taaaaaaaac | 540 | |
| gacctttgaa aaccagtaag gaggactcgt tcggtattca gttttaaagt tcaaggttaa | 600 | |
| aaatcgaact gacgtgcaaa acaccctggg ggttaaaatc aaaacacaca atttggaaa | 660 | |
| atgagcaggc atgacttatg ttgtgtccgt tgaagtgccg tggctccatg gcacggtgga | 720 | |
| actttacatt agtgcggtag tgtcactgtg gcagtaaagc ccacttattt tccattagag | 780 | |
| agagggagat taaaaacgtg gctttacaca ttctgaaact aattgtgagt ttgtgactct | 840 | |
| tggcttgcct gcagtgtccg cctgcacctt ctataagtac agtcgcgagc tcagctata | 900 | |
| caaaccaact agcgcatagt atctcctgag ctccattcat catcccaagt cttcactggt | 960 | |
| cttagatcac | 970 | |

<210> SEQ ID NO 35
<211> LENGTH: 1995
<212> TYPE: DNA
<213> ORGANISM: Zea mays

<400> SEQUENCE: 35

| | | |
|---|---|---|
| tctggagtcc caccggacca caaaagcaac cacttgtttg cgcatgtcaa gtaggccagg | 60 | |
| gcaagcagat tgtttgttgc aggtgaccta atccagcgga aatgtcttct gatgcgact | 120 | |
| gcaggagatg gtgccagacc acaattcatg tgtcatgagt aattcagctc aggacatgcc | 180 | |

```
aacagagaca gtggcctcca gcgaggggca tccaacccaa taaaacaacg ttcaagttcc    240
taatccgaga cacacatcgg taaaagtagg gggtgttgaa gatctatcca gttacagtgc    300
tcacgtatgc gtaaagcaag cccaagtgct aacattcaag acaaagcaag gccagtgccc    360
tctgtacatt cttacatcac acatcagttg tgaccaatgg gccataacct cttctccaca    420
ggataataca acaacaatta aagacagaaa tgtcagtgcg caatcataaa tgaactgcga    480
caatgaagaa caggtagcaa gccttatttc tagcaaacag tcagctcagc gctaagaaac    540
taactactat actagatcat gtaattctaa gaaaagggca tgattctgaa tacacaagtt    600
ttacttagca ttctgggact caattttaga tgaatctaat ttccgtcaac catatttccg    660
agagaaagct ggaatcttcc agttcaagca actgccaagc taaatgctat ggtgcagtga    720
attgcgacta cagtaacgaa gcgagcaaga atcatggaag ggagggaaca tgggtacgcg    780
tgttacccac ccgggagcag ccgagttttg gaggcccatt ttgcgcttac ggatatctgt    840
taagaggagg tccaaaagaa tccgtaaacc aatctcaaaa caaatattag tagagaatag    900
tgatcttctt tgctccaaac agctccccta ttctcctctc caaaatttcg tatccctcat    960
ctacctcctt cgctcccgta tattttgca tgattgatgg ctccacacgc gctggcgttt   1020
ttgtttctcg cacatagact tgtttcgatg gagacatcaa ccaggaagct gtttggaggt   1080
tacgaaggcc tacatttcca aatattgcga agggcccata tacatgtgca aagtgggctg   1140
ccaggagggc gttttatttt aaatttgagt ccagtttttt ggtttttcag ttttgactgt   1200
tggagtagac acaatatttc acccctaaaa aattttaggc ccctttgaaa tgcatgattg   1260
ataaaatgca ggaatagaaa aaaaaaaacg taggaatgga gttgtactac aactacaatc   1320
atacaagaat taaaaatact tgaaaacatc aaatagagtg tttagatgca gcgtataaag   1380
aacaaatgag ttagaggaga gagatacaca caaaggaacg ttttcgagg ttggacctct    1440 tgttataaat cctccaaaat tttactacaa tgaataattt tatagggatt ttatagaatt   1500
tgtaggaact taatccttta ttctaaaagg ctatatagga aaatttccta tatgattcca   1560
atcctctaaa atcccactac ttttcatttg ttctaaagga ggccctagcc ctattccgat   1620
aacatctttt ctttgaaaca ttttaggttt ttttttttgga gttgctctaa atggagctag   1680
gcaaaaagag cgatactcct ctcaatttgg aacttgggac gtatttattg catgcatgcg   1740
gaccggggag gagttgaaca gacaggccgg cgtcggggga ggaaacgatg caattgaaat   1800
tgaatgaata gaatataatg caaatgaaat tgaaccgaaa cgacagccaa tccgatccgc   1860
ttgccttcct gcgcgcctct accacttcca ccaactgagt gaatagtata cagtatacat   1920
accgctaggc gctagcttct ccaaatctct accacaccaa cctgcctcgc tctccaacaa   1980
acatagcagc cagcc                                                   1995
```

<210> SEQ ID NO 36
<211> LENGTH: 7579
<212> TYPE: DNA
<213> ORGANISM: Zea mays
<220> FEATURE:
<221> NAME/KEY: misc_feature
<222> LOCATION: (686)..(785)
<223> OTHER INFORMATION: n is a, c, g, or t
<220> FEATURE:
<221> NAME/KEY: misc_feature
<222> LOCATION: (1937)..(2036)
<223> OTHER INFORMATION: n is a, c, g, or t
<220> FEATURE:
<221> NAME/KEY: misc_feature
<222> LOCATION: (7521)..(7579)

<223> OTHER INFORMATION: n is a, c, g, or t

<400> SEQUENCE: 36

| | |
|---|---|
| gcaagtgatg cacatattca gggggagttg tgctacaact tgacccttg agactaaccg | 60 |
| tttgcttgag tttgcttgat ttagtctcaa aggaagtttg aaagggaaaa ggtggacttg | 120 |
| gaccatgaaa gacttccact acactccgat gagagggtaa cttattccaa gttcatctca | 180 |
| tgtactctta ttgcctttgt attcttattt gaagattttg gtgaggcaat ggggttattg | 240 |
| ggccaagatt ggtcccgttt tggtgcttga tgccaaaggg ggagaaaata aaggccaaag | 300 |
| caataaatgg atcagatacc acttgagagt tttttgaaa atagtagaat agagcttttt | 360 |
| gtttgtcaaa aagcttttat tgtctctctt gtcaaaagtt ggcttcttgt ggggagaagt | 420 |
| gttgattatg ggaaaagggg ggagttttg aaatcttgaa tcaatttctc ttggaatgac | 480 |
| tctctttatg tcttaacaag tatgtttgac ttagagatag aaatttgagt ttgatttgca | 540 |
| aaaataaacc aagtggtggc aaagagtgat ccatatatgc caaatatgaa tcaaaacaat | 600 |
| tttgagttct catttgcatc cctcttcccc ttgttctagt tgctttatgt tgtgtggcat | 660 |
| aaatcaacga attccaaagg tctagnnnnn nnnnnnnnnn nnnnnnnnnn nnnnnnnnnn | 720 |
| nnnnnnnnnn nnnnnnnnnn nnnnnnnnnn nnnnnnnnnn nnnnnnnnnn nnnnnnnnnn | 780 |
| nnnnnttaag gttgttgttg ggcataaaat cacccaaaaa gggggagga attgaaaggg | 840 |
| gccatttcta agtattttgg ggattgaatg caacacaagt gctttgtgta atctatgcaa | 900 |
| agtggtggac aaagtgcaaa tcatgtcaaa ggtatgtttc tggacttagt acattgtttt | 960 |
| attgactaat gtattgtatc taagtgctgg aaacaggaaa aattgaattg gaaatgagat | 1020 |
| ggctacgttc agcctaagtc agctcggtct gggtgcaccg acagtgtcc ggtggtgcac | 1080 |
| cggacagtgt ctggtgcgcc aggctggctc tagcgaacag gctgctctcg ggacttcgac | 1140 |
| gacggcgtac ggctaaaatt caccggactg cccggtggtg caccggactg tccggtgagc | 1200 |
| caacggtctg ccggggcaac agtcggccga ggattccgcg cgtgacgcgt ggccgagcca | 1260 |
| acgatcacat tggagcaccg gactgtccgg tgtgcaccgg acagtgtccg gtgcgccaac | 1320 |
| ggctcccagg cgccaacggt cggcttcgct aaataaggaa agagatccgc accggacagt | 1380 |
| gtacggtggt gcaccggact gtccggtgcg ccaggcggca gaaggcaaga tcagccttcc | 1440 |
| tggaatgctc tcaacggctc ctagctgcat tggggctata aaagggaccc taggcacatg | 1500 |
| gaggagatac ccaagcatac tcaaagcatt cctaagcacc aagacttctt ttccacgcat | 1560 |
| ttgtttcttc gtgatagcat ctagagctct tgttgagttg tgaactcgtc gggttgtgtt | 1620 |
| gcgagctctt gttgccactt gtgtgcgtgt tgacattctg acttcgtgtc ttgtgtgcgt | 1680 |
| tgatcatccc tcccttactc cgtgcttctt tgtgaacttt aagtgtaagg gcgagagact | 1740 |
| ccaagttgtg gagattcctc gcggaaggga ttaagaaaag caaagcaaaa caccgtggta | 1800 |
| ttcaagtggg tctttggacc gcttgagagg ggttgattgc aaccctcgtc catttggacg | 1860 |
| ccacaacgtg gagtaggcaa gtgttggtat tggccgaacc cacgggataa ccaccgtgcc | 1920 |
| cacataaaaa gaaggannnn nnnnnnnnnn nnnnnnnnnn nnnnnnnnnn nnnnnnnnnn | 1980 |
| nnnnnnnnnn nnnnnnnnnn nnnnnnnnnn nnnnnnnnnn nnnnnnnnnn nnnnnnctaa | 2040 |
| ggattcaagc tttgaattcg ttgctacaag cagaaatggt aagttgaact gagttagaag | 2100 |
| aggactgatt atataatcag cgtggataaa tattgtttct aaccaagctt tctatcctat | 2160 |
| atttgcatgt tcttcaaagg gatgtatatg gaccttccaa atacactaga cttttgcaag | 2220 |
| caaccaaaga tactctcaga gaagaaggtt tgccttgcct tgaatacttc ttgacttatg | 2280 |

```
tcatattgag catttgagct attgagaaac atactaatac agacattgtt gatcttgcac    2340
ttgcatgcct ctatgtaata ggctaaacta agcagcattg tataggatac tggtactttt    2400
gcacttgcat tatctcttct tgctaggtag agtcctaccc catagtctgg aactagaaga    2460
attctgattt tccttttagg aatcaatgtc tatttgagct ttgtttggtc agaaatgcat    2520
tgtagaaaaa tttagatggt gagatttta  tctttgttct cattttttatt cattgtagta    2580 taatttttt  cagaggttgt tctcatttat ctataacttt ttattttttt tacgaaaagc    2640
cggtgcatgc tgattatgca ccaagaaaca tagttacagg cagatacttg ttgtagtgct    2700
ctctttacaa tttatgtgta ctatatgctg tattctcagg tagtctggct gaacggctgc    2760
cccagtggaa gagatgaccg cgcagtgcag tgcagcactg cgttggtgga tgatcgatcg    2820
tccagttgta tgtgactaaa acgccatgcc ctgtgcatta gaagatag   agaatcgcca    2880 tgccctgtac aggacagtga gccaaattct tgttcttttt gcactatgat acagattgat    2940
tcattaggcc ctaggttgga ggttgtgact gatgagttgg gaagggatta cttgattggt    3000
ggtgtacaat tcttggacag gatacaggtt ccagttttttg gtccattagt tcaggaattg    3060
tttcatttac atgtatattc agtacactcg tataatggaa acagacaaaa tctctatctc    3120
attctttagt tatcgtgtta ttatatggtt ccgttgcaac gcacgggcac ccacctagta    3180
atatattgtg catgttgcga ttgtaaaata cctatggtac cgcagttaag taaaatacct    3240
atggccgacg gagtgcttca tttgagaact ggaaggtctg gtagtaattt cacattgatt    3300
caaactcacg tgtgtttcta aaatacggca gttcaaacga acacgcggct ctcgacttcc    3360
gttgcattgc caatgccaat gcggctgcat tgcatgtggt gttggttcac attcgctcat    3420
caatatacgg cccggccaga gctggttgct tggcaaagca accgttcaat ctccctctcc    3480
ctctcctctg tagtatatat agtagtatac aactagcagt attcaagaag tcacatctct    3540
gagctctatg gcaactcgtt gtcagtctgc tggtttcatc gaattcaagc tcgacttcgc    3600
agcatccaac caccttgccg tcggcgacat cgtccgctcc gacgatttct cggcaggcgg    3660
gcacttatgg agagtaattt gctacccaaa gggagacgag gttggtaatg gcaattacct    3720
ctctctctac ctacggctcg tcagcgactc caagtccgag aaaatcaagg ccatcatcga    3780
cgctttccta ctcggcagaa acggcgcacc gtcatcatct tcgcatggaa agcgttgggt    3840
gcatgtgtat tcttcacccg atggctcgcg atcacgtggg tttccagagt tcgtgaaacg    3900
gagcgtccta gatcagtctg actgcgtcac ggacggcttc gtcacattca tggttgtagt    3960
catagttctt agggatagcc ccatggccat acccgtacca tcttctgaca tcgccgacca    4020
tcttggccgc ctcctggatc acgctaatga cggttccacc gacgtgacct tcactgtcgg    4080
caccgagacg ttccacgcgc acagggccgt gctcgctgcc cggtcgccgg tgttcaaagc    4140
gcagctcttc ggctctatgg cggacgccaa gatcacgctg caaggcatcc gtccggaggt    4200
gttccggatc ctgctgcggt tcatgtacac cgatgcgttt ccgggcgacg acagcgacaa    4260
cgacaacgat gacgctgaag attcgttgcc gagagacgac gacgatgaag acgagcagga    4320
gggttattcc gacatcgacc tgttccagga tttgctcgcg gcagctgaca tgtaccacct    4380
ggaccggctg aagctcatgt gcgcccgcaa gctgtggacc gcgtatcgg  gagagactgt    4440 agccaagctt cttgtctgcg ctgaactgcg tgactgctcg gagctcaaga gcgcctgcct    4500
cgacttcttt cttgtcgaga aaaatttcaa ggtggctgta ctaacagatg ggtatttgca    4560
gcttatgcag agctttccat ccgtcatcgc cgagataaaa gcgcgggttc gtcagatcta    4620
```

```
aataagacat agcgtgcgtg cgagctatat tatatagttt gcagtttctt taatatttag    4680
gccagaatga tgctttcgtc agatctgaat aaagacatat atatgatgcg tccgatctac    4740
aatattataa tggtatgctg tttctcagaa tctgtaagac cgaatgttgc tttatcagag    4800
tacattatat attatgtgtc gaggaaacat gaaattatgc ctacctcata aaaaatgacc    4860
ataaatccta aacactaaac aagacaatct aaatctctac tacatattaa gacaataaag    4920
gtagtctgtc tcccctcgtt tttccgtttt gccgtccatc gatctggacc gtccgtatcc    4980
tatcgttcgt ctgcgtctcc cacgctccat ccccctccac cgcacgaccg cacccaatcc    5040
ctaacctttc cccgcacgtt cctctcctct caatgccacg ttgcctgccc cctgcccctg    5100
ccgcgataga tgcctcgcgg cccccgacaa cgacaaccgc gccaccatga cctcccatcg    5160
cctccatgaa agagaaatgt gcccttgggc catttctaag tattttggtg atttagtgtc    5220
caacacaagt gcttaagtga taaacaagtg cttaagtgat aaactatgtc aaatgatgga    5280
taaaggtgca aatcaataca aagatatgat tctagactta gtacattggt ttttgtgtgc    5340
taacatgttt gtctaagtgt tagaatcaga gaaaatgcaa ttgaaaaaga gtggcttgaa    5400
gcagccaaga gtctgctcag tctgggtgca ccggaccgtc cggtggtgta ccggacagtg    5460
tccggtgcgc caggttggct ctggcgaact ggctgctctc aggacttcga cggcggcata    5520
cgactataaa tcaccagact gtccggtggt gcaccgggta gaatccgcgc gcgacgcgtg    5580
gcaagtgcca acggtcagat gggggcaccgg actgtccggt gcgccaacgg ctccaaagcg    5640
ccaacggtcg gcttcgccaa agaaggaaag aaatccgcac cggacagtgt ccggtgcgcc    5700
aggcgacaga aggcaagaat tgccttcctg gaatgcactc aacggctcct agctgcctta    5760
gggctataaa agggaccct aggcgcatgg aggaggaacc caaacattct ctaagcattc    5820
ctaagcacca agacttcgat tccgcgcatt tgattctttg tgatagcaac tagagctcca    5880
ttttagttgt gaacttgtcg ggttgtgttg tgagatcttg ttgtgacttg tgtgcatgtt    5940
ggttctctga tttcgtgtct tgtgtgcgtt gctcatccct tccttactcc gtgcttcttt    6000
gtgaacatca aagtgtaagg gcgagaggct ccaagttgtg gagattcctc gcaaacggga    6060
tatagtaaag caaagcaaaa caccgtggta ttcaagtggt cttagaccg cttgagaggg    6120 gttgattgca accctcgtcc gttgggacgc cacaacgtgg agtaggcaag tgttgaactt    6180
ggccgaacca cggatgataaac cactgtgtct atctgtgatt gatcttcttg tggttatcgt    6240
gtcttgcaaa gactcttatc tagccacttg gctttattgt gctaactcct aaccaagttt    6300
tgtggcatta aagtttaagt tttacaggat cacctattca cccccctcta ggtgctctca    6360
attggtatcg gagccgttct cttcaagaaa gggactaatc gcccgaagag atggatccta    6420
agggcaaggg gatggtggtc aacgataagg agaaggagtc ctttgtcaat gatccaaagg    6480
aggacaagcc tactgactcg ggctcgagcc acaaaagaaa agatgggagg aagaagaaaa    6540
caaggcgcat caaagagata gtctactacg acagcgacga atcctcttct tcccaaaagg    6600
acgacgacaa cgactatgag aaaaagaaga cggttaattc aaacttctct tttgattatt    6660
ctcgtattcc tcaaagtacc aatgctcatt tactttccat tccacttggt aaacctcctc    6720
attttgatgg agagtactag ggattttgga gtcacaaaat gcgtagtcac ttgttctctc    6780
tccatcctag tatatgggag atagtagaga gtggaatgaa atttgatagc tcggatagtc    6840
ctttgtttat caatgaacag attcataaaa atgcacaagc tactactgtg ttgttagcct    6900
cattgtgcag ggacgagtac cataagttga gcggcttgga caatgccaag cagatctggg    6960
acaccctcaa gatctcacat gaggggaacg acgtcaccat gctcaccaag atggagttgg    7020
```

```
tggaaggcga actcgggaga ttcgcgatga taagagggga ggagccaacc catacataca    7080
acaggctcaa gactctcgtc aacaagataa ggagctatgg aagcacgcga tggacggacc    7140
acgacgtcgt ccgcctaatg ctaaggtcct ttactgtact tgatccacat ctggtgaaca    7200
atatttgtga aaatcctagg tacaccaaga tgtcgcccga agaaattctt gggaaatttg    7260
taaccgggcg gatgatgatc aaggaggcga gatacgtgga tgatgcattg aatggcccaa    7320
tccacgagcc tcaaaccgtt gctctcaagg cgacaaggag caaggaggca ctacctagca    7380
aggtggcgca agttgaggcg gtcgggctta atgaggaaga aatggcccct atcatcaagc    7440
ggttcaagat ggcgctaaag ggtcgcaagg agcaccccaa caagaacaag acgaagggaa    7500
gacgaatctt tagatttccc nnnnnnnnnn nnnnnnnnnn nnnnnnnnnn nnnnnnnnnn    7560
nnnnnnnnnn nnnnnnnnn                                                 7579

<210> SEQ ID NO 37
<211> LENGTH: 2000
<212> TYPE: DNA
<213> ORGANISM: Zea mays

<400> SEQUENCE: 37
ttgcaatcgt gtgtgtgtat atatatatat atatatatat atatatatat atatatatat      60
ataatctgct tttgtatttc acatttactt cacatctagt ctttctaaga taatgttcat     120
tgtgtatata ctaaattgat tcatttcagc tactaactcc tactgctata tattgtttaa     180
tcacactgct atgctatgct actagcattg aactatataa ttgtgtaacc atataaacta     240
aaatgtgtgt caattggtat tacttgcagt gtgttaagtg gaagcaacac atgaagcgga     300
catggagaag gaagctggca tgacactaaa acgcataaag ttgacatgtg acgttcatgt     360
tttagatgtc ttattctact gccaaacttc ataatactcc attttttatac tatattgtct     420 atctgtacgt gtgaatggag atgatgatat tatgtgatgt gatgatggat ggattagctt     480
cgttgaatat tagatgatat tatgtgatga tgatattaaa cgggcattgc agtattgata     540
catgcttcat atttctggat ttttagtgat gttttattgt ttatgagttt ctaaatatt      600 ccttattttt gtttgatttt ttctaaattt ttgatgtatt ttttgctcaa gaggggtatt     660
tagccccttt cttcccaaac aacgccagga aaatatatcc gggagggag attctctccg      720 ggaaataagg tgacatctaa aatccctcc agggttagtt tccaagggat attttttctct     780 tcactgccaa actagccctc agcgtccttc tcgatctccg tggattggta agtggctgct     840
ggcatttcat ccccaatatc aacatactca tccacctgct cagccactgt agtactcttc     900
acaggttcct cgctctcctg caaaaataat aaataaacaa actagcatca gcgcccaatt     960
catatgtcca ctagctgcaa ccaaaaacaa acgtgctgct cttattgtca ttaccgcatc    1020
gtcgttgtca accaatgtag gcacatcgcc cacaggtgca gtgtcatcct cagccacagc    1080
agtactggtt acatcagcaa cgccaccatt gatcatcgca gcacgctggg acttcttgag    1140
cgccttgttg aagttagtaa cgaaacgatc aagctcccac tgtgtctcaa catccatcac    1200
atcaatatca agctcgatct catccccaag catctccggg ttgttgttcc tcttgcgcac    1260
aatctgaagc acattgtgca tcttctcttc gggcaggctc accagcccca gcctgagcat    1320
gttcttctcc tctaggctca tctccctctt gttaggctcc ctcgccttag ggcttccgca    1380
tcctcacatt ccctgctctc gtcttagcct tcgcctcgac aggctcaact gccgcggag     1440 gtggcagctc agccgccact ggcctcggcg gctcaaggcg cttgtgctct tcatcgaaac    1500
```

| | |
|---|---|
| aagcgtaaca tactgttatg catttattaa gtgaaattta aattatagac gcatcggtca | 1560 |
| cctcagcctt aaattccacc taggcgaccc ttcgtcttct gcacctatgc atcgcactcg | 1620 |
| cagctcaagc gtcaataaaa tgcaggcggc agcgaaatca tactcacacc acagacccgc | 1680 |
| tcgcggcctc accaacgttt tcgtatggct aatgtttcac aggccgtagc tatgccgtcc | 1740 |
| tcctcccgcc gccacggtgg tcgccacaga gcagaacctc ctcgcattca ccagcgccca | 1800 |
| gcgagccgag ggactggacg gcgctgcctc aggacatcct gataaccgtc ttccttaagc | 1860 |
| ttgggccccg cgagatcatg ctgggcgcag agttcgtgtg cacgacgtgg cggcgtgtag | 1920 |
| ccgtcggcga ggctctgctg tggcgccgca tcgacatggg catagacaaa atttcggttt | 1980 |
| ttcaccccgc taggcgcgcg | 2000 |

<210> SEQ ID NO 38
<211> LENGTH: 1799
<212> TYPE: DNA
<213> ORGANISM: Zea mays

<400> SEQUENCE: 38

| | |
|---|---|
| tttctccggg tgcccctga gaacttgccg tggggtgggg ttccctggtg ccccgggaca | 60 |
| gtccggttgt cccacgggac agtccgtgct ccacgcacag acagtctgta ggcaacacac | 120 |
| ttggactttc ttagatcttt ttattgtctt cttttgaggg tgttgctttc ctcaattcct | 180 |
| tagtccaaag ttaatcttag catcctgtga actacaaaca caaacacaaa cactagaaaa | 240 |
| cttattagtt cacgaattgt gttgatcatc aaacaccaaa actcaattag ccaaatggcc | 300 |
| cggggtccat tttccttaca ccccacaaat gcggtttgat ggcagtgcaa aagtgtttca | 360 |
| aagcctcatg tgccgtagat tcaccagtgc gtatgtattc gtcaacggca tccgcaggaa | 420 |
| cacggtatgc aaggatacga acaacagcaa caactttctg cagagcagat agacctagct | 480 |
| caccggcaca gtttggtcgt tgaacgaagt agggatcgac ttgttgcaca tcatgaacca | 540 |
| ggtgctcaaa cacatggcga cgcatgcgaa acctataatg gaaaatacag tgagtacaag | 600 |
| tgtgaagcac gtattatgga cgtaagaata gatgggcgta cgaaaaaaga tacctccttg | 660 |
| ggaattgagc atccatgtac accggttggg cgcaaaagta gttcgctcgg attcttgcat | 720 |
| cgccactcat atggtcacga tggattcgaa catgaccggg aattgaacca gcataccgac | 780 |
| gctcgttgcg tgcacgacgc ctaagatgtt ggtacgtcgc aacctccaac tcatgttctt | 840 |
| catcttccat gtcttgcgtc atcctaagaa aaatattgca atctacgtac cggttcattg | 900 |
| ttgtggagca ctctaagtga agtgttgaag cgtgagtgat tatttataga acggataggc | 960 |
| ttcggagaca agccatcctc ttgttgtgca gacgaagcta gtcgatggct tgttcaagaa | 1020 |
| gtgtcatggc ttacggtaga agcatgtgaa tttgcaaaca tattttgata ctaataaaat | 1080 |
| actatgcgac attttatcga caacaattac acactaaata acatcgaatg ttaattaatt | 1140 |
| tttacaattc gaattatta atcaagcatt gttttggaga ttattattc gaaaattagt | 1200 |
| aaatacatta ttttgtgcat cctttgtata gcgtgaaatg ggaagaaaac aaagaaaata | 1260 |
| gaaaatgaaa tggaaaaaag aaatctgtta acactgtagc tttagatgac cgaatttaga | 1320 |
| ggacgttact ggagaataag aagatataga ggacataatc ttttagagtg tgctgtaaag | 1380 |
| aacagataat aatctttag gggatggaat ttaggggacg ctactggaga caaccttatt | 1440 |
| ctctggttcc tgaactctat tccatttaac aagattagtt tagtctttgc agtacacaga | 1500 |
| attggtggca ctcaattaat attctttcta acgttggac tgccctttgg acagcgttaa | 1560 |
| ttcgttgctg caatgaaatt tctctctatt tgttcttgcg tgcgttagct caaccgacgt | 1620 |

| | | |
|---|---|---|
| tctcgagaaa | cccatttcag tttagctcca cccatgaata ctgatcaatg ataatgaatg | 1680 |
| ctgctgtagt | acttagtaac tcccaatcct agctgttgta tataacaggc acgacacgta | 1740 |
| cggccatacg | cagcatctgc acacagacaa gtctcgaatc ttccaatccc aacacggca | 1799 |

<210> SEQ ID NO 39
<211> LENGTH: 2000
<212> TYPE: DNA
<213> ORGANISM: Zea mays

<400> SEQUENCE: 39

| | | |
|---|---|---|
| cattcgtaat | cttctctgtg ttcgtcttct ccatagcctc gtaaaaccta gctagtgcag | 60 |
| ggtcaacaac | cttcttctct ttaaccatat agtaagaact tgtgcgaatg ccgaagctcg | 120 |
| caaatcaaac | aaaagctggc agagcaagaa atccaagct tgaaaaatgg cacaagtggt | 180 |
| tgagatggca | catcaaatgc tatcaatgcg ggttcctatt tatatgccca gcgtatcaca | 240 |
| acttggtggc | ctccacatgt cattgacttt cactattcta gcgaaggaaa ggtgttttt | 300 |
| aaaccttcga | ctaaaggcct tgttcacgt cgtagtccaa atttgttaat acaaaaacaa | 360 |
| attaatactg | tgatgggcta ctgttggggg ccttcctctt ccgaaggccc tcaaaacgta | 420 |
| actaatgtgt | ttttcggtat aacatagact gttacaggag gcttcggctt tgagatgaag | 480 |
| gtgtgcgtga | tatgaaggta cggtctgaag gaagggtgaa cgagcgccga agctgtggct | 540 |
| gaaggacctt | cggtttagta tgacgacgaa ggtggaagat gaaaccgacc taaaagggga | 600 |
| tagactactt | agcccttgat agctcgccct acgattacca gtaaatgtca gggatataaa | 660 |
| tgtaattttg | tctgggctgt gtcctgtgcc tataaataga tgaacagtaa caccgtacaa | 720 |
| ttcacgctgc | attgtaattg ctcccgcgtc attcactttc tcaccttttg tcaagccgaa | 780 |
| ggtatcaatg | aaatataaat attgtgaaca tctattcatg tttatgaaat aaaataagaa | 840 |
| tgtaaacaat | tcattgctat attgttatca tttacattct tcttctgtat ttcatttcgt | 900 |
| gtttcctcat | ttatatttat ttacttacca agatgatgaa gatacgtctt tcattacctt | 960 |
| cgtctaaaga | ttattatata caaaagaaaa taatgtttcg gaggacgaag atctttaatc | 1020 |
| attaaataat | cgtgttgctt tgttttttgt gtataacatt cgagaacaag gaacatcaat | 1080 |
| agtccaagcc | acttttcctg ccatctggcg cacattagtg atcggtccat catttcctct | 1140 |
| gaaaatgtaa | attatttcat gttttccata aattgtgtaa tttcatttgc ttaattatgt | 1200 |
| aattggatag | atttttattt tcataaatta tgtgtttcat gtcaattaac agtctataaa | 1260 |
| atgaaactaa | cgtaatggtg agatagctgc aaactagcgc taaaggttgt acactaaaac | 1320 |
| gttaggtaga | taaagataga caaaaatcaa tagtacactt aataattaat aatacagtca | 1380 |
| atagctaagg | ccaaatataa ccctaaaata tcagttcggt ttttttaagt ataaaagatg | 1440 |
| gttaaaagat | tatatgatac aaccttaaga ctatgaatca taaatgtagc tgaaagataa | 1500 |
| cgtgtacgga | aaattatgaa cagatgttct attcacgaaa agtatgtccc ttatgttttc | 1560 |
| tcacttagct | ctttagagac cactcaagac agggtttaca catgccctaa tgtgccacga | 1620 |
| tcggatggta | aacataaaca tagaacatct gaatttcgag catcctttta gctagccgaa | 1680 |
| ctgtgatgag | ttctcgcagt cggtcaaaat tgtcatgaaa accgtgaag gcgttagtat | 1740 |
| gaccacaatt | tcccacaaaa aattaattac cgcctcgctc aaaatgacga cgagtcgacg | 1800 |
| actcttcggg | attgcgcttt gacgctccga gttatcagac actaatcact cagacggatc | 1860 |
| agctcgtgca | tgcgcagcac atttcacact agttatcacc agtatataaa tacgagagct | 1920 |

| caatagcatg gtagtcttat tcttcacaaa gaagtagcct gctcttgtta gttcttacta | 1980 |
| gcagtccaac agcagccaca | 2000 |

<210> SEQ ID NO 40
<211> LENGTH: 2000
<212> TYPE: DNA
<213> ORGANISM: Zea mays

<400> SEQUENCE: 40

| tatcttatat aatacactag gtgagtgccc gtgcgtcaca ggcccgagtt tctcttcgat | 60 |
| gtcatctcgg acagctcgta tatgtcatcc tttatctcat aactatataa cacatatgtg | 120 |
| catatataag ttatcgagat attatatatc cccgttgcaa cgcacgggta ctgacctagt | 180 |
| taaataaaga gagagagtgg tgctatctat aagcctagag taagcctaaa cacataaatc | 240 |
| gagatggtgc agagagtgaa ttaagtatta aaaacagcta tagatttttt tttgattatg | 300 |
| gaaacaagag ttccggcttt agcatacaaa tgcgtacagc cattacataa cgattattgg | 360 |
| accatagagc agttgcttga ataattaaac taactcaaag aaaacaaaat gccatgacta | 420 |
| tagaaaacac tagccatctt caattcttgc attcgagcgc catccatgca ttgcaaaaac | 480 |
| ttccatcgcc accacctcca aagctcgaca ggcatcgaga atttgttggt gttttccctc | 540 |
| cttctgtaga agtctccaaa atctgaacca gtgagtaacc ctgaaaataa cctacacaat | 600 |
| tgatggtatt ggtttatgat aaacaccac ctcatttcga cagagccaga tggaccaaaa | 660 |
| taaagctgat attccagtca gtaataatgt tttgtatgcc agagcattat tagattccca | 720 |
| agacccaata atatgattaa tgctaatggg catgtctatt tttaaagcaa agtaaatgat | 780 |
| tctccatata cttttggcaa tgtaacagtc aaaaaagaga tgatgtatac tctcattgtt | 840 |
| gttgcaaaag ctacaggtca agctaccatt ccaacgcctt ctagctaaat tatctttagt | 900 |
| gaggatcgct ccccgacata aattccacag taaaactttt attttttagag ggagcttaag | 960 |
| tctccaaagc atcttactcc gattgctgtt aggattattc atcaaaagat ggtacatcaa | 1020 |
| ttggacagag aaaatttcat tcttatgacc atcccaaaca aaattgtccc tagtcggatt | 1080 |
| cagagtaacc gtagtagca agtttaacaa gttatgtcat tccaccattt taattccct | 1140 |
| aattgttcgg cgaaaagata aattaagatt tgaatctgaa aagacgtcta caaccaaggc | 1200 |
| cgatttgtta cgcactatat taaaggttcg ggaattgctc actgagaggt cgactggtta | 1260 |
| accatatatc cttccagaat ctggtagcat gaccattcct cacttgaaag tgacctcatt | 1320 |
| taagaaattg atccttaata ttcattagac ctgaccaaaa gtgtgaattg tccggtcttc | 1380 |
| tagatatttg agtaagagat ttatgtccta agtatttgtt tttaagtagc tgttgtcacc | 1440 |
| tcccctcttc attgagtaat ttaaatagtc atttgctgag taagctaata tttttttaaag | 1500 |
| ccagattaga gacacctaag cctcctaacg ctttgggttg acaaacaata tagatagcat | 1560 |
| agatgttata gatatctact gtagatacat cattgcaaag atttactata gtatagtagt | 1620 |
| atatagatgg catagatgtt attagagatg tgatatatct atatacctgt ctcttcgatt | 1680 |
| ttcgttctgt aaaaaacgaa atggttactc ccgtctataa tctcttcgat ctccgctctg | 1740 |
| tctcttttac taacaaatta atcctgccaa gcaagtccca ataacaacac atcgtctctg | 1800 |
| gttttgttcc ggagacgacg gtccatctcc tccgttactt caatcgtcgt tcttcgctgc | 1860 |
| tcggagctac atgcgtcgtt gacgtacacc cagttctcga atggccgtag tatacactag | 1920 |
| tatgtgctag gtgtctctat ttatatctac cattatattc tagtatctcg tccagcaagc | 1980 |
| actccagcta ctgtgtagac | 2000 |

<210> SEQ ID NO 41
<211> LENGTH: 2000
<212> TYPE: DNA
<213> ORGANISM: Zea mays

<400> SEQUENCE: 41

| | | |
|---|---|---|
| tttttaagta catgttttta gctttctaat tttttaaatg agtgaaacaa agaaatattc | 60 |
| cacatttgtt ttaatagaga taaagacaaa gatttacact tgtttgaatc aaacaagttt | 120 |
| tagcattctc ataacttaca cctacaacaa cttttatag cttatagtta tagttttct | 180 |
| ttcaccgcca cgacttaaca aaatagccct tatacaatga gcagacaaag tgctaacgcc | 240 |
| aaactcatct caacccaatc actatatata aatatttgat atatttttag aataaataga | 300 |
| caaatagagc acgcttgacc agagcatggt aacatagatt ttccaacttt gtcaaatgca | 360 |
| agattagatt gctttgcaac tattttggat cctagaaaaa aacttgatgg gttacaaact | 420 |
| gctttagaag gaattggcga cttgctagat atggactatt catatgcttt caatcatgtg | 480 |
| aaagatgaat tatttcgtgt ttttggcttt tattataaca aatatggtga agtgatgtt | 540 |
| gcaggaacaa cgactgaaca tgacatagaa cattcagata gttctttgac agctcactta | 600 |
| tggaagagat ctaaggggaa agaatctgct aactctacaa caaatcaaag gtggaatcct | 660 |
| aatgctgaat tgaatcatta tctatctact aactttgcag cgactgatcg cacccttgaag | 720 |
| ggtgataagg taaaattact tgatggtgga gggaacacaa gtatagtttt ccagtattat | 780 |
| ctcattttgc tagagatatt cttcttgttc ctgtttcgac ggtttcctct gaagcaacat | 840 |
| ttagcacagt gggtagaatt attgaagaaa ggaggtcctc tctttcacct gagacagtgg | 900 |
| aggccattac ctgccttaag gattggaaaa gagcatatga tagaaagcaa catcaacttg | 960 |
| aagatcctga ggttgaacaa gcttttgctg atttcagcca tgattagtgt tacttttatc | 1020 |
| tagttcatgt ggactgttat tgtaatatgg actggacatt aaaatttttt ccgatctgta | 1080 |
| ctcttttcct tacagaggga gccccacact gggttgtaag gttttttaacg aggcagatcg | 1140 |
| aggaataaaa aacatttttcc ctctaaaatt tgtttgtgtt gtctaattta ttgtaactgt | 1200 |
| ttatttaaat aaatgacttg tttatgtatt ttaactgttt ttaattggac tgttgttat | 1260 |
| gttgcctgag aggtttggac ttgtttctgt atctgaccta gtcatatgat gattaattgc | 1320 |
| gggccgggtc tgggccagca cagcccaatg taagcccgtc gtgctttaga gccgtgttga | 1380 |
| gcctacgttt taggaggtca gcacgttttg gcccggctcg aaagaaattt atgctagcac | 1440 |
| gacccaaagt atttaagcct aaagcacgat ggcccggccc ggcctaactt gcaggactag | 1500 |
| ctggacggat tgagtcaacg agttgtttcc tccgtagatc cctactgagt gctagttggc | 1560 |
| gtcgttactc ttatgaacaa aaaaagtagg aacaattgga tctataccat taaaagatcc | 1620 |
| aaactttaga tatataccat ggaccccaca tgtcattgac tcatgtggac ccacatgtaa | 1680 |
| gtgagatagt aatggtatgg attcaaagtg gtgatctttt aatggtatgg atccaaattt | 1740 |
| cccaaaagt aataataata aacatatgta atgaagaaaa ataagttaca tgcacgtaac | 1800 |
| ttcatcaact aatggattta atttatgaga cacagaaggt tgaattataa ctcatgccgc | 1860 |
| tagaaataaa caccattaat gactatagct ccgttacaga tatgtagctg gaattaacta | 1920 |
| cactttctca tataaagcta gaccacccat gactgaagca ccaacacaat ttctaccctc | 1980 |
| aaaactgttt tggagaaaca | 2000 |

<210> SEQ ID NO 42

<211> LENGTH: 2000
<212> TYPE: DNA
<213> ORGANISM: Zea mays

<400> SEQUENCE: 42

```
ttgcgtgccg tgttagaatt ttgaaggcag gaattgacta gccatgcttc ggatcgcaca      60
aagtttctgc aacttgggag cggtgcagag tcgataatgg aggaacggcg gtggagagga     120
gaatattccg gcgatactgc cgatcgggtc caatattcct tccagctgat gatcggaggt     180
ctggccactg ccgatcggat cgaccacgca ggcagccgtg tggtgtggtg tggtgtgggt     240
ggcctgcgac ggaacgtcga cggagcatgt gaccgtgacc tctgcctctg cctgctgtgt     300
caggtcaggg gctccgttgc ctctactgta ccggggcgcc agaaaaagac aggccttgac     360
tgtgtcgcgt cgcgtgtgtc catcgtccat gcttggatct gtactgtacg aacgagatgc     420
catgtgaacg tactgtatgc gtgagaggcg gatgcataga ctggccagat ggtaactttt     480
ttaaaaaaaa aaaatcgctt catatcactc gttataaaaa aaatacactc tccgctcaat     540
ttataattta tttaactttt ttttaccaaa tttgaataac acgtcttatt caaaaaaaac     600
ataattatta ttaagttcta ctatgttacc gtttagtata taatatattt taaataaagc     660
tttgaatttt tcgttttctc gcaaatattt gaattagacg agccgtttga taaagaaagt     720
taaacgaatt ataaaattaa gatagagcga gtaaaaattt actcgtcttt cattgacgtg     780
cccttaatcc tcgatgctcc tcttccgata cgctggtgcc aaaagcaacc cgtccccca     840
tcggagccat atccacgact ccacgagcgc cgtcctcact agcgagctct gcctcacacc     900
tcatctcgtg cgcttaacga gaggaccaca cctatgctcg tgccaacgca tggttgtgca     960
tgtgcctaca ccacgccagc acgcgggggc cactccatgc gcctccatag aggtcacgtc    1020
cctctagagc ttgttcggtt gccgggagat tgaaggggat taaatcctct cctattcaat    1080
tttgaatagg agggaattta atccccttca atcccgtca aaccactaat aaccgaacat    1140
gaccctaggc gtttctgagc acagggctat tctaagcggc gcagcgcagt agccaagggg    1200
gcgggtaggg gccttggccc ctctcgcgta aatatatata gacaaataga gaacatataa    1260
attgtatagt ttttgttgat taaaataaac aaattgttta aataagtcgt catgtttcct    1320
aaaatattaa attcgccgct aataataaaa ttcatgaatt ttaaataaag ttgtcatcag    1380
atagttgttg tgtatacgac gaatttgaca tgtacgtgcg caaattgacg aattttcagg    1440
gatcctcgag gctaattaga tttttgaatt ctcttaaaaa attgttagct gcctcgtgca    1500
tactagagtc attatataaa aagttaaatc tcatcataat agtaaataac atccacgcac    1560
gtgccatata tgttagttta tttggccatg ccatgcatct gcagaccatc gtgcaaaaaa    1620
gttttctgaa tagttattat ttgatagctg agagaaatgc atagaaaaga tatgcacgtt    1680
ttttatgcaa ctccatcaaa taactcctaa gttattaacc tttttctgtc gattaaactc    1740
ctaaggttat ttggccaaat taacagggtt tattaactag ctagagcgta actcctgtca    1800
taaatagaat cctcattaat taaacaaatc cgctaataac gccaccgcag tttcataaat    1860
agaatcttta ttattttata tgaaatattt ccacctataa aaaccaggtg ttccttcctc    1920
gtcctagacc agtgcaagtc gttccatcca ctacaccttc ttacacaacg cacgaccatc    1980
accaagccgt gaagaacgaa                                                 2000
```

<210> SEQ ID NO 43
<211> LENGTH: 2000
<212> TYPE: DNA
<213> ORGANISM: Zea mays

<400> SEQUENCE: 43

```
ggaccttcgt cgggaacttc tagggcacct acaagctcca tggaagctcc tggaccttaa      60
gaggtgcacc caaaagagca gtgagagcct tcgggactac atccgaaggt tctcaaagaa     120
aatgagcgaa ctcctagatg tcaccgccgt tgacgtggtg agtgcattca cctacgacac     180
caccaacgag tcgtccacga gcttggacag gggtgacaaa agatggccac cgacctcttc     240
gacatagcgg tcgctgacga ggaagacgtg gtggggcaa ttttccgcaa gagaaaaaac      300
tcgcgtgatg ccgacgagcc cagcggcgaa acgagggatc aacgagagca ccctggtaga     360
cgtcagataa accactgccc cacacgaacc gaggaaggag aagacactgt cgcggaccgg     420
tcgctagggg tgggcgttcg ggttacccga aattttcggg tcgggtaatt cgggttttta     480
aaatttcggg ttttgagaat tgatacccga aattacaatg ggttttgcaa tacccgaaaa     540
ttcgggtacc cggaatttcg ggttcgggtt cgggtattcc cgaactaccc gaactattat     600
gttggcttca taaaaacaca tatacgctat taaattagta taaaaacata gtttgaataa     660
tgatatacat ggacatataa aacataagct atctacaatc acaagttatg cacacttaca     720
cataattata gatgtacaaa ttaataatta atcatgacat gagtatatga cacatgaaag     780
ttcgggtaat tcgggtaccc gaattttccg aaataaattc gggttttgta agttgctacc     840
cgaaattctc gaacaaaatt cgggtatttc gagttcaggt tcgggtattc cggattcggg     900
tttcgggtta cgggtttttt gctcagcctt accggccgcc cacacaactg gcgaagaacg     960
acaacgacca cttatagagt ggaaataacct atagagtgga aattttttgac acgaggcggt    1020
ggctgtatgg acaggaccgg aggaggatgc gcggtacgta ggccgattgt gccagcctat    1080
tagggcatgt acagtgggtg ttttaagttg tgtcttacaa cgtgtctaga ggggtgaatg    1140
taaaaaaact taagacacgt atcttgacga agacacagtg tcttagctct atgttcgaga    1200
cagaagacta gctgattggt cattttaatt tattgaatgc tctgattggt acaatgaata    1260
tcgtaagaca catgttttag atatgaccac tgtattatgt tgtgttttag ttgtatcttg    1320
tacttggagt accgtgcagc agtatctggg ttgtacgtgc ccttatgtag gggaagggag    1380
tagaaatacg atcaatgcga acgcacgttg atgacggtga aaacggtaga aaccggtgga    1440
agtagagatt acagcaaaca tggagggacg gctttcgtcc acccaccggt ccttggcgcg    1500
cgcgcggcga gcctacgatc caaaagccgc gaccgcttgg tgttttggct gacgcttggg    1560
aacctgccgc agctgcattt cttgctttgg gagccatgta cggcgaactc atacttttga    1620
cgtcggttct ttttcgaaaa aacttttgac ggtcagtttt ccccactccc gctatattta    1680
aaaccccca ccactccccc aatatttatg acttgacaac aattcccaca tcgattcatt    1740
gtcacttgcc agaagtcggg cggccatcga tcccactccc accgcttaca gccggcccag    1800
tcctcgtcgg cgccggacgg ggcgaaggta accccaagc ttccagattc tctgtcaact    1860
tcagttatgc gttttctttt aagatgaac ctgaaacatt ttagctttag atcaccggag    1920
tcatttttt ttttcattag gcgattggag ttaaaacagg ccgagtggga gaatttcctg    1980
gatcttatct gttctccatc                                                2000
```

<210> SEQ ID NO 44
<211> LENGTH: 2000
<212> TYPE: DNA
<213> ORGANISM: Zea mays

<400> SEQUENCE: 44

```
agtcatgact tgagctcgaa acacaacaca cggagttcgc aactcaaatg gagctcaaat      60
cactagcaca gagaatcaaa tgtgtggagt cggagtctgg gagttttaaa atgtttcttg     120
aaagcttggt gtactcctcc attcgcctag ggtccctttt tatagcccca aggcagctag     180
gagccattgg agacaatctt ggaaggcaat tcctgccttc tatcgagtgg tgcaccagac     240
agtccggtgc accaccggac aaccactttt catgtccggt gcacgatctc cttccaaatc     300
aggtgcatcc tccgggccca ttggcgcacc ggacactgtc cggtgcacac cagacagtcc     360
ggtgtgccca accgaccgtt ggagcgagac acgcgtcgcc cgcagattgc gcggctgacc     420
gttggcgctg cgaccgttg gctcaccgga cagtccggtg aattatagcc acatcgtctt     480
ttccgtttcc cgagagcggc gagttcgtcg cagacgactc accggacagt ctggtgcacc     540
accggacagt ccggtgaatt atagtcgtac aactccatcg attcccgaga ccggctactt     600
caccgttgac cagcctggcg caccggacac tgtccggtgt gccaggcccg agcagatact     660
tggctgttca cagccaagcc ttttccaatg cgtttcttct tttgttggcc ctgtttctag     720
cacttaggca aacacattag tgtacaaaat aatatactaa gtctagaaac ataccttgta     780
cattgatttg cacttttcac ccatttagca cataagtgct caattagtgt gttgtgcatc     840
taatcaccaa aatacttata gaaattgccc aggggcacat ttccctttca gctgcttctg     900
accgtctacg gactgtccga ccattatagc cggaccgtct gcttctgtct cggaccgttc     960
ggccttagta cccggaccgt ccggcgtacg caggacaagt gaccgtgatc gggtgtccga    1020
tcgtgcttgc ccccggtgcc ttcggtcttt cttttgtctg gagctttctg agtaactatt    1080
ctgcgtgaca tatttggtgt gcggggatca ccaatgacga tatttttatc tttgctttta    1140
tcggccgcac aaggccgaat tatggccttt ttgctcgttg gcaaaaatgt ggtgacaggg    1200
acatatggcc catcaatttt cacctctttt taaacctcaa tgggtcttcg tttatagcca    1260
attgtatttg ccgacggaag acgacacaat cattggtgtt atggggaaag gagccatgtc    1320
atttgcatta tacgcgccat ttgcaatata cacaatctta gttgactaaa aattgctagt    1380
gaaattagca agttaacaaa tagctatcta actattagtt aatttactaa aaataggtaa    1440
tagctaaagt attagttgta ctgtttggat gtctcgacta attttagtaa ctaactatta    1500
gttttattgt attcaagcac cacttgagta gttaagatag ctgccataac aagtgattca    1560
cgggctcttg ccctgatggg cttggagggc cgatttatgg gcctatgttg gctgaaagcc    1620
tgttatggat agtatcacgg actagttttt ttttttttg ataaaaaagt attgatttaa    1680
cagtatgaat tggcgtcggt aggaaatgca gttcacacga ctaggaagga taaaatcgca    1740
gccctaaact gtaaattctc cttgtgtaaa ctggaaaacg agaagtttct gaagtaaatt    1800
agcttcaatg cccgactctt cgtgcgaact ggaagaggct tttgtcgttt cgttttctga    1860
attgtgacct gtcagattcc agggcgattc agcgcatgct gcacgcacca gatattttaa    1920
gggtcacact tgcttgtttc atgtactagc acaagaagta accgtaccac ttcttcaagc    1980
caaatcgcca gcaatccacc                                                2000

<210> SEQ ID NO 45
<211> LENGTH: 2000
<212> TYPE: DNA
<213> ORGANISM: Zea mays

<400> SEQUENCE: 45
gaggtctttt atctctttag tggacccagg ggatatctat cccccactgc acgtgaagga      60
gaagaagatc aaaatatgaa tgagttccgt gattggatcg caaactggtt gtttgcaaga    120
```

```
gcctggagta catgttttgt aataaaaagt atttggacta tatgtacttt ggtatttgaa        180
ctacatgtac tttggcatgg tatgaacatg tgtgtacaca attctgtgcg tttgtttcct        240
gtgaacctgg caccaagttt ctgcgtgtcc aaaattgttg tgtttggtgc caagcatgtg        300
tacctggaat ccaaattgtt ggcgccaaga gcacccactt tattattacg ggtaatgcaa        360
tctttatgca ttgtaattag tgcacttcag tgaaatttag tcaatagaac taaacatggt        420
attttagtga ttaaacttta gtcattaaat tttaatcggg tgagtaaatg aatcaaatga        480
agttttaata ataaagtcaa tcgctagcta taagactgtc ttcagcggtt accctaaatt        540 tctccccta tattccactc acgtgccacg tcagcgttct cttcccctat atctccaccc         600
tgtatagcgg ttcccctaaa tccttcctct ataccccact acaaccataa aatatcattt        660
tctataccta cttttcacct cctatcaatt tttcatctac taataattgg aagtgggccc        720
acgtgaacag tgttagaggg ggagagagac gcacgccaga acgagggaga gagagaagct        780
tgctagggga acctctgcgt agggcgcccg ctagagtgaa acgttgagcg tatgtcgtgt        840
gtactgtagc cgttgtattt ggcgtgtggg agcgatagcg agaaccgttg aagacggtct        900
aaggatcctt atagccacct atttaaccca tctatatatc agtttacctt ttaatattaa        960
tgcaagacct cacatgtctc tctcacaaag cttcttaggc cccgtttggt ttgagggact       1020
aaaaattagt tcctctgttt tagtccctaa attactaaac ggtagggcta aaacaagaat       1080
taaactgttt tagtatctag ttgctcaaga ggtgactaaa agagactaaa tcatataaaa       1140
tttatttttt tgtcatcctt tatttcagtt gtactaatga caaagaatg ttaagagatg        1200 ttttaatcat cttatgattt atttaatgtg ttttgaatag ttttagtcgt tataatcaat       1260
attataatca acatggtaga gactaaactt taatttaatg actaaacttt agtcaagcct       1320
tagggcctgt ttggttcgtg gctaactgtg ccacactttg cctaaggtta gtcgttcgaa       1380
ttgaagaact aaccttaggc agaaaagtta ggcaaagggg ccgtaataaa tagcaacaat       1440
acacaaagat taaatgaag caagaaatat ccggctacca ataataaatg cccttcgcga        1500
cgtattctac tttatctatt ctatttattt attatcacta aatttataaa aaatatatta       1560
aatatttata tctctaaata aaattactac cgataattaa tttattaata atatttaata       1620
tctactgtga atattaatat ttttatatat gtggtacaag ttaaacacgt ggcactggta       1680
attatgggac gggaggtagt acgtcggaag ccggaacgaa ccgcctacta gcctagtccc       1740
agtgccagcc taggctgcga gttcaagcag cgccgctgcg acttcctatg cacagcactc       1800
gcacagctcc cggagcgcgc tgctcgcccc ttcgccttcc caggtctcag cggctgcact       1860
cctcgggagt cgggcctcgc catataaaca tgcctgggct aaaacatctc acacgtcgcc       1920
gactcgcgtc aagaaccagc agccacacta caacgccacc acatagttcc cagttcccac       1980
cattgtttgc acttggcaac                                                    2000

<210> SEQ ID NO 46
<211> LENGTH: 501
<212> TYPE: DNA
<213> ORGANISM: Zea mays

<400> SEQUENCE: 46
atccatctag ctagactgct gctgctactt cacaagcttg ggacgatgtg tgatgatgca         60
tgcttggact gtcatcagtc tctatgtagc ttctgaataa aataaatgt aacgatgctc         120 gattgggttt cacttgctcg cttgttccag ccaagttatt atatatatca tcaggctcgt        180
```

```
acgccagcta tatatatatg catgcaggtg catggattgt gcaacgcgaa cgcgtgattg      240
tgctaatccg ttagttgatg cgttctgttg ctttgatatg taatccggcc actcattaag      300
catgtcaagg tgcaatgatc agaagtcaat atgtagttac tagttagtag tctctgaaca      360
agcagtacgg ccagcccttt taattaaaca accctccaga ccaagaggag tcaaagaacg      420
tactagcatt ttttagtatc aagatcttcc acgagctaga tgaaatgaag tgtttgaaag      480
attagatatc atattttgc t                                                 501

<210> SEQ ID NO 47
<211> LENGTH: 501
<212> TYPE: DNA
<213> ORGANISM: Zea mays

<400> SEQUENCE: 47
gtatagctag caggtgttgt gtaccggcgt cgtgtcttgc aggcaccgtc ttatttcctc       60
acccgctgtt ggtaaataaa agtacggagt cgtagcgtag tagctagcag ctcactagtt      120
cagtaaggat ttggctttgt tgggaagtca agacgatagt tgtatgagat gggcgttaga      180
ctttgtttgg gaaagcttct aagtgctctc taaatccatc aaaataacta tatacctttt      240
ttccccaagc acttctctat cgaagaatct ggattcttga aaaattcagg tctaaggcca      300
catccatgga ttttatagag tattgctccg aaaacacaag ttttgtactt ctgataaggt      360
cttgttatcc gtatcgaatg ggattgaaag gaaatgaatc ccattctatt tctatttaat      420
tttaactagg aagggctcgt tttggtagag ttctgctcca tgattctcta gtttcgagag      480
ctctaataga gtgatttcga g                                                501

<210> SEQ ID NO 48
<211> LENGTH: 501
<212> TYPE: DNA
<213> ORGANISM: Zea mays

<400> SEQUENCE: 48
gctcgcgatg atggttttcg ttgacagtct tagtattact actatcttcc tcatgcatgt       60
aacgagttgc ttcgttttctc gtattatggt tatggttttcc cttggatgca tgatgaacta      120
gtgcttgcag ttgattttcc ccttattagt ttgagctgct taattcttag tagccctttt      180 tttttttcttg tgcttgtcat gcacgtatgc acacacacat gagacgggca gctagcattt      240
tctgtggttc tatctcctct cggttttgtg cctgtcattt ggggcttaaa tgtatcagtt      300
gtcttttctc gtgcttggca tgcatagtat atatatgccc acatgagcaa actgctgctg      360
cttcagttcc aagtagtaca aaagattcaa attaaaattc catcgtattt aaccctagat      420
tttaattgaa tatattagat ccgcatagtt ataccaacat gactgattac acatgatacg      480
tgccctttag ttttatatca a                                                501

<210> SEQ ID NO 49
<211> LENGTH: 500
<212> TYPE: DNA
<213> ORGANISM: Zea mays

<400> SEQUENCE: 49
atccatcgag ctagactgct agcaagctag ctgcttgttg catggcaatc tagcgtggga       60
tttgtgatcc tgaatgaatg tatggaccgt cgtcagtctc cgtagcctct aaataaaatg      120
ttaagctgct cgatcgtttc tgggtatcat ttgctcgcat gtttacgata gaagtttatt      180
atatgtcatt aggcaggctc gtacgtcatc agctatttac ccgatatatt tcgatatatc      240
```

```
ctgttatatc catatatatc ccaatatttg cacttttgga gaatcctagg gataaatctc    300
ttatctcgct atttaaaaca atggttcgat tgagttagtt ccagaaaaaa aaatcttacc    360
gccattgttt tcttatctga taattcagct actagaagct cattgagttg ggttagtgga    420
tggcctagtg catgtacata tgtctcgttt gctcagttaa tcagtttatt gatgagaaac    480
cagtgtagga gaacatgcaa                                                500

<210> SEQ ID NO 50
<211> LENGTH: 500
<212> TYPE: DNA
<213> ORGANISM: Zea mays

<400> SEQUENCE: 50
atctatcgag ctagatgcta gctagctagc tgcttgttgc atggcaagct agcatgggat     60
ttgtgatcct gaatgaatgt atggatcgtc gtcagtcttc ttagcctcta aataaaatgt    120
taagctgatt gatcgtttct gggtatcatt tgctcgcatg tttatcgata caagtttatt    180
atatatcatt atcaggccat ttaaaacact tttggagaag cctaaggata aatctcttat    240
cctgctattt aaaacactgg ttcattgagt tagtgccaga aaaaaaatct taccgccatt    300
gttttcttgc ttgataattc agctactagg agctcattga gttgggttat tggatggtct    360
agtgcttgta catatgtctc gtgtgctctg ttaatcagtt tagtgatgag aaaccagtgt    420
aggagactag cacacctgca agaatgttga gatctgttcc attaggcaga gatcaaaaaa    480
gctctcattg accacatttt                                                500

<210> SEQ ID NO 51
<211> LENGTH: 500
<212> TYPE: DNA
<213> ORGANISM: Zea mays

<400> SEQUENCE: 51
ataaatcttg ctagacttgt tagcaagcta gctgcttgtt gcatgacaag ctagcgtggg     60
atttgtgatc ctgaatgaat gtatgggccg tcatcagtct ccgtagccct ctaaataaaat    120 gttaagctgc ttgatcgttt ttggacatca tttgctcaga tgtttacgag ataagattat    180
tatatatcat caggtaggct cgtacgtcat cagctaaata tatatagtat gggtctttta    240
aattggtgct cttagacctt agttttggtg gtgtgctcac ctatacgatg tagcgcttgt    300
gtggtcaacc aacgcaaatg aatgattgtg ttaatccgtt agtagcttga tgctagcatg    360
ctgcttgtct ttttcatata taacctgtct accttgtgag agaagtagga atttctttga    420
gcacgagacg gtggtggcaa tgacaagcta gcagcttcag ttctgctgtt gacaagaggt    480
tcgtgttcac cgattaatga                                                500

<210> SEQ ID NO 52
<211> LENGTH: 500
<212> TYPE: DNA
<213> ORGANISM: Zea mays

<400> SEQUENCE: 52
tgaacgtgtc catgcgttgt ttcgatcgga caaaaataaa cagccagcgt tatggtacag     60
tgaagaaatt ttacatgtat tttttatatt ttacttaaaa gggtgcaggt gcagtgcagt    120
ggtgcacaca gcaaagcaag caaggtatgc tggctagcta gtcatgctgc tgctgggatt    180
ttcacttgcc attgccatgt atgagagtta tgattcttac ctgatcttgt gttcatccct    240
```

| | |
|---|---|
| gtcatgctat caattcatct tttttgccgt ctggttcacg aaacgtaacg aaacgtaacg | 300 |
| taaatggtaa tagtaatgat tcacactcga ttaccagtag ttacaagttt gaatataaca | 360 |
| ttttatcagt ttctagtgca gcacctgatt atggttgaac ttaaccagac atggtttaac | 420 |
| gttatcggtt atcatttacg ttacaaatat gtgaatcaaa caacacctta tatttgtgat | 480 |
| atgtatggtt tgaagtgtgc | 500 |

<210> SEQ ID NO 53
<211> LENGTH: 500
<212> TYPE: DNA
<213> ORGANISM: Zea mays

<400> SEQUENCE: 53

| | |
|---|---|
| tagtcgtcgt tgttgcttta ctctataatt agccccaata ataacaatct atgtctgtgt | 60 |
| tttcctgctg aatttgtaag ttatcatttt ggccactggt acttggtaac tactataaca | 120 |
| gttcgagcat ataataaact agtgcatcag gcgcgcccat gcgcgcgtac caagcagctg | 180 |
| tcaattattt tttatattta gttttagtaa ggtaatataa tggtatattc tatatacact | 240 |
| tgtagcagtt attttaacat aagtataaga gcaaatttaa actggtagta gtgattacat | 300 |
| aaggtgcacc gagtttataa ttgtagtgat tacaatctat attagactga agaaccaca | 360 |
| catattacat tgtgtttcag caatgtgttg catgagtgac agattacata gagcataggt | 420 |
| taaactgaca aggtttcatc agctttgttt tatgtacgca aaagcatttg agcttcacgt | 480 |
| cacatggtca gtggcggagc | 500 |

<210> SEQ ID NO 54
<211> LENGTH: 500
<212> TYPE: DNA
<213> ORGANISM: Zea mays

<400> SEQUENCE: 54

| | |
|---|---|
| ctatggatca ggatgtggat gtgttcgttc gatcgtttcc acgtccaatc tcgctgaata | 60 |
| aattgtctcg agaaagtttg gctttgccga gataaataat agtgataatt cttactcctg | 120 |
| ctacaaactg ttttccttga agcaactatg agcatcttcc atagattcgc gacacgattt | 180 |
| aaatttttaaa aataacatttt ttaaaaaaat gtgtcacggt tacacaactt ttttttttaac | 240 |
| actagttgcg ccccgcgtcc aagcttactc cctgaaattg cattcaaaact ctcgattcat | 300 |
| gtctgccctt ctcaccttct gtgtgcctgt gtgggctcga cgtctagtcg tcttcggctc | 360 |
| ttcgcctaca tcagtcacct cctcacacga cgtgtctgcg acacaggccg cggcatagag | 420 |
| cacgggcatg tagttttgaa caagtgcatg ttgctacctc gactatgatc atgcaaaata | 480 |
| ttttttttat tatttataga | 500 |

<210> SEQ ID NO 55
<211> LENGTH: 500
<212> TYPE: DNA
<213> ORGANISM: Zea mays

<400> SEQUENCE: 55

| | |
|---|---|
| ggtctgcatg ttgtgtcccg cccagagtgc agtacaaaaa cctgatattt atttgcattt | 60 |
| cctatcagct gggctctccg aacattatta ctaccaagtt tctttttttgt ttgtatggtc | 120 |
| gttgcccaat ttggttttga gtagcaggga ggttttgaat tgggaacgag aatacttctt | 180 |
| ctgtggtgcg tagcggcaga cttaacgct gttttttgtgg cggttggttt tgatgatgct | 240 |
| agtatctgtt agacgatata acttttgttg aaatttggat gtggcacaaa aattccggcg | 300 |

```
gagaagtgca aaagtgtata acttgtgttc atctaattaa cctggatata tgaatcgtcg    360
ggctgcagat tctgtctagc ttaattccgt aatgggacac aatccggccc aaccccactc    420
caatcctata agtttaaaaa gtcaacccag cctacttaaa tccaaattga tttggtacag    480
ttcaatccaa tccgtttttt                                                 500
```

<210> SEQ ID NO 56
<211> LENGTH: 500
<212> TYPE: DNA
<213> ORGANISM: Zea mays

<400> SEQUENCE: 56

```
ataagacata gcgtgcgtgc gagctatatt atatagtttg cagtttcttt aatatttagg    60
ccagaatgat gctttcgtca gatctgaata aagacatata tatgatgcgt ccgatctaca    120
atattataat ggtatgctgt ttctcagaat ctgtaagacc gaatgttgct ttatcagagt    180
acattatata ttatgtgtcg aggaaacatg aaattatgcc tacctcataa aaaatgacca    240
taaatcctaa acactaaaca agacaatcta atctctact acatattaag acaataaagg    300
tagtctgtct cccctcgttt ttccgttttg ccgtccatcg atctggaccg tccgtatcct    360
atcgttcgtc tgcgtctccc acgctccatc cccctccacc gcacgaccgc acccaatccc    420
taacctttcc ccgcacgttc ctctcctctc aatgccacgt tgcctgcccc ctgcccctgc    480
cgcgatagat gcctcgcggc                                                500
```

<210> SEQ ID NO 57
<211> LENGTH: 500
<212> TYPE: DNA
<213> ORGANISM: Zea mays

<400> SEQUENCE: 57

```
agaattgatc atggtggaag agatggcctt gattataata gctgggagat tccttgcaac    60
taaatggctg tgccatctgt catcaagttt tatatacatg aacttgccac tacttgggat    120
gatcttaaat gcactgtatc cttttgcaaa tgtatgtcgt cagttatgca tggatgttaa    180
tgctagattt aagtattttc acttttcag tgtggtgcta gatgtattta tatgggttca    240
aatcttgttg ccacaattaa catccacagc gcaagtgctt aagccgccat tgcacctgca    300
cggctgtttt cgtgcctgac agcaccattg cgttttggcg caattttgct ggcgcgtaat    360
ggctgtttcc cgtcctgccc tcagccaata tgcagacttg ctgatctgca tctgctccac    420
tctcatgctc ggctgtgtat cttagtatcg taataaaacg actcatcatt cccctaccta    480
caagttgccc accctgatta                                                500
```

<210> SEQ ID NO 58
<211> LENGTH: 500
<212> TYPE: DNA
<213> ORGANISM: Zea mays

<400> SEQUENCE: 58

```
attgcatgct ggaacgtctt caaccccgtg ctcgtcggat tgttcgtcat ctggcgatta    60
tcttagcatt gtcgtctgct tgcagtggct agcgccctg tttatcttat ccaaattaga    120
taattaaata aatgtatcga actaccttt aatataatta tttaaatttc gtctagtagc    180
agataaaaac taattctgat attagatata tggcgtacag tcattctctt gctttccact    240
gttatcgtct tgctaatatt atgtacagct ggttgttcta ctgctgtacc aagagtcgta    300
```

| | |
|---|---|
| gtggccttat tattatttat taccggtagc tcattttgct agtaaccatc atgaaattga | 360 |
| tctccgtatt ggagtcaccg agcattccgt tagattttgg aaagcacact tttgatcttg | 420 |
| atttatcttt caaacttcca tgttattcat tgaagagaga ctctagaaag taagcttgtg | 480 |
| acattgagtc agctactagt | 500 |

<210> SEQ ID NO 59
<211> LENGTH: 500
<212> TYPE: DNA
<213> ORGANISM: Zea mays

<400> SEQUENCE: 59

| | |
|---|---|
| aggtcaggtc agcagcatgt atataatgca tgctagtcaa tggatgtagt actagtacca | 60 |
| gctttattca tggtattttg ataagttcga caaatgatat ctgatgaagt ctattggaaa | 120 |
| gtgttttgag ttttctgttt tcaagtgtcc tactattatc ttattactat catgattttt | 180 |
| ttttctgttg gtatttcgaa ttcttggctc cataaaaaaa tgctatttta tcactctcag | 240 |
| cgtgggctat ctgttattat gtctccctat gtctatgact tgtgggacca ttgtgtctat | 300 |
| gatttgtaag tccgatggtc aaatagaaa gcgcataact gagagtgaca aaatagcaaa | 360 |
| tgcccaaaaa aaagtgatgc aaaacatgtt aatagtggcc catagagcag gtgtcggcgg | 420 |
| ttcatgtgca cagacgccat tccagggggt gctgagcttg ggggactcct accgagatgt | 480 |
| tgaagagcat ttgttggttg | 500 |

<210> SEQ ID NO 60
<211> LENGTH: 500
<212> TYPE: DNA
<213> ORGANISM: Zea mays

<400> SEQUENCE: 60

| | |
|---|---|
| acagacactc ttttatcata tagttttgac agcgacgacg aacacggccg ggtgtgtcca | 60 |
| gcatatatga actggtgctg tatttgttat atgctgcgtc aaccatgtaa gctagcgttc | 120 |
| aaataaatgt cgagcacacg accacacgtg atcattcaac atcaacaaaa tgggactcag | 180 |
| tattgttgtc taaaagttag acaactgtgc aggattggat ttaatttaca gatataaata | 240 |
| atgagataag agattgagag tacaaccgtc tcgactctcg tgaacccgat tcacatacac | 300 |
| gcgcatgaga tttaagatt atactgtcgg gcaccggctc ttgcgcatct ccccttccgc | 360 |
| ctatggtttc ctttactacg ggaatccggc attttggtga atgttcaacg ctttgtcgag | 420 |
| tatattttgt cggacactcg acaaagcagt ctttatatta ctgtccggca ccggctcttg | 480 |
| cgcatctccc cttccgccta | 500 |

<210> SEQ ID NO 61
<211> LENGTH: 500
<212> TYPE: DNA
<213> ORGANISM: Zea mays

<400> SEQUENCE: 61

| | |
|---|---|
| ctaagcgaca catctcgtgg ccaagtgtag tcaggcaacg gtgttgtcgg gaccataatt | 60 |
| aggggtaccc tcaagacgcc taattctcag ctggtaaccc ccatcagcat aaagctgcaa | 120 |
| aggcctgatg ggtacgatta agtcagggat cagtccacac gagtgactcg atcacgcttc | 180 |
| acccgagcct agcctcggcc aagggcagcc gacctcgaga gacttccgtc tcgcccgagg | 240 |
| cccccctttt tacggcggac acacctccgg ctcgcccgag gccttggctt cgctcagaag | 300 |
| caaccctgac taaatcgcca caccgactga ccaagttgca ggagcattta acgcaaaggt | 360 |

```
ggcctgacac ctttatcctg acacgcgccc cccggcagag ccgaagtgac cgccgtcact      420
ccaccgctcc actgaccagt ctgacagaag gacagcgtcg cctgcgccac tccgactgca      480
gtgccactcg acagagtgag                                                  500
```

<210> SEQ ID NO 62
<211> LENGTH: 500
<212> TYPE: DNA
<213> ORGANISM: Zea mays

<400> SEQUENCE: 62

```
gctcgcgatg atggttttcg ttgacagtct tagtattact actatcttcc tcatgcatgt       60
aacgagttgc ttcgtttctc gtattatggt tatggtttcc cttggatgca tgatgaacta      120
gtgcttgcag ttgattttcc ccttattagt ttgagctgct taattcttag tagcccttttt     180 ttttttcttg tgcttgtcat gcacgtatgc acacacacat gagacgggca gctagcattt      240
tctgtggttc tatctcctct cggttttgtg cctgtcattt ggggcttaaa tgtatcagtt      300
gtcttttctc gtgcttggca tgcatagtat atatatgccc acatgagcaa actgctgctg      360
cttcagttcc aagtagtaca aaagattcaa attaaaattc catcgtattt aaccctagat      420
tttaattgaa tatattagat ccgcatagtt ataccaacat gactgattac acatgatacg      480
tgccctttag ttttatatca                                                  500
```

<210> SEQ ID NO 63
<211> LENGTH: 500
<212> TYPE: DNA
<213> ORGANISM: Zea mays

<400> SEQUENCE: 63

```
actttgtgag gcgaatccaa acaaaaagg tggatgcgag aaaggcgaag tatatgtaag        60
ccggaaggcg aatttcctgg ttactgatga cctgcgtgtt cttccactct cattagcatc      120
cactgttaag attgttagtg attccaaaat ccagacctcg aatcttgtgg tcaaagaaat      180
cacattaaca aagtccaagg tatctatatc tgctacataa ctcacattat ttgcattgtg      240
ctagactacc tattcacttg gtcttgtgta actgaatctt ggaacaggtt atggagctac      300
agagggctgt cctgctgctg agtcgcaaca tactcagctc cgtgcttctg catcctaaga      360
agaacaagaa gctgcaccat taccatcgca tgtattagcc gtcgttgttg ctttactcta      420
tgattagcca caatgataac tatgtactat gtctgttttt ctgctgaatt tgtaagttat      480
cattttggcc actggtattc                                                  500
```

<210> SEQ ID NO 64
<211> LENGTH: 500
<212> TYPE: DNA
<213> ORGANISM: Zea mays

<400> SEQUENCE: 64

```
gcatgtcatg gtgtgctctg cgtgacattg acttttgggt tgcgttccca gccgtatgga       60
ctttgttaag gtttacatgc tatgtttctg ttttaatgca tgttactatc gtttagattg      120
ttatgtttta tctcatcact gttcatggtg gctacctatg gttaacggtg gcttgttcgc      180
gccttggcga cccataagtg ctgtgttttg ttgtttgttt ggtcactgtt ttttctttgc      240
gagaccagta ttaaagccag taaaatgcct ttttgtttc taggagtaca tccctaatta      300
aagccaataa atgagttact ttttttttgga atgaaggacg tctttcgagt ttcgatcggt     360
```

| | |
|---|---:|
| agttttagtt ccaaaatctt ctgacttgag cccctctgga tgtccacgcc tactaaagct | 420 |
| ctaattatgt aaaaaaatcc tgagctcagt aacagattag gccttgaaag tgcaaaatgt | 480 |
| tcatataaat tatactgcat | 500 |

<210> SEQ ID NO 65
<211> LENGTH: 2000
<212> TYPE: DNA
<213> ORGANISM: Glycine max

<400> SEQUENCE: 65

| | |
|---|---:|
| taattaaaaa gataatattt tatattatgt aataatatat tatttattat aaaattttca | 60 |
| taattagatt ttaattttaa tattaagtag taacaataaa tattatatta ctacttatgc | 120 |
| atatttttaa aaattagtta ctgtaaaata tatttcatga aaagtaatat tccttaatat | 180 |
| tattacagaa ttttataatt aaatattaat tttgataatt gatattaagt aataatatgt | 240 |
| catttactat acaattctga taattaattt tttattaaat aataatatta attaaatatt | 300 |
| atgaaaataa tgaaataaat atgaaatatg taattagata tcaattaatt aatactaaaa | 360 |
| tacatagata atcaaataca tttttaacta ttatttctca taaaaaatat ttaaaataat | 420 |
| aaaatgagca gatgaaaaaa ttaatgtgtt tttaatcttt tgtgtgtaat attttttaaaa | 480 |
| tattaaaata aatattttat ttattcacta ttaattattg ttcgtgttta ttaagtataa | 540 |
| tatataatta attttatgtt ttattttttga aataaaaatt atatttctat tatgaaaaca | 600 |
| aaaatataat attattgtat gtaattttga taattaaaaa ttaattttaa tatttatcct | 660 |
| aagtaatagt atactactta ttatacagtt ttaatattct aattaaatat caattttgat | 720 |
| aattttgata ttaagtagta taattaaata ttatattgtt atctacgcta attttttaaaa | 780 |
| ttacttattt taaaatatat ttcaagaaaa ataataattt aaaagtgtca attttaaaaa | 840 |
| tacgtattta aatttaaaat aattcgtaat atataataat taagaatata aattaataaa | 900 |
| ttaattatta tgtatacata tcaatgtaat ttattttaaa tttagttatt taaataaatt | 960 |
| ttgctaacag taataattaa aagtaatcat ttaaaagtga cgtgagtatt taatgaatat | 1020 |
| ttgagctttt aatatgtaat tttagttttt ttataatttc taatcaatga ttttaatttt | 1080 |
| ttttttttgta atttttagtc ttcttatggt aaaaatttta taattttgat caaatcctca | 1140 |
| attttacata tattttattt ctcaattaaa aattaataat tatcttgatc aattttttaca | 1200 |
| taattatttt aatatgttat taaatatttt aatttttaat tttatcaata tatatatata | 1260 |
| tatatatata tatatattat aaaatactac atacaaatat aaaattatat ttttgaatcc | 1320 |
| aactcgtaca tgatacacga gtttaaaatc tatgagatgt aatcgtttcc ttccaagtat | 1380 |
| ataggcagaa aaaacatgca ttcgtctgtt cttatactac aattgtaaat ttattgctta | 1440 |
| ttacgaagat gtcactaaaa acctcttggc tacctttca tcttccaaca acgtgcatat | 1500 |
| actactctct tgttacattt caactgcttt aacgctaagt tttctaatta atgtgtcaat | 1560 |
| aattgtttta aaactgatag gtgataatta ttctctggta atatctgatg ggttttttttt | 1620 |
| taggtatact agtatttgtt aataaaagaa gtatattgtg taagcctctg agatgtttta | 1680 |
| ttcatggtat agagcaaaaa gtgtaacaca aatttaaat attgataaaa tcctatcctt | 1740 |
| aaaacatgaa ataaatccta aaatactcac aacaaattca taatatttta aatctaaaat | 1800 |
| aatatcctaa aaatttaaaa cagatatttt ttttaaagat aaacaaatta tttctttcta | 1860 |
| aactaaatat atgagacaaa ttcttttacaa tatctactat gtagacctct atatataccc | 1920 |
| tgcccttttca gtccacatta cagcacagat attttctcaa agggaaatag caccatttgg | 1980 |

-continued

| | |
|---|---|
| cattttacaa tttccaagct | 2000 |

<210> SEQ ID NO 66
<211> LENGTH: 2000
<212> TYPE: DNA
<213> ORGANISM: Glycine max

<400> SEQUENCE: 66

| | |
|---|---|
| ataaggagtg ataagctgca aaaccaacc atgtgacatg aaagtattta cccctagga | 60 |
| ttgaggatcc acaaaaagac acaaaagtta aactcataat taaattcaat ttcacttgtt | 120 |
| ttcacattat aattttaatc aaattattaa aattaatatt tttgtccaac atttgaatcc | 180 |
| tatatactat ctttcaattt atagctaaat tcaactcact actgatattt taattctaca | 240 |
| atcgcccacg tgcattatca cttagaatca aaacataata tatatttcaa agatttcgaa | 300 |
| ttcaatttca aatcataata tcgtaaaatt caaaaccaat ttccacggtg aacagaaacc | 360 |
| tatcttcatt tgttatcacc tatatctttc ccattttttcc attcccgaac agattcgctg | 420 |
| acgagaaagt ttctgctgta gctttaattt taatgctaat agtttggaat agaaatctct | 480 |
| gacatctcag ggagtcagaa cgtgacatat ttataggaaa tatataatct aaataaacgt | 540 |
| ttgaatttct tccaaaaata tttgaaaata tatcagaa tattattaat gaagaaccaa | 600 |
| taaaaaattg caatttgtat atgtttaata tttaaataca ttatatttat caaataaaca | 660 |
| taaaaaaata taatactaat tatttataat aaatctttca caatcaaatt gtgtgttctt | 720 |
| tagctagcct ctatgtagta caaatgtaaa taactcatta gaaaacatttt agtaaaggaa | 780 |
| aacaccgatc ttatcttcat ggaataatga atttgtttgg ttgttcattg aactgaaatg | 840 |
| ttctgctagc tccgggcgct cttttttaata ataataaaaa aagaactaaa gtattttatt | 900 |
| ttttttaatt taagattttg atgcattcac atgtgaggac ataatttat ttaatggaaa | 960 |
| agtacttgct tgatttatat catgtataac attttcatgg attaacaata attacacatc | 1020 |
| acaaacgaaa ttatttaaa atcctgtgtg gtgggaacta atgatttgat aataaaaaaa | 1080 |
| acaaaagttt ttttttttta atgaaaatac ttcttctttt actttttttt attagaatct | 1140 |
| attgtgaagt gtctcagctt tcattttatt taattttaaa caaacaatt actccttctcg | 1200 |
| ttatcataaa aaatactccg ttctaaaata agtgtaatgt ttaatttta tataatatta | 1260 |
| atttttctttt cagtgatact cataatatgt gtgctttaac ttttttaacgt gtcgctttaa | 1320 |
| ttttttaata taatattaat agtaaggtta atttttataag attattactt tttttatttat | 1380 |
| ttattattat taatttctct ttatctatgt aaaataactt acaacaacac ttaagttaaa | 1440 |
| atatgtcatg tgaaggagtg ctgccatgca cagtcattaa tacataattt ttattagtta | 1500 |
| aaagatatta aaaatacaaa attataagtg ccaaaagtga gttagaaaag tttgcctatt | 1560 |
| actaacattt tcctaatcca tgtataatcc ccatttacac cattttgtca tttctcgctg | 1620 |
| tggtaggtgt atcatttaac aatcccgcac tggactcgct gaagtatgct ttttaagga | 1680 |
| tttcttgatt ccttattggt acgcacaata aatatttctt ggagatgaaa ttctcttttt | 1740 |
| catgggacca gtctaaaaaa tcactaggta ttttttttctt ctattggcat tttcttctat | 1800 |
| ggtcgaccaa cgtaaaataa aattggtctt aattttttc cgcagcacac gtcttagtgc | 1860 |
| ctctataaat tcagcaatat gtagctgtag taatccacat aaaatccaat tcataataca | 1920 |
| ggttaaccca tttcccacta gcgatcttgt tctctaagcc taatattact cccttgatca | 1980 |
| gtctttgcat atttagaaaa | 2000 |

<210> SEQ ID NO 67
<211> LENGTH: 2000
<212> TYPE: DNA
<213> ORGANISM: Glycine max

<400> SEQUENCE: 67

| | | | | | |
|---|---|---|---|---|---|
| tagttggttc | actaaaagaa | tctattattt | tatataatat | tacattaatt | tcttatatat | 60 |
| aaatttagat | attaattcaa | tatcttattc | ataaaaataa | atcaatatac | taagaaacta | 120 |
| aatcatcatt | cattgacatg | attttttata | ttatatttac | ttattcttat | ttcgttacaa | 180 |
| aattctcaat | tttttatttt | agattttgat | ttttttttctt | ctaaaatccc | agtttaatta | 240 |
| cttttaaagt | tttattgtta | tattaaaaac | atattttttca | tttatacatt | caaaaacgtt | 300 |
| ttttcgtatt | ttctatttttt | ctaataaatt | aaagttactt | atattttga | cttatttatt | 360 |
| taaattaatt | ataaactatt | ttttttatgaa | tttcaatttt | ggtaattta | tttttatttaa | 420 |
| aaatgactga | cgcacaaaat | acatacaagt | acattcttta | cataacattt | ctttaaatga | 480 |
| cgaacgcgtc | gatttctagt | cattacccctt | taactaatac | aaggtaaggt | cgcgttaagt | 540 |
| tttcacgtaa | aaaagttact | atataaacac | ttctctaaag | acccactggc | atttgtttaa | 600 |
| attaggaacc | aaacacattc | atttttcaact | catccttgag | ataaaattta | ctttttgaag | 660 |
| taaatattaa | aaatcgtgac | gatgttcaat | atcattcgga | aagagacata | ctaatccgca | 720 |
| ttgacgcatt | ttcatgccac | tatttttgctt | tacgcatgaa | acttccaaat | tctccgttgg | 780 |
| tcgctttcaa | cttttgcaact | ttcaaaccca | aatttataaa | gagatcaatt | ttttcttttc | 840 |
| tttttgaagg | atagagagag | agatcaattt | ttaaatatat | atagatattt | tatttaattg | 900 |
| ctaaacattc | attagttagt | aatatgtaaa | atatatttga | attaaaattc | ataataaata | 960 |
| aatatttttat | aacatataag | ttatatttta | aaattgtaat | aaatatttat | atcatgatac | 1020 |
| aaattttattt | ttaactatag | gtaaattctt | tttgaaatat | tttaaaattc | aatatgaaaa | 1080 |
| taatatatta | gaaaagataa | aaaagattaa | gaaaaatttc | taaaaacatc | atgattgaag | 1140 |
| aaaaactctc | attaaaaatt | agattctaaa | aacattctca | ttcaagataa | ctattagtat | 1200 |
| aattttttaac | ttaggaaaca | ttgttttttga | gaatatttct | tacaaatttt | ttctcatgag | 1260 |
| ggaaatgttt | taatgctatc | aaaataccaa | ataaccctta | ttaactcatt | taataaaatt | 1320 |
| atataaaatt | ttgaattagt | ttccttactaa | aagtgataaa | taaataaata | aatttaagaa | 1380 |
| taagaaatac | taataaaaat | tcttagcatg | tttcttatcg | ttttaagaat | attattgcag | 1440 |
| aaacatcatg | gaaatatttt | ttagaaaatg | taaaaaaaaa | aaaatctaac | atagagcaaa | 1500 |
| tgataaattt | tgtgatgtta | aaattaaata | gaaatatgaa | aaatcataca | aaccttttttg | 1560 |
| taattttttaa | attcatgaaa | aattttattt | tataacaaaa | cttatccaaa | ttatagttga | 1620 |
| tcgaattaat | tttaaaattt | aacttaattt | acgtgcaaga | aaatgttata | ataaattatt | 1680 |
| tatgaatgtt | attatccaac | tagtaatact | agataatttt | cattattcta | taaaaaaaat | 1740 |
| ataatttgca | ttaaaaataa | aaataaattt | cactacaatt | tatttatttt | gaaatttaat | 1800 |
| tctaataaac | aatttaattc | ttattttttta | aaaaatgggt | tgtcaaccgg | gagagagttg | 1860 |
| gtgatttcaa | tcttagtaat | gacgtgggag | attccattcc | agtgtgtgtg | ctttttctct | 1920 |
| ccctactact | ataaagccat | gttagtgtct | gcttcaactc | aagtatctct | ttgtgttcat | 1980 |
| agcaattctc | tattctgaag | | | | | 2000 |

<210> SEQ ID NO 68
<211> LENGTH: 2000

<212> TYPE: DNA
<213> ORGANISM: Glycine max

<400> SEQUENCE: 68

```
gcattgcatt caaaatgtaa agtttacaga aatttaaaat ggttcacaaa caaacataca      60
ttctccttgt gtactcgttt ctctctgcgc tgggtacttt gagtgtataa ggatttgtat     120
aaatgaattg cgaccacgaa atctaactaa aaactgctat atatagattt cgaaaataa      180
actgccctaa cggtcgaacg ctatcctaat gccaagtgtc ctgctacgta cccttgcat     240
gcacacataa ctgctcccta gaacggttat ccacattact cgaaatcgaa atgatttggt    300
gaagatttgt tcagaaacta cgctaagtcc agaactcttg ctgcctcgac ttcgactcgt    360
ccatacacca gttcgaattg cccaatggct cgaagtcctc tttcttgtct tagctttgta    420
cttcgtaaat acttctttga acctgggaat tccttcttaa agacttttct ctcttttcga    480
ttcgagcagg tcctgaccag actcttgctc tgtaatacgc ttcgaacctc gagacgacat    540
ccaatgcata cttagagcat attttagctc gtcgaaaata tgggccaaca gatatttaga    600
atttttttc tttcgtttaa aaataatatt taatttctct tatcttttta gttgtttaaa     660
gtggaataaa aaatggaaaa caattttggg aagaacaaaa aaagttgact ttccttcctc    720
gatcaaattg ttaaaaaata aagttttatt aaacattttt ttatttgata tgtatctctt    780
agtgttagtt agttggaaat taggttaggt agttagaact agtggtaatt agttgatgtt    840
gtaataataa catcaagact ttatattatt gagtaattaa tcttacatct tcattttgtg    900
tctcttgatt tcgatcttaa gggtgaacaa tcatcttctt ctcttataac attattgatg    960
tttgaatttt gaaccttgta aagtttgtgt ccaggtgggt acccatgctt cttgtaacaa   1020
tcatcagtat gattataaaa atcataatat gtgcaaatct tgtttccttt tactcctgaa   1080
tttcctttgt cgtaagtttc ctttttctgga agcatacttc tgagaaaaac catgcttcct   1140
atagcatcta tcaatagtgt gattatcttt cccacaatag gtacatgaag gcctagaatt   1200
caatgaattg ctgcaaattt gttttaattg tcaattcatc atcccgagtg attctcaatc   1260
ttgtgaagta atcggtaatg ctttgatcac cttgtttgat agaagtcatt tcttgctaca   1320
aatttaaaat tctcaacaga tctccttatg agtatcttaa ctttaagtcc ttccaaatgt   1380
ctctagcatt atccatctat aagatacttt gtcttatcga gggtaaaacc gagtggacaa   1440
gccaagaaac caccatattg ttacatctcc tccaagctgc atgaagagga tgaattgatg   1500
cacatttttg aattgatcca tctataaatt caattttatt tttcgcgctt aatgcagtaa   1560
gcatcgaaca attccatgag ttctagtttg tcggatcaag aatcgaagaa atcaatgcaa   1620
ttgcaagatt ttcacctgga tgaaggtagt ataggctatg gacatttagg gattggtctt   1680
gtgaagaaat ctcattggtc ataattaaga aaatgaaaaa aaagatttag gttcaagatc   1740
agggagttac gtaaaagagc actaatgcct tgataccatc ataaatattg tgcctaccat   1800
ctttgaatgt aaaattaacc aaaaaagctt gcaagagaaa ctagaaagaa actaggaag    1860
aaatgaatga aattctatgt attgaaaatt agttctaact acaaccaatt tcaaccaact   1920
aaactaagtt ccgactaagt aacaagatcg agtatcttta atcaatttgc ccattgatta   1980
ttcttacatt ttaatttgga                                               2000
```

<210> SEQ ID NO 69
<211> LENGTH: 2000
<212> TYPE: DNA
<213> ORGANISM: Glycine max

<400> SEQUENCE: 69

```
acactttata cacataataa ttaatataaa tttttattta tatatagaga gctaactcaa      60
ttttaaaag tttggatgtg agtttctttc actcaaaact agacaacctt tatagtttct     120
agttttcgca tcgtcttaca gataagtaat aataataata atataaaaaa ccctcatgcc     180
tgtcgtttcg aaggtgcaac aggttcaaaa accattagtt tcaatgactt ttcacttatt     240
cagtatgtgt gaaaagtgag gagataaagg caataataca tgggactcat gcaaaataat     300
ttcactactg cattattgtc gggaagaaaa cttggaagag aagaacaaaa taaccatttg     360
tcaattttgt tttatataaa cataaaaaaa tgtcatctaa ttaatatgat tatattttc      420
ttttaatttt ttttatcta tatatataac ctaaaattta ttatttatt ttcagttttc       480
ctacttcatt ttatattatt tcttttcctc tacttctccc atgcaagcat aatgttacgg     540
cttaatttga gaaaagaag agagataaca ttcaaaccc agtgatctcc ccatgcggtt       600
acagtcgcac aatatatctc gctctgtgtt gaattgaaaa ggatgtgtaa ttaagggtct     660
ccacgcgtga agtaaatgaa gtagaacata tgcacaaatg ctcttagtaa ttttagggca     720
gattcctgcc ttaatttgtg gtgaccgtga ctaaatggg aatgtcctag atacaaagtt      780
agcatgcttc ttctattgaa ttatatatac actgggtcaa tcaagaacat taatcatggt     840
acatagcatc accgtagcac atggacttta aatgaagata gatacatgta accatttcat     900
taattaattc atgtcgttaa cactcaacga aaaatagaac taaattaaag aaaatttgtt     960
gatgtgagga atgagtatga aacgtattaa ggggatggt agattaatga tgatattgac     1020
atacaggtgc ggatatgtgc ctgatagttt aatgcacaag taagaccgta ccaaatcaaa    1080
gtgcaacttg agcctttcgc tgtctagttt ctaaactact atcaagctgg attgaaaaaa   1140
tatgaatata gacaaacttg tacaacctgg tcattaaatt aaactactgt aaatgtacca    1200
aatgtaggtt ttcatattaa gagttcaata tatttatata aaacattttt acattaatct   1260
aaataagatt taattatttt atcaggttat tttattcatt aacatgctgt gacgataaaa    1320
aatttcttgt tagatgttta gaaaaatatt ttacatgcaa aattgcaaat caaaccttt     1380
tcaaattcat cgcgggaaag gaatcgatat ttctgtggac actatataca cggtatgacc    1440
attaattgga catggaccaa acaagcaata acgtcaaaat ttgtagttgt cgatgaatga   1500
atcttgcaga caaggtgtc caaaatcatc caaagcacgg gcatatgtag ctacttaatc   1560
ttattgtggg ggggagacta gggtcccgta gaagatacct tttggggata tatagataac    1620
tttttgagag gtctggatat aatttgaagt tttaaacatc cataaattat actcttcttg    1680
tttttttgac aaacataaat tatactccaa cactatatca atactagtgt cttgatattc    1740
aaaaggtgtt cccatgattt taaatagtga tctaccatcg caatcgcaat tatgataata   1800
atatcaaagt attttgattt tccgtaatcg tacaacaatc gtaataatga ctatattaca   1860
ttttttttca taatataaaa gttttctaaa tgatcaacca caagtcaatt tatgagagct    1920
agttaacgaa tatcacagcc tgtatatatt ccctatttaa acatcacatt tgttctatac   1980
acattcacct taatccgatg                                               2000
```

<210> SEQ ID NO 70
<211> LENGTH: 500
<212> TYPE: DNA
<213> ORGANISM: Glycine max

<400> SEQUENCE: 70

```
cgggaataaa ccggaaaaaa gatgtcttgt ttagagatat ttttactatt ttactctata     60
```

```
ggctacgttt gatttccaaa gcttattact acattctact aggtgctgta aggaatagga    120
agtttattat tcactgttgt ggtctttgta tttcatgaag attagtactt tgttatttca    180
ttacctaatg aaaatatact aggtttcaat tataagatta cttttatggc tatattgttg    240
tctctttatt tcatgtttac tttgtctgta tttcacgacg tgacgaaaat aaacaataca    300
aggtttcaat cgcaaagaaa ttaaaataaa aaaataaaaa ttcaatagca aaaaatagtt    360
ctaaaatcta aatggaatgg ggcattccga gaattgaact cgggacctct cgcaccctaa    420
gcgagaatca taccactaga ccaaatgccc tttggaagtg gtttgtgaaa gttaactaat    480
ttaattagta aaatcaatgc                                                500

<210> SEQ ID NO 71
<211> LENGTH: 500
<212> TYPE: DNA
<213> ORGANISM: Glycine max

<400> SEQUENCE: 71
ttccattaca aaaagttaag tagcaagtat tatatattat acatattgaa taattattga     60
ggctatgata gtggttcaca attatgaatt tattaattta caatatgtaa tggatggtat    120
gtatccttca tttacgataa attgttggtt tgaaaattcc ttttgtattg attctaaaga    180
ggtacgtaca atttcttttt taatcctcag ttcttttcat gattcttttt gtagcaagaa    240
aaatcacaac tcttatatca aatataggaa tgatatattt aattaactcg gaaatgtaga    300
acatgcggag aagaacatca aaacagtgga tatatacgtg tatatatata tatatatata    360
tatataagac aattccaatg taaaacaata aaaaaaatgg accaaactta actgtaaaat    420
tttatgtaca tgttttttga gttattgtcg aatcaaaatg gagttttaca ttagcaaatt    480
acgtaagagt tgtatcaaat                                                500

<210> SEQ ID NO 72
<211> LENGTH: 500
<212> TYPE: DNA
<213> ORGANISM: Glycine max

<400> SEQUENCE: 72 tttttttctta agttgacttg acatggctga tagggctttc tcataaggaa atcctagcaa     60
aataatgccc tgcaacttat gatgttatag attgtcaatg agttgttagg caaggaatgt    120
tggatgtaaa atggttggga tagcatatat aatcccatat atatggtaca acataatcta    180
tatataaact ttatttttt acatttttact atattttttt tgtccaaact ataattttgt    240
ttttcataag ctacaacata cgcatttaca gatgtaaaca ttaacattgg ctgaaaaggg    300
atgctctaca ttacgttgag atagatgaat gaatatacac aatagtatgt ctatggacta    360
tggatattca taggtcgatt agttgtgaaa atgagacga aaaacaaaa ttaaacaaaa    420 gaacgtaaga aaaaatgtga ttgaaataaa ttttaaatct aatataatta aatttaaatt    480
aaattttaaa tagttataat                                                500

<210> SEQ ID NO 73
<211> LENGTH: 500
<212> TYPE: DNA
<213> ORGANISM: Glycine max

<400> SEQUENCE: 73
cgtggaggaa aaaggaattg tttggtgggg aaatgatggt gaccaatgta agcttgccaa     60
```

```
atgtccaaca gcgaaaggtg tagttactga agggtgtcct gtgttttgat ttccatttcg      120 acatctata ttttctggtt agttaagaat taagatggtg agtgggggag taatatttct       180
gcaaatacca gttgaattag attgttttaa gcgctttaat ttggtggacc tttatgttgt      240
ggttgtgtgc aacttctcca gaacagatcg ttgttttttt tttttttttt tttatatagc      300
tagtcatttt taatttcatt ctatttcttc ttctttttt tttaacagaa tttcgttcta       360
tttcatcatc actatcattt agaattgaca atgttttagt tgctagataa ccgcgagata      420
ttgggagttc caacatacta gtattatatt agtatcaaac tttcaagaat tataaacctt      480
ttatttccgt ttcgtgatag                                                  500

<210> SEQ ID NO 74
<211> LENGTH: 500
<212> TYPE: DNA
<213> ORGANISM: Glycine max

<400> SEQUENCE: 74
atcaatatgt atagtgacgg agacatatat catatatggt ttcatatgaa tcaagttaaa      60
aatgcacatc aactaaacaa atcttctata tggaacataa taataatttc tcaccagact      120
aacataggtt tcgatgattc cggaaataac gttgattctt tatgctccaa ttattttttat     180 tatatatata tatatatata tatatatata tatatatatt ttttttttt                  240 tttttcttt tatcacgcca gttattatat ttacttttt tttcttcttc caatccgata        300
tatacatacc attagaagat gtgaaaaatc gcctatgttt aatatatgaa ataattcta       360 attgtttatg gcatctctat tttatactta tctgaacctc ctgttgttta atactattaa      420
ttagcactca tcgtatttat cattttttgt tctattttgt ctgtatccgt tgttcactt       480 gagatgtgtg ctttttttaaa                                                 500

<210> SEQ ID NO 75
<211> LENGTH: 592
<212> TYPE: DNA
<213> ORGANISM: Arabidopsis thaliana

<400> SEQUENCE: 75
acaaagactg gtcggtcggt tttggtagac aattgaaatt agatggatgg tccggttcgg      60
tatactataa gattaaaaac agttttaaat tcagctaaac cgaactcatt tgattttatt      120
aaaccggaat catccgattc gagtttgtaa aaaataccga aattgaaaac actaaacaaa      180
aactgtatta aactgttact gaaataagag aatctcccaa ttcggtttac gtactactct      240
tcagaaatca gaaccaaaaa ttcagaaatc ggattgaacc aaacttaaat tgacggtccg      300
gttagtcttc ggctctacaa attaaaggcc caagttctg ctttaaaaga acgaaatagt      360
taatgggctc aaaccataga ccaggtaagt catgggcttg gttagtccgg gtcaacccgg      420
tagacccgat tcctgaagaa aacctagtgg aaggtttaaa gttgtaaact ttccgaccaa      480
ataaacaaaa tcgttttcca gcttcttccg tcgccactaa accctgaggc taaacctaga      540
cgagtcaaag tgtaaaatcg ttaaacccta agagggagtg agagagagaa ga              592

<210> SEQ ID NO 76
<211> LENGTH: 459
<212> TYPE: DNA
<213> ORGANISM: Arabidopsis thaliana

<400> SEQUENCE: 76
ttatgatttc ttcggtttca agatgatcaa atagttatag atttcatgct cacacatgct      60
```

```
cattagatgt gtacatactt tacttaccca aatctatttt ctcgcaaaga ttttgatggt    120
aaagctgatt tggttctatt gaactaaatc aaacgagttt cagactgagt gattctaatc    180
cggcccatta gcccctaaac agacccacta attacgcagc ttttaataga gtaattacac    240
ctagtttacc cactaaacca ctaagcacta attatctcac aatctaatga gcttccctcg    300
taattacttg ggctttcact ctaccattta tttgtaacag tcaagtctct actgtctcta    360
tataaactct ctaaagttaa cacacaattc tcatcacaaa caaatcaacc aaagcaactt    420
ctactctttc ttctttcgac cttatcaatc tgttgagaa                          459

<210> SEQ ID NO 77
<211> LENGTH: 667
<212> TYPE: DNA
<213> ORGANISM: Arabidopsis thaliana

<400> SEQUENCE: 77
cagagaaact aggagacttg agaatataca ttcttgtata tttgtattcg agattgtgaa     60
aatttgacca taagttttaaa ttcttaaaaa gatatatctg atctagatga tggttataga   120
ctgtaatttt accacatgtt taatgatgga tagtgacaca catgcacat cgacaacact    180 atagcatctt atttagatta caacatgaaa tttttctgta atacatgtct ttgtacataa    240
tttaaaagta attcctaaga aatatattta tacaaggagt ttaaagaaaa catagcataa   300
agttcaatga gtagtaaaaa ccatatacag tatatagcat aaagttcaat gagtttatta   360
caaaagcatt ggttcacttt ctgtaacacg acgttaaacc ttcgtctcca ataggagcgc   420
tactgattca acatgccaat atatactaaa tacgtttcta cagtcaaatg ctttaacgtt   480
tcatgattaa gtgactattt accgtcaatc ctttcccatt cctcccacta atccaacttt   540
ttaattactc ttaaatcacc actaagcttc gaatccatcc aaaccacaa tataaaaaca    600 gaactctcgt aactcaatca tcgcaaaaca aacaaaaca aaacaaaaac cccaaaaaga   660
aagaata                                                              667

<210> SEQ ID NO 78
<211> LENGTH: 479
<212> TYPE: DNA
<213> ORGANISM: Arabidopsis thaliana

<400> SEQUENCE: 78
cattatgttt gaactcttat atgggttctt cccatgttac aatacgtacc agggtgctct     60
aaaatatcca attggtcccg atctatatat gtatgtagag actcttcctt ggatagatat   120
ttggtgaatc caaaaataaa gttttacaag agatgacgaa acaaaggata gtaaaagaaa   180
tcagaatctt gattattgaa attttttaaa gacagaatca gcctttataa agaaacaata   240
ttctttattc atttccttcc aaaatctctc ttctttaaga tgatctacac aattaaatac   300
cgtcgatttc gaaaattgaa gtttaaaatc aatatgagga tttgaaataa gagcttacat   360
gcacacacac atatctctct atatataagt gagtaggttt acatggttta attttctata   420
acacgacaca cacgaaaaag agaagcaagc acaacacaat ttttttttata acaactaaa    479

<210> SEQ ID NO 79
<211> LENGTH: 2345
<212> TYPE: DNA
<213> ORGANISM: Arabidopsis thaliana

<400> SEQUENCE: 79
```

```
ctgctgtaaa tgtgaaggtg ttgggagtaa accctcttga taccatttgc tcaaaacagt        60
ttattgcatc cctgaagagt tcattgcatc cataagcctc tataatggcg gtccatgtca       120
gagagccctt gacagcaaca gcatcgaaag agaaattagc acttctgaga tctccacatt       180
ttccatacat cttgatgatt cttgcagaaa caaatgggat cgactcaaat tccttttca       240 gaatgtgccc atgaagctct tccccaact ttaatgcttt gagatcactg caaacagtca       300
aaaccctacc catcgtaaca gaatctggcc tgtgttttga taacagcatc aatctgaata       360
cctcaatccc tgctcttaaa tcacaatttt ccacatagca gtcaatcata gcggtccatg       420
ctttcacatt cctttgttcc aacctgtcaa acagtctgat aggatactct ggaacaccgc       480
actttgagta catcaccatc aaggaagtga ccagggatac attcggcaag aagagattct       540
ttaaagcata acaatgaatc tccttccctt gctttatagc cctcagctct gcgcaaacag       600
gaagaacagt agcaattgta acaacatctg gcctaaaacc ttcctgctgc atccaaacaa       660
tcgacctcaa agcttgatca aatctaccgt tggctgcgta tccagacatc aatgcagtcc       720
aagatatggc attcctctgt ttggatccat agaacacacg tctcccagaa gccatatccc       780
cacacttgca gtataaatca atcaaaccag agtgaacaaa cggctgttcc acgtaattct       840
tcgatttcaa tacatgggca tggacctcct tccccagttt cagtgcctta acatccccaa       900
gtacgggaag aatcgttgta agtataactg agtttggata tatctttct tcactaatca       960 tcgtcctaaa cagtcccaac gcttcccact gcctttatt gtgagccaat ccagcaatca      1020
tcgcccccca aacaactata tctctctcta caatctcatc aaaaactcga cgtgcaagcc      1080
ctactttacc acacttaaaa tacatatcaa caagagaagt cttaagaaag acactattaa      1140
acaaaccatt cttaatcgca agtgcatgcg tcttcaatcc ctgtctcaaa gcagatgcac      1200
cagcaaaact cttaaacaca ttagataaac tataaacatt caaatcaaca ccaagctctc      1260
tcatttctgt aaacgtagaa agaacatctt gataccgctt cttccctgat ataacagtcc      1320
ctctaagcaa cgcattccaa gagtaaacat ttgagctagt actttcatcg aacaccttct      1380
gtgcatcttt aaccgaacca caagcagtat acatatgaac aagcttggtc cttagaaact      1440
cattactctc caacccatta atacgtatat gaacatggac ttgtttaccg tgaagcaacg      1500
acttccggcg aacacacgcc tctaaaagag cagagaaagt tgtcgcattt acaggaatcc      1560
ctctctgttc gagataatca agaatcgtga gagcgacttc gagattgttc tgcctcgcaa      1620
aaatttgaat atctctgtgg ataatgtagg ggttcttgga gtggagagga agagaagaag      1680
ggaaagcatc tctttcccta aaaggtttcg gcttttggc gggagaagtg gaaggtcgtc      1740
tagttctgct tggtctaatc ggagatttcg ccggagcgcc atctttatcg gaacgatgag      1800
gacggtggtt gagactcgtc gtcacggaga gggacgccgg gaggtctcgg attccgagag      1860
acgacactac ttccattgtg accactaacc acttgattaa gctaaaggtc gttagtattt      1920
atatgtagct ttaaactatt tttataaagt atgcaattga aattgaaagc taatatttgg      1980
gccagaaaat tgaaatatgg gcttagggcc cccaaaacaa ttgtagccca tcagttcaca      2040
cacggtttcg tttttaaaaa aagcatgtat ttagaattta ttggctttta ttttggtggt      2100
tgcttcaatc ttcctcgttt aaaaacaatt catgtcaact tggacaagtt acaaaaaaaa      2160
cgtttcatat ttttgtcact aaaaatattc agttaaataa agtaattgac tcttcgtttt      2220
cccgacgata ctgtataaat aaacatcatg tttctacttg ttcacatatc gactctttgt      2280
ttgtccgatt ctatctctct ctttagaaac tttatctagt ctcttcgaac ttaatcttaa      2340
cgacg                                                                 2345
```

<210> SEQ ID NO 80
<211> LENGTH: 289
<212> TYPE: DNA
<213> ORGANISM: Arabidopsis thaliana

<400> SEQUENCE: 80

```
tcttgttata caatcttcaa agtttctata tttatcaagt aaccattgac tcttcgcttg      60
tatctttccg ttaagaccac ctattcaatc attctctaag ttacatgatt taagatttaa     120
gtaaaatcat taactctctg ccctctccca cttcctccac taaaaaccat ctttaatcat     180
aattaaacct caaaaatcct ttcataatca cagtattata aatagcagct cttaccaaat     240
cctctaaacc atcacacaat acaacacaaa atcttcaaaa gaaaacaca                 289
```

<210> SEQ ID NO 81
<211> LENGTH: 267
<212> TYPE: DNA
<213> ORGANISM: Arabidopsis thaliana

<400> SEQUENCE: 81

```
ttttgttgct cttgctgcat caaatacata tttaaattaa aagtaaaacc tttcgtatgc      60
attgtctgtt actcatcttc atcagaagcc ttaatcgcac catccaccac taatcattta     120
ctttcactta tccctcccca ctaataaacc ttttaattac tctttaatat ccactaacac     180
aacaaatcct tccacaaaca cactataaat accaaaccat cacaagctag tctaatcaca     240
ctaaaattcc aaacaaaaac cacacca                                         267
```

<210> SEQ ID NO 82
<211> LENGTH: 287
<212> TYPE: DNA
<213> ORGANISM: Arabidopsis thaliana

<400> SEQUENCE: 82

```
atactaaact aaacataata atttatttat tttaatgggt ttccataaag cccaatttag      60
ttggcccaat agcttgcaaa actgggcgta acggataatt taataaagac acggtaaatg     120
cttagataga ggattagagg gtaattaaat taaccacgat cactgtgata attactacaa     180
cattaaacga caaaaaaact tttcgtctcc ctcataatct tctactatat attcgtcaca     240
tcacactcat aatctcttac aaaaaatcca taacacaaaa agaagca                   287
```

<210> SEQ ID NO 83
<211> LENGTH: 2821
<212> TYPE: DNA
<213> ORGANISM: Arabidopsis thaliana

<400> SEQUENCE: 83

```
tgaatcatga atggtatgat cgatcttgtc ccgttgtaac cacaagcaag atcagaagcg      60
atgcatgcgt agcaaatttt aaagagagaa aaaacaagt ttttggatgt gagtgttaaa     120
ttatttagca aattttttgta tgtaaatact actgcttgct aaacactatt ttatacctac    180
ataaccaaaa tatctttact agataattaa taataaaaaa tttattggag ctctttatgt     240
ttgacatgta agataaaata ctcatttcag aataatgttc ttatattttt ttttgttgcc     300
aaaactatca gattatgatg accaactcat tcttaaaaat tagttcttca aatgtaacag     360
ttattatcac taaaaaccta gaagacggat cctattcatt tatatacagt cagataaaga     420
gagcatctcc tgatgataaa ggtgggagtg tcattattta tattaaaaaa gtaagaataa     480
```

```
tatcatatgg aaaaaaaaat ttggtctgtt acaaaagtaa agcctatggt ttataaatcc      540
ttgacaaaga aaataaaaat aaaaaatcaa attaggaaaa acaaaaatcg gcatgatcat      600
ggctaattag gttttgatca tcttctagat tcttaatagt tttttttgct tgtagtagta      660
atgacgaaca cattttgcac actgtaactc tagaccaatg tcgtaaaata ctttacaatt      720
tgaggtaatg atacaaatat aaagattaaa gcaatgctaa tatattgaat caaagcaaat      780
attaacatta ataaaatgtt ttgaaagata attgttttga cttttgacta gtcgtaagta      840
gcaatttact agagatgagg aattgtataa gattaaggat gtatttcact atgagatttt      900
agagttagct ttgaagagtg tcaaattgga atatcatgtt ggtggaaaat tattatgctt      960
tgaaggttgg aataagcatt ggaaagccga tgatgttgag atatacatttt acaatggtct     1020 cgtaatcagg tgctaaatat tgcaaggaca tgcgttgtgt aattatcatt gatttcacaa     1080
taacccatgg ggtaaatgtg gtaatttgca aaagtagtaa gggagtggaa tttggtaatt     1140
gtggatacat tgctgtcaat gttgaaataa tgctaacttt ggttggtgct gcaaaaaaaa     1200
aggtcagcca aatatgtgta gaacgaagcc gcaatatcta ctacaagatt gctactctat     1260
agatgttgaa tggggttccc aaccacttat aaaagtggat caagatcaag aaaaggagaa     1320
catgaagttt aaggtttgtg tgtgtggata ttccttcatt tgaatgtggc ttcctagatg     1380
ttgagttcat gttttttgttt tcttacatca ttaggtagca actgattgtt ttggtagctt     1440
gtttgctcat atatatcaaa attctgatag aattggaaac acatgtttgt tgttatggta     1500
ttagcatatg ttactcatta tacacacaag tacataagtt tattgtgaca aaagtgctga     1560
tattatgtga aggttatgta gagaatccgt ggagggttgg tgacgttaat gactgttgtg     1620
gatgtgttaa atctttggta atgtttcttt ccagctttaa ttacatcctc aaatgccaat     1680
gattcaatag tagtgtaatc tcctgcacaa ccgcaagaca cctgctcaaa accaaaacaa     1740
acaaaaattg ttttcgaatt gcttttaact ttggtttctc gtacaaaaaa actaatacaa     1800
aggtgcatga gtagtagtaa ctgaataaat aataagtgca aatagttgac ttaaaataag     1860
aagttgaaag agttgaatga tttcatctca cttttttacca tttgagataa ataagtttga     1920
aaattgattc aacttattca accacaaaaa ttagaaaact aaaccaatta taaaaaacga     1980
attgttcaac cctttcatct actattttgg agaggaattg attaaatgat gttcaacttt     2040
tttttcaaac tcaaattttt cctatcattt atatatctag caattcattt gcaactgaaa     2100 tgttttttc gtgtcaaact ctaggtttga aacccgtata catcaccaac aataactaga      2160
gtttgaaatc aaataatatt ttttcatata taaaacaatt taaaatttct tttagataat     2220
taataaaaaa tgtatgacac acagacacag ctggttgatt tgtttatttg aattttttgac    2280 taggattaag aacattaatc atcaaccgtt gattatataa gcaagttgaa gaaaaggcac     2340
ggttcagatt cacctcttct catatgatgc gttacataag atcctttccc tctttccctc     2400
attttcaggt tcagcgccat cgtcaaaaac ttttggcggt cgatcaaaaa atttcgaaat     2460
ttgaagattt cgccggcaaa tacacaaacc cgaaaatgaa taacacttca aaattttcat     2520
taccagaaga aagaaatcaa ataccttcag atctctatct tcctcattca cacaccctct     2580
ctctcttctc cttttctctc ttctcctttt ctctatctcc ctctttgttc cgttcgcatc     2640
ctctaatcat cgtcaacaag ccgacgaaga gagaaacgaa tccaaagttc gttacttgaa     2700
agctacccag aagaattcaa atctcaggta cttttcctgt ggatttgatc tgggcactgc     2760
ttattaggga tttgattgga tctacaaaat tctgccttct gggtgattca atttcacgga     2820
a                                                                    2821
```

<210> SEQ ID NO 84
<211> LENGTH: 400
<212> TYPE: DNA
<213> ORGANISM: Arabidopsis thaliana

<400> SEQUENCE: 84

| | | |
|---|---|---|
| tttaagctta ttattatgtg tgttgcgaac tcttttaac tcttttgtta aattcttatg | 60 |
| ttttcttaac tcgtttgttc gtcaccattg ctttctcttc aaataatggc tgattttttt | 120 |
| ctataatttt ggatttgttg aatgctttct tttaaaagaa tcagattttg gacttttgac | 180 |
| caaagaaaat aataatatca gacgataaaa tagacggctc tcgataaaac taaccctaaa | 240 |
| aataaggaaa taagttcctc tttgaaccaa attttctttc tttgaccaat agatctttt | 300 |
| gtcaacctct taaatatatt cttagtcaat cttctaataa acccattggc cattaccaaa | 360 |
| aattcctcgg aaacgctgaa taaaaaacat tctatcatct | 400 |

<210> SEQ ID NO 85
<211> LENGTH: 386
<212> TYPE: DNA
<213> ORGANISM: Arabidopsis thaliana

<400> SEQUENCE: 85

| | | |
|---|---|---|
| gcaagcaatg tgatgacgtg ttcatctata aaactcaaag ctcgtttagt tcttttgcca | 60 |
| tgagcttttg cagattaacc ataaaatcga acctttatgt ttacaagatc cttttgtctc | 120 |
| caagtctact ggtccgttga agtttaaaga ttagatcagt agattaccct ttttgcccct | 180 |
| acgttaaagt ttgtttattt aaatacaagt ccttgtgatt tttatcactt tctcacttct | 240 |
| tcaacgacac tgattcgttt tcaaagcatt tgcgttcttg atcttttca cgagggcgat | 300 |
| ttctgaagaa cacgagaatt tgaattctgg gaaaagcttt ctcgaacttt atctgagtaa | 360 |
| attgacagag agaatcgaaa agaaa | 386 |

<210> SEQ ID NO 86
<211> LENGTH: 3433
<212> TYPE: DNA
<213> ORGANISM: Arabidopsis thaliana

<400> SEQUENCE: 86

| | | |
|---|---|---|
| gatttatact atcatgtaac tcaaatttaa atttatacta taatgtgttt cacgttttg | 60 |
| tgttgttgac aaaacaaaat cccaaaccaa tactatgatt tcgtagtaa aaaaagttga | 120 |
| gtctttctct ttaagaaata tgcatgtaaa aggatgtttt gatcctagca aaaagcatat | 180 |
| tacataaatt ctaggacatc ctaggattta ggaccggctc cacctcttcc aaaagtctca | 240 |
| ttgtaccttt ttcaccgcta tgatcgatta atcgttataa tattagtatt tgattttctt | 300 |
| ctattcctac tttagagttt tagataatac cttcggaaga taaaagagca aaggcaacga | 360 |
| acgtgcaaac aggttacgac agtacgttaa tgttgtctga atcctaaaaa atagtaaact | 420 |
| tagcatacga agaatgcagc aaataggtac aaaaaaagta taatacgtgt ataaacatag | 480 |
| aatgtgatgt tacatacata cgtgtaaaag tttggctaca agtgtcttct acacccaacg | 540 |
| acaacacaca aaggagacaa aattgccttt tacggcagtt acgacttata cgtgtataaa | 600 |
| atggtatata cgtctatcgt tcagcttaaa aattcagatt cacaaatgat aataataata | 660 |
| gtgcagagca aatggattag atgaaactca tagaacaatt aaaagaaatg ttttgcaaga | 720 |
| aaatcactca attttttat tataatagaa atacagagac cactaaaatt atagataaat | 780 |

```
aaaactgcca tcgtgatatt cattaattct tatcagaatt aaacgaaaac aagaagtaaa    840
atatctgctg aacgaatcaa gttggctcaa atttcactaa aacatgaaaa tcaatgaaga    900
gattggagag tgttatactt atatgtctca ctctttctcg aggcaaatct ctgctcctat    960
agattcgtag gtgcctaaaa ggctcaattt gaagccatgc atgtcttttg ctttcacaat   1020
ttgtcattcc ccatgccaac ttttcacaaa tttttacagt ccatatatgt atatgcatat   1080
tgcacattta tatatctaaa gttggtggcg taacacgatg aatttttaact aattgatagt   1140
cgcacaatgg catccttatg ttagtctgaa atcagtactg tatcaaattt aattctgact   1200
tttatttgac ttgtctagtt ttcagttgaa gcgaaactat aatggttaaa tgatgttttt   1260
cttatgatta tacaaaaaaa aaattcaaaa aaattcataa tgtttgataa aacgcaataa   1320
tgcaggattt gcgttttgt ctaaaaaaaa gtaaaaactt attatgtaaa taatgatta    1380
tggttatgtt atgaagtctt attccgttag tctgcacata tatctatccg tacaatgtga   1440
tttttcggc gaatagttat ctaatatttt tcattctaaa acttgtatta ttatgtacaa    1500
tagttatgca atattttatt ttcccttttg atcttaaaag ttcaatgttt tgagtttttt   1560
ttttgttcca caattattga tattctacat caacatcatt attattttta ttgttgacca    1620
ataaaaataa gaaaaaaata tagttaatat tattaaacta ataaaataat aatattaaaa   1680
tgtaaaagtt attttttaa tttgtatgaa aatttcacaa catcagactt gataaacttg    1740
atgtaataga gggaatacta aagagtcaat atgtagttag ccatgagccc atgattgtga   1800
tgtaaaaata tgtgttgaaa aatataaaac aattaaacac gagggaattc aacaattaaa   1860
gtagtatgtt tcactatgct acattacaaa ttatttagag aaaattaaat taaaataaga   1920
ggatgaggaa atgatgtgat aaaaatgttc taaagtacgt atgtaccgtg aaaagtgcaa   1980
ttatatggaa gaaaaacacc acaaacacga cactgaaacg ttgtacatac gattgcttca   2040
tctgcaagta tagaacgaat atttgtttta ttttgtctta aagtatcgat tagttccaaa   2100
aaacagcttt ctgaaaccat ttttcatttg tatggattta ttatattttg tagttttaca   2160
gatagatatc attcttaaat agtttttaatt agaaaaatta tgttctatat ttcaaaatta   2220
tgtttttattt tatacctata gttccaactt ccaaataaac gttttgtgcc taggttaagc   2280
atatcggtga tttgcgctca actaacgtct gctatatttg agaaacttaa attttttactg   2340
aaaaacctac gaaaaaccta cgaaaatatc tcgtacggat atgatcaata agattctatc   2400
tgaaagaaaa tgacggtcca tacttgaact cgccatttcc tcttcaacta ggaaaaaatt   2460
ggatcgacat tggatttaag aaaggaaatg aaaccacgag gcgaaagaac taagccacta   2520
gagttctcta ttttgacggt ttactaaata taatcaagag tttgtttctt tgctcgaatc   2580
ttttgaattt ttttcctgtt cgttaagaaa tcgaagagcc aagctactgg acttcatatt   2640
gtcgtgttat ataaatacaa atattataaa caaaatatga tagtactata atataagata   2700
tgtcaatttc cgaagcaaac tagatatgta ggcttctcat gacctacaaa gaacacaatc   2760
caaccagcta tcttttgccg ccctatcata tttaacgttc gtatttatcc tctctttcat   2820
ttccaaaact taatggttct tcttcattaa tacacttcaa aaaaaaaaca tccgtaatcc   2880
ccagaaagaa taagaaaaac taataaagtc acaagtcaca actaacaatt atacaccgta   2940
tctactggaa aataaagaga gagttatatc cattattcac atagaaaaaa catttttaca   3000
tgttaaagac aagtattact gtgttatctc tttttctatt tgccgcattt tgataaatta   3060
attataaaat gcaacatgct tttttttttt ttccgcgtat gtgccaatgc aacatgcttt   3120
tattaaaaaa aaaacgaata gatccaaaat gttttttttt cctttctatt tgtcttctca   3180
```

```
taaaaaagta gcctcttttt taccatctca gccgctccac gcgatgtttt cagagtctcc    3240
agcgcaaaaa acaacacgca tgtcactatc tctctcttca tttgactctg ttccaatccc    3300
tcactaactc gctatataaa tatgagagcc tccccatgaa tttcatgcat cattcaaccc    3360
ccataaccta catgcaaacc atcgtcttaa aaccctagtt ctccataaaa aaatatcct     3420 tgaacacaaa taa                                                       3433

<210> SEQ ID NO 87
<211> LENGTH: 292
<212> TYPE: DNA
<213> ORGANISM: Arabidopsis thaliana

<400> SEQUENCE: 87
atcttaaaac gtaaggctta agataagtag tatatggtgg atatggaacc cgcgtaatca      60
tctagaggct ctacaaatat ttattttgta tttccttctt attttgtatt tgcctacgtg     120
gcattataca acgtatttaa cttgaaacca gattatggcc caatgggtc gggtcgaccc      180 gaccgatttt aaactgcgct cctaactaaa aaaagtcaa acccttga aaaacctaaa       240 aacgcaattt gcttcgtcgt ctctcatctc tttctctttc tccgtcgcca cc            292

<210> SEQ ID NO 88
<211> LENGTH: 494
<212> TYPE: DNA
<213> ORGANISM: Arabidopsis thaliana

<400> SEQUENCE: 88
ttgattactg tggatctagc tagagagaag taatggcacg gacgaagaaa gctaaaaagc      60
agggagattg ttaacttacg ttttttgtcct tctcttagct taaaacggtc tgataattaa    120
acttcgaatc taaacaattt aatattttac agcataatcc cagtttaact gtaatctaaa    180
caaggccaat aataaatat gcaagccat aactacagtt tggcccatta gttttttccc       240
gcgccaaatt tgccctagtt cctttcttct ttcccgctat ttccaaaatc tcccaaaagg     300
tcaagttcca gcaaaatgac acaatctttg taatcaacat tgttctccgt caagcttctc    360
cttcaaaatt cgtaagcttt ctgttctcta actctttttg gtttcagtat atgaatcaat    420
ccgactttgg aatctctact taaaaataaa aatcgatctt tttgctgccc agatagtgaa    480
taaccttaaa atcg                                                      494

<210> SEQ ID NO 89
<211> LENGTH: 297
<212> TYPE: DNA
<213> ORGANISM: Arabidopsis thaliana

<400> SEQUENCE: 89
gtatttcatt gggataaatg aagcgttgtt atggatagtt ttgagttgct aaaaagccaa      60
agatctaatc gcaagtcata tagggattac atttccttgt agctcttgaa gttttttgctc    120 cctttttttgt ttgttccttg taccattttt tcttaatacg agagataaga acttatcatt    180
ttgaggctct gaagaatcaa agaggataac agttcccaat ttttcattc tctcagtaaa     240 gcttttttgtt tcgttttccc aaatgttgaa gataagtata tgaaaggca aattatt       297

<210> SEQ ID NO 90
<211> LENGTH: 138
<212> TYPE: DNA
<213> ORGANISM: Arabidopsis thaliana
```

<400> SEQUENCE: 90

```
gtcttagtat tcatctttac actcctgcta tgttttcttt tgctaagaga attttaatct    60
ttatgtaact ggtgacgaat gcttgaaaaa tagcgtctct gttattactt ttgagaataa   120
aagatcatca ttactcac                                                 138
```

<210> SEQ ID NO 91
<211> LENGTH: 575
<212> TYPE: DNA
<213> ORGANISM: Arabidopsis thaliana

<400> SEQUENCE: 91

```
tgtatgcaaa ctccagtaat gattttgtta taatatatgg tttttaaatg ataatggc     60
atctcccttt ggattttcc gtgtgactaa aaccgcattt ataatttata cctggacaaa   120
gaacaaaaac agtgttgcca agaaacagag catagtaaga acagagaaag tttctattca  180
agtaacttgt aaaacaagct agtagattca tgttttttgca aaaccctaga aaagtcatag 240
tttcattgct tctaaacaat taacagaaaa aaacagggga cagaacatat agaaagaaaa  300
gacaagtaac aagtccaaca agaaaacgga ttcatgattt tgtaaccatg ctcaagaaaa  360
tctcagaatc tagacgtgat cgagactcca tggtccacct gctccgttaa aatctcagct  420
gacgactcag ggagtaaaga gttggccaca tcgatcacga accggtacct gacatcagat  480
ttagccaaac ggtccatcgc agagttgata tcactcatct ttatgagctc aatatccgaa  540
acgattttat gcttggcaca gaactcaagc atctc                             575
```

<210> SEQ ID NO 92
<211> LENGTH: 190
<212> TYPE: DNA
<213> ORGANISM: Arabidopsis thaliana

<400> SEQUENCE: 92

```
ttgttatttc tttgactaat gtcattaatt ttctctagaa taaaacttcg aaaattgaaa    60
tgtgatgtgc acaatcattt ctgttttctt tatttggttg ataagcaaat ttggctattt  120
atgttttttt tttaacggat gcctatatat gatactgcat tgcagtgttt ttggtctttc  180
cataaaaata                                                         190
```

<210> SEQ ID NO 93
<211> LENGTH: 267
<212> TYPE: DNA
<213> ORGANISM: Arabidopsis thaliana

<400> SEQUENCE: 93

```
gaacttttcg atagtgacgt gcatggcttg agtttgattt tctcgttttt atttatgtta    60
taattattgt gttccatcta tgaatgtaaa agatttatga aggattcgat ttttttctct   120
ttttttaaag attattataa acgtctttca taaccatctc tttattcatt atatgttcag   180
gagtgaaaaa acaaaatcta aaaaatagggg ttaaatgttt gcttagcttc tctctttatg  240
tagatttgag aaccgatgaa caagaat                                      267
```

<210> SEQ ID NO 94
<211> LENGTH: 276
<212> TYPE: DNA
<213> ORGANISM: Arabidopsis thaliana

<400> SEQUENCE: 94

```
taaatgttcc tcgctgacgt aagaagacat tagtaatggt tataatatat agctttctat    60
```

```
gaatgtatgg tgagaaaatg tctgttcact gatttttgagt ttggaataaa agcatttgcg    120
tttggtttat cattgcgttt atacaaggac agagatccac tgagctggaa tagcttaaaa    180
ccattatcag aacaaaataa accatttttt gttaagaatc agagcatagt aaacaacaga    240
aacaacctaa gagaggtaac ttgtccaaga agatag                              276
```

<210> SEQ ID NO 95
<211> LENGTH: 110
<212> TYPE: DNA
<213> ORGANISM: Arabidopsis thaliana

<400> SEQUENCE: 95

```
tagtaacttt catatcaatt aataaacgct catgtttaaa tgatcacaat ccaatgattc     60
tgcatattga gattctttaa aatcataaag agtttaaagc tgtttaggtt                110
```

<210> SEQ ID NO 96
<211> LENGTH: 135
<212> TYPE: DNA
<213> ORGANISM: Arabidopsis thaliana

<400> SEQUENCE: 96

```
tagctttccc tttatatttt aagttaaata aaagttacca gtgaactatg tttccttttt     60
atgtgtaaca ttttctgatt tatctttgtt aaattttgtt aatcacggtc taaatcgatt    120
taaaatcgtt ttggt                                                    135
```

<210> SEQ ID NO 97
<211> LENGTH: 248
<212> TYPE: DNA
<213> ORGANISM: Arabidopsis thaliana

<400> SEQUENCE: 97

```
catagtctca ttgttcttcg attcagtgtg ttttctttta tagttttcag ttttatctca     60
ctgtttgcat ttttttacgag cctgtgtaat aggcacaatc tgttatcaat catgtaactt   120
gtttaatcaa ataaccatag agttttatgt gaaaaggtcc tttactcatt tggtgttaac   180
tctttacctc ttcaggtctt taactctgtt tatataaaac atctaatgaa caatctgtgt   240
tttgaacg                                                            248
```

<210> SEQ ID NO 98
<211> LENGTH: 285
<212> TYPE: DNA
<213> ORGANISM: Arabidopsis thaliana

<400> SEQUENCE: 98

```
agagcattgt gttaatgata tgccattgtt gtgttttctt ctacagtttg agttttgcag     60
gaacttttct tttgtacata gccagccaaa cgtttgaatg tgttgtaata aggacttgat    120
cattttaata tgtgcaggtt ttgtctttct taacatgttg aatcgcttta tgattttacc    180
ggaacgaacc ggttgctatg gtttcggtat gatttgattt ctcgttatag gccttagtcg    240
gcccaataac gaagattctc tataaataaa tgaacataaa caagg                    285
```

<210> SEQ ID NO 99
<211> LENGTH: 392
<212> TYPE: DNA
<213> ORGANISM: Arabidopsis thaliana

<400> SEQUENCE: 99

-continued

```
gatctatttg taccggttat caagttttt ggatcataga aattgtatag gcttttgaca      60
ttgaaatatt ttcatagaca aaacaaagaa gcataggcaa atgtgattac actctggaac    120
aaatcttagg tttgggaaag aaattcaata acaaaacaca caaagcacaa aaagagagaa    180
tcccaattca gaaaagagg taaaggaaa tgagtgcgac gaacttacag ccttacaaaa      240
gtaataatca atcatctttt ctttaggctt cttcttcttc ttcgtcctcc tcgtactcct    300
cttcaccgac tgtagcatct tgatattgct gatactctgc aacaagatca ttcatgttac    360
tctctgcttc agtgaactcc atctcgtcca tt                                  392

<210> SEQ ID NO 100
<211> LENGTH: 297
<212> TYPE: DNA
<213> ORGANISM: Arabidopsis thaliana

<400> SEQUENCE: 100
cgaaggttta atgaaattat aaattttatg taatcattag ttgttttaaa aagtatttca     60
aactgtggag aaactcatga acattttgaa acgaaacgta actatatatt ttggtcgaat   120
ttaaaggtta aatcactctc attaaacaag tcaattattt caatgaattt caatttcatt   180
tattaattaa aaaaattctt ctaaaattaa atttaagtac taattaaact tggtaatgaa   240
taaacttaat tcatatagtg atacatctat aggaggccga catagacatt ctataaa      297

<210> SEQ ID NO 101
<211> LENGTH: 319
<212> TYPE: DNA
<213> ORGANISM: Arabidopsis thaliana

<400> SEQUENCE: 101
gcaagggaag aagctaaaga agctccattt tgtttcttga ggccctgctt agtaaggaac     60
taagaataga aatgttgaag agtgtcagag gatgaatcgg ccaagttgtg aggaagtatg   120
tttccttcca tatgtatgcc taaaattttg taagagcctt aaatgagttt tgtttctttt   180
ctttgttttc aatacaatag tggatattga gctttgtata gctcatacct agatttatac   240
tatattaaga acttcttttt gttttttgccg tttgtgttct cttcattttt atgagtcaat   300
ccattgtgtt taacttcga                                                 319

<210> SEQ ID NO 102
<211> LENGTH: 202
<212> TYPE: DNA
<213> ORGANISM: Arabidopsis thaliana

<400> SEQUENCE: 102
ccttagtaag gtttataacc tgcttatttc agtcttagtt ttgatttcag tttggttcag     60
tttgtaatgt acaagtttct ctaagcttta taatctatca gtagagtctc tctatcttgt   120
tgtggtgttt cctaagaaaa ttatagcctt tgagcgagtg attgaatata tttatatggt   180
aatgaatcac accgagtcac cg                                             202
```

US 11,981,900 B2

INCREASING GENE EDITING AND SITE-DIRECTED INTEGRATION EVENTS UTILIZING MEIOTIC AND GERMLINE PROMOTERS

CROSS-REFERENCE TO RELATED APPLICATIONS

This application claims priority to U.S. Provisional Patent Application No. 63/076,705, filed Sep. 10, 2020, which is incorporated herein by reference in its entirety.

FIELD

The present disclosure relates to compositions and methods related to expressing guided nucleases and guide nucleic acids in egg cells and embryo tissues in plants.

INCORPORATION OF SEQUENCE LISTING

A sequence listing contained in the file named "P34738US01_SL.txt" which is 175,235 bytes (measured in MS-Windows®) and created on Sep. 9, 2021, is filed electronically herewith and incorporated by reference in its entirety.

BACKGROUND

CRISPR (Clustered Regularly Interspaced Short Palindromic Repeats) nucleases (e.g., Cas12a, CasX, Cas9) are proteins guided by guide RNAs to a target nucleic acid molecule, where the nuclease can cleave one or two strands of a target nucleic acid molecule.

SUMMARY

In one aspect, this disclosure provides a plant comprising (a) a first nucleic acid sequence encoding a guided nuclease operably linked to a heterologous egg cell-preferred or embryo tissue-preferred promoter; and (b) a second nucleic acid sequence encoding at least one guide nucleic acid operably linked to a heterologous second promoter, where the at least one guide nucleic acid is capable of forming a complex with the guided nuclease and hybridizing to a target sequence within a genome of the plant and wherein the complex induces modification of the target sequence. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line. Several embodiments relate to a seed produced by the plant. In some embodiments, the seed comprises at least one mutation in a gene of interest comprising the target sequence as compared to a seed from a control plant of the same variety that lacks the first nucleic acid sequence or second nucleic acid sequence In one aspect, this disclosure provides a plant comprising (a) a first nucleic acid sequence encoding a guided nuclease operably linked to a heterologous meiotic cell-preferred promoter; and (b) a second nucleic acid sequence encoding at least one guide nucleic acid operably linked to a heterologous second promoter, where the at least one guide nucleic acid is capable of forming a complex with the guided nuclease and hybridizing to a target sequence within a genome of the plant and wherein the complex induces modification of the target sequence. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous egg cell-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one modification within the target sequence in the at least one egg cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous meiotic cell-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one modification within the target sequence in the at least one meiotic cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the meiotic cell is from a haploid inducer line.

In one aspect, this disclosure provides a method of editing a genome of a plant cell comprising: (a) crossing a first plant with a second plant, where the first plant comprises a first nucleic acid sequence encoding a guided nuclease operably linked to a heterologous embryo tissue-preferred promoter, and where the second plant comprises a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one modification within the target sequence in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a method of editing a genome of a plant cell comprising: (a) crossing a first plant with a second plant, where the first plant comprises a first nucleic acid sequence encoding a guided nuclease operably linked to a heterologous meiotic-cell preferred promoter, and where the second plant comprises a second nucleic acid sequence encoding at least one guide nucleic acid operably linked to a heterologous second promoter, where the at least one guide nucleic acid is capable of forming a complex with the guided nuclease and hybridizing to a target sequence within the genome; and (b) obtaining at least one embryo from the crossing of step (a), where the guided nuclease and the at least one guide nucleic acid form a ribonucleoprotein within the at least one meiotic cell, and where the ribonucleoprotein generates at least one modification within the target sequence in the at least one meiotic cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of editing a genome of a plant comprising: (a) introducing to a plant cell: (i) a first nucleic acid sequence encoding a guided nuclease operably linked to a heterologous embryo tissue-preferred promoter; and (ii) a second nucleic acid sequence encoding at least one guide nucleic acid operably linked to a heterologous second promoter, where the at least one guide nucleic acid is capable of forming a complex with the guided nuclease and hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one modification within the target sequence in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a method of generating a site-directed integration in a plant comprising: (a) introducing to a plant cell: (i) a first nucleic acid sequence encoding a guided nuclease operably linked to a heterologous egg cell-preferred promoter; (ii) a second nucleic acid sequence encoding one or more guide nucleic acids operably linked to a heterologous second promoter, where the one or more guide nucleic acids are (A) capable of forming a complex with the guided nuclease and hybridizing to a target sequence within a genome of the plant; and (B) capable of hybridizing to a first site and a second site flanking a nucleic acid sequence encoding a gene of interest; and (iii) a third nucleic acid sequence encoding the gene of interest; and (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO:

7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line.

In one aspect, this disclosure provides a method of generating a site-directed integration in a plant comprising: (a) introducing to a plant cell: (i) a first nucleic acid sequence encoding a guided nuclease operably linked to a heterologous embryo tissue-preferred promoter; (ii) a second nucleic acid sequence encoding one or more guide nucleic acids operably linked to a heterologous second promoter, where the one or more guide nucleic acids are (A) capable of forming a complex with the guided nuclease and hybridizing to a target sequence within a genome of the plant; and (B) capable of hybridizing to a first site and a second site flanking a nucleic acid sequence encoding a gene of interest; (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo. In some embodiments, the guided nuclease is a CRISPR effector protein. In some embodiments, the modification is a staggered cut within a double-stranded DNA molecule of the genome. In some embodiments, the modification is an insertion of a transgene. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the first plant. In some embodiments, the first plant is a hybrid inducer.

In one aspect, this disclosure provides a recombinant DNA construct comprising (a) a first nucleic acid sequence encoding a guided nuclease operably linked to a heterologous egg cell-preferred promoter, meiotic cell preferred promoter or embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first nucleic acid sequence, the second nucleic acid sequence, or both, are stably integrated into a genome of the plant. In some embodiments, the first nucleic acid sequence, the second nucleic acid sequence, or both, are stably integrated into a genome of a haploid inducer line. In some embodiments, the recombinant DNA construct is integrated into the genome of a haploid inducer line.

Several embodiments relate to a recombinant DNA construct comprising (a) a first nucleic acid sequence encoding a DNA modification enzyme operably linked to one or more one or more TALE binding sites and a minimal promoter; and (b) a second nucleic acid sequence encoding a TALE operably linked to a egg cell-preferred promoter, meiotic cell-preferred promoter or embryo tissue-preferred promoter, wherein the minimal promoter does not drive expression of the DNA modification enzyme in the absence of TALE binding to the to one or more one or more TALE binding sites. In some embodiments, the recombinant DNA construct further comprises a third nucleic acid sequence encoding a guide nucleic acid operably linked to a third promoter. In some embodiments, the DNA modification enzyme is a guided nuclease. In some embodiments, the guided nuclease is a CRISPR effector protein. In some embodiments, the first nucleic acid sequence encoding a DNA modification enzyme and the minimal promoter are operably linked 1, 2, 3, 4, 5, 6, 7, 8, 9, 10 or more TALE binding sites. In some embodiments, the CRISPR effector protein is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for expression in a plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the third promoter is a Pol III promoter. In some embodiments, the third promoter is selected from the group consisting of a tissue-preferred promoter, a tissue-specific promoter, an inducible promoter, and a constitutive promoter. In some embodiments, the third promoter is a meiotic cell-preferred, an egg cell-preferred or an embryo tissue-preferred promoter. In some embodiments, the third promoter is meiotic cell-specific, an egg cell-specific or an embryo tissue-specific promoter. In some embodiments, the third promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the third promoter comprises a nucleic acid sequence at least 90% identical to a nucleic acid sequence selected from the group consisting of SEQ ID NOs: 1-6, 21-45 and 65-88 or a functional fragment thereof. In some embodiments, the third promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the third nucleic acid sequence encoding at least one guide nucleic acid is operably linked to one or more self-cleaving ribozymes. In some embodiments, the first nucleic acid sequence, the second nucleic acid sequence, and/or the third nucleic acid sequence, are stably integrated into a genome of the plant. In some embodiments the plant is from a haploid inducer line. In some embodiments the guide nucleic acid is provided to the plant by bombardment. Several embodiments relate to a plant comprising the recombinant DNA construct. Several embodiments relate to a seed produced by a plant comprising the recombinant DNA construct. In some embodiments, the recombinant DNA construct is integrated into the genome of a haploid inducer line.

Several embodiments relate to a recombinant DNA construct comprising (a) a first nucleic acid sequence encoding at least one guide nucleic acid operably linked to one or more one or more TALE binding sites and a minimal promoter; and (b) a second nucleic acid sequence encoding a TALE operably linked to an egg cell-preferred promoter, a meiotic cell-preferred promoter or an embryo tissue-preferred promoter, wherein the minimal promoter does not drive expression of the guide nucleic acid in the absence of TALE binding to the to one or more one or more TALE binding sites. In some embodiments, the recombinant DNA construct further comprises a third nucleic acid sequence encoding a guided nuclease operably linked to a third promoter. In some embodiments, the guided nuclease is a CRISPR effector protein. In some embodiments, the first nucleic acid sequence encoding guide nucleic acid and the minimal promoter are operably linked 1, 2, 3, 4, 5, 6, 7, 8, 9, 10 or more TALE binding sites. In some embodiments, the CRISPR effector protein is selected from the group consisting of Cas9, Cas12a (e.g., LbCas12a, FnCas12a) and CasX. In some embodiments, the third nucleic acid sequence comprises a nucleic acid sequence at least 90% identical to SEQ ID NO: 7. In some embodiments, the third nucleic acid sequence is codon-optimized for expression in a plant. In some embodiments, the third nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the third promoter is selected from the group consisting of a tissue-preferred promoter, a tissue-specific promoter, an inducible promoter, and a constitutive promoter. In some embodiments, the third promoter is a meiotic cell-preferred, an egg cell-preferred or an embryo tissue-preferred promoter. In some embodiments, the third promoter is meiotic cell-specific, an egg cell-specific or an embryo tissue-specific promoter. In some embodiments, the third promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the third promoter comprises a nucleic acid sequence at least 90% identical to a nucleic acid sequence selected from the group consisting of SEQ ID NOs: 1-6, 21-45 and 65-88 or a functional fragment thereof. In some embodiments, the third promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the first nucleic acid sequence encoding the at least one guide nucleic acid is operably linked to one or more self-cleaving ribozymes. In some embodiments, the first nucleic acid sequence, the second nucleic acid sequence, and/or the third nucleic acid sequence, are stably integrated into a genome of the plant. In some embodiments the plant is from a haploid inducer line. Several embodiments relate to a plant comprising the recombinant DNA construct. Several embodiments relate to a seed produced by a plant comprising the recombinant DNA construct. In some embodiments, the recombinant DNA construct is integrated into the genome of a haploid inducer line.

Several embodiments relate to a recombinant DNA construct comprising (a) a first nucleic acid sequence encoding a guided nuclease; (b) a second nucleic acid sequence encoding a first promoter; and (c) a third nucleic acid sequence encoding DNA modification enzyme operably linked to an egg cell-preferred promoter, a meiotic cell-preferred promoter or an embryo tissue-preferred promoter, wherein the third nucleic acid is positioned between the first nucleic acid and the second nucleic acid, and wherein the third nucleic acid comprises a first target site for the DNA modification enzyme at the 5' end and a second target site for the DNA modification enzyme at the 5' end. In some embodiments, the recombinant DNA construct further comprises a fourth nucleic acid sequence encoding one or more guide nucleic acids operably linked to a third promoter. In some embodiments, the DNA modification enzyme is a recombinase. In some embodiments, the first and second target sites are Lox sites. In some embodiments, the DNA modification enzyme is an endonuclease. In some embodiments, the DNA modification enzyme is a CRISPR effector protein. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the first promoter is a meiotic cell-preferred, an egg cell-preferred or an embryo tissue-preferred promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments the third promoter is a Pol III promoter. Several embodiments relate to a plant comprising the recombinant DNA construct. Several embodiments relate to a seed produced by a plant comprising the recombinant DNA construct. In some embodiments the plant is from a haploid inducer line. In some embodiments, the recombinant DNA construct is integrated into the genome of a haploid inducer line.

In several embodiments, high levels of egg, embryo, and/or meiotic tissue specific expression of a DNA modification enzyme such as a guided nuclease (e.g., a CRISPR/Cas system), is achieved by providing to a plant cell: 1) an expression construct comprising a promoter as described in Table 1 operably linked to a sequence encoding a CRISPR effector protein, such as a dCas12a or dCas9 fused to a transcription activator; 2) an expression construct comprising one or more target sites operably linked to a minimal promoter and a sequence encoding the DNA modification enzyme; and 3) an expression construct encoding a guide RNA that hybridizes with the one or more target sites; and generating a plant therefrom. In some embodiments, 1, 2, 3, 4, 5, 6, 7, 8, 9, 10 or more target sites are operably linked to the minimal promoter. In some embodiments, the plant cell is from a haploid inducer line. In some embodiments, a female plant is generated that expresses high levels of the DNA modification enzyme in egg, embryo, and/or meiotic tissue. In some embodiments, the female plant is outcrossed and a population of R1 plants comprising unique edits are identified.

In several embodiments, high levels of egg, embryo, and/or meiotic tissue specific expression of a DNA modification enzyme such as a guided nuclease (e.g., a CRISPR/Cas system), is achieved by providing to a plant cell: 1) an expression construct comprising a promoter as described in Table 1 operably linked to a sequence encoding a TALE and 2) and an expression construct comprising one or more TALE binding sites (TB) operably linked to a minimal promoter and a sequence encoding the DNA modification enzyme and generating a plant therefrom. In some embodiments, an expression construct encoding one or more guide nucleic acids is further provided. In some embodiments, 1, 2, 3, 4, 5, 6, 7, 8, 9, 10 or more TBs are operably linked to the minimal promoter. In some embodiments, the plant cell is from a haploid inducer line. In some embodiments, a female plant is generated that expresses high levels of the DNA modification enzyme in egg, embryo, and/or meiotic tissue. In some embodiments, the female plant is outcrossed and a population of R1 plants comprising unique edits are identified.

Several embodiments relate to a method of generating two or more progeny plants with unique edits from a single transformed plant cell, the method comprising: (a) introducing to the plant cell: a first nucleic acid sequence encoding a guided nuclease operably linked to a heterologous meiosis-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one meiotic cell of the first plant, and wherein the ribonucleoprotein generates at least one modification within the target sequence in the at least one meiotic cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

Several embodiments relate to a method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous meiosis-preferred promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one meiotic cell of the first plant, and wherein the ribonucleoprotein generates at least one modification within the target sequence in the at least one meiotic cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the meiotic cell-preferred promoter is selected from the group consisting of a DMC1 promoter, a Mps1 promoter, and an Adf1 promoter. In some embodiments, the meiotic cell-preferred promoter comprises a nucleic acid sequence at least 90% identical to a nucleic acid sequence selected from the group consisting of SEQ ID NOs: 4-6 and 83-85 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous egg cell-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one egg cell of the first plant, and wherein the ribonucleoprotein generates at least modification within the target sequence in the at least one egg cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous egg cell-preferred promoter, wherein the at least one guide nucleic acid is capable of hybridizing to a target sequence within the genome; and (b) regenerating a first plant from the plant cell of step (a), wherein the guided nuclease and at least one guide nucleic acid form a ribonucleoprotein within at least one egg cell of the first plant, and wherein the ribonucleoprotein generates at least one modification within the target sequence in the at least one egg cell; (c) pollinating the first plant of step (b); (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the egg cell-preferred promoter is selected from the group consisting of an EA1 promoter and an ES4 promoter. In some embodiments, the egg cell-preferred promoter comprises a nucleic acid sequence at least 90% identical to a nucleic acid sequence selected from the group consisting of SEQ ID NOs: 2-3, 21-38, 41-45, and 65-82 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, an ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous embryonic cell-preferred promoter; and a second nucleic acid sequence encoding at least one guide nucleic acid operably linked to a heterologous second promoter, wherein the at least one guide nucleic acid is capable of hybridizing to a target sequence within the genome; and (b) regenerating a first plant from the plant cell of step (a), (c) pollinating the first plant of step (b), wherein the guided nuclease and at least one guide nucleic acid form a ribonucleoprotein within embryonic cells, and wherein the ribonucleoprotein generates at least one modification within the target sequence in the embryonic cells; (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the second promoter is a Pol III promoter. In some embodiments, the second promoter is selected from the group consisting of a tissue-preferred promoter, a tissue-specific promoter, an inducible promoter, and a constitutive promoter. In some embodiments, the second promoter is a meiotic cell-preferred, an egg cell-preferred or an embryo tissue-preferred promoter. In some embodiments, the second promoter is meiotic cell-specific, an egg cell-specific or an embryo tissue-specific promoter. In some embodiments, the second promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the second promoter comprises a nucleic acid sequence at least 90% identical to a nucleic acid sequence selected from the group consisting of SEQ ID NOs: 1-6, 21-45 and 65-88 or a functional fragment thereof. In some embodiments, the second promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is outcrossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

A method of generating two or more progeny plants with unique edits from a single transformed plant cell, the method comprising: (a) introducing to the plant cell: a first nucleic acid sequence encoding a guided nuclease operably linked to a heterologous first promoter; and a second nucleic acid sequence encoding at least one guide nucleic acid operably linked to a heterologous embryonic cell-preferred promoter, wherein the at least one guide nucleic acid is capable of hybridizing to a target sequence within the genome; and (b) regenerating a first plant from the plant cell of step (a), (c) pollinating the first plant of step (b), wherein the guided nuclease and at least one guide nucleic acid form a ribonucleoprotein within embryonic cells, and wherein the ribonucleoprotein generates at least one modification within the target sequence in the embryonic cells; (d) germinating two or more seeds produced from step (c) to produced two or more progeny plants with unique edits. In some embodiments, the modification is a staggered cut within a double-stranded DNA molecule of the genome. In some embodiments, the target sequence comprises genic DNA. In some embodiments, the target sequence comprises intergenic DNA. In some embodiments, the target sequence is within a gene of interest. In some embodiments, the gene of interest encodes a protein or a non-protein-coding RNA. In some embodiments, the gene of interest encodes a non-protein-coding RNA is selected from the group consisting of a microRNA, a small interfering RNA (siRNA), a trans-acting siRNA, or a precursor thereof. In some embodiments, the guided nuclease is a CRISPR effector protein. In some embodiments, the guided nuclease is selected from the group consisting of Cas9, Cas12a (e.g., LbCas12a, FnCas12a) and CasX. In some embodiments, the first nucleic acid sequence comprises a nucleic acid sequence at least 90% identical to SEQ ID NO: 7. In some embodiments, the first nucleic acid sequence is codon-optimized for the plant. In some embodiments, the first nucleic acid sequence encodes at least one nuclear localization signal. In some embodiments, the at least one nuclear localization signal comprises a nucleic acid sequence selected from the group consisting of SEQ ID NOs: 8 and 9. In some embodiments, the embryo tissue-preferred promoter is selected from the group consisting of a DSUL1 promoter, an EA1 promoter, an ES4 promoter, and an EAL1 promoter. In some embodiments, the embryo tissue-preferred promoter comprises a nucleic acid sequence at least 90% identical to a nucleic acid sequence selected from the group consisting of SEQ ID NOs: 1-3, 29-40, 43-45 and 86-88 or a functional fragment thereof. In some embodiments, the first promoter is selected from the group consisting of a tissue-preferred promoter, a tissue-specific promoter, an inducible promoter, and a constitutive promoter. In some embodiments, the first promoter is a meiotic cell-preferred, an egg cell-preferred or an embryo tissue-preferred promoter. In some embodiments, the first promoter is meiotic cell-specific, an egg cell-specific or an embryo tissue-specific promoter. In some embodiments, the first promoter is selected from the group consisting of a DSUL1 promoter, an EA1 promoter, a ES4 promoter, a DMC1 promoter, a Mps1 promoter, an Adf1 promoter and an EAL1 promoter. In some embodiments, the first promoter comprises a nucleic acid sequence at least 90% identical to a nucleic acid sequence selected from the group consisting of SEQ ID NOs: 1-6, 21-45 and 65-88 or a functional fragment thereof. In some embodiments, the first promoter is a constitutive promoter selected from the group consisting of a CaMV 35S promoter, an Actin promoter, a Rab15 promoter, and a Ubiquitin promoter. In some embodiments, the at least one guide nucleic acid comprises at least one guide RNA. In some embodiments, the second nucleic acid sequence encoding at least one guide nucleic acid is operably linked to one or more self-cleaving ribozymes. In some embodiments, the first plant is self-pollinated. In some embodiments the first plant is out-crossed. In some embodiments, the plant cell is from a haploid inducer line. In some embodiments, the progeny plants are haploid. In some embodiments, the method further comprises screening the haploid progeny for modifications at the target site. In some embodiments, the method further comprises inducing doubling of the genome of the haploid plants.

DETAILED DESCRIPTION

Figure 1:
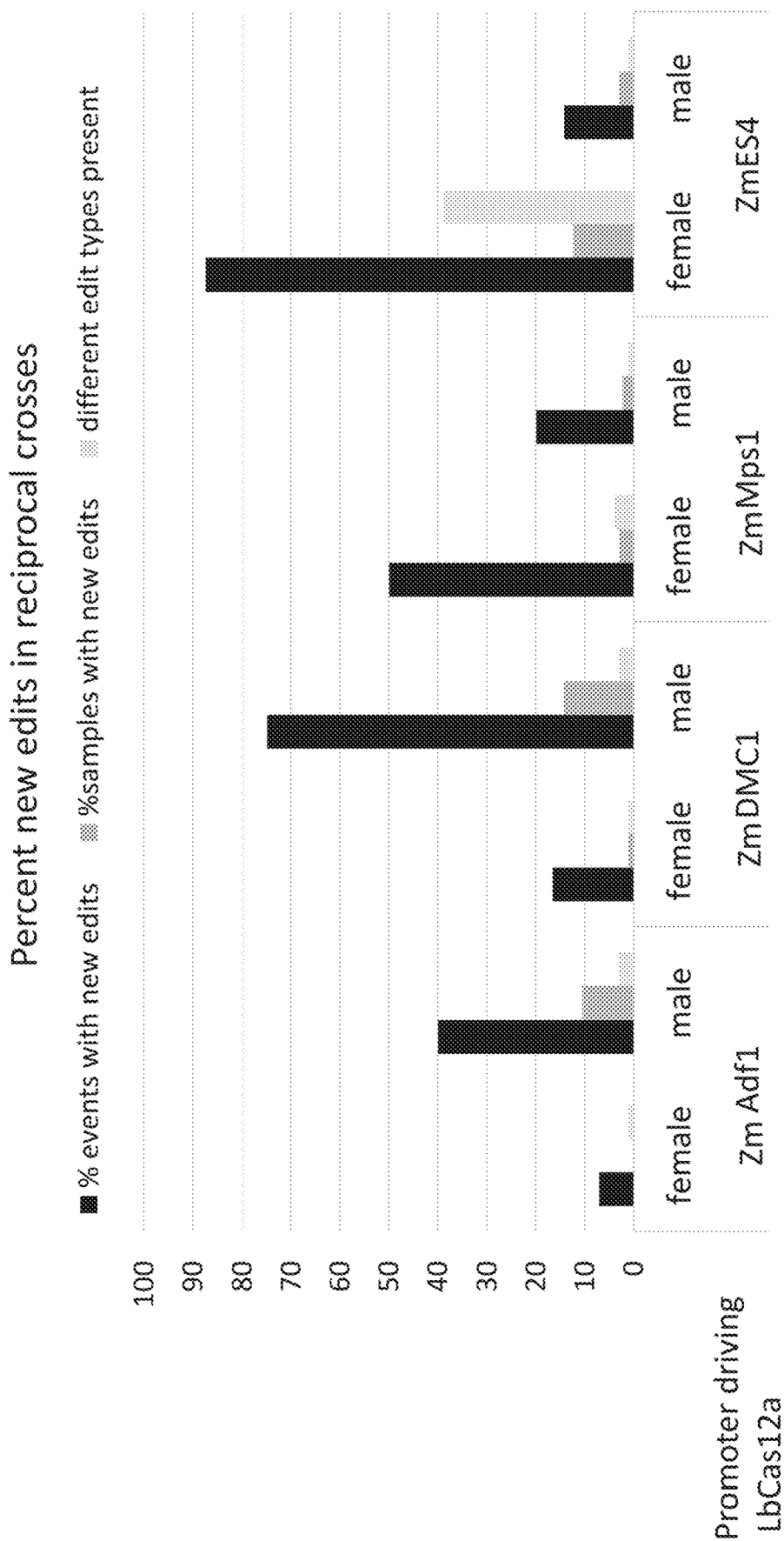
FIG. 1. Editing in reciprocal F1 plants with reproductive promoters. Transgenic R1 lines were used as either the female or male to generate reciprocal F1s. The black bars represent percent of events with an active LbCas12a when provided by the female or male parent, as indicated by new edits being present in F1 plants. The grey bars are the percent of F1 individuals containing new edits. The light grey bars are the number of unique edits found in the F1s.

Unless defined otherwise, all technical and scientific terms used have the same meaning as commonly understood by one of ordinary skill in the art to which this disclosure belongs. Where a term is provided in the singular, the inventors also contemplate aspects of the disclosure described by the plural of that term. Where there are discrepancies in terms and definitions used in references that are incorporated by reference, the terms used in this application shall have the definitions given herein. Other technical terms used have their ordinary meaning in the art in which they are used, as exemplified by various art-specific dictionaries, for example, "The American Heritage® Science Dictionary" (Editors of the American Heritage Dictionaries, 2011, Houghton Mifflin Harcourt, Boston and New York), the "McGraw-Hill Dictionary of Scientific and Technical Terms" (6th edition, 2002, McGraw-Hill, New York), or the "Oxford Dictionary of Biology" (6th edition, 2008, Oxford University Press, Oxford and New York). The inventors do not intend to be limited to a mechanism or mode of action. Reference thereto is provided for illustrative purposes only.

The practice of this disclosure includes, unless otherwise indicated, conventional techniques of biochemistry, chemistry, molecular biology, microbiology, cell biology, plant biology, genomics, biotechnology, and genetics, which are within the skill of the art. See, for example, Green and Sambrook, Molecular Cloning: A Laboratory Manual, 4th edition (2012); Current Protocols In Molecular Biology (F. M. Ausubel, et. al. eds., (1987)); Plant Breeding Methodology (N. F. Jensen, Wiley-Interscience (1988)); the series Methods In Enzymology (Academic Press, Inc.): PCR 2: A Practical Approach (M. J. MacPherson, B. D. Hames and G. R. Taylor eds. (1995)); Harlow and Lane, eds. (1988) Antibodies, A Laboratory Manual; Animal Cell Culture (R. I. Freshney, ed. (1987)); Recombinant Protein Purification: Principles And Methods, 18-1142-75, GE Healthcare Life Sciences; C. N. Stewart, A. Touraev, V. Citovsky, T. Tzfira eds. (2011) Plant Transformation Technologies (Wiley-Blackwell); and R. H. Smith (2013) Plant Tissue Culture: Techniques and Experiments (Academic Press, Inc.).

Any references cited herein, including, e.g., all patents, published patent applications, and non-patent publications, are incorporated herein by reference in their entirety.

When a grouping of alternatives is presented, any and all combinations of the members that make up that grouping of alternatives is specifically envisioned. For example, if an item is selected from a group consisting of A, B, C, and D, the inventors specifically envision each alternative individually (e.g., A alone, B alone, etc.), as well as combinations such as A, B, and D; A and C; B and C; etc.

As used herein, terms in the singular and the singular forms "a," "an," and "the," for example, include plural referents unless the content clearly dictates otherwise.

Any composition, nucleic acid molecule, polypeptide, cell, plant, etc. provided herein is specifically envisioned for use with any method provided herein.

Several embodiments described herein relate to compositions and methods for expressing a DNA modification enzyme, for example a guided nuclease, preferentially in the egg, meiotic, and/or embryonic cells of a plant. In some embodiments, compositions and methods are provided for preferential expression of components of a CRISPR/Cas editing system in egg, meiotic, and/or embryonic cells of a plant. Several embodiments relate to compositions and methods for producing offspring with unique edits from a parent comprising an expression cassette that preferentially provides a DNA modification enzyme, for example a guided nuclease, in egg, meiotic, and/or embryonic cells. In some embodiments, a female parent plant is provided that preferentially expresses a DNA modification enzyme, for example a guided nuclease, preferentially in egg, meiotic, and/or embryonic cells. In some embodiments, a male parent plant is provided that preferentially expresses a DNA modification enzyme, for example a guided nuclease, preferentially in egg, meiotic, and/or embryonic cells. In some embodiments, a population of seeds wherein 2 or more of the seeds comprise unique edits is provided wherein the population of seeds is produced from a parent expressing a DNA modification enzyme, for example a guided nuclease, preferentially in egg, meiotic, and/or embryonic cells. Non-limiting examples of expression elements useful in the composition and methods described herein are provided in Table 1.

As used herein, an "egg cell" refers to a haploid egg cell produced by the female gametophyte of a plant. Upon fertilization by a haploid pollen cell, a diploid zygote is formed, which gives rise to an embryo. As used herein, "embryo tissue" refers to diploid tissue comprising precursor tissues for leaf, stem, and root tissue, as well as one or more cotyledons. Embryo tissue is eventually incorporated into a seed. Once the embryo begins to germinate, a seedling or plantlet is generated. As used herein, meiosis refers to a process of cell division in sexually-reproducing organisms that produces gametes. Meiosis involves two rounds of cell division that ultimately result in four haploid cells. A meiotic cell refers to a cell undergoing meiosis.

In an aspect, this disclosure provides a recombinant DNA construct comprising a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within a genome of a plant cell.

In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an embryo tissue-preferred promoter, where the at least one guide nucleic acid is capable of hybridizing to a target sequence within a genome of a plant. In an aspect, this disclosure provides a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an meiotic-preferred promoter, where the at least one guide nucleic acid is capable of hybridizing to a target sequence within a genome of a plant cell.

In an aspect, this disclosure provides a plant comprising a recombinant DNA construct comprising a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous embryo tissue-preferred promoter; and (b) a second nucleic acid sequence encoding at least one guide nucleic acid operably linked to a heterologous second promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within a genome of the plant.

In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an embryo tissue-preferred promoter, where the at least one guide nucleic acid is capable of hybridizing to a target sequence within a genome of the plant. In an aspect, this disclosure provides a plant comprising a recombinant DNA construct comprising a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an meiosis-preferred promoter, where the at least one guide nucleic acid is capable of hybridizing to a target sequence within a genome of the plant.

In an aspect, this disclosure provides a seed of any plant provided herein.

Nucleic Acids and Amino Acids

The use of the term "polynucleotide" or "nucleic acid molecule" is not intended to limit the present disclosure to polynucleotides comprising deoxyribonucleic acid (DNA). For example, ribonucleic acid (RNA) molecules are also envisioned. Those of ordinary skill in the art will recognize that polynucleotides and nucleic acid molecules can comprise deoxyribonucleotides, ribonucleotides, or combinations of ribonucleotides and deoxyribonucleotides. Such deoxyribonucleotides and ribonucleotides include both naturally occurring molecules and synthetic analogues. The polynucleotides of the present disclosure also encompass all forms of sequences including, but not limited to, single-stranded forms, double-stranded forms, hairpins, stem-and-loop structures, and the like. In an aspect, a nucleic acid molecule provided herein is a DNA molecule. In another aspect, a nucleic acid molecule provided herein is an RNA molecule. In an aspect, a nucleic acid molecule provided herein is single-stranded. In another aspect, a nucleic acid molecule provided herein is double-stranded.

As used herein, the term "recombinant" in reference to a nucleic acid (DNA or RNA) molecule, protein, construct, vector, etc., refers to a nucleic acid or amino acid molecule or sequence that is man-made and not normally found in nature, and/or is present in a context in which it is not normally found in nature, including a nucleic acid molecule (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other.

In one aspect, methods and compositions provided herein comprise a vector. As used herein, the term "vector" refers to a DNA molecule used as a vehicle to carry exogenous genetic material into a cell.

In an aspect, one or more polynucleotide sequences from a vector are stably integrated into a genome of a plant. In an aspect, one or more polynucleotide sequences from a vector are stably integrated into a genome of a plant cell.

In an aspect, a first nucleic acid sequence and a second nucleic acid sequence are provided in a single vector. In another aspect, a first nucleic acid sequence is provided in a first vector, and a second nucleic acid sequence is provided in a second vector.

As used herein, the term "polypeptide" refers to a chain of at least two covalently linked amino acids. Polypeptides can be encoded by polynucleotides provided herein. An example of a polypeptide is a protein. Proteins provided herein can be encoded by nucleic acid molecules provided herein.

Nucleic acids can be isolated using techniques routine in the art. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

Without being limiting, nucleic acids can be detected using hybridization. Hybridization between nucleic acids is discussed in detail in Sambrook et. al. (1989, Molecular Cloning: A Laboratory Manual, 2nd Ed., Cold Spring Harbor Laboratory Press, Cold Spring Harbor, N.Y.).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

The terms "percent sequence complementarity" or "percent complementarity" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

For optimal alignment of sequences to calculate their percent identity, various pair-wise or multiple sequence alignment algorithms and programs are known in the art, such as ClustalW or Basic Local Alignment Search Tool (BLAST®), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et. al., "Multiple sequence alignment with the Clustal series of programs," *Nucleic Acids Research* 31: 3497-3500 (2003); Thompson J D et. al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et. al., "Clustal W and Clustal X version 2.0," *Bioinformatics* 23: 2947-48 (2007); and Altschul, S. F., Gish, W., Miller, W., Myers, E. W. & Lipman, D. J. (1990) "Basic local alignment search tool." *J. Mol. Biol.* 215:403-410 (1990), the entire contents and disclosures of which are incorporated herein by reference.

As used herein, a first nucleic acid molecule can "hybridize" a second nucleic acid molecule via non-covalent interactions (e.g., Watson-Crick base-pairing) in a sequence-specific, antiparallel manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymine (T), adenine (A) pairing with uracil (U), and guanine (G) pairing with cytosine (C). In addition, it is also known in the art that for hybridization between two RNA molecules (e.g., dsRNA), guanine base pairs with uracil. For example, G/U base-pairing is partially responsible for the degeneracy (i.e., redundancy) of the genetic code in the context of tRNA anti-codon base-pairing with codons in mRNA. In the context of this disclosure, a guanine of a protein-binding segment (dsRNA duplex) of a subject DNA-targeting RNA molecule is considered complementary to an uracil, and vice versa. As such, when a G/U base-pair can be made at a given nucleotide position a protein-binding segment (dsRNA duplex) of a subject DNA-targeting RNA molecule, the position is not considered to be non-complementary, but is instead considered to be complementary.

Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer nucleotides) the position of mismatches becomes important (see Sambrook et. al.). Typically, the length for a hybridizable nucleic acid is at least 10 nucleotides. Illustrative minimum lengths for a hybridizable nucleic acid are: at least 15 nucleotides; at least 18 nucleotides; at least 20 nucleotides; at least 22 nucleotides; at least 25 nucleotides; and at least 30 nucleotides). Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST® programs (basic local alignment search tools) and PowerBLAST programs known in the art (see Altschul et. al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Generating Edits

Several embodiments described herein relate to compositions and methods for producing heritable edits in the genome of a progeny plant by expressing a DNA modification enzyme, for example a guided nuclease, preferentially in egg, meiotic, and/or embryonic cells of a parent plant. In some embodiments, the parent plant expressing the DNA modification enzyme is female. In some embodiments, the parent plant expressing the DNA modification enzyme is male.

As used herein, the term "genome editing" or "editing" refers to any modification of a nucleotide sequence in a site-specific manner. In the present disclosure genome editing techniques include the use of DNA modification enzymes, such as endonucleases, recombinases, transposases, deaminases, methylases, helicases and any combination thereof. In an aspect, a "modification" comprises the hydrolytic deamination of cytidine or deoxycytidine to uridine or deoxyuridine, respectively. In some embodiments, a sequence-specific editing system comprises an adenine deaminase. In an aspect, a "modification" comprises the hydrolytic deamination of adenine or adenosine. In an aspect, a "modification" comprises the hydrolytic deamination of adenosine or deoxyadenosine to inosine or deoxyinosine, respectively. In an aspect, a "modification" comprises the insertion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the insertion of one or more transgenes. In another aspect, a "modification" comprises the deletion of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In a further aspect, a "modification" comprises the inversion of at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the substitution of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In still another aspect, a "modification" comprises the duplication of at least 1, at least 2, at least 3, at least 4, at least 5, at least 6, at least 7, at least 8, at least 9, at least 10, at least 15, at least 25, at least 50, at least 100, at least 200, at least 300, at least 400, at least 500, at least 750, at least 1000, at least 1500, at least 2000, at least 3000, at least 4000, at least 5000, or at least 10,000 nucleotides. In some embodiments, a "modification" comprises the substitution of an "A" for a "C", "G" or "T" in a nucleic acid sequence. In some embodiments, a "modification" comprises the substitution of an "C" for a "A", "G" or "T" in a nucleic acid sequence. In some embodiments, a "modification" comprises the substitution of an "G" for a "A", "C" or "T" in a nucleic acid sequence. In some embodiments, a "modification" comprises the substitution of an "T" for a "A", "C" or "G" in a nucleic acid sequence. In some embodiments, a "modification" comprises the substitution of an "C" for a "U" in a nucleic acid sequence. In some embodiments, a "modification" comprises the substitution of an "G" for a "A" in a nucleic acid sequence. In some embodiments, a "modification" comprises the substitution of an "A" for a "G" in a nucleic acid sequence. In some embodiments, a "modification" comprises the substitution of an "T" for a "C" in a nucleic acid sequence.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous meiosis-preferred promoter; and (b) a second nucleic acid sequence encoding at least one guide nucleic acid operably linked to a heterologous second promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one double-stranded break within the target sequence in the at least one meiotic cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to a heterologous meiosis-preferred promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one meiotic cell of the plant, and where the ribonucleoprotein generates at least one double-stranded break within the target sequence in the at least one meiotic cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous egg cell-preferred promoter; and (b) a second nucleic acid sequence encoding at least one guide nucleic acid operably linked to a heterologous second promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one double-stranded break within the target sequence in the at least one egg cell.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (b) a second nucleic acid sequence encoding at least one guide nucleic acid operably linked to an egg cell-preferred promoter, where the at least one guide nucleic acid is capable of hybridizing to a target sequence within the genome; and (b) regenerating at least one plant from the plant cell of step (a), where the guided nuclease and at least one guide nucleic acid form a ribonucleoprotein within at least one egg cell of the plant, and where the ribonucleoprotein generates at least one double-stranded break within the target sequence in the at least one egg cell.

In an aspect, this disclosure provides a method of editing a genome of a plant cell comprising: (a) crossing a first plant with a second plant, where the first plant comprises a first nucleic acid sequence encoding a guided nuclease capable of generating a staggered cut in a double-stranded DNA molecule operably linked to a heterologous embryo tissue-preferred promoter, and where the second plant comprises a second nucleic acid sequence encoding at least one guide nucleic acid operably linked to a heterologous second promoter, wherein the at least one guide nucleic acid is capable of hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one double-stranded break within the target sequence in the at least one embryo.

In an aspect, this disclosure provides a method of editing a genome of a plant cell comprising: (a) crossing a first plant with a second plant, where the first plant comprises a first nucleic acid sequence encoding a guided nuclease capable of generating a staggered cut in a double-stranded DNA molecule operably linked to a heterologous promoter, and where the second plant comprises a second nucleic acid sequence encoding at least one guide nucleic acid operably linked to an embryo tissue-preferred promoter, wherein the at least one guide nucleic acid is capable of hybridizing to a target sequence within the genome; and (b) obtaining at least one embryo from the crossing of step (a), where the guided nuclease and the at least one guide nucleic acid form a ribonucleoprotein within the at least one embryo, and where the ribonucleoprotein generates at least one double-stranded break within the target sequence in the at least one embryo.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous embryo tissue-preferred promoter; and (ii) a second nucleic acid sequence encoding at least one guide nucleic acid operably linked to a heterologous second promoter, where the at least one guide nucleic acid is capable of hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one double-stranded break within the target sequence in the at least one embryo.

In an aspect, this disclosure provides a method of editing a genome of a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding at least one guide nucleic acid operably linked to an embryo tissue-preferred promoter, where the at least one guide nucleic acid is capable of hybridizing to a target sequence within the genome; (b) regenerating at least one plant from the plant cell of step (a); and (c) fertilizing the at least one plant to create at least one embryo, where the guided nuclease and at least one guide nucleic acid form a ribonucleoprotein within the at least one embryo from step (c), and where the ribonucleoprotein generates at least one double-stranded break within the target sequence in the at least one embryo.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous meiosis-preferred promoter; and (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one meiotic cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding one or more guide nucleic acids operably linked to a meiosis-preferred second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one meiotic cell of the plant, where the ribonucleoprotein generates a double-stranded break within the target sequence, the first site, and the second site, and where the gene of interest is integrated into the target site in the at least one meiotic cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous egg cell-preferred promoter; and (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; and (ii) a second nucleic acid sequence encoding one or more guide nucleic acids operably linked to an egg cell-preferred second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); where the guided nuclease and at least one guide RNA form a ribonucleoprotein within at least one egg cell of the plant, where the ribonucleoprotein generates a double-stranded break within the target sequence, the first site, and the second site, and where the gene of interest is integrated into the target site in the at least one egg cell.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous embryo tissue-preferred promoter; (ii) a second nucleic acid sequence encoding one or more guide nucleic acids operably linked to a heterologous second promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo.

In an aspect, this disclosure provides a method of generating a site-directed integration in a plant comprising: (a) introducing to a plant cell: (i) a first nucleic acid sequence encoding a guided nuclease capable of generating a staggered cut in a double-stranded DNA molecule operably linked to a heterologous promoter; (ii) a second nucleic acid sequence encoding one or more guide nucleic acids operably linked to an embryo tissue-preferred promoter, wherein the one or more guide nucleic acids are (A) capable of hybridizing to a target sequence within a genome of the plant; and (B) capable of hybridizing to a first site and a second site flanking a nucleic acid sequence encoding a gene of interest; and (iii) a third nucleic acid sequence encoding the gene of interest; (b) regenerating at least one plant from the plant cell of step (a); and (c) fertilizing the at least one plant from step (b) to create at least one embryo; where the guided nuclease and at least one guide RNA form a ribonucleoprotein within at least one embryo, where the ribonucleoprotein generates a double-stranded break within the target sequence, the first site, and the second site, and where the gene of interest is integrated into the target site in the at least one embryo.

Regulatory Elements

Regulatory elements such as promoters, leaders (also known as 5' UTRs), enhancers, introns, and transcription termination regions (or 3' UTRs) play an integral part in the overall expression of genes in living cells. The term "regulatory element," as used herein, refers to a DNA molecule having gene-regulatory activity. The term "gene-regulatory activity," as used herein, refers to the ability to affect the expression of an operably linked transcribable DNA molecule, for instance by affecting the transcription and/or translation of the operably linked transcribable DNA molecule. Regulatory elements, such as promoters, leaders, enhancers, introns and 3' UTRs that function in plants are useful for modifying plant phenotypes through genetic engineering. Regulatory elements may be characterized by their gene expression pattern, e.g., positive and/or negative effects such as constitutive expression or temporal, spatial, developmental, tissue, environmental, physiological, pathological, cell cycle, and/or chemically responsive expression, and any combination thereof, as well as by quantitative or qualitative indications. As used herein, a "gene expression pattern" is any pattern of transcription of an operably linked DNA molecule into a transcribed RNA molecule. The transcribed RNA molecule may be translated to produce a protein molecule or may provide an antisense or other regulatory RNA molecule, such as a double-stranded RNA (dsRNA), a transfer RNA (tRNA), a ribosomal RNA (rRNA), a microRNA (miRNA), a small interfering RNA (siRNA), and the like. As used herein, the term "protein expression" is any pattern of translation of a transcribed RNA molecule into a protein molecule. Protein expression may be characterized by its temporal, spatial, developmental, or morphological qualities, as well as by quantitative or qualitative indications.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter may be initially isolated from the 5' untranslated region (5' UTR) of a genomic copy of a gene. A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, cell cycle-specific, inducible, etc.

In some embodiments, a promoter is operably linked 5' to a leader sequence. As used herein, the term "leader" refers to a DNA molecule isolated from the untranslated 5' region (5' UTR) a gene and defined generally as a nucleotide segment between the transcription start site (TSS) and the protein coding sequence start site. Alternately, leaders may be synthetically produced or manipulated DNA elements. A leader can be used as a 5' regulatory element for modulating expression of an operably linked transcribable DNA molecule. Leader molecules may be used with a heterologous promoter or with their native promoter.

As used herein, "operably linked" refers to a functional linkage between two or more elements. For example, an operable linkage between a polynucleotide of interest and a regulatory sequence (e.g., a promoter) is a functional link that allows for expression of the polynucleotide of interest. Operably linked elements may be contiguous or non-contiguous.

Promoters that express within a specific tissue(s) of an organism, with no expression in other tissues, are referred to as "tissue-specific" promoters. Promoters that drive enhanced expression in certain tissues of an organism relative to other tissues of the organism are referred to as "tissue-preferred" promoters. Thus, a "tissue-preferred" promoter causes relatively higher or preferential expression in a specific tissue(s) of a plant, but with lower levels of expression in other tissue(s) of the plant. In another aspect, a promoter provided herein is a tissue-specific promoter. In a further aspect, a promoter provided herein is a tissue-preferred promoter. In an aspect, a tissue-preferred promoter comprises a tissue-specific promoter.

Promoters that express within a meiotic cell(s) of an organism, with no expression in non-meiotic cells, are referred to as "meiotic cell-specific" or "meiosis-specific" promoters. Promoters that drive enhanced expression in meiotic cells of an organism relative to other cells of the organism are referred to as "meiotic cell-preferred" or "meiosis-preferred" promoters. Thus, a "meiotic cell-preferred" or "meiosis-preferred" promoter causes relatively higher or preferential expression in cells of a plant undergoing meiosis, but with lower levels of expression in other cell(s) of the plant. In another aspect, a promoter provided herein is a meiosis-specific promoter. In a further aspect, a promoter provided herein is a meiosis-preferred promoter. In an aspect, a meiosis-preferred promoter comprises a meiosis-specific promoter. Promoters that express in a cell cycle dependent manner, are referred to as "cell cycle-specific" promoters. In another aspect, a promoter provided herein is a cell cycle-specific promoter. In a further aspect, a promoter provided herein is a cell cycle-preferred promoter. In an aspect, a cell cycle-preferred promoter comprises a cell cycle-specific promoter.

Determination of promoter activity can be performed using any method standard in the art. For example, without being limiting, a promoter of interest can be used to drive expression of a fluorophore or other reporting molecule, and the concentration of the expressed molecule can be used to determine promoter activity in different cell or tissue types.

Several embodiments described herein relate to expression of a DNA modification enzyme, for example a guided nuclease, preferentially in egg, meiotic, and/or embryonic cells of a plant. Nonlimiting examples of expression elements useful in the composition and methods described herein are provided in Table 1.

TABLE 1

Plant Egg, Embryo, and Meiotic Cell Promoters

| Source | Gene name/ID | Expected Expression | Promoter and leader SEQ ID NO: | 3'UTR SEQ ID NO: |
|---|---|---|---|---|
| Corn | ZmDSUL 1 | Embryo | 1 | — |
| Corn | ZmEA1 | Egg/Embryo | 2 | — |
| Corn | ZmES4 | Egg/Embryo | 3 | — |
| Corn | ZmDMC1 | Meiocyte | 4 | — |
| Corn | ZmMps1 | Meiocyte | 5 | — |
| Corn | ZmAdf1 | Meiocyte | 6 | — |
| Corn | GRMZM2G141762 | Ovary (including Egg) | 21 | — |
| Corn | A1ZM025370 | Egg | 22 | — |
| Corn | GRMZM2G119150 | Ovary (including Egg) | 23 | — |
| Corn | Zm.AC185611 | Egg and zygote | 24 | 46 |
| Corn | GRMZM2G025133 | Zygote and egg | 25 | 47 |
| Corn | GRMZM2G103251 | Zygote | 26 | 48 |
| Corn | P-Zm.EAL1:1 GRMZM2G456746 | Egg | 27 | — |
| Corn | P-ZmES2/3 GRMZM2G128301 | Egg and zygote | 28 | — |
| Corn | GRMZM2G466856 | Egg and Embryo | 29 | 49 |
| Corn | GRMZM2G075386 | Egg and Embryo | 30 | 50 |
| Corn | GRMZM2G466848 | Egg and Embryo | 31 | 51 |
| Corn | GRMZM2G047842 | Egg and Embryo | 32 | 52 |
| Corn | GRMZM2G025720 | Egg and Embryo | 33 | 53 |
| Corn | GRMZM2G083190 | Egg and Embryo | 34 | 54 |
| Corn | GRMZM2G536120 | Egg and Embryo | 35 | 55 |
| Corn | GRMZM2G125162 | Egg and Embryo | 36 | 56 |
| Corn | AC211413.4_FG001 | Egg and Embryo | 37 | 57 |
| Corn | GRMZM2G457612 | Egg and Embryo | 38 | — |
| Corn | GRMZM2G328205 | Embryo | 39 | 58 |
| Corn | GRMZM2G337139 | Embryo | 40 | 59 |
| Corn | AC215302.3 FG001 | Egg specific | 41 | 60 |
| Corn | GRMZM2G417287 | Egg specific | 42 | 61 |
| Corn | GRMZM2G103251 | Egg and Embryo | 43 | 62 |
| Corn | GRMZM2G035685 | Egg and Embryo | 44 | 63 |
| Corn | GRMZM2G150827 | Egg and Embryo | 45 | 64 |
| Soy | Glyma.05G128300 | Ovule | 65 | 70 |
| Soy | Glyma.03G037900 | Ovule | 66 | 71 |
| Soy | Glyma.04G248800 | Ovule | 67 | 72 |
| Soy | Glyma.04G090700 | Ovule | 68 | 73 |
| Soy | Glyma.07G050200 | Ovule | 69 | 74 |
| Arabidopsis | Yao AT4G05410 | Egg | 75 | 89 |
| Arabidopsis | EC1.1 AT1G76750 | Egg | 76 | 90 |
| Arabidopsis | DD45 AT2G21740 | Egg | 77 | 91 |
| Arabidopsis | DD33 AT2G20070 | Egg | 78 | 92 |
| Arabidopsis | AtP5p AT1G71470 | Egg | 79 | 93 |
| Arabidopsis | EC1.3 AT2G21750 | Egg | 80 | 94 |
| Arabidopsis | EC1.4 AT4G39340 | Egg | 81 | 95 |
| Arabidopsis | EC1.5 AT5G64720 | Egg | 82 | 96 |
| Arabidopsis | CDC45 AT3G25100 | Meiotic | 83 | 97 |
| Arabidopsis | MGE1p AT4G40020 | Meiotic | 84 | 98 |
| Arabidopsis | MGE2p AT4G20900 | Meiotic | 85 | 99 |
| Arabidopsis | WOX2 AT5G59340 | Early embryo | 86 | 100 |
| Arabidopsis | F17L21.26 AT1G27470 | Early embryo | 87 | 101 |
| Arabidopsis | POLA3 AT5G41880 | Early embryo | 88 (Promoter + 5'UTR intron + leader) | 102 |

In one embodiment, fragments of a promoter sequence disclosed in Table 1 are provided. Promoter fragments may comprise egg, embryo, and/or meiotic expression activity, as described above, and may be useful alone or in combination with other promoters and promoter fragments, such as in constructing chimeric promoters, or in combination with other expression elements and expression element fragments. In some embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, or at least about 1000 contiguous nucleotides, or longer, of a DNA molecule having promoter activity as disclosed herein. In some embodiments, fragments of a promoter are provided comprising at least about 50, at least about 75, at least about 95, at least about 100, at least about 125, at least about 150, at least about 175, at least about 200, at least about 225, at least about 250, at least about 275, at least about 300, at least about 500, at least about 600, at least about 700, at least about 750, at least about 800, at least about 900, at least about 1000, at least about 1050, at least about 1100, or at least about 1150 contiguous nucleotides, of a DNA sequence comprising a TATA box and having at least about 85 percent identity, at least about 86 percent identity, at least about 87 percent identity, at least about 88 percent identity, at least about 89 percent identity, at least about 90 percent identity, at least about 91 percent identity, at least about 92 percent identity, at least about 93 percent identity, at least about 94 percent identity, at least about 95 percent identity, at least about 96 percent identity, at least about 97 percent identity, at least about 98 percent identity, at least about 99 percent identity, or at least about 100 percent identity to SEQ ID NO. 1-6, 21-45, 65-69 or 75-88, having promoter activity as disclosed herein. Methods for producing such fragments from a starting promoter molecule are well known in the art.

In an aspect, a meiosis cell-preferred or meiosis-preferred promoter comprises a DMC1 promoter. In an aspect, a meiotic cell-preferred or meiosis-preferred promoter comprises an Mps1 promoter. In an aspect, a meiotic cell-preferred or meiosis-preferred promoter comprises an Adf1 promoter. In an aspect, a meiotic cell-preferred or meiosis-preferred promoter comprises a promoter selected from the group consisting of a DMC1 promoter, a Mps1 promoter, and an Adf1 promoter.

In an aspect, an expression element described in Table 1 is operably linked to a nucleic acid encoding a DNA modification enzyme, such as a guided nuclease. In an aspect, an expression element described in Table 1 is operably linked to a nucleic acid encoding a Cas9 nuclease. In an aspect, an expression element described in Table 1 is operably linked to a nucleic acid encoding a Cas12a nuclease. In an aspect, an expression element described in Table 1 is operably linked to a nucleic acid encoding a CasX nuclease. In an aspect, an expression element described in Table 1 is operably linked to a nucleic acid encoding a guide nucleic acid. In an aspect, an expression element described in Table 1 is operably linked to a nucleic acid encoding a guide RNA. In an aspect, an expression element described in Table 1 is operably linked to a nucleic acid encoding a single-guide RNA. In some embodiments, the guide RNA acid is flanked by self-cleaving ribozymes. In an aspect, an expression element described in Table 1 is operably linked to a nucleic acid encoding a recombinase (e.g., Cre recombinase). In an aspect, an expression element described in Table 1 is operably linked to a nucleic acid encoding a TALE.

In an aspect, a DMC1 promoter is operably linked to a nucleic acid encoding a guided nuclease. In an aspect, a DMC1 promoter is operably linked to a nucleic acid encoding a Cas9 nuclease. In an aspect, a DMC1 promoter is operably linked to a nucleic acid encoding a Cas12a nuclease. In an aspect, a DMC1 promoter is operably linked to a nucleic acid encoding a CasX nuclease. In an aspect, a DMC1 promoter is operably linked to a nucleic acid encoding a guide nucleic acid. In an aspect, a DMC1 promoter is operably linked to a nucleic acid encoding a guide RNA. In an aspect, a DMC1 promoter is operably linked to a nucleic acid encoding a single-guide RNA. In some embodiments, the guide RNA acid is flanked by self-cleaving ribozymes. In an aspect, a DMC1 promoter is operably linked to a nucleic acid encoding a recombinase (e.g., Cre recombinase). In an aspect, a DMC1 promoter is operably linked to a nucleic acid encoding a TALE.

In an aspect, a Mps1 promoter is operably linked to a nucleic acid encoding a guided nuclease. In an aspect, a Mps1 promoter is operably linked to a nucleic acid encoding a Cas9 nuclease. In an aspect, a Mps1 promoter is operably linked to a nucleic acid encoding a Cas12a nuclease. In an aspect, a Mps1 promoter is operably linked to a nucleic acid encoding a CasX nuclease. In an aspect, a Mps1 promoter is operably linked to a nucleic acid encoding a guide nucleic acid. In an aspect, a Mps1 promoter is operably linked to a nucleic acid encoding a guide RNA. In an aspect, a Mps1 promoter is operably linked to a nucleic acid encoding a single-guide RNA. In some embodiments, the guide RNA acid is flanked by self-cleaving ribozymes. In an aspect, a Mps1 promoter is operably linked to a nucleic acid encoding a recombinase (e.g., Cre recombinase). In an aspect, a Mps1 promoter is operably linked to a nucleic acid encoding a TALE.

In an aspect, an Adf1 promoter is operably linked to a nucleic acid encoding a guided nuclease. In an aspect, an Adf1 promoter is operably linked to a nucleic acid encoding a Cas9 nuclease. In an aspect, an Adf1 promoter is operably linked to a nucleic acid encoding a Cas12a nuclease. In an aspect, an Adf1 promoter is operably linked to a nucleic acid encoding a CasX nuclease. In an aspect, an Adf1 promoter is operably linked to a nucleic acid encoding a guide nucleic acid. In an aspect, an Adf1 promoter is operably linked to a nucleic acid encoding a guide RNA. In an aspect, an Adf1 promoter is operably linked to a nucleic acid encoding a single-guide RNA. In some embodiments, the guide RNA acid is flanked by self-cleaving ribozymes. In an aspect, an Adf1 promoter is operably linked to a nucleic acid encoding a recombinase (e.g., Cre recombinase). In an aspect, an Adf1 promoter is operably linked to a nucleic acid encoding a TALE.

In an aspect, a DMC1 promoter comprises a nucleic acid sequence at least 80% identical to SEQ ID NO: 4, or a functional fragment thereof. In an aspect, a DMC1 promoter comprises a nucleic acid sequence at least 85% identical to SEQ ID NO: 4, or a functional fragment thereof. In an aspect, a DMC1 promoter comprises a nucleic acid sequence at least 90% identical to SEQ ID NO: 4, or a functional fragment thereof. In an aspect, a DMC1 promoter comprises a nucleic acid sequence at least 95% identical to SEQ ID NO: 4, or a functional fragment thereof. In an aspect, a DMC1 promoter comprises a nucleic acid sequence at least 96% identical to SEQ ID NO: 4, or a functional fragment thereof. In an aspect, a DMC1 promoter comprises a nucleic acid sequence at least 97% identical to SEQ ID NO: 4, or a functional fragment thereof. In an aspect, a DMC1 promoter comprises a nucleic acid sequence at least 98% identical to SEQ ID NO: 4, or a functional fragment thereof. In an aspect, a DMC1 promoter comprises a nucleic acid sequence at least 99% identical to SEQ ID NO: 4, or a functional fragment thereof. In an aspect, a DMC1 promoter comprises a nucleic acid sequence 100% identical to SEQ ID NO: 4, or a functional fragment thereof.

In an aspect, a Mps1 promoter comprises a nucleic acid sequence at least 80% identical to SEQ ID NO: 5, or a functional fragment thereof. In an aspect, a Mps1 promoter comprises a nucleic acid sequence at least 85% identical to SEQ ID NO: 5, or a functional fragment thereof. In an aspect, a Mps1 promoter comprises a nucleic acid sequence at least 90% identical to SEQ ID NO: 5, or a functional fragment thereof. In an aspect, a Mps1 promoter comprises a nucleic acid sequence at least 95% identical to SEQ ID NO: 5, or a functional fragment thereof. In an aspect, a Mps1 promoter comprises a nucleic acid sequence at least 96% identical to SEQ ID NO: 5, or a functional fragment thereof. In an aspect, a Mps1 promoter comprises a nucleic acid sequence at least 97% identical to SEQ ID NO: 5, or a functional fragment thereof. In an aspect, a Mps1 promoter comprises a nucleic acid sequence at least 98% identical to SEQ ID NO: 5, or a functional fragment thereof. In an aspect, a Mps1 promoter comprises a nucleic acid sequence at least 99% identical to SEQ ID NO:5, or a functional fragment thereof. In an aspect, a Mps1 promoter comprises a nucleic acid sequence 100% identical to SEQ ID NO: 5, or a functional fragment thereof.

In an aspect, an Adf1 promoter comprises a nucleic acid sequence at least 80% identical to SEQ ID NO: 6, or a functional fragment thereof. In an aspect, an Adf1 promoter comprises a nucleic acid sequence at least 85% identical to SEQ ID NO: 6, or a functional fragment thereof. In an aspect, an Adf1 promoter comprises a nucleic acid sequence at least 90% identical to SEQ ID NO: 6, or a functional fragment thereof. In an aspect, an Adf1 promoter comprises a nucleic acid sequence at least 95% identical to SEQ ID NO: 6, or a functional fragment thereof. In an aspect, an Adf1 promoter comprises a nucleic acid sequence at least 96% identical to SEQ ID NO: 6, or a functional fragment thereof. In an aspect, an Adf1 promoter comprises a nucleic acid sequence at least 97% identical to SEQ ID NO: 6, or a functional fragment thereof. In an aspect, an Adf1 promoter comprises a nucleic acid sequence at least 98% identical to SEQ ID NO: 6, or a functional fragment thereof. In an aspect, an Adf1 promoter comprises a nucleic acid sequence at least 99% identical to SEQ ID NO: 6, or a functional fragment thereof. In an aspect, an Adf1 promoter comprises a nucleic acid sequence 100% identical to SEQ ID NO: 6, or a functional fragment thereof.

In an aspect, a meiocyte-preferred promoter comprises a nucleic acid sequence at least 80% identical to a nucleic acid sequence selected from the group consisting of SEQ ID NOs: 4-6, 83-85 or a functional fragment thereof. In an aspect, a meiocyte-preferred promoter comprises a nucleic acid sequence at least 85% identical to a nucleic acid sequence selected from the group consisting of SEQ ID NOs: 4-6, 83-85 or a functional fragment thereof. In an aspect, a meiocyte-preferred promoter comprises a nucleic acid sequence at least 90% identical to a nucleic acid sequence selected from the group consisting of SEQ ID NOs: 4-6, 83-85 or a functional fragment thereof. In an aspect, a meiocyte-preferred promoter comprises a nucleic acid sequence at least 95% identical to a nucleic acid sequence selected from the group consisting of SEQ ID NOs: 4-6, 83-85 or a functional fragment thereof. In an aspect, a meiocyte-preferred promoter comprises a nucleic acid sequence at least 96% identical to a nucleic acid sequence selected from the group consisting of SEQ ID NOs: 4-6, 83-85 or a functional fragment thereof. In an aspect, a meiocyte-preferred promoter comprises a nucleic acid sequence at least 97% identical to a nucleic acid sequence selected from the group consisting of SEQ ID NOs: 4-6, 83-85 or a functional fragment thereof. In an aspect, a meiocyte-preferred promoter comprises a nucleic acid sequence at least 98% identical to a nucleic acid sequence selected from the group consisting of SEQ ID NOs: 4-6, 83-85 or a functional fragment thereof. In an aspect, a meiocyte-preferred promoter comprises a nucleic acid sequence at least 99% identical to a nucleic acid sequence selected from the group consisting of SEQ ID NOs: 4-6, 83-85 or a functional fragment thereof. In an aspect, a meiocyte-preferred promoter comprises a nucleic acid sequence 100% identical to a nucleic acid sequence selected from the group consisting of SEQ ID NOs: 4-6, 83-85 or a functional fragment thereof.

As used herein, an "egg cell-preferred promoter" refers to a promoter that exhibits higher or preferential expression in an egg cell as compared to other cell or tissue types of the plant. Egg cell-preferred promoters can exhibit expression in nearby cells such as, without being limiting, synergids, antipodal cells, central cells, integument cells, stigma cells, and style cells. An egg cell-preferred promoter can also exhibit expression in other ovary cells, for example the ovule. An egg cell-preferred promoter can also exhibit expression in other plant tissues, such as, without being limiting, pollen cells, root cells, embryo cells, stem cells, meristem cells, floral cells, and leaf cells, as long as the egg cell-preferred promoter exhibits higher or preferential expression in an egg cell.

As used herein, an "egg cell-specific promoter" refers to a promoter that exhibits expression exclusively in an egg cell. In an aspect, an egg cell-preferred promoter comprises an egg cell-specific promoter.

As used herein, an "ovule tissue preferred promoter" refers to a promoter that exhibits higher or preferential expression in at least one or all of the ovule tissue as compared to other cell or tissue types of the plant. In seed plants, the ovule is the structure that gives rise to and contains the female reproductive cells. As used herein, the ovule is initially composed of unreduced tissue that gives rise to the haploid tissue of the female gametophyte. The female gametophyte further develops into the "mature egg sac", comprised of four unique cell types: one egg cell, a central cell, two synergids and three or more antipodal cells. As used herein, the ovule preferred promoter can exhibit expression in pre or post pollinated ovule. An ovule preferred promoter can also exhibit expression in other ovary cells.

As used herein, an "ovule tissue-specific promoter" refers to a promoter that exhibits expression exclusively in ovule. In an aspect, an ovule tissue-preferred promoter comprises an ovule tissue-specific promoter.

As used herein, an "embryo tissue-preferred promoter" refers to a promoter that exhibits higher or preferential expression in embryo tissue as compared to other cell or tissue types of the plant. Embryo tissue-preferred promoters can exhibit expression in nearby cells such as, without being limiting, endosperm cells, cotyledon cells, and seed coat cells. An embryo tissue-preferred promoter can also exhibit expression in other plant tissues, such as, without being limiting, pollen cells, root cells, egg cells, stem cells, meristem cells, floral cells, and leaf cells, as long as the embryo tissue-preferred promoter exhibits higher or preferential expression in embryo tissue.

As used herein, an "embryo tissue-specific promoter" refers to a promoter that exhibits expression exclusively in embryo tissue. In an aspect, an embryo tissue-preferred promoter comprises an embryo tissue-specific promoter.

As used herein, an "zygote cell-preferred promoter" refers to a promoter that exhibits higher or preferential expression in zygotes as compared to other cell or tissue types of the plant. Upon fertilization of an egg cell by a haploid pollen cell, a diploid zygote is formed, which gives rise to an embryo. A zygote cell-preferred promoter can also exhibit expression in other plant cells, such as, without being limiting, pollen cells, egg cells, stem cells, meristem cells, endosperm cells, cotyledon cells, floral cells, leaf cells and embryo tissue as long as the zygote tissue-preferred promoter exhibits higher or preferential expression in the zygote.

As used herein, an "zygote cell-specific promoter" refers to a promoter that exhibits expression exclusively in the zygote. In an aspect, a zygote cell-preferred promoter comprises a zygote cell-specific promoter.

It will be appreciated that the same promoter can be both egg cell-preferred, zygote cell-preferred and embryo-tissue preferred, as a fertilized egg upon pollination will develop into a zygote which will give rise to embryo tissue.

In an aspect, an embryo tissue-preferred or embryo tissue-specific promoter comprises a DSUL1 promoter. In an aspect, an egg cell-preferred or embryo tissue-preferred promoter comprises an EA1 promoter. In an aspect, an egg cell-preferred or embryo tissue-preferred promoter comprises an ES4 promoter. In an aspect, an egg cell-preferred or embryo tissue-preferred promoter comprises an EAL1 promoter. In an aspect, an egg cell-preferred or embryo tissue-preferred promoter comprises a promoter selected from the group consisting of a DSUL1 promoter, an EA1 promoter, an ES4 promoter, and an EAL1 promoter.

In an aspect, a DSUL1 promoter is operably linked to a nucleic acid encoding a guided nuclease. In an aspect, a DSUL1 promoter is operably linked to a nucleic acid encoding a Cas9 nuclease. In an aspect, a DSUL1 promoter is operably linked to a nucleic acid encoding a Cas12a nuclease. In an aspect, a DSUL1 promoter is operably linked to a nucleic acid encoding a CasX nuclease. In an aspect, a DSUL1 promoter is operably linked to a nucleic acid encoding a guide nucleic acid. In an aspect, a DSUL1 promoter is operably linked to a nucleic acid encoding a guide RNA. In an aspect, a DSUL1 promoter is operably linked to a nucleic acid encoding a single-guide RNA. In some embodiments, the guide RNA acid is flanked by self-cleaving ribozymes. In an aspect, a DSUL1 promoter is operably linked to a nucleic acid encoding a recombinase (e.g., Cre recombinase). In an aspect, a DSUL1 promoter is operably linked to a nucleic acid encoding a TALE.

In an aspect, an EA1 promoter is operably linked to a nucleic acid encoding a guided nuclease. In an aspect, an EA1 promoter is operably linked to a nucleic acid encoding a Cas9 nuclease. In an aspect, an EA1 promoter is operably linked to a nucleic acid encoding a Cas12a nuclease. In an aspect, an EA1 promoter is operably linked to a nucleic acid encoding a CasX nuclease. In an aspect, an EA1 promoter is operably linked to a nucleic acid encoding a guide nucleic acid. In an aspect, an EA1 promoter is operably linked to a nucleic acid encoding a guide RNA. In an aspect, an EA1 promoter is operably linked to a nucleic acid encoding a single-guide RNA. In some embodiments, the guide RNA acid is flanked by self-cleaving ribozymes. In an aspect, an EA1 promoter is operably linked to a nucleic acid encoding a recombinase (e.g., Cre recombinase). In an aspect, an EA1 promoter is operably linked to a nucleic acid encoding a TALE.

In an aspect, an ES4 promoter is operably linked to a nucleic acid encoding a guided nuclease. In an aspect, an ES4 promoter is operably linked to a nucleic acid encoding a Cas9 nuclease. In an aspect, an ES4 promoter is operably linked to a nucleic acid encoding a Cas12a nuclease. In an aspect, an ES4 promoter is operably linked to a nucleic acid encoding a CasX nuclease. In an aspect, an ES4 promoter is operably linked to a nucleic acid encoding a guide nucleic acid. In an aspect, an ES4 promoter is operably linked to a nucleic acid encoding a guide RNA. In an aspect, an ES4 promoter is operably linked to a nucleic acid encoding a single-guide RNA. In some embodiments, the guide RNA acid is flanked by self-cleaving ribozymes. In an aspect, an ES4 promoter is operably linked to a nucleic acid encoding a recombinase (e.g., Cre recombinase). In an aspect, an ES4 promoter is operably linked to a nucleic acid encoding a TALE.

In an aspect, an EAL1 promoter is operably linked to a nucleic acid encoding a guided nuclease. In an aspect, an EAL1 promoter is operably linked to a nucleic acid encoding a Cas9 nuclease. In an aspect, an EAL1 promoter is operably linked to a nucleic acid encoding a Cas12a nuclease. In an aspect, an EAL1 promoter is operably linked to a nucleic acid encoding a CasX nuclease. In an aspect, an EAL1 promoter is operably linked to a nucleic acid encoding a guide nucleic acid. In an aspect, an EAL1 promoter is operably linked to a nucleic acid encoding a guide RNA. In an aspect, an EAL1 promoter is operably linked to a nucleic acid encoding a single-guide RNA. In some embodiments, the guide RNA acid is flanked by self-cleaving ribozymes. In an aspect, an EAL1 promoter is operably linked to a nucleic acid encoding a recombinase (e.g., Cre recombinase). In an aspect, an EAL1 promoter is operably linked to a nucleic acid encoding a TALE.

In an aspect, a DSUL1 promoter comprises a nucleic acid sequence at least 80% identical to SEQ ID NO: 1, or a functional fragment thereof. In an aspect, a DSUL1 promoter comprises a nucleic acid sequence at least 85% identical to SEQ ID NO: 1, or a functional fragment thereof. In an aspect, a DSUL1 promoter comprises a nucleic acid sequence at least 90% identical to SEQ ID NO: 1, or a functional fragment thereof. In an aspect, a DSUL1 promoter comprises a nucleic acid sequence at least 95% identical to SEQ ID NO: 1, or a functional fragment thereof. In an aspect, a DSUL1 promoter comprises a nucleic acid sequence at least 96% identical to SEQ ID NO: 1, or a functional fragment thereof. In an aspect, a DSUL1 promoter comprises a nucleic acid sequence at least 97% identical to SEQ ID NO: 1, or a functional fragment thereof. In an aspect, a DSUL1 promoter comprises a nucleic acid sequence at least 98% identical to SEQ ID NO: 1, or a functional fragment thereof. In an aspect, a DSUL1 promoter comprises a nucleic acid sequence at least 99% identical to SEQ ID NO: 1, or a functional fragment thereof. In an aspect, a DSUL1 promoter comprises a nucleic acid sequence 100% identical to SEQ ID NO: 1, or a functional fragment thereof.

In an aspect, an EA1 promoter comprises a nucleic acid sequence at least 80% identical to SEQ ID NO: 2, or a functional fragment thereof. In an aspect, an EA1 promoter comprises a nucleic acid sequence at least 85% identical to SEQ ID NO: 2, or a functional fragment thereof. In an aspect, an EA1 promoter comprises a nucleic acid sequence at least 90% identical to SEQ ID NO: 2, or a functional fragment thereof. In an aspect, an EA1 promoter comprises a nucleic acid sequence at least 95% identical to SEQ ID NO: 2, or a functional fragment thereof. In an aspect, an EA1 promoter comprises a nucleic acid sequence at least 96% identical to SEQ ID NO: 2, or a functional fragment thereof. In an aspect, an EA1 promoter comprises a nucleic acid sequence at least 97% identical to SEQ ID NO: 2, or a functional fragment thereof. In an aspect, an EA1 promoter comprises a nucleic acid sequence at least 98% identical to SEQ ID NO: 2, or a functional fragment thereof. In an aspect, an EA1 promoter comprises a nucleic acid sequence at least 99% identical to SEQ ID NO: 2, or a functional fragment thereof. In an aspect, an EA1 promoter comprises a nucleic acid sequence 100% identical to SEQ ID NO: 2, or a functional fragment thereof.

In an aspect, an ES4 promoter comprises a nucleic acid sequence at least 80% identical to SEQ ID NO: 3, or a functional fragment thereof. In an aspect, an ES4 promoter comprises a nucleic acid sequence at least 85% identical to SEQ ID NO: 3, or a functional fragment thereof. In an aspect, an ES4 promoter comprises a nucleic acid sequence at least 90% identical to SEQ ID NO: 3, or a functional fragment thereof. In an aspect, an ES4 promoter comprises a nucleic acid sequence at least 95% identical to SEQ ID NO: 3, or a functional fragment thereof. In an aspect, an ES4 promoter comprises a nucleic acid sequence at least 96% identical to SEQ ID NO: 3, or a functional fragment thereof. In an aspect, an ES4 promoter comprises a nucleic acid sequence at least 97% identical to SEQ ID NO: 3, or a functional fragment thereof. In an aspect, an ES4 promoter comprises a nucleic acid sequence at least 98% identical to SEQ ID NO: 3, or a functional fragment thereof. In an aspect, an ES4 promoter comprises a nucleic acid sequence at least 99% identical to SEQ ID NO: 3, or a functional fragment thereof. In an aspect, an ES4 promoter comprises a nucleic acid sequence 100% identical to SEQ ID NO: 3, or a functional fragment thereof.

In an aspect, an egg cell-preferred promoter, ovule tissue-preferred promoter, zygote cell-preferred or an embryo tissue-preferred promoter comprises a nucleic acid sequence at least 80% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 85% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 90% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 95% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 96% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 97% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 98% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence at least 99% identical to a nucleic acid sequence selected from the group consisting of SEQ ID NOs: 1-3, 21-45, 65-69, 75-82, 86-88 or a functional fragment thereof. In an aspect, an egg cell-preferred promoter or an embryo tissue-preferred promoter comprises a nucleic acid sequence 100% identical to a nucleic acid sequence selected from the group consisting of SEQ ID NOs: 1-3, 21-45, 65-69, 75-82, 86-88 or a functional fragment thereof.

It is appreciated in the art that a fragment of a promoter sequence can function to drive transcription of an operably linked nucleic acid molecule. For example, without being limiting, if a 1000 bp promoter is truncated to 500 bp, and the 500 bp fragment is capable of driving transcription, the 500 bp fragment is referred to as a "functional fragment."

In an aspect, an egg cell-preferred promoter is operably linked to a nucleic acid sequence encoding a DNA modification enzyme, such as a guided nuclease. In an aspect, an egg cell-preferred promoter is operably linked to a nucleic acid sequence encoding a Cas9 nuclease. In an aspect, an egg cell-preferred promoter is operably linked to a nucleic acid sequence encoding a Cas12a nuclease. In an aspect, an egg cell-preferred promoter is operably linked to a nucleic acid sequence encoding a CasX nuclease. In an aspect, an egg cell-preferred promoter is operably linked to a nucleic acid sequence encoding a guide nucleic acid. In an aspect, an egg cell-preferred promoter is operably linked to a nucleic acid sequence encoding a guide RNA. In an aspect, an egg cell-preferred promoter is operably linked to a nucleic acid sequence encoding a single-guide RNA. In some embodiments, the guide RNA acid is flanked by self-cleaving ribozymes. In an aspect, an egg cell-preferred promoter is operably linked to a nucleic acid sequence encoding a recombinase (e.g., Cre recombinase). In an aspect, an egg cell-preferred promoter is operably linked to a nucleic acid sequence encoding a TALE.

In an aspect, an egg cell-specific promoter is operably linked to a nucleic acid sequence encoding a DNA modification enzyme, such as a guided nuclease. In an aspect, an egg cell-specific promoter is operably linked to a nucleic acid sequence encoding a Cas9 nuclease. In an aspect, an egg cell-specific promoter is operably linked to a nucleic acid sequence encoding a Cas12a nuclease. In an aspect, an egg cell-specific promoter is operably linked to a nucleic acid sequence encoding a CasX nuclease. In an aspect, an egg cell-specific promoter is operably linked to a nucleic acid sequence encoding a guide nucleic acid. In an aspect, an egg cell-specific promoter is operably linked to a nucleic acid sequence encoding a guide RNA. In an aspect, an egg cell-specific promoter is operably linked to a nucleic acid sequence encoding a single-guide RNA. In some embodiments, the guide RNA acid is flanked by self-cleaving ribozymes. In an aspect, an egg cell-specific promoter is operably linked to a nucleic acid sequence encoding a recombinase (e.g., Cre recombinase). In an aspect, an egg cell-specific promoter is operably linked to a nucleic acid sequence encoding a TALE.

In an aspect, an embryo tissue-preferred promoter is operably linked to a nucleic acid sequence encoding a DNA modification enzyme, such as a guided nuclease. In an aspect, an embryo tissue-preferred promoter is operably linked to a nucleic acid sequence encoding a Cas9 nuclease. In an aspect, an embryo tissue-preferred promoter is operably linked to a nucleic acid sequence encoding a Cas12a nuclease. In an aspect, an embryo tissue-preferred promoter is operably linked to a nucleic acid sequence encoding a CasX nuclease. In an aspect, an embryo tissue-preferred promoter is operably linked to a nucleic acid sequence encoding a guide nucleic acid. In an aspect, an embryo tissue-preferred promoter is operably linked to a nucleic acid sequence encoding a guide RNA. In an aspect, an embryo tissue-preferred promoter is operably linked to a nucleic acid sequence encoding a single-guide RNA. In some embodiments, the guide RNA acid is flanked by self-cleaving ribozymes. In an aspect, an embryo tissue-preferred promoter is operably linked to a nucleic acid sequence encoding a recombinase (e.g., Cre recombinase). In an aspect, an embryo tissue-preferred promoter is operably linked to a nucleic acid sequence encoding a TALE.

In an aspect, an embryo tissue-specific promoter is operably linked to a nucleic acid sequence encoding a DNA modification enzyme, such as a guided nuclease. In an aspect, an embryo tissue-specific promoter is operably linked to a nucleic acid sequence encoding a Cas9 nuclease. In an aspect, an embryo tissue-specific promoter is operably linked to a nucleic acid sequence encoding a Cas12a nuclease. In an aspect, an embryo tissue-specific promoter is operably linked to a nucleic acid sequence encoding a CasX nuclease. In an aspect, an embryo tissue-specific promoter is operably linked to a nucleic acid sequence encoding a guide nucleic acid. In an aspect, an embryo tissue-specific promoter is operably linked to a nucleic acid sequence encoding a guide RNA. In an aspect, an embryo tissue-specific promoter is operably linked to a nucleic acid sequence encoding a single-guide RNA. In some embodiments, the guide RNA acid is flanked by self-cleaving ribozymes. In an aspect, an embryo tissue-specific promoter is operably linked to a nucleic acid sequence encoding a recombinase (e.g., Cre recombinase). In an aspect, an embryo tissue-specific promoter is operably linked to a nucleic acid sequence encoding a TALE.

Several embodiments described herein relate to methods and compositions for providing egg, embryo, and/or meiotic plant tissue preferred or specific expression of a DNA modification enzyme, such as a guided nuclease (e.g., a CRISPR/Cas system), from a constitutive promoter. In some embodiments, a transcribable polynucleotide encoding a DNA modification enzyme, such as a guided nuclease (e.g., a CRISPR/Cas system) is operably linked to a constitutive promoter by excision of a intervening polynucleotide sequence preferentially or specifically in egg, embryo, and/ or meiotic plant tissue. In some embodiments, the intervening sequence is excised by a recombinase that is preferentially or selectively expressed in egg, embryo, and/or meiotic plant tissue. In some embodiments, the intervening sequence is excised by Cre-mediated excision of an intervening Cre expression cassette, where Cre is preferentially or selectively expressed in egg, embryo, and/or meiotic plant tissue.

Promoters that drive expression in all or most tissues of the plant are referred to as "constitutive" promoters. Promoters that drive expression during certain periods or stages of development are referred to as "developmental" promoters. An "inducible" promoter is a promoter that initiates transcription in response to an environmental stimulus such as heat, cold, drought, light, or other stimuli, such as wounding or chemical application. A promoter can also be classified in terms of its origin, such as being heterologous, homologous, chimeric, synthetic, etc.

As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature.

In an aspect, a promoter provided herein is a constitutive promoter. In still another aspect, a promoter provided herein is an inducible promoter. In another aspect, a promoter provided herein is selected from the group consisting of a constitutive promoter, a tissue-specific promoter, a tissue-preferred promoter, and an inducible promoter.

RNA polymerase III (Pol III) promoters can be used to drive the expression of non-protein coding RNA molecules, such as guide RNAs. In an aspect, a promoter provided herein is a Pol III promoter. In another aspect, a Pol III promoter provided herein is operably linked to a nucleic acid molecule encoding a non-protein coding RNA. In yet another aspect, a Pol III promoter provided herein is operably linked to a nucleic acid molecule encoding a guide nucleic acid. In still another aspect, a Pol III promoter provided herein is operably linked to a nucleic acid molecule encoding a single-guide RNA. In a further aspect, a Pol III promoter provided herein is operably linked to a nucleic acid molecule encoding a CRISPR RNA (crRNA). In another aspect, a Pol III promoter provided herein is operably linked to a nucleic acid molecule encoding a tracer RNA (tracrRNA). In some embodiments, a nucleic acid molecule encoding a non-protein coding RNA (e.g., a gRNA, a single-guide RNA, a crRNA, a tracrRNA, etc.) is operably linked to a Pol III promoter by excision of a intervening polynucleotide sequence preferentially or specifically in egg, embryo, and/or meiotic plant tissue. In some embodiments, the intervening sequence is excised by a recombinase that is preferentially or selectively expressed in egg, embryo, and/or meiotic plant tissue. In some embodiments, the intervening sequence is excised by Cre-mediated excision of an intervening Cre expression cassette, where Cre is preferentially or selectively expressed in egg, embryo, and/or meiotic plant tissue.

Non-limiting examples of Pol III promoters include a U6 promoter, an H1 promoter, a 5S promoter, an Adenovirus 2 (Ad2) VAI promoter, a tRNA promoter, and a 7SK promoter. See, for example, Schramm and Hernandez, 2002, Genes & Development, 16:2593-2620, which is incorporated by reference herein in its entirety. In an aspect, a Pol III promoter provided herein is selected from the group consisting of a U6 promoter, an H1 promoter, a 5S promoter, an Adenovirus 2 (Ad2) VAI promoter, a tRNA promoter, and a 7SK promoter. In another aspect, a guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a single-guide RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a CRISPR RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter. In another aspect, a tracer RNA provided herein is operably linked to a promoter selected from the group consisting of a U6 promoter, an H1 promoter, a 5S promoter, an Adenovirus 2 (Ad2) VAI promoter, a tRNA promoter, and a 7SK promoter.

In an aspect, a promoter provided herein is a Dahlia Mosaic Virus (DaMV) promoter. In another aspect, a promoter provided herein is a U6 promoter. In another aspect, a promoter provided herein is an actin promoter. In an aspect, a promoter provided herein is a Cauliflower Mosaic Virus (CaMV) 35S promoter. In an aspect, a promoter provided herein is a ubiquitin promoter.

In an aspect, a constitutive promoter is selected from the group consisting of a CaMV 35S promoter, an actin promoter, and a ubiquitin promoter.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et. al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et. al., *Plant Molecular Biology* (1987) 9: 315-324), the CaMV 35S promoter (Odell et. al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences, USA* (1990) 87: 4144-4148), the R gene complex promoter (Chandler et. al., *Plant Cell* (1989) 1: 1175-1183), and the chlorophyll a/b binding protein gene promoter, PC1SV (U.S. Pat. No. 5,850,019), and AGRtu.nos (GenBank Accession V00087; Depicker et. al., *Journal of Molecular and Applied Genetics* (1982) 1: 561-573; Bevan et. al., 1983) promoters.

Promoter hybrids can also be used and constructed to enhance transcriptional activity (see U.S. Pat. No. 5,106,739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

In an aspect, a constitutive promoter is operably linked to a nucleic acid sequence encoding a guided nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a Cas9 nuclease by Cre-mediated excision of an intervening Cre expression cassette, where Cre is preferentially or selectively expressed in egg, embryo, and/ or meiotic plant tissue. In an aspect, a constitutive promoter is operably linked to a nucleic acid sequence encoding a Cas12a nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a CasX nuclease by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a guide nucleic acid by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a guide RNA by Cre-mediated excision of an intervening Cre expression cassette, where Cre is preferentially or selectively expressed in egg, embryo, and/or meiotic plant tissue. In an aspect, a constitutive promoter is operably linked to a nucleic acid sequence encoding a single-guide RNA by Cre-mediated excision of an intervening Cre expression cassette, where Cre is preferentially or selectively expressed in egg, embryo, and/or meiotic plant tissue.

In an aspect, an inducible promoter is operably linked to a nucleic acid sequence encoding a guided nuclease. In an aspect, an inducible promoter is operably linked to a nucleic acid sequence encoding a Cas9 nuclease. In an aspect, an inducible promoter is operably linked to a nucleic acid sequence encoding a Cas12a nuclease. In an aspect, an inducible promoter is operably linked to a nucleic acid sequence encoding a CasX nuclease. In an aspect, an inducible promoter is operably linked to a nucleic acid sequence encoding a guide nucleic acid. In an aspect, an inducible promoter is operably linked to a nucleic acid sequence encoding a guide RNA. In an aspect, an inducible promoter is operably linked to a nucleic acid sequence encoding a single-guide RNA. In some embodiments, the guide RNA acid is flanked by self-cleaving ribozymes. In an aspect, an inducible promoter is operably linked to a nucleic acid sequence encoding a recombinase (e.g., Cre recombinase). In an aspect, an inducible promoter is operably linked to a nucleic acid sequence encoding a TALE.

In an aspect, a developmental promoter is operably linked to a nucleic acid sequence encoding a guided nuclease. In an aspect, a developmental promoter is operably linked to a nucleic acid sequence encoding a Cas9 nuclease. In an aspect, a developmental promoter is operably linked to a nucleic acid sequence encoding a Cas12a nuclease. In an aspect, a developmental promoter is operably linked to a nucleic acid sequence encoding a CasX nuclease. In an aspect, a developmental promoter is operably linked to a nucleic acid sequence encoding a guide nucleic acid. In an aspect, a developmental promoter is operably linked to a nucleic acid sequence encoding a guide RNA. In an aspect, a developmental promoter is operably linked to a nucleic acid sequence encoding a single-guide RNA. In some embodiments, the guide RNA acid is flanked by self-cleaving ribozymes. In an aspect, a developmental promoter is operably linked to a nucleic acid sequence encoding a recombinase (e.g., Cre recombinase). In an aspect, a developmental promoter is operably linked to a nucleic acid sequence encoding a TALE.

As used herein the term "leader" refers to a nucleotide segment between the transcription start site (TSS) and protein coding sequence start site of a gene. It is isolated from the untranslated 5' region of the genomic copy of a gene. Leaders can be used as 5' regulatory elements to regulate the expression of operably linked transcribable polynucleotide molecules. The leader molecule can be used with a heterologous promoter or with its native promoter.

As used herein, the term "3' transcription termination molecule" or "3' UTR" refers to a DNA sequence that is used during transcription to produce the 3' untranslated region (3' UTR) of an mRNA molecule. The 3' untranslated region of an mRNA molecule may be generated by specific cleavage and 3' polyadenylation, a.k.a. polyA tail. A 3' UTR may be operably linked to and located downstream of a transcribable polynucleotide molecule and may include polynucleotides that provide a polyadenylation signal and other regulatory signals capable of affecting transcription, mRNA processing, or gene expression. PolyA tails are thought to function in mRNA stability and in initiation of translation. Examples of 3' transcription termination molecules in the art are the nopaline synthase 3' region (see, Fraley, et. al., Proc. Natl. Acad. Sci. USA, 80: 4803-4807 (1983)); wheat hsp17 3' region; pea rubisco small subunit 3' region; cotton E6 3' region (U.S. Pat. No. 6,096,950); 3' regions disclosed in WO0011200A2; and the coixin 3' UTR (U.S. Pat. No. 6,635,806). 3' UTRs typically find beneficial use for the recombinant expression of specific genes. 3'UTRs can be used as 3'regulatory elements to regulate the expression of operably linked transcribable polynucleotide molecules. 3'UTRs can be used as 3' regulatory elements to regulate the tissue/cell preferred expression of operably linked transcribable polynucleotide molecules. 3' UTRs can be used with a heterologous promoter or with its native promoter. Non-limiting examples of 3' UTRs useful in practicing the various embodiments described here include SEQ ID NOs 46-64, 70-74, 89-102

DNA Modification Enzymes

Several embodiments relate to compositions and methods for preferential or specific expression of one or more components of a genome editing system in egg, embryo, and/or meiotic plant tissue. Several embodiments relate to a gene regulatory element as described in Table 1 operably linked to a heterologous transcribable DNA molecule encoding one or more components of a genome editing system. Genome editing systems may be used to introduce one or more insertions, deletions, substitutions, base modifications, translocations, or inversions to a genome of a host cell. In some embodiments, a gene regulatory element as described in Table 1 is operably linked to a heterologous transcribable DNA molecule encoding a sequence-specific DNA modification enzyme, such as a CRISPR-Cas effector protein, a zinc finger protein, or a transcription activator (TAL) protein. In some embodiments, the sequence-specific DNA modification enzyme may be a fusion protein. In some embodiments, the sequence-specific DNA modification enzyme may be a guided nuclease.

Guided nucleases are nucleases that form a complex (e.g., a ribonucleoprotein) with a guide nucleic acid molecule (e.g., a guide RNA), which then guides the complex to a target site within a target sequence. One non-limiting example of guided nucleases are CRISPR nucleases.

CRISPR (Clustered Regularly Interspaced Short Palindromic Repeats) nucleases (e.g., Cas9, CasX, Cas12a (also referred to as Cpf1), CasY) are proteins found in bacteria that are guided by guide RNAs ("gRNAs") to a target nucleic acid molecule, where the endonuclease can then cleave one or two strands the target nucleic acid molecule. Although the origins of CRISPR nucleases are bacterial, many CRISPR nucleases have been shown to function in eukaryotic cells.

While not being limited by any particular scientific theory, a CRISPR nuclease forms a complex with a guide RNA (gRNA), which hybridizes with a complementary target site, thereby guiding the CRISPR nuclease to the target site. In class II CRISPR-Cas systems, CRISPR arrays, including spacers, are transcribed during encounters with recognized invasive DNA and are processed into small interfering CRISPR RNAs (crRNAs). The crRNA comprises a repeat sequence and a spacer sequence which is complementary to a specific protospacer sequence in an invading pathogen. The spacer sequence can be designed to be complementary to target sequences in a eukaryotic genome.

In some embodiments, a gene regulatory element as described herein is operably linked to a heterologous transcribable DNA molecule encoding a CRISPR-Cas effector protein. In some embodiments, the CRISPR-Cas effector protein is selected from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. Examples of CRISPR-Cas effector proteins include, but are not limited to, Cas9, C2c1, C2c3, C2c4, C2c5, C2c8, C2c9, C2c10, Cas12a (also referred to as Cpf1), Cas12b, Cas12c, Cas12d, Cas12e, Cas12h, Cas12i, Cas12g, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), Csf5, Cas14a, Cas14b, and Cas14c effector protein. In some embodiments, a gene regulatory element as described herein is operably linked to a CRISPR-Cas effector protein comprising a mutation in its nuclease active site (e.g., RuvC, HNH, and/or NUC domain). A CRISPR-Cas effector protein having a mutation in its nuclease active site, and therefore, no longer comprising nuclease activity, is commonly referred to as "dead," e.g., dCas. In some embodiments, a CRISPR-Cas effector protein domain or polypeptide having a mutation in its nuclease active site may have impaired activity or reduced activity as compared to the same CRISPR-Cas effector protein without the mutation. In some embodiments, a gene regulatory element as described herein is operably linked to a CRISPR-Cas effector protein having a mutation in its nuclease active site to generate a nickase activity operably linked to a reverse transcriptase enzyme.

CRISPR effector proteins associate with their respective crRNAs in their active forms. CasX, similar to the class II endonuclease Cas9, requires another non-coding RNA component, referred to as a trans-activating crRNA (tracrRNA), to have functional activity. Nucleic acid molecules provided herein can combine a crRNA and a tracrRNA into one nucleic acid molecule in what is herein referred to as a "single guide RNA" (sgRNA). Cas12a does not require a tracrRNA to be guided to a target site; a crRNA alone is sufficient for Cas12a. The gRNA guides the active CRISPR nuclease complex to a target site, where the CRISPR nuclease can cleave the target site.

When a CRISPR effector protein and a guide RNA form a complex, the whole system is called a "ribonucleoprotein." Ribonucleoproteins provided herein can also comprise additional nucleic acids or proteins.

In an aspect, a CRISPR effector protein and a guide nucleic acid form a ribonucleoprotein in an egg cell. In another aspect, a CRISPR effector protein and a guide nucleic acid form a ribonucleoprotein in embryo tissue. In an aspect, a Cas9 nuclease and a guide nucleic acid form a ribonucleoprotein in an egg cell. In another aspect, a Cas9 nuclease and a guide nucleic acid form a ribonucleoprotein in embryo tissue. In an aspect, a Cas12a nuclease and a guide nucleic acid form a ribonucleoprotein in an egg cell. In another aspect, a Cas12a nuclease and a guide nucleic acid form a ribonucleoprotein in embryo tissue. In an aspect, a CasX nuclease and a guide nucleic acid form a ribonucleoprotein in an egg cell. In another aspect, a CasX nuclease and a guide nucleic acid form a ribonucleoprotein in embryo tissue. In an aspect, a CRISPR effector protein and a guide RNA form a ribonucleoprotein in an egg cell. In another aspect, a CRISPR effector protein and a guide RNA form a ribonucleoprotein in embryo tissue. In an aspect, a Cas9 nuclease and a guide RNA form a ribonucleoprotein in an egg cell. In another aspect, a Cas9 nuclease and a guide RNA form a ribonucleoprotein in embryo tissue. In an aspect, a Cas12a nuclease and a guide RNA form a ribonucleoprotein in an egg cell. In another aspect, a Cas12a nuclease and a guide RNA form a ribonucleoprotein in embryo tissue. In an aspect, a CasX nuclease and a guide RNA form a ribonucleoprotein in an egg cell. In another aspect, a CasX nuclease and a guide RNA form a ribonucleoprotein in embryo tissue. In an aspect, a guided nuclease and a single-guide RNA form a ribonucleoprotein in an egg cell. In another aspect, a guided nuclease and a single-guide RNA form a ribonucleoprotein in embryo tissue. In another aspect, a CasX nuclease and a single-guide RNA form a ribonucleoprotein in embryo tissue. In another aspect, a Cas9 nuclease and a single-guide RNA form a ribonucleoprotein in embryo tissue.

In an aspect, a ribonucleoprotein generates at least one double-stranded break within a target site in an egg cell. In an aspect, a ribonucleoprotein generates at least one double-stranded break within a target site in embryo tissue. In an aspect, a ribonucleoprotein generates at least one single-stranded break within a target site in an egg cell. In an aspect, a ribonucleoprotein generates at least one single-stranded break within a target site in embryo tissue.

A prerequisite for cleavage of the target site by a CRISPR ribonucleoprotein is the presence of a conserved Protospacer Adjacent Motif (PAM) near the target site. Depending on the CRISPR nuclease, cleavage can occur within a certain number of nucleotides (e.g., between 18-23 nucleotides for Cas12a) from the PAM site. PAM sites are only required for type I and type II CRISPR associated proteins, and different CRISPR endonucleases recognize different PAM sites. Without being limiting, Cas12a can recognize at least the following PAM sites: TTTN, and YTN; and CasX can recognize at least the following PAM sites: TTCN, TTCA, and TTC (where T is thymine; C is cytosine; A is adenine; Y is thymine or cytosine; and N is thymine, cytosine, guanine, or adenine).

Cas12a is an RNA-guided nuclease of a class II, type V CRISPR/Cas system. Cas12a nucleases generate staggered cuts when cleaving a double-stranded DNA molecule. Staggered cuts of double-stranded DNA produce a single-stranded DNA overhang of at least one nucleotide. This is in contrast to a blunt-end cut (such as those generated by Cas9), which does not produce a single-stranded DNA overhang when cutting double-stranded DNA.

In an aspect, a Cas12a nuclease provided herein is a Lachnospiraceae bacterium Cas12a (LbCas12a) nuclease. In another aspect, a Cas12a nuclease provided herein is a *Francisella novicida* Cas12a (FnCas12a) nuclease. In an aspect, a Cas12a nuclease is selected from the group consisting of LbCas12a and FnCas12a.

In an aspect, a Cas12a nuclease, or a nucleic acid encoding a Cas12a nuclease, is derived from a bacteria genus selected from the group consisting of *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium, Acidaminococcus, Peregrinibacteria, Butyrivibrio, Parcubacteria, Smithella, Candidatus, Moraxella,* and *Leptospira.*

In an aspect, a Cas12a nuclease is encoded by a polynucleotide comprising a sequence at least 80% identical to a polynucleotide selected from the group consisting of SEQ ID NO: 7. In another aspect, a Cas12a nuclease is encoded by a polynucleotide comprising a sequence at least 85% identical to a polynucleotide selected from the group consisting of SEQ ID NO: 7. In another aspect, a Cas12a nuclease is encoded by a polynucleotide comprising a sequence at least 90% identical to a polynucleotide selected from the group consisting of SEQ ID NO: 7. In another aspect, a Cas12a nuclease is encoded by a polynucleotide comprising a sequence at least 95% identical to a polynucleotide selected from the group consisting of SEQ ID NO: 7. In another aspect, a Cas12a nuclease is encoded by a polynucleotide comprising a sequence at least 96% identical to a polynucleotide selected from the group consisting of SEQ ID NO: 7. In another aspect, a Cas12a nuclease is encoded by a polynucleotide comprising a sequence at least 97% identical to a polynucleotide selected from the group consisting of SEQ ID NO: 7. In another aspect, a Cas12a nuclease is encoded by a polynucleotide comprising a sequence at least 98% identical to a polynucleotide selected from the group consisting of SEQ ID NO: 7. In another aspect, a Cas12a nuclease is encoded by a polynucleotide comprising a sequence at least 99% identical to a polynucleotide selected from the group consisting of SEQ ID NO: 7. In another aspect, a Cas12a nuclease is encoded by a polynucleotide comprising a sequence 100% identical to a polynucleotide selected from the group consisting of SEQ ID NO: 7.

CasX is a type of class II CRISPR-Cas nuclease that has been identified in the bacterial phyla Deltaproteobacteria and Planctomycetes. Similar to Cas12a, CasX nucleases generate staggered cuts when cleaving a double-stranded DNA molecule. However, unlike Cas12a, CasX nucleases require a crRNA and a tracrRNA, or a single-guide RNA, in order to target and cleave a target nucleic acid.

In an aspect, a CasX nuclease provided herein is a CasX nuclease from the phylum Deltaproteobacteria. In another aspect, a CasX nuclease provided herein is a CasX nuclease from the phylum Planctomycetes. Without being limiting, additional suitable CasX nucleases are those set forth in WO 2019/084148, which is incorporated by reference herein in its entirety.

In an aspect, a guided nuclease capable of generating a staggered cut in a double-stranded DNA molecule is selected from the group consisting of Cas12a and CasX. In an aspect, a guided nuclease is selected from the group consisting of Cas12a and CasX.

In an aspect, a guided nuclease is a RNA-guided nuclease. In another aspect, a guided nuclease is a CRISPR nuclease. In another aspect, a guided nuclease is a Cas12a nuclease. In another aspect, a guided nuclease is a CasX nuclease.

As used herein, a "nuclear localization signal" (NLS) refers to an amino acid sequence that "tags" a protein for import into the nucleus of a cell. In an aspect, a nucleic acid molecule provided herein encodes a nuclear localization signal. In another aspect, a nucleic acid molecule provided herein encodes two or more nuclear localization signals.

In an aspect, a CRISPR effector protein provided herein comprises a nuclear localization signal. In an aspect, a Cas9 effector protein provided herein comprises a nuclear localization signal. In an aspect, a nuclear localization signal is positioned on the N-terminal end of a Cas12a nuclease. In a further aspect, a nuclear localization signal is positioned on the C-terminal end of a Cas9 effector protein. In yet another aspect, a nuclear localization signal is positioned on both the N-terminal end and the C-terminal end of a Cas9 effector protein.

In an aspect, a Cas12a effector protein provided herein comprises a nuclear localization signal. In an aspect, a nuclear localization signal is positioned on the N-terminal end of a Cas12a effector protein. In a further aspect, a nuclear localization signal is positioned on the C-terminal end of a Cas12a effector protein. In yet another aspect, a nuclear localization signal is positioned on both the N-terminal end and the C-terminal end of a Cas12a effector protein.

In an aspect, a CasX effector protein provided herein comprises a nuclear localization signal. In an aspect, a nuclear localization signal is positioned on the N-terminal end of a CasX effector protein. In a further aspect, a nuclear localization signal is positioned on the C-terminal end of a CasX effector protein. In yet another aspect, a nuclear localization signal is positioned on both the N-terminal end and the C-terminal end of a CasX effector protein.

In an aspect, a ribonucleoprotein comprises at least one nuclear localization signal. In another aspect, a ribonucleoprotein comprises at least two nuclear localization signals. In an aspect, a nuclear localization signal provided herein is encoded by SEQ ID NO: 8 or 9.

Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www[dot]kazusa[dot] or[dot]jp[forwards slash]codon and these tables can be adapted in a number of ways. See Nakamura et. al., 2000, *Nucl. Acids Res.* 28:292. Computer algorithms for codon optimizing a particular sequence for expression in a particular plant cell are also available, such as Gene Forge (Aptagen; Jacobus, Pa.), are also available.

As used herein, "codon optimization" refers to a process of modifying a nucleic acid sequence for enhanced expression in a plant cell of interest by replacing at least one codon (e.g., at least 1, 2, 3, 4, 5, 10, 15, 20, 25, 50, or more codons) of a sequence with codons that are more frequently or most frequently used in the genes of the plant cell while maintaining the original amino acid sequence (e.g., introducing silent mutations).

In an aspect, one or more codons (e.g., 1, 2, 3, 4, 5, 10, 15, 20, 25, 50, or more, or all codons) in a sequence encoding a guided nuclease correspond to the most frequently used codon for a particular amino acid. In another aspect, one or more codons (e.g., 1, 2, 3, 4, 5, 10, 15, 20, 25, 50, or more, or all codons) in a sequence encoding a Cas9 effector protein, a Cas12a effector protein or a CasX effector protein correspond to the most frequently used codon for a particular amino acid. As to codon usage in plants, reference is made to Campbell and Gowri, 1990, *Plant Physiol.*, 92: 1-11; and Murray et. al., 1989, *Nucleic Acids Res.*, 17:477-98, each of which is incorporated herein by reference in their entireties.

In an aspect, a nucleic acid molecule encodes a guided nuclease that is codon optimized for a plant. In an aspect, a nucleic acid molecule encodes a Cas9 effector protein that is codon optimized for a plant. In an aspect, a nucleic acid molecule encodes a Cas12a effector protein that is codon optimized for a plant. In an aspect, a nucleic acid molecule encodes a CasX effector protein that is codon optimized for a plant.

In another aspect, a nucleic acid molecule provided herein encodes a guided nuclease that is codon optimized for a plant cell. In another aspect, a nucleic acid molecule provided herein encodes a guided nuclease that is codon optimized for a monocotyledonous plant species. In another aspect, a nucleic acid molecule provided herein encodes a guided nuclease that is codon optimized for a dicotyledonous plant species. In a further aspect, a nucleic acid molecule provided herein encodes a guided nuclease that is codon optimized for a gymnosperm plant species. In a further aspect, a nucleic acid molecule provided herein encodes a guided nuclease that is codon optimized for an angiosperm plant species. In a further aspect, a nucleic acid molecule provided herein encodes a guided nuclease that is codon optimized for a corn cell. In a further aspect, a nucleic acid molecule provided herein encodes a guided nuclease that is codon optimized for a soybean cell. In a further aspect, a nucleic acid molecule provided herein encodes a guided nuclease that is codon optimized for a rice cell. In a further aspect, a nucleic acid molecule provided herein encodes a guided nuclease that is codon optimized for a wheat cell. In a further aspect, a nucleic acid molecule provided herein encodes a guided nuclease that is codon optimized for a cotton cell. In a further aspect, a nucleic acid molecule provided herein encodes a guided nuclease that is codon optimized for a sorghum cell. In a further aspect, a nucleic acid molecule provided herein encodes a guided nuclease that is codon optimized for an alfalfa cell. In a further aspect, a nucleic acid molecule provided herein encodes a guided nuclease that is codon optimized for a sugarcane cell. In a further aspect, a nucleic acid molecule provided herein encodes a guided nuclease that is codon optimized for an *Arabidopsis* cell. In a further aspect, a nucleic acid molecule provided herein encodes a guided nuclease that is codon optimized for a tomato cell. In a further aspect, a nucleic acid molecule provided herein encodes a guided nuclease that is codon optimized for a cucumber cell. In a further aspect, a nucleic acid molecule provided herein encodes a guided nuclease that is codon optimized for a potato cell. In a further aspect, a nucleic acid molecule provided herein encodes a guided nuclease that is codon optimized for an onion cell.

In another aspect, a nucleic acid molecule provided herein encodes a Cas12a effector protein that is codon optimized for a plant cell. In another aspect, a nucleic acid molecule provided herein encodes a Cas12a effector protein that is codon optimized for a monocotyledonous plant species. In another aspect, a nucleic acid molecule provided herein encodes a Cas12a effector protein that is codon optimized for a dicotyledonous plant species. In a further aspect, a nucleic acid molecule provided herein encodes a Cas12a effector protein that is codon optimized for a gymnosperm plant species. In a further aspect, a nucleic acid molecule provided herein encodes a Cas12a effector protein that is codon optimized for an angiosperm plant species. In a further aspect, a nucleic acid molecule provided herein encodes a Cas12a effector protein that is codon optimized for a corn cell. In a further aspect, a nucleic acid molecule provided herein encodes a Cas12a effector protein that is codon optimized for a soybean cell. In a further aspect, a nucleic acid molecule provided herein encodes a Cas12a effector protein that is codon optimized for a rice cell. In a further aspect, a nucleic acid molecule provided herein encodes a Cas12a effector protein that is codon optimized for a wheat cell. In a further aspect, a nucleic acid molecule provided herein encodes a Cas12a effector protein that is codon optimized for a cotton cell. In a further aspect, a nucleic acid molecule provided herein encodes a Cas12a effector protein that is codon optimized for a sorghum cell. In a further aspect, a nucleic acid molecule provided herein encodes a Cas12a effector protein that is codon optimized for an alfalfa cell. In a further aspect, a nucleic acid molecule provided herein encodes a Cas12a effector protein that is codon optimized for a sugar cane cell. In a further aspect, a nucleic acid molecule provided herein encodes a Cas12a effector protein that is codon optimized for an *Arabidopsis* cell. In a further aspect, a nucleic acid molecule provided herein encodes a Cas12a effector protein that is codon optimized for a tomato cell. In a further aspect, a nucleic acid molecule provided herein encodes a Cas12a effector protein that is codon optimized for a cucumber cell. In a further aspect, a nucleic acid molecule provided herein encodes a Cas12a effector protein that is codon optimized for a potato cell. In a further aspect, a nucleic acid molecule provided herein encodes a Cas12a effector protein that is codon optimized for an onion cell.

In another aspect, a nucleic acid molecule provided herein encodes a CasX effector protein that is codon optimized for a plant cell. In another aspect, a nucleic acid molecule provided herein encodes a CasX effector protein that is codon optimized for a monocotyledonous plant species. In another aspect, a nucleic acid molecule provided herein encodes a CasX effector protein that is codon optimized for a dicotyledonous plant species. In a further aspect, a nucleic acid molecule provided herein encodes a CasX effector protein that is codon optimized for a gymnosperm plant species. In a further aspect, a nucleic acid molecule provided herein encodes a CasX effector protein that is codon optimized for an angiosperm plant species. In a further aspect, a nucleic acid molecule provided herein encodes a CasX effector protein that is codon optimized for a corn cell. In a further aspect, a nucleic acid molecule provided herein encodes a CasX effector protein that is codon optimized for a soybean cell. In a further aspect, a nucleic acid molecule provided herein encodes a CasX effector protein that is codon optimized for a rice cell. In a further aspect, a nucleic acid molecule provided herein encodes a CasX effector protein that is codon optimized for a wheat cell. In a further aspect, a nucleic acid molecule provided herein encodes a CasX effector protein that is codon optimized for a cotton cell. In a further aspect, a nucleic acid molecule provided herein encodes a CasX effector protein that is codon optimized for a sorghum cell. In a further aspect, a nucleic acid molecule provided herein encodes a CasX effector protein that is codon optimized for an alfalfa cell. In a further aspect, a nucleic acid molecule provided herein encodes a CasX effector protein that is codon optimized for a sugar cane cell. In a further aspect, a nucleic acid molecule provided herein encodes a CasX effector protein that is codon optimized for an *Arabidopsis* cell. In a further aspect, a nucleic acid molecule provided herein encodes a CasX effector protein that is codon optimized for a tomato cell. In a further aspect, a nucleic acid molecule provided herein encodes a CasX effector protein that is codon optimized for a cucumber cell. In a further aspect, a nucleic acid molecule provided herein encodes a CasX effector protein that is codon optimized for a potato cell. In a further aspect, a nucleic acid molecule provided herein encodes a CasX effector protein that is codon optimized for an onion cell.

Guide Nucleic Acids

As used herein, a "guide nucleic acid" refers to a nucleic acid that forms a ribonucleoprotein (e.g., a complex) with a CRISPR effector protein (e.g., without being limiting, Cas9, Cas12a, CasX) and then guides the ribonucleoprotein to a specific sequence in a target nucleic acid molecule, where the guide nucleic acid and the target nucleic acid molecule share complementary sequences. In an aspect, a ribonucleoprotein provided herein comprises at least one guide nucleic acid.

In an aspect, a guide nucleic acid comprises DNA. In another aspect, a guide nucleic acid comprises RNA. In an aspect, a guide nucleic acid comprises DNA, RNA, or a combination thereof. In an aspect, a guide nucleic acid is single-stranded. In another aspect, a guide nucleic acid is at least partially double-stranded.

When a guide nucleic acid comprises RNA, it can be referred to as a "guide RNA." In another aspect, a guide nucleic acid comprises DNA and RNA. In another aspect, a guide RNA is single-stranded. In another aspect, a guide RNA is double-stranded. In a further aspect, a guide RNA is partially double-stranded.

In an aspect, a guide nucleic acid comprises a guide RNA. In another aspect, a guide nucleic acid comprises at least one guide RNA. In another aspect, a guide nucleic acid comprises at least two guide RNAs. In another aspect, a guide nucleic acid comprises at least three guide RNAs. In another aspect, a guide nucleic acid comprises at least five guide RNAs. In another aspect, a guide nucleic acid comprises at least ten guide RNAs.

In another aspect, a guide nucleic acid comprises at least 10 nucleotides. In another aspect, a guide nucleic acid comprises at least 11 nucleotides. In another aspect, a guide nucleic acid comprises at least 12 nucleotides. In another aspect, a guide nucleic acid comprises at least 13 nucleotides. In another aspect, a guide nucleic acid comprises at least 14 nucleotides. In another aspect, a guide nucleic acid comprises at least 15 nucleotides. In another aspect, a guide nucleic acid comprises at least 16 nucleotides. In another aspect, a guide nucleic acid comprises at least 17 nucleotides. In another aspect, a guide nucleic acid comprises at least 18 nucleotides. In another aspect, a guide nucleic acid comprises at least 19 nucleotides. In another aspect, a guide nucleic acid comprises at least 20 nucleotides. In another aspect, a guide nucleic acid comprises at least 21 nucleotides. In another aspect, a guide nucleic acid comprises at least 22 nucleotides. In another aspect, a guide nucleic acid comprises at least 23 nucleotides. In another aspect, a guide nucleic acid comprises at least 24 nucleotides. In another aspect, a guide nucleic acid comprises at least 25 nucleotides. In another aspect, a guide nucleic acid comprises at least 26 nucleotides. In another aspect, a guide nucleic acid comprises at least 27 nucleotides. In another aspect, a guide nucleic acid comprises at least 28 nucleotides. In another aspect, a guide nucleic acid comprises at least 30 nucleotides. In another aspect, a guide nucleic acid comprises at least 35 nucleotides. In another aspect, a guide nucleic acid comprises at least 40 nucleotides. In another aspect, a guide nucleic acid comprises at least 45 nucleotides. In another aspect, a guide nucleic acid comprises at least 50 nucleotides.

In another aspect, a guide nucleic acid comprises between 10 nucleotides and 50 nucleotides. In another aspect, a guide nucleic acid comprises between 10 nucleotides and 40 nucleotides. In another aspect, a guide nucleic acid comprises between 10 nucleotides and 30 nucleotides. In another aspect, a guide nucleic acid comprises between 10 nucleotides and 20 nucleotides. In another aspect, a guide nucleic acid comprises between 16 nucleotides and 28 nucleotides. In another aspect, a guide nucleic acid comprises between 16 nucleotides and 25 nucleotides. In another aspect, a guide nucleic acid comprises between 16 nucleotides and 20 nucleotides.

In an aspect, a guide nucleic acid comprises at least 70% sequence complementarity to a target site. In an aspect, a guide nucleic acid comprises at least 75% sequence complementarity to a target site. In an aspect, a guide nucleic acid comprises at least 80% sequence complementarity to a target site. In an aspect, a guide nucleic acid comprises at least 85% sequence complementarity to a target site. In an aspect, a guide nucleic acid comprises at least 90% sequence complementarity to a target site. In an aspect, a guide nucleic acid comprises at least 91% sequence complementarity to a target site. In an aspect, a guide nucleic acid comprises at least 92% sequence complementarity to a target site. In an aspect, a guide nucleic acid comprises at least 93% sequence complementarity to a target site. In an aspect, a guide nucleic acid comprises at least 94% sequence complementarity to a target site. In an aspect, a guide nucleic acid comprises at least 95% sequence complementarity to a target site. In an aspect, a guide nucleic acid comprises at least 96% sequence complementarity to a target site. In an aspect, a guide nucleic acid comprises at least 97% sequence complementarity to a target site. In an aspect, a guide nucleic acid comprises at least 98% sequence complementarity to a target site. In an aspect, a guide nucleic acid comprises at least 99% sequence complementarity to a target site. In an aspect, a guide nucleic acid comprises 100% sequence complementarity to a target site. In another aspect, a guide nucleic acid comprises between 70% and 100% sequence complementarity to a target site. In another aspect, a guide nucleic acid comprises between 80% and 100% sequence complementarity to a target site. In another aspect, a guide nucleic acid comprises between 90% and 100% sequence complementarity to a target site. In an aspect, a guide nucleic acid is capable of hybridizing to a target site.

As noted above, some guided nucleases, such as CasX and Cas9, require another non-coding RNA component, referred to as a trans-activating crRNA (tracrRNA), to have functional activity. Guide nucleic acid molecules provided herein can combine a crRNA and a tracrRNA into one nucleic acid molecule in what is herein referred to as a "single guide RNA" (sgRNA). The gRNA guides the active CasX complex to a target site within a target sequence, where CasX can cleave the target site. In other embodiments, the crRNA and tracrRNA are provided as separate nucleic acid molecules. In an aspect, a guide nucleic acid comprises a crRNA. In another aspect, a guide nucleic acid comprises a tracrRNA. In a further aspect, a guide nucleic acid comprises a sgRNA.

Target Sites

As used herein, a "target sequence" refers to a selected sequence or region of a DNA molecule in which a modification (e.g., cleavage, deamination, site-directed integration) is desired. A target sequence comprises a target site.

As used herein, a "target site" refers to the portion of a target sequence that is modified (e.g., cleaved) by a CRISPR effector protein. In contrast to a non-target nucleic acid (e.g., non-target ssDNA) or non-target region, a target site comprises significant complementarity to a guide nucleic acid or a guide RNA.

In an aspect, a target site is 100% complementary to a guide nucleic acid. In another aspect, a target site is 99% complementary to a guide nucleic acid. In another aspect, a target site is 98% complementary to a guide nucleic acid. In another aspect, a target site is 97% complementary to a guide nucleic acid. In another aspect, a target site is 96% complementary to a guide nucleic acid. In another aspect, a target site is 95% complementary to a guide nucleic acid. In another aspect, a target site is 94% complementary to a guide nucleic acid. In another aspect, a target site is 93% complementary to a guide nucleic acid. In another aspect, a target site is 92% complementary to a guide nucleic acid. In another aspect, a target site is 91% complementary to a guide nucleic acid. In another aspect, a target site is 90% complementary to a guide nucleic acid. In another aspect, a target site is 85% complementary to a guide nucleic acid. In another aspect, a target site is 80% complementary to a guide nucleic acid.

In an aspect, a target site comprises at least one PAM site. In an aspect, a target site is adjacent to a nucleic acid sequence that comprises at least one PAM site. In another aspect, a target site is within 5 nucleotides of at least one PAM site. In a further aspect, a target site is within 10 nucleotides of at least one PAM site. In another aspect, a target site is within 15 nucleotides of at least one PAM site. In another aspect, a target site is within 20 nucleotides of at least one PAM site. In another aspect, a target site is within 25 nucleotides of at least one PAM site. In another aspect, a target site is within 30 nucleotides of at least one PAM site.

In an aspect, a target site is positioned within genic DNA. In another aspect, a target site is positioned within a gene. In another aspect, a target site is positioned within a gene of interest. In another aspect, a target site is positioned within an exon of a gene. In another aspect, a target site is positioned within an intron of a gene. In another aspect, a target site is positioned within 5'-UTR of a gene. In another aspect, a target site is positioned within a 3'-UTR of a gene. In another aspect, a target site is positioned within intergenic DNA.

In an aspect, a target DNA molecule is single-stranded. In another aspect, a target DNA molecule is double-stranded.

In an aspect, a target sequence comprises genomic DNA. In an aspect, a target sequence is positioned within a nuclear genome. In an aspect, a target sequence comprises chromosomal DNA. In an aspect, a target sequence comprises plasmid DNA. In an aspect, a target sequence is positioned within a plasmid. In an aspect, a target sequence comprises mitochondrial DNA. In an aspect, a target sequence is positioned within a mitochondrial genome. In an aspect, a target sequence comprises plastid DNA. In an aspect, a target sequence is positioned within a plastid genome. In an aspect, a target sequence comprises chloroplast DNA. In an aspect, a target sequence is positioned within a chloroplast genome. In an aspect, a target sequence is positioned within a genome selected from the group consisting of a nuclear genome, a mitochondrial genome, and a plastid genome.

In an aspect, a target sequence comprises genic DNA. As used herein, "genic DNA" refers to DNA that encodes one or more genes. In another aspect, a target sequence comprises intergenic DNA. In contrast to genic DNA, "intergenic DNA" comprises noncoding DNA, and lacks DNA encoding a gene. In an aspect, intergenic DNA is positioned between two genes.

In an aspect, a target sequence encodes a gene. As used herein, a "gene" refers to a polynucleotide that can produce a functional unit (e.g., without being limiting, for example, a protein, or a non-coding RNA molecule). A gene can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "gene sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a gene encodes a non-protein-coding RNA molecule or a precursor thereof. In another aspect, a gene encodes a protein. In some embodiments, the target sequence is selected from the group consisting of: a promoter, an enhancer sequence, a leader sequence, a transcriptional start site, a transcriptional stop site, a polyadenylation site, an exon, an intron, a splice site, a 5'-UTR, a 3'-UTR, a protein coding sequence, a non-protein-coding sequence, a miRNA, a pre-miRNA and a miRNA binding site.

Non-limiting examples of a non-protein-coding RNA molecule include a microRNA (miRNA), a miRNA precursor (pre-miRNA), a small interfering RNA (siRNA), a small RNA (18 to 26 nucleotides in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single guide RNA (sgRNA). In an aspect, a non-protein-coding RNA molecule comprises a miRNA. In an aspect, a non-protein-coding RNA molecule comprises a siRNA. In an aspect, a non-protein-coding RNA molecule comprises a ta-siRNA. In an aspect, a non-protein-coding RNA molecule is selected from the group consisting of a miRNA, a siRNA, and a ta-siRNA.

As used herein, a "gene of interest" refers to a polynucleotide sequence encoding a protein or a non-protein-coding RNA molecule that is to be integrated into a target sequence, or, alternatively, an endogenous polynucleotide sequence encoding a protein or a non-protein-coding RNA molecule that is to be edited by a ribonucleoprotein. In an aspect, a gene of interest encodes a protein. In another aspect, a gene of interest encodes a non-protein-coding RNA molecule. In an aspect, a gene of interest is exogenous to a targeted DNA molecule. In an aspect, a gene of interest replaces an endogenous gene in a targeted DNA molecule.

Mutations

In an aspect, a ribonucleoprotein or method provided herein generates at least one mutation in a target sequence of an egg, embryo, and/or meiotic cell.

In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to an egg cell-preferred promoter or a second nucleic acid encoding at least one guide nucleic acid operably linked to a heterologous second promoter. In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to an embryo tissue-preferred promoter or a second nucleic acid encoding at least one guide nucleic acid operably linked to a heterologous second promoter. In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to a heterologous promoter or a second nucleic acid encoding at least one guide nucleic acid operably linked to an egg cell-preferred promoter. In an aspect, a seed produced from a plant provided herein comprises at least one mutation in a gene of interest comprising a target site as compared to a seed of a control plant of the same line or variety that lacks a first nucleic acid sequence encoding a guided nuclease operably linked to a heterologous promoter or a second nucleic acid encoding at least one guide nucleic acid operably linked to an embryo tissue-preferred promoter.

As used herein, a "mutation" refers to a non-naturally occurring alteration to a nucleic acid or amino acid sequence as compared to a naturally occurring reference nucleic acid or amino acid sequence from the same organism. It will be appreciated that, when identifying a mutation, the reference sequence should be from the same nucleic acid (e.g., gene, non-coding RNA) or amino acid (e.g., protein). In determining if a difference between two sequences comprises a mutation, it will be appreciated in the art that the comparison should not be made between homologous sequences of two different species or between homologous sequences of two different varieties of a single species. Rather, the comparison should be made between the edited (e.g., mutated) sequence and the endogenous, non-edited (e.g., "wildtype") sequence of the same organism.

Several types of mutations are known in the art. In an aspect, a mutation comprises an insertion. An "insertion" refers to the addition of one or more nucleotides or amino acids to a given polynucleotide or amino acid sequence, respectively, as compared to an endogenous reference polynucleotide or amino acid sequence. In another aspect, a mutation comprises a deletion. A "deletion" refers to the removal of one or more nucleotides or amino acids to a given polynucleotide or amino acid sequence, respectively, as compared to an endogenous reference polynucleotide or amino acid sequence. In another aspect, a mutation comprises a substitution. A "substitution" refers to the replacement of one or more nucleotides or amino acids to a given polynucleotide or amino acid sequence, respectively, as compared to an endogenous reference polynucleotide or amino acid sequence. In another aspect, a mutation comprises an inversion. An "inversion" refers to when a segment of a polynucleotide or amino acid sequence is reversed end-to-end. In an aspect, a mutation provided herein comprises a mutation selected from the group consisting of an insertion, a deletion, a substitution, and an inversion.

In an aspect, a plant or seed comprises at least one mutation in a gene of interest, where the at least one mutation results in the deletion of one or more amino acids from a protein encoded by the gene of interest as compared to a wildtype protein.

In an aspect, a plant or seed comprises at least one mutation in a gene of interest, where the at least one mutation results in the substitution of one or more amino acids within a protein encoded by the gene of interest as compared to a wildtype protein.

In an aspect, a plant or seed comprises at least one mutation in a gene of interest, where the at least one mutation results in the insertion of one or more amino acids within a protein encoded by the gene of interest as compared to a wildtype protein.

Mutations in coding regions of genes (e.g., exonic mutations) can result in a truncated protein or polypeptide when a mutated messenger RNA (mRNA) is translated into a protein or polypeptide. In an aspect, this disclosure provides a mutation that results in the truncation of a protein or polypeptide. As used herein, a "truncated" protein or polypeptide comprises at least one fewer amino acid as compared to an endogenous control protein or polypeptide. For example, if endogenous Protein A comprises 100 amino acids, a truncated version of Protein A can comprise between 1 and 99 amino acids.

Without being limited by any scientific theory, one way to cause a protein or polypeptide truncation is by the introduction of a premature stop codon in an mRNA transcript of an endogenous gene. In an aspect, this disclosure provides a mutation that results in a premature stop codon in an mRNA transcript of an endogenous gene. As used herein, a "stop codon" refers to a nucleotide triplet within an mRNA transcript that signals a termination of protein translation. A "premature stop codon" refers to a stop codon positioned earlier (e.g., on the 5'-side) than the normal stop codon position in an endogenous mRNA transcript. Without being limiting, several stop codons are known in the art, including "UAG," "UAA," "UGA," "TAG," "TAA," and "TGA."

In an aspect, a seed or plant comprises at least one mutation, where the at least one mutation results in the introduction of a premature stop codon in a messenger RNA encoded by the gene of interest as compared to a wildtype messenger RNA.

In an aspect, a mutation provided herein comprises a null mutation. As used herein, a "null mutation" refers to a mutation that confers a complete loss-of-function for a protein encoded by a gene comprising the mutation, or, alternatively, a mutation that confers a complete loss-of-function for a small RNA encoded by a genomic locus. A null mutation can cause lack of mRNA transcript production, a lack of small RNA transcript production, a lack of protein function, or a combination thereof.

A mutation provided herein can be positioned in any part of an endogenous gene. In an aspect, a mutation provided herein is positioned within an exon of an endogenous gene. In another aspect, a mutation provided herein is positioned within an intron of an endogenous gene. In a further aspect, a mutation provided herein is positioned within a 5'-untranslated region of an endogenous gene. In still another aspect, a mutation provided herein is positioned within a 3'-untranslated region of an endogenous gene. In yet another aspect, a mutation provided herein is positioned within a promoter of an endogenous gene.

In an aspect, a mutation is positioned at a splice site within a gene. A mutation at a splice site can interfere with the splicing of exons during mRNA processing. If one or more nucleotides are inserted, deleted, or substituted at a splice site, splicing can be perturbed. Perturbed splicing can result in unspliced introns, missing exons, or both, from a mature mRNA sequence. Typically, although not always, a "GU" sequence is required at the 5' end of an intron and a "AG" sequence is required at the 3' end of an intron for proper splicing. If either of these splice sites are mutated, splicing perturbations can occur.

In an aspect, a seed or plant comprises at least one mutation, where the at least one mutation comprises the deletion of one or more splice sites from a gene of interest. In another aspect, a seed or plant comprises at least one mutation, where the at least one mutation is positioned within one or more splice sites from a gene of interest.

In an aspect, a mutation comprises a site-directed integration. In an aspect, a site-directed integration comprises the insertion of all or part of a desired sequence into a target sequence.

As used herein, "site-directed integration" refers to all, or a portion, of a desired sequence (e.g., an exogenous gene, an edited endogenous gene) being inserted or integrated at a desired site or locus within the plant genome (e.g., target sequence). As used herein, a "desired sequence" refers to a DNA molecule comprising a nucleic acid sequence that is to be integrated into a genome of a plant or plant cell. The desired sequence can comprise a transgene or construct. In an aspect, a nucleic acid molecule comprising a desired sequence comprises one or two homology arms flanking the desired sequence to promote the targeted insertion event through homologous recombination and/or homology-directed repair.

In an aspect, a method provided herein comprises site-directed integration of a desired sequence into a target sequence.

Any site or locus within the genome of a plant can be chosen for site-directed integration of a transgene or construct of the present disclosure. In an aspect, a target sequence is positioned within a B, or supernumerary, chromosome.

For site-directed integration, a double-strand break (DSB) or nick may first be made at a target sequence via a guided nuclease or ribonucleoprotein provided herein. In the presence of a desired sequence, the DSB or nick can then be repaired by homologous recombination (HR) between the homology arm(s) of the desired sequence and the target sequence, or by non-homologous end joining (NHEJ), resulting in site-directed integration of all or part of the desired sequence into the target sequence to create the targeted insertion event at the site of the DSB or nick.

In an aspect, site-directed integration comprises the use of NHEJ repair mechanisms endogenous to a cell. In another aspect, site-directed integration comprises the use of HR repair mechanisms endogenous to a cell.

In an aspect, repair of a double-stranded break generates at least one mutation in a gene of interest as compared to a control plant of the same line or variety.

In an aspect, a mutation comprises the integration of at least 5 contiguous nucleotides of a desired sequence into a target sequence. In an aspect, a mutation comprises the integration of at least 10 contiguous nucleotides of a desired sequence molecule into a target sequence. In an aspect, a mutation comprises the integration of at least 15 contiguous nucleotides of a desired sequence into a target sequence. In an aspect, a mutation comprises the integration of at least 20 contiguous nucleotides of a desired sequence into a target sequence. In an aspect, a mutation comprises the integration of at least 25 contiguous nucleotides of a desired sequence into a target sequence. In an aspect, a mutation comprises the integration of at least 50 contiguous nucleotides of a desired sequence into a target sequence. In an aspect, a mutation comprises the integration of at least 100 contiguous nucleotides of a desired sequence into a target sequence. In an aspect, a mutation comprises the integration of at least 250 contiguous nucleotides of a desired sequence into a target sequence. In an aspect, a mutation comprises the integration of at least 500 contiguous nucleotides of a desired sequence into a target sequence. In an aspect, a mutation comprises the integration of at least 1000 contiguous nucleotides of a desired sequence into a target sequence. In an aspect, a mutation comprises the integration of at least 2000 contiguous nucleotides of a desired sequence into a target sequence.

In an aspect, a mutation comprises the integration of between 5 contiguous nucleotides and 3500 contiguous nucleotides of a desired sequence into a target sequence. In an aspect, a mutation comprises the integration of between 5 contiguous nucleotides and 2500 contiguous nucleotides of a desired sequence into a target sequence. In an aspect, a mutation comprises the integration of between 5 contiguous nucleotides and 1500 contiguous nucleotides of a desired sequence into a target sequence. In an aspect, a mutation comprises the integration of between 5 contiguous nucleotides and 750 contiguous nucleotides of a desired sequence into a target sequence. In an aspect, a mutation comprises the integration of between 5 contiguous nucleotides and 500 contiguous nucleotides of a desired sequence into a target sequence. In an aspect, a mutation comprises the integration of between 5 contiguous nucleotides and 250 contiguous nucleotides of a desired sequence into a target sequence. In an aspect, a mutation comprises the integration of between 5 contiguous nucleotides and 150 contiguous nucleotides of a desired sequence into a target sequence. In an aspect, a mutation comprises the integration of between 25 contiguous nucleotides and 2500 contiguous nucleotides of a desired sequence into a target sequence. In an aspect, a mutation comprises the integration of between 25 contiguous nucleotides and 1500 contiguous nucleotides of a desired sequence into a target sequence. In an aspect, a mutation comprises the integration of between 25 contiguous nucleotides and 750 contiguous nucleotides of a desired sequence into a target sequence. In an aspect, a mutation comprises the integration of between 50 contiguous nucleotides and 2500 contiguous nucleotides of a desired sequence into a target sequence. In an aspect, a mutation comprises the integration of between 50 contiguous nucleotides and 1500 contiguous nucleotides of a desired sequence into a target sequence. In an aspect, a mutation comprises the integration of between 50 contiguous nucleotides and 750 contiguous nucleotides of a desired sequence into a target sequence. In an aspect, a mutation comprises the integration of between 100 contiguous nucleotides and 2500 contiguous nucleotides of a desired sequence into a target Sequence. In an aspect, a mutation comprises the integration of between 100 contiguous nucleotides and 1500 contiguous nucleotides of a desired sequence into a target Sequence. In an aspect, a mutation comprises the integration of between 100 contiguous nucleotides and 750 contiguous nucleotides of a desired sequence into a target Sequence.

In an aspect, a method provided herein comprises detecting an edit or a mutation in a target sequence. The screening and selection of mutagenized or edited plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the above-referenced techniques are known in the art.

Recombinases

Several embodiments described herein relate to methods and compositions for preferably or specifically inducing site-specific recombination in egg, embryo, and/or meiotic plant tissue. Several embodiments described herein relate to methods and compositions for providing egg, embryo, and/or meiotic plant tissue preferred or specific expression of a recombinase. Several embodiments described herein relate to methods and compositions for preferably or specifically expressing a DNA modification enzyme, such as a guided nuclease (e.g., a CRISPR/Cas system), in egg, embryo, and/or meiotic plant tissue by inducing site-specific recombination to operably linking a polynucleotide encoding a DNA modification enzyme to a constitutive promoter. In some embodiments, a transcribable polynucleotide encoding a DNA modification enzyme, such as a guided nuclease (e.g., a CRISPR/Cas system) is operably linked to a constitutive promoter by recombinase-mediated excision of a intervening polynucleotide sequence preferentially or specifically in egg, embryo, and/or meiotic plant tissue.

Site-specific recombination occurs when DNA strand exchange takes place between DNA segments possessing at least some sequence homology with each other. Site-specific recombinases are able to recognize and bind to "recombination sites," which are short, specific DNA sequences which are cleaved by the recombinase, allowing the exchange of DNA strands, which is followed by strand repair. Typically, each recombinase protein binds to a specific, and unique, recombination site. As used herein, a "recombinase" refers to an enzyme that is capable of catalyzing site-specific recombination events within DNA. Recombinases are capable of excising DNA, inserting DNA, inverting DNA, translocating DNA, and/or exchanging DNA.

In an aspect, this disclosure provides methods and compositions for specifically or preferentially providing a recombinase in egg, embryo, and/or meiotic plant tissue. In an aspect, this disclosure provides a nucleic acid sequence encoding a recombinase operably linked to a promoter as described in Table 1. In an aspect, a recombinant nucleic acid construct comprises a sequence encoding at least one recombinase operably linked to a promoter as described in Table 1. In an aspect, a recombinant nucleic acid construct comprising a sequence encoding at least one recombinase operably linked to a promoter as described in Table 1 is provided to a plant cell in combination with a recombinant nucleic acid construct comprising a polynucleotide encoding a DNA modification enzyme, an intervening sequence flanked by recombination sites, and a constitutive promoter, wherein excision of the intervening sequence operably links polynucleotide encoding a DNA modification enzyme to the constitutive promoter preferentially in egg, embryo, and/or meiotic tissue.

In an aspect, a recombinase is a tyrosine recombinase. In an aspect, a tyrosine recombinase is selected from the group consisting of a Cre recombinase and a Flp recombinase.

In an aspect, a recombinase is Cre recombinase. Cre-lox is a site-specific recombination system derived from the bacteriophage P1. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete.

In an aspect, a recombinase is Flippase (Flp). The Flp-FRT site-specific recombination system comes from the 2μ plasmid from the baker's yeast *Saccharomyces cerevisiae* and is similar to the Cre-lox system. Flp is capable of inducing recombination between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites.

In an aspect, a recombination site is a lox site. In an aspect, a lox site is selected from the group consisting of a loxP site, a lox 2272 site, a loxN site, a lox 511 site, a lox 5171 site, a lox71 site, a lox66 site, a loxLTR site, an M2 site, an M3 site, an M7 site, and an M11 site. In an aspect, a recombination site is an FRT site.

Tale

Several embodiments provided herein relate to the use of TALE activators to preferentially express a DNA modification enzyme, such as a guided nuclease (e.g., a CRISPR/Cas system), in egg, embryo, and/or meiotic plant tissue. In several embodiments, high levels of egg, embryo, and/or meiotic tissue specific expression of a DNA modification enzyme such as a guided nuclease (e.g., a CRISPR/Cas system), by providing to a plant cell: 1) an expression construct comprising a promoter as described in Table 1 operably linked to a sequence encoding a TALE and 2) and an expression construct comprising one or more TALE binding sites (TB) operably linked to a minimal promoter and a sequence encoding the DNA modification enzyme and generating a plant therefrom. In some embodiments, an expression construct encoding one or more guide nucleic acids is further provided. In some embodiments, levels of egg, embryo, and/or meiotic tissue specific expression of a DNA modification enzyme can be modulated by altering the number of TBs.

As used herein, "TALE protein" refers to a transcription activator-like effector (TALE) protein or a homolog thereof. TALE proteins were originally identified as a virulence factor from the phytopathogenic bacterial genera *Xanthomonas* or *Ralstonia*. These proteins are secreted by the phytopathogenic bacteria to alter transcription of host genes in plant cells. TALE proteins bind DNA in the nucleus, via a domain of DNA-binding repeats, where they act as transcriptional activators thereby contributing to virulence. The TALE moves to the nucleus, where it recognizes and binds to a specific DNA sequence in the regulatory region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs. As used herein, a "TALE binding site" (TBS) refers to a specific DNA sequence that is recognized and bound by the "TALE DNA-binding domain" of the TALE protein.

Plants

Any plant or plant cell can be used with the methods and compositions provided herein. In an aspect, a plant is selected from the group consisting of a corn plant, a rice plant, a sorghum plant, a wheat plant, an alfalfa plant, a barley plant, a millet plant, a rye plant, a sugarcane plant, a cotton plant, a soybean plant, a canola plant, a tomato plant, an onion plant, a cucumber plant, an *Arabidopsis* plant, and a potato plant. In an aspect, a plant is an angiosperm. In an aspect, a plant is a gymnosperm. In an aspect, a plant is a monocotyledonous plant. In an aspect, a plant is a dicotyledonous plant. In an aspect, a plant is a plant of a family selected from the group consisting of Alliaceae, Anacardiaceae, Apiaceae, Arecaceae, Asteraceae, Brassicaceae, Caesalpiniaceae, Cucurbitaceae, Ericaceae, Fabaceae, Juglandaceae, Malvaceae, Mimosaceae, Moraceae, Musaceae, Orchidaceae, Papilionaceae, Pinaceae, Poaceae, Rosaceae, Rutaceae, Rubiaceae, and Solanaceae.

In an aspect, a plant cell is selected from the group consisting of a corn cell, a rice cell, a sorghum cell, a wheat cell, an alfalfa cell, a barley cell, a millet cell, a rye cell, a sugarcane cell, a cotton cell, a soybean cell, a canola cell, a tomato cell, an onion cell, a cucumber cell, an *Arabidopsis* cell, and a potato cell. In an aspect, a plant cell is an angiosperm plant cell. In an aspect, a plant cell is a gymnosperm plant cell. In an aspect, a plant cell is a monocotyledonous plant cell. In an aspect, a plant cell is a dicotyledonous plant cell. In an aspect, a plant cell is a plant cell of a family selected from the group consisting of Alliaceae, Anacardiaceae, Apiaceae, Arecaceae, Asteraceae, Brassicaceae, Caesalpiniaceae, Cucurbitaceae, Ericaceae, Fabaceae, Juglandaceae, Malvaceae, Mimosaceae, Moraceae, Musaceae, Orchidaceae, Papilionaceae, Pinaceae, Poaceae, Rosaceae, Rutaceae, Rubiaceae, and Solanaceae.

As used herein, a "variety" refers to a group of plants within a species (e.g., without being limiting *Zea mays*) that share certain genetic traits that separate them from other possible varieties within that species. Varieties can be inbreds or hybrids, though commercial plants are often hybrids to take advantage of hybrid vigor. Individuals within a hybrid cultivar are homogeneous, nearly genetically identical, with most loci in the heterozygous state.

As used herein, the term "inbred" means a line that has been bred for genetic homogeneity. In an aspect, a seed provided herein is an inbred seed. In an aspect, a plant provided herein is an inbred plant.

As used herein, the term "hybrid" means a progeny of mating between at least two genetically dissimilar parents. Without limitation, examples of mating schemes include single crosses, modified single cross, double modified single cross, three-way cross, modified three-way cross, and double cross wherein at least one parent in a modified cross is the progeny of a cross between sister lines. In an aspect, a seed provided herein is a hybrid seed. In an aspect, a plant provided herein is a hybrid plant.

Transformation

Methods can involve transient transformation or stable integration of any nucleic acid molecule into any plant or plant cell provided herein.

As used herein, "stable integration" or "stably integrated" refers to a transfer of DNA into genomic DNA of a targeted cell or plant that allows the targeted cell or plant to pass the transferred DNA to the next generation of the transformed organism. Stable transformation requires the integration of transferred DNA within the reproductive cell(s) of the transformed organism. As used herein, "transiently transformed" or "transient transformation" refers to a transfer of DNA into a cell that is not transferred to the next generation of the transformed organism. In a transient transformation the transformed DNA does not typically integrate into the transformed cell's genomic DNA. In one aspect, a method stably transforms a plant cell or plant with one or more nucleic acid molecules provided herein. In another aspect, a method transiently transforms a plant cell or plant with one or more nucleic acid molecules provided herein.

In an aspect, a nucleic acid molecule encoding a guided nuclease is stably integrated into a genome of a plant. In an aspect, a nucleic acid molecule encoding a Cas12a nuclease is stably integrated into a genome of a plant. In an aspect, a nucleic acid molecule encoding a CasX nuclease is stably integrated into a genome of a plant. In an aspect, a nucleic acid molecule encoding a guide nucleic acid is stably integrated into a genome of a plant. In an aspect, a nucleic acid molecule encoding a guide RNA is stably integrated into a genome of a plant. In an aspect, a nucleic acid molecule encoding a single-guide RNA is stably integrated into a genome of a plant.

Numerous methods for transforming cells with a recombinant nucleic acid molecule or construct are known in the art, which can be used according to methods of the present application. Any suitable method or technique for transformation of a cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants.

In an aspect, a method comprises providing a cell with a nucleic acid molecule via *Agrobacterium*-mediated transformation. In an aspect, a method comprises providing a cell with a nucleic acid molecule via polyethylene glycol-mediated transformation. In an aspect, a method comprises providing a cell with a nucleic acid molecule via biolistic transformation. In an aspect, a method comprises providing a cell with a nucleic acid molecule via liposome-mediated transfection. In an aspect, a method comprises providing a cell with a nucleic acid molecule via viral transduction. In an aspect, a method comprises providing a cell with a nucleic acid molecule via use of one or more delivery particles. In an aspect, a method comprises providing a cell with a nucleic acid molecule via microinjection. In an aspect, a method comprises providing a cell with a nucleic acid molecule via electroporation.

In an aspect, a nucleic acid molecule is provided to a cell via a method selected from the group consisting of *Agrobacterium*-mediated transformation, polyethylene glycol-mediated transformation, biolistic transformation, liposome-mediated transfection, viral transduction, the use of one or more delivery particles, microinjection, and electroporation.

Other methods for transformation, such as vacuum infiltration, pressure, sonication, and silicon carbide fiber agitation, are also known in the art and envisioned for use with any method provided herein.

Methods of transforming cells are well known by persons of ordinary skill in the art. For instance, specific instructions for transforming plant cells by microprojectile bombardment with particles coated with recombinant DNA (e.g., biolistic transformation) are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Delivery vehicles, vectors, particles, nanoparticles, formulations and components thereof for expression of one or more elements of a nucleic acid molecule are as used in WO 2014/093622. In an aspect, a method of providing a nucleic acid molecule or a protein to a cell comprises delivery via a delivery particle. In an aspect, a method of providing a nucleic acid molecule to a plant cell or plant comprises delivery via a delivery vesicle. In an aspect, a delivery vesicle is selected from the group consisting of an exosome and a liposome. In an aspect, a method of providing a nucleic acid molecule to a plant cell or plant comprises delivery via a viral vector. In an aspect, a viral vector is selected from the group consisting of an adenovirus vector, a lentivirus vector, and an adeno-associated viral vector. In another aspect, a method providing a nucleic acid molecule to a plant cell or plant comprises delivery via a nanoparticle. In an aspect, a method providing a nucleic acid molecule to a plant cell or plant comprises microinjection. In an aspect, a method providing a nucleic acid molecule to a plant cell or plant comprises polycations. In an aspect, a method providing a nucleic acid molecule to a plant cell or plant comprises a cationic oligopeptide.

In an aspect, a delivery particle is selected from the group consisting of an exosome, an adenovirus vector, a lentivirus vector, an adeno-associated viral vector, a nanoparticle, a polycation, and a cationic oligopeptide. In an aspect, a method provided herein comprises the use of one or more delivery particles. In another aspect, a method provided herein comprises the use of two or more delivery particles. In another aspect, a method provided herein comprises the use of three or more delivery particles.

Suitable agents to facilitate transfer of nucleic acids into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning includes (a) surfactants, (b) organic solvents, aqueous solutions, or aqueous mixtures of organic solvents, (c) oxidizing agents, (e) acids, (f) bases, (g) oils, (h) enzymes, or combinations thereof.

Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e.g., plant-sourced oils, crop oils (such as those listed in the 9$^{th}$ Compendium of Herbicide Adjuvants, publicly available on line at www(dot)herbicide (dot)adjuvants(dot)com) can be used, e.g., paraffinic oils, polyol fatty acid esters, or oils with short-chain molecules modified with amides or polyamines such as polyethyleneimine or N-pyrrolidine.

Examples of useful surfactants include sodium or lithium salts of fatty acids (such as tallow or tallowamines or phospholipids) and organosilicone surfactants. Other useful surfactants include organosilicone surfactants including nonionic organosilicone surfactants, e.g., trisiloxane ethoxylate surfactants or a silicone polyether copolymer such as a copolymer of polyalkylene oxide modified heptamethyl trisiloxane and allyloxypolypropylene glycol methylether (commercially available as Silwet® L-77).

Useful physical agents can include (a) abrasives such as carborundum, corundum, sand, calcite, pumice, garnet, and the like, (b) nanoparticles such as carbon nanotubes or (c) a physical force. Carbon nanotubes are disclosed by Kam et. al. (2004) Am. Chem. Soc, 126 (22):6850-6851, Liu et. al. (2009) Nano Lett, 9(3): 1007-1010, and Khodakovskaya et. al. (2009) ACS Nano, 3(10):3221-3227. Physical force agents can include heating, chilling, the application of positive pressure, or ultrasound treatment. Embodiments of the method can optionally include an incubation step, a neutralization step (e.g., to neutralize an acid, base, or oxidizing agent, or to inactivate an enzyme), a rinsing step, or combinations thereof. The methods of the invention can further include the application of other agents which will have enhanced effect due to the silencing of certain genes. For example, when a polynucleotide is designed to regulate genes that provide herbicide resistance, the subsequent application of the herbicide can have a dramatic effect on herbicide efficacy.

Agents for laboratory conditioning of a plant cell to permeation by polynucleotides include, e.g., application of a chemical agent, enzymatic treatment, heating or chilling, treatment with positive or negative pressure, or ultrasound treatment. Agents for conditioning plants in a field include chemical agents such as surfactants and salts.

In an aspect, a transformed or transfected cell is a plant cell. Recipient plant cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a guard cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U.S. Patent Application Publication 2004/0216189, all of which are incorporated herein by reference. Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction. In one aspect, this disclosure provides a non-reproductive plant cell.

Use of Haploids/Haploid Induction Lines

Several embodiments relate to the use of the methods and compositions as described herein in combination with haploid induction techniques. As used herein, a "haploid" cell or nucleus comprises a single set of unpaired chromosomes (x). In contrast, a "diploid" cell or nucleus comprises two complete sets of chromosomes (2x) that are capable of homologous pairing. As used herein, a "haploid plant" describes a sporophyte comprising a plurality of cells comprising a haploid nuclear genome. A haploid plant provided herein can be a maternal haploid plant, meaning it has lost its paternal nuclear genome while retaining its maternal nuclear genome. Alternatively, a haploid plant provided herein can be a paternal haploid plant, meaning it has lost its maternal nuclear genome while retaining its paternal nuclear genome. Typically, maternal mitochondria and plastid (e.g., chloroplast) genomes are retained in both maternal and paternal haploid plants.

In some embodiments, a 'doubled haploid (DH)' method is used to rapidly produce homozygous plants. Progenies of DH plants are genetically homogeneous material, allowing breeders to evaluate their traits of interest on genetically fixed material at an early stage of the breeding cycle, thus increasing breeding efficiency (see Gilles L M et. al. Curr Biol. 2017 Oct. 23; 27(20):R1095-R1097. The DH technology relies on two main steps: (1) a haploid induction system to generate haploid embryos or plantlets, and (2) a chromosome doubling step to restore diploidy of these plantlets.

"Haploid induction (HI)" is a phenomena in some plants characterized by loss of the parental inducer chromosomes during embryo development. As used herein, a "haploid induction (HI) plant" is a plant capable of inducing haploidization in a progeny plant by eliminating one set of chromosomes. Maternal haploid induction is triggered by the pollinator (male) parent. Paternal haploid induction is triggered by the female parent.

Haploid inducer lines are routinely used in plant breeding especially for maize. A number of known haploid-inducing maize lines exist including but not limited to: stock 6, MHI (Moldovian Haploid Inducer), indeterminate gametophyte (ig 1) mutation, KEMS, RWK, ZEM, ZMS, KMS. Haploid inducer lines have also been created in *Arabidopsis thaliana, Brassica juncea* and maize by the use of engineered centromeric histone 3 (CENH3) variants (See Ravi and Chan. 2010. Nature. 464:615-6190). In some aspects, the haploid induction lines described here include the Maize Stock 6 line, maize plants harboring mutations in the ig-1 locus, MHI inducer lines, KEMS inducer lines, RWK inducer lines, ZEM inducer lines, ZMS inducer lines, KMS inducer lines. In some aspects the Haploid inducer line comprises a modified MATRILINEAL/NOT LIKE DAD/ZmPHOSPHOLIPASE-A1 (MATL/NLD/ZmPLA1) gene. In some aspects, the haploid inducer line described herein comprises a modified CEN H3 variant.

The benefits offered by haploid induction systems to crop breeding programs are diverse, as DH technology can be used in conjunction with several different molecular techniques to overcome various constraints to crop improvement. One example is the use of haploid induction systems to expand the application of genome editing technologies to crops. The genome editing component (for e.g., the guided nuclease) could be introduced into the Haploid Inducer line which is then crossed to a non-inducer maize line. The haploid progeny is then screened for nuclease-induced mutations and genome doubling is subsequently induced to produce diploid, editing component-free, genome-edited cultivars. This methodology has been described in detail in US20190169596 (U.S. application Ser. No. 16/275,200) and is incorporated herein by reference in its entirety.

The present disclosure will now be described with reference to the following examples. It should be appreciated that these examples are not intended to limit the scope of the claims to the present disclosure; but are rather intended to be examples of certain embodiments. Any variations in the exemplified methods that occur to the skilled artisan are intended to fall within the scope of the present disclosure.

EXAMPLES

Example 1. Expression of Cas12a in Meiotic Egg Cells or Embryo Tissue to Generate Germinal Mutations or Targeted Integration of Template DNA Several *Agrobacterium* T-DNA vectors were generated to preferentially express Cas12a in corn egg cells and/or corn embryo cells undergoing meiosis (meiocytes). See Table 2.

TABLE 2

Cassettes designed to express Cas12a preferentially, or solely, in corn egg cells and/or corn embryo cells and/or cells undergoing meiosis.

| Construct | Promoter::LbCas12a | Expression | Promoter SEQ ID NO. |
|---|---|---|---|
| 1 | ZmDSUL1::LbCas12a | Embryo | 1 |
| 2 | ZmEA1::LbCas12a | Egg/Embryo | 2 |
| 3 | ZmES4::LbCas12a | Egg/Embryo | 3 |
| 4 | ZmDMC1::LbCas12a | Meiocyte | 4 |
| 5 | ZmMps1::LbCas12a | Meiocyte | 5 |
| 6 | ZmAdf1::LbCas12a | Meiocyte | 6 |

The plant codon optimized LbCas12a sequence (SEQ ID NO: 7) in these cassettes was flanked by NLS sequences at the 5' and 3' ends (SEQ ID:8 and SEQ ID:9) and operably linked to a transcription terminator sequence from a rice Lipid transfer protein (LTP) gene (described in US20200080096 as SEQ ID NO:8). Each vector also contained an expression cassette encoding a Cas12a gRNA targeting a unique corn genomic site (ZmTS1) under the control of the Pol III ZmU6 promoter (SEQ ID NO: 10); an expression cassette flanked by ZmTS1 target sites, where the cassette comprised a constitutive promoter operably linked to a Gene of Interest (GOI); and an expression cassette for a selectable marker conferring resistance to the herbicide glyphosate. Corn 01DKD2 cultivar embryos were transformed with the vectors described above by *agrobacterium*-mediated transformation and R0 plants were regenerated from the transformed corn cells. DNA was extracted from leaf samples from 59-153 R0 seedlings generated from each construct. The genomic target site was sequenced and analyzed for the presence of targeted mutations. A Taqman based assay was also performed to identify the copy number of the Cas12a carrying construct. For all reproductive promoters except ZmDSUL, no mutations were detected at ZmTS1 site in the R0 generation. The ZmDSUL:LbCas12a (Construct 1), showed about a 32% target site mutation rate in the R0 seedlings (See Table 3). Lack of mutations at the ZmTS1 target site in the newly transformed (or R0) plants is expected where LbCas12a expression is confined to the reproductive tissue.

20 R0 lines from each transformed construct were grown to maturity and at least one ear from each transformed corn plant was self-pollinated. 10 R1 lines were selected and up to 16 seedlings per line were germinated, screened for mutations in ZmTS1 and the mutation rates (cutting rates) were calculated. Taqman assays were also performed to determine the presence and copy number of the LbCas12a expression cassette. The overall target site mutation rate among all lines generated from Constructs 2-5 ranged from about a 1.1% to 14%. The average mutation rates are shown in Table 3. 4 R1 seedlings expressing ZmDSUL::LbCas12a (Construct 1) were tested and no mutations were observed. Co-expression of Cas12a and its cognitive gRNA in cells undergoing meiosis are expected to generate a double stranded break at the ZmTS1 target site and subsequent imperfect DNA repair generates unique mutations in egg cells and embryos created by the pollination.

TABLE 3

Average mutation rates observed at ZmTS1 target site in R0 and R1 plants

| | Promoter | | | | | |
|---|---|---|---|---|---|---|
| Construct | ZmDMC1 4 | ZmMps1 5 | ZmAdf1 6 | ZmES4 3 | ZmEA1 2 | DSUL1 1 |
| Expression | Meiotic | Meiotic | Meiotic | Egg/Embryo | Egg/Embryo | Embryo |
| R0 Events tested | 153 | 110 | 153 | 81 | 115 | 59 |
| R0 Cutting Rate (Avg.) | 0% | 0% | 0% | 0% | 0% | 32% |
| R1 Cutting (Avg.) | 7.69% | 2.67% | 1.10% | 14.04% | 3.60% | 0.00% |

Mutation rates in R1 plants generated from individual R0 lines can vary as shown in Tables 4-8. For example, in the highest cutting promoter, ZmES4, some lines with single copy Cpf1 cassette showed 0% mutation rate, while another line showed about an 11% mutation rate. The highest mutation rate observed was 46%, which originated from an R0 line that had two copies of ZmES4:LbCas12a. In the ZmES4:Cas12a plants, consistently among all lines tested, R0 lines with 2 copies of Cas12a had a higher target mutation rate than one copy R0 lines (see Table 7).

TABLE 4

Mutation rates in R1 seedlings from pZmDMC1::LbCas12a transformed Corn plants.

| R0 Event | Number of R1 plants | Number Cas12a+ plants | Number Cas12a+ Mutation+ | % mutations in Cas12a+ plants | Cas12a Copy number |
|---|---|---|---|---|---|
| ZM_S22307337 | 13 | 10 | 0 | 0.00% | 1 |
| ZM_S22307366 | 12 | 8 | 0 | 0.00% | 1 |
| ZM_S22307385 | 15 | 11 | 0 | 0.00% | 1 |
| ZM_S22307402 | 16 | 14 | 0 | 0.00% | 1 |
| ZM_S22307410 | 16 | 14 | 3 | 21.43% | 1 |
| ZM_S22307411 | 16 | 13 | 1 | 7.69% | 1 |
| ZM_S22307475 | 14 | 11 | 1 | 9.09% | 1 |

TABLE 4-continued

Mutation rates in R1 seedlings from pZmDMC1::LbCas12a transformed Corn plants.

| R0 Event | Number of R1 plants | Number Cas12a+ plants | Number Cas12a+ Mutation+ | % mutations in Cas12a+ plants | Cas12a Copy number |
|---|---|---|---|---|---|
| ZM_S22307488 | 12 | 11 | 1 | 9.09% | 1 |
| ZM_S22307495 | 15 | 12 | 1 | 8.33% | 2 |

TABLE 5

Mutation rates in R1 seedlings from pZmMPS4::LbCas 12a transformed Corn plants.

| R0 Event | Number of R1 plants | Number Cas12a+ plants | Number Cas12a+ Mutation+ | % Mutant in Cas12a+ plants | Cas12a copy number |
|---|---|---|---|---|---|
| ZM_S22324677 | 15 | 12 | 1 | 8.33% | 2 |
| ZM_S22324740 | 16 | 12 | 0 | 0.00% | 1 |
| ZM_S22324702 | 13 | 8 | 0 | 0.00% | 1 |
| ZM_S22324681 | 16 | 9 | 0 | 0.00% | 1 |
| ZM_S22324728 | 16 | 14 | 0 | 0.00% | 2 |
| ZM_S22324698 | 15 | 11 | 0 | 0.00% | 1 |
| ZM_S22324652 | 14 | 10 | 1 | 10.00% | 2 |
| ZM_S22324654 | 16 | 9 | 1 | 11.11% | 1 |
| ZM_S22324675 | 15 | 14 | 1 | 7.14% | 1 |
| ZM_S22324723 | 13 | 10 | 0 | 0.00% | 1 |

TABLE 6

Mutation rates in R1 seedlings from pZmAdf1::LbCas 12a transformed Corn plants.

| R0 Event | Number of R1 plants | Number Cas12a+ plants | Number Cas12a+ Mutation+ | % mutant in Cas12a+ plants | Cas12a copy number |
|---|---|---|---|---|---|
| ZM_S22309320 | 16 | 12 | 1 | 8.33% | 2 |
| ZM_S22309333 | 11 | 8 | 0 | 0.00% | 1 |
| ZM_S22309363 | 14 | 9 | 0 | 0.00% | 1 |
| ZM_S22309387 | 16 | 13 | 0 | 0.00% | 1 |
| ZM_S22309393 | 15 | 9 | 0 | 0.00% | 1 |
| ZM_S22309410 | 14 | 9 | 0 | 0.00% | 1 |
| ZM_S22309419 | 12 | 10 | 0 | 0.00% | 1 |
| ZM_S22309422 | 14 | 10 | 0 | 0.00% | 1 |
| ZM_S22309465 | 14 | 11 | 0 | 0.00% | 1 |

TABLE 7

Mutation rates in R1 seedlings from pZmES4::LbCas12a transformed Corn plants.

| R0 Event | Number of R1 plants | Number Cas12a+ plants | Number Cas12a + Mutation+ | % mutant in Cas12a+ plants | LbCas12a Copy Number |
|---|---|---|---|---|---|
| ZM_S22321323 | 16 | 13 | 6 | 46.15% | 2 |
| ZM_S22321283 | 15 | 9 | 0 | 0.00% | 1 |
| ZM_S22321299 | 15 | 11 | 4 | 36.36% | 2 |
| ZM_S22321291 | 15 | 8 | 1 | 12.50% | 2 |
| ZM_S22321261 | 15 | 11 | 0 | 0.00% | 1 |
| ZM_S22321307 | 13 | 12 | 3 | 25.00% | 2 |
| ZM_S22321298 | 16 | 12 | 1 | 8.33% | 1 |
| ZM_S22321335 | 13 | 9 | 3 | 33.33% | 2 |
| ZM_S22321326 | 10 | 9 | 1 | 11.11% | 1 |
| ZM_S22321262 | 14 | 13 | 1 | 7.69% | 1 |

TABLE 8

Mutation rates in R1 seedlings from pZmEA1::LbCas12a transformed Corn plants.

| R0 Event | Number of R1 plants | Number Cas12+a plants | Number Cas12a+ Mutation+ | % Mutations in Cas12a+ plants | Cas12a copy number |
|---|---|---|---|---|---|
| ZM_S22317328 | 12 | 9 | 1 | 11.11% | 1 |
| ZM_S22317003 | 14 | 10 | 1 | 10.00% | 1 |
| ZM_S22317338 | 14 | 10 | 2 | 20.00% | 1 |
| ZM_S22317300 | 15 | 10 | 0 | 0.00% | 1 |
| ZM_S22317305 | 13 | 9 | 0 | 0.00% | 1 |
| ZM_S22316987 | 16 | 12 | 1 | 8.33% | 1 |
| ZM_S22317322 | 15 | 10 | 0 | 0.00% | 1 |
| ZM_S22317345 | 16 | 11 | 0 | 0.00% | 1 |
| ZM_S22316989 | 13 | 11 | 0 | 0.00% | 1 |
| ZM_S22317296 | 10 | 8 | 0 | 0.00% | 1 |

TABLE 9

Mutation rates in R1 seedlings from pZmEDSUL1::LbCas 12a transformed Corn plants.

| R0 Event | Number of R1 plants | Number Cas12a+ plants | Number Cas12a+ Mutation+ | % mutations in Cas12a+ plants | Cas12a copy number |
|---|---|---|---|---|---|
| ZM_S22307430 | 13 | 10 | 0 | 0.00% | 1 |
| ZM_S22307433 | 12 | 8 | 0 | 0.00% | 1 |
| ZM_S22307451 | 14 | 10 | 0 | 0.00% | 1 |
| ZM_S22307456 | 15 | 7 | 0 | 0.00% | 1 |

To increase confidence in the targeted mutation rate, three R0 lines were selected from ZmES4:LbCas12a transformants. For the selected lines, 152, 112, and 86 R1 seedlings were screened. The mutation rates were 74.2%, 49.4%, and 8.3%, respectively. The lines with 74.2% and 49.4% observed mutation rates were R1 seeds from a R0 line that had 2 copies of ZmES4:Cas12a.

Unique targeted mutations in R1 plants: Two R0 lines (ZM_S22321326 and ZM_S22321323) from ZmES4::LbCas12a, which is expected to selectively express LbCas12a in egg and synergid cells, were analyzed to assess the types of mutations created. Five mutant plants were produced from the ZM_S22321326 line. The sequencing results from the ZmTS1 gRNA target loci indicated that all five plants had unique mutations at the target site. 49 mutant seedlings were analyzed from the ZM_S22321323 R0 line which had two copies of ZmES4:LbCas12a. Out of 49 mutant seedlings, 56 target site mutations were identified. This suggests that some plants contained heterologous mutations. The 49 plants had a total of 23 unique mutations.

TABLE 10

Type and number of unique mutations observed in R1 plants from ZmES4::LbCas12a R0 ZM_S22321326 event.

| | ZM_S22321326 | |
|---|---|---|
| Mutation | Mutation Type | # of Mutations |
| 1 | 1 bp deletion at nucleotide 16 of the target site | 1 |
| 2 | 9 bp deletion at nucleotide 16 of the target site | 1 |
| 3 | 8 bp deletion at nucleotide 17 of the target site | 1 |
| 4 | 7 bp deletion at nucleotide 15 of the target site | 1 |
| 5 | 2 bp deletion at nucleotide 23 of the target site | 1 |
| | Total | 5 |

TABLE 11

Type and number of unique mutations observed in R1 plants from ZmES4::LbCas12a R0 ZM_S22321323 event.

ZM_S22321323

| Mutation | Mutation Type | # of Mutations |
|---|---|---|
| 1 | 8 bp deletion at nucleotide 17 of the target site | 9 |
| 2 | 10 bp deletion at nucleotide 15 of the target site | 6 |
| 3 | 7 bp deletion at nucleotide 15 of the target site | 4 |
| 4 | 2 bp deletion at nucleotide 15 of the target site | 2 |
| 5 | 12 bp deletion at nucleotide 16 of the target site | 1 |
| 6 | 35 bp deletion at nucleotide 2 of the target site | 2 |
| 7 | 240 bp deletion at nucleotide 15 of the target site | 1 |
| 8 | 229 bp deletion at nucleotide 15 of the target site | 2 |
| 9 | 9 bp deletion at nucleotide 16 of the target site | 10 |
| 10 | 7 bp deletion at nucleotide 20 of the target site | 1 |
| 11 | 13 bp deletion at nucleotide 15 of the target site | 2 |
| 12 | 10 bp deletion at nucleotide 13 of the target site | 2 |
| 13 | Inucletide substitution at position 15 of the target site and a 12 bp deletion starting at position 16 of the target site | 1 |
| 14 | 14 bp deletion at nucleotide 14 of the target site | 2 |
| 15 | 10 bp deletion at nucleotide 16 of the target site | 1 |
| 16 | 11bp deletion at nucleotide 10 of the target site | 1 |
| 17 | 1 bp deletion at nucleotide 1 of the target site | 1 |
| 18 | 6 bp deletion at nucleotide 15 of the target site | 1 |
| 19 | 17 bp deletion at nucleotide 13 of the target site | 1 |
| 20 | 13 bp deletion at nucleotide 15 of the target site | 3 |
| 21 | 1 nucleotide substitution at position 8 of the target site | 1 |
| 22 | 8 bp deletion at nucleotide 14 of the target site | 1 |
| 23 | 8 bp deletion at nucleotide 18 of the target site | 1 |
| | Total | 56 |

Testing for Site Directed Integration of Template DNA in Plants Expressing Cas12a.

In addition to the Cas12a and gRNA expression cassette, each vector also contained an expression cassette for a gene of interest (GOI) that was flanked by the ZmTS1 gRNA target sequences. Expression of Cas12a in reproductive tissues is expected to create double stranded breaks on both sides of the GOI cassette releasing it from the T-DNA. This released DNA could serve as a donor for targeted insertion at the genomic ZmTS1 target site. When the CRISPR-Cpf1 complex cuts the target site within the genome, the non-homologous end joining (NHEJ) DNA repair pathway could insert the donor GOI cassette into the genomic target site. This form of SDI is also known as trans-fragment targeting (TFT). To test for SDI by TFT, flank PCR assays similar to those described in WO2019084148 were used to identify putative targeted insertions. Primers were designed to PCR amplify the expected insertion flanking sequence. Four separate PCR reactions were carried out: a left flank PCR and a right flank PCR for potential inserts that were positioned in the sense orientation, and a left flank PCR and a right flank PCR for inserts that were positioned in the antisense direction. In the initial screen of R0 lines, two plants showed flank positive PCRs. Both were identified in ZmES4:LbCas12a line and both produced only one flank PCR product. While one flank positive plant was in a line with an established mutation rate (11.11%), the other flank positive plant was in a line that had 0% mutation rate.

Taken together, the data shows that reproductive editing can be achieved when LbCas12a is expressed under the control of the promoter DMC1, Mps1 or Adf1 that preferentially or solely express in cells undergoing meiosis. Reproductive editing can also be achieved when LbCas12a is expressed by the Egg or Embryo expressing promoters like ZmES4 and ZmEA1. Additionally, the data demonstrates that a single R0 plant can produce many R1 offspring each with unique target site edits. This suggests that these promoters can be used to drive the expression of nucleases so as to increase the frequency of unique edits produced per transformed plants.

Germinal Mutations are Heritable to the F1 Generation

Two R1 individuals from the ZmES4::LbCas12a R0 event ZM_S22321323 were grown to maturity and cross pollinated with a wild type 01DKD2 tester. R1 plant-1 comprised a 7 bp deletion at nucleotide 15 of the target site (see mutation 3 in Table 11) and R1 plant-2 comprised a 9 bp deletion at nucleotide 16 of the target site (see mutation 9 in Table 11). 32 seedlings for each of the F1 lines were planted and screened for inheritance of mutations in ZmTS1 target site. 11 of the 32 F1 seedlings from Plant-1 cross germinated and 6 of them inherited the R1 event specific mutation. 5 of the 32 seedlings from plant-2 cross germinated and 3 of them inherited the R1 event specific mutation.

Example 2. Expression of Cas12a in Cells Undergoing Meiosis to Generate Germinal Mutations Several constructs are generated to preferentially express Cas12a in corn cells undergoing meiosis, in corn egg cells and/or corn embryos. See Table 12.

TABLE 12

Cassettes designed to express Cas12a preferentially, or solely, in cells undergoing meiosis, corn egg cells and/or in corn embryos.

| Construct | Promoter::LbCas12a | Expression | Promoter SEQ ID NO. |
|---|---|---|---|
| 7 (Control) | ZmUbqM1::LbCas12a | Constitutive | 11 |
| 8 | ZmDSUL1::LbCas12a | Embryo | 1 |
| 9 | ZmEA1::LbCas12a | Egg/Embryo | 2 |
| 10 | ZmES4::LbCas12a | Egg/Embryo | 3 |
| 11 | ZmDMC1::LbCas12a | Meiotic | 4 |
| 12 | ZmMps1::LbCas12a | Meiotic | 5 |
| 13 | ZmAdf1::LbCas12a | Meiotic | 6 |

The plant codon optimized LbCas12a sequence (SEQ ID NO: 7) in the expression cassettes described in Table 12 is flanked by NLS sequences at the 5' and 3' ends (SEQ ID:8 and SEQ ID: 9). Each construct described in Table 12 is introduced simultaneously with a construct ("gRNA construct") encoding a gRNA complementary to a target site under the control of the Pol III ZmU6 promoter (SEQ ID NO: 10) into corn cells using biolistic transformation methods routinely used in the art. Alternatively, the constructs described in Table 12 can be transformed either biolistically or through an *Agrobacterium* T-DNA vector into cells containing a gRNA construct. The resulting transformed corn cells comprise one of constructs 7-13, as well as the gRNA construct. Corn plants are regenerated from the transformed corn cells and grown to maturity. At least one ear from each transformed corn plant is pollinated. Seed resulting from the pollination is screened for mutations in the target site and the number and types of mutations produced using constructs 8-13 is compared to the transformed corn plants produced using construct 7. Co-expression of Cas12a from constructs 8-13 and its cognitive guide RNA from the gRNA construct is expected to result in double stranded breaks in the genomic DNA at the target site, with subsequent DNA repair generating one or more unique mutations.

Example 3. Expression of gRNA in Egg or Embryo Tissue with a Constitutively-Expressed Cas12a to Generate Germinal Mutations Several constructs are generated to preferentially express a guide RNA (gRNA) complementary to a target site under the control of a Pol II promoter in meiotic cells, corn egg cells and/or corn embryos. See Table 3. Following transcription, Pol-II products are rapidly modified with a 5' cap and poly-A tail and exported from the nucleus. These modifications and altered localization could prevent efficient use of gRNA. To optimize the gRNA availability and performance, self-cleaving ribozymes are incorporated into the gRNA cassette design. It has been reported that self-cleaving ribozymes facilitate cleavage/processing of the gRNA transcript from Pol II expressed transcripts to produce the precise guide molecule (see Wang et. al., 2018, J. of Integrative Plant Biol, 60:8, 626-631).

TABLE 13

Constructs designed to express a gRNA preferentially, or solely, in corn egg cells and/or corn embryos.

| Construct | Promoter::gRNA | Promoter SEQ ID NO. |
|---|---|---|
| 14 (Control) | ZmUbqM1::ribozyme-gRNA-ribozyme | 11 |
| 15 | ZmDSUL1::ribozyme-gRNA-ribozyme | 1 |
| 16 | ZmEA1::ribozyme-gRNA-ribozyme | 2 |
| 17 | ZmES4::ribozyme-gRNA-ribozyme | 3 |
| 18 | ZmDMC1::ribozyme-gRNA-ribozyme | 4 |
| 19 | ZmMps1::ribozyme-gRNA-ribozyme | 5 |
| 20 | ZmAdf1::ribozyme-gRNA-ribozyme | 6 |

The constructs described in Table 13 are stably introduced into corn cells using transformation methods routinely used in the art. Additionally, a construct ("Cas12a construct") comprising a plant codon optimized nucleic acid sequence encoding a Cas12a protein (SEQ ID NO: 1) flanked by NLS sequences at the 5' and 3' ends (SEQ ID:2 and SEQ ID:3) and under the control of a ubiquitous ZmUbqM1 promoter (SEQ ID NO: 11) is co-introduced with each construct provided in Table 13. The resulting transformed corn cells comprise one of constructs 14-20, as well as the Cas12a construct. Corn plants are regenerated from the transformed corn cells and grown to maturity. At least one ear from each transformed corn plant is pollinated. Seed resulting from the pollination is screened for mutations in the target site, and the number and type of mutations produced using constructs 15-20 is compared to the transformed corn plants produced using construct 14. Selective expression of gRNA is expected to generate one or more unique mutations in each meiotic cell, egg cell, or in each embryo created by the pollination.

Example 4. Expression of Cas12a and gRNA as a Single Transcript in Cells Undergoing Meiosis, Egg Cells or Embryo Tissue to Generate Germinal Mutations Several constructs are generated to preferentially express LbCas12a and a guide RNA (gRNA) complementary to a target site as a single transcript in cells undergoing meiosis, corn egg cells and/or corn embryos. See Table 14.

TABLE 14

Constructs designed to express a LbCas12a and a gRNA flanked by self-cleaving ribozymes in a single transcript in meiotic cells, corn egg cells and/or corn embryos.

| Construct | Promoter::gRNA | Promoter SEQ ID NO. |
|---|---|---|
| 21 (Control) | ZmUbqM1::LbCas12a-ribozyme-gRNA-ribozyme | 11 |
| 22 | ZmDSUL1::LbCas12a-ribozyme-gRNA-ribozyme | 1 |
| 23 | ZmEA1::LbCas12a-ribozyme-gRNA-ribozyme | 2 |
| 24 | ZmES4::LbCas12a-ribozyme-gRNA-ribozyme | 3 |
| 25 | ZmDMC1::LbCas12a-ribozyme-gRNA-ribozyme | 4 |
| 26 | ZmMps1::LbCas12a-ribozyme-gRNA-ribozyme | 5 |
| 27 | ZmAdf1::LbCas12a-ribozyme-gRNA-ribozyme | 6 |

Each construct described in Table 14 is stably introduced into corn cells using biolistic transformation methods or agrobacterium transformation methods routinely used in the art. The resulting transformed corn cells comprise one of constructs 21-27. Corn plants are regenerated from the transformed corn cells and grown to maturity. At least one ear from each transformed corn plant is pollinated. The LbCas12a and gRNA are transcribed as part of a single transcript in cells where the promoter expresses. Subsequently, ribozyme mediated cleavage occurs releasing the gRNA segments. LbCas12a protein transcribed from the transcript forms ribonucleoproteins (RNPs) with the gRNAs. The RNPs will generate a double-stranded break at the target site and subsequent repair will generate one or more unique mutations in each meiotic cell, egg cell, or in each embryo created by the pollination. Seed resulting from the pollination is screened for mutations in the target site and the number and type of mutations produced using constructs 22-27 is compared to the transformed corn plants produced using construct 21.

Example 5. Generating Mutations Via Crossing

Transgenic corn plants comprising one of Constructs 8-13 (see Example 2, Table 2) are generated and grown to flowering stage. An additional transgenic corn plant comprising the gRNA construct of Example 2 is also generated and grown to flowering stage. The corn plants comprising one of Constructs 8-13 are crossed with the corn pant comprising the gRNA construct, generating progeny corn plants comprising Cas12a and the gRNA being expressed in the resulting embryos.

Alternatively, transgenic corn plants comprising one of Constructs 15-20 (see Example 3, Table 13) are generated and grown to flowering stage. An additional transgenic corn plant comprising the Cas12a construct of Example 3 is also generated and grown to flowering stage. The corn plants comprising one of Constructs 15-20 are crossed with the corn pant comprising the Cas12a construct, generating progeny corn plants comprising Cas12a and the gRNA being expressed in the resulting embryos.

Co-expression of Cas12a and the gRNA generate a double-stranded break within the target site, thereby generating a unique mutation in each cell where the both components of the CRISPR system are expressed. Resulting embryos, or plants arising from the resulting embryos, are screened to identify mutations in the target site.

Example 6. Expression of Cas12a During Meiosis, in Egg Cells or Embryo Tissue of Reciprocal F1s to Generate Different Germinal Mutations R1 seeds containing T-DNA vectors that preferentially express Cas12a in corn meiotic tissue, egg and/or corn embryo cells as described in Example 1 were planted. See Table 15 for a list of constructs.

TABLE 15

Cassettes to express Cas12a preferentially, or solely, in corn zygotes or embryos.

| Construct | Promoter::LbCas12a::terminator (3'UTR) | Promoter SEQ ID NO. |
|---|---|---|
| 6 | ZmAdf1::LbCas12a::OsLTP$_{Term}$ | 6 |
| 5 | ZmMps1::LbCas12a::OsLTP$_{Term}$ | 5 |
| 4 | ZmDMC1::LbCas12a::OsLTP$_{Term}$ | 4 |
| 3 | ZmES4::LbCas12a::OsLTP$_{Term}$ | 3 |

30 R1 individuals from each transformed construct representing 4-10 independent events per construct were grown to maturity and reciprocal crosses were attempted with all individuals. F1 seeds were recovered from 6-29 crosses per direction per construct. Up to 72 seedlings from each F1 ear were germinated, screened for mutations in the ZmTS1 target site and the mutation rates (cutting rates) were calculated. See Table 16.

TABLE 16

Total events and samples screened in F1 reciprocal cross progeny

| Promoter driving Cas12a | Event parent | Total events | Total F1 samples |
|---|---|---|---|
| ZmAdf1 | female | 14 | 508 |
|  | Male | 10 | 85 |
| ZmDMC1 | female | 6 | 94 |
|  | Male | 4 | 21 |
| ZmMps1 | female | 6 | 169 |
|  | Male | 5 | 43 |
| ZmES4 | female | 8 | 652 |
|  | Male | 7 | 194 |

Taqman assays were performed to determine the copy number of the LbCas12a expression cassette. The overall target site mutation rate among all F1s ranged from 0 to 14%, and showed directional expression (FIG. 1 and Table 16).

F1 mutation rate was compared to the mutation rate from the event parent (R1) in order to determine how many new edits (present in F1 and not in the R1 parent) were generated. These data are summarized in FIG. 1. The ZmES4: LbCas12a construct showed the highest rate of cutting from the female (average of 12% of samples containing new edits). ZmDMC1:LbCas12a showed the highest rate of cutting from the male (average of 14% of samples containing new edits).

ZmES4:LbCas12a not only produced a high percentage of F1 plants with new edits when carried by the female parent, it also produced a high number of unique edits in the F1 plants (FIG. 1, Table 17). When carried by the female parent, ZmES4:LbCas12a produced 39 different mutation types as detected in F1 plants. The other promoters tested produced a maximum of 4 unique edits types in 1 progeny (see FIG. 1).

The new edits observed in the ZmES4:LbCas12a F1 plants were highly abundant. Sequencing of the target site showed 40%-100% of the sequencing reads containing the mutant alleles, indicating these edits are made early in embryo/zygote development and are thus fixed in the plant (Table 17). Edits that become fixed in the plant will be present in that plant's germline and thus inherited in its progeny.

ZmES4 retains high embryo/zygote expression generation after generation, and many independent events show functional activity of LbCas12a. Nearly every edited plant in each event contains a unique edit (Table 17). Moreover, all but one ZmES4 event tested produced new edits, with mutation rates per event of up to 20% (Table 17).

TABLE 17

ZmES4::LbCas12a editing summary in F1s by event.

| Event | Event parent | Total Samples (Cas12a+) | Total samples with edits* | Total samples with new** edits | Total samples with new heritable edits$ | % samples with edits | % samples with new edits | % samples with new heritable edits | Different edits<sup>&</sup> in total edited samples | Different new edits | Different heritable edits |
|---|---|---|---|---|---|---|---|---|---|---|---|
| ZM_S22 | female | 55 | 26 | 11 | 11 | 47.27 | 20.00 | 20.00 | 12 | 9 | 9 |
| 321294 | male | 12 | 0 | 0 | 0 | 0.00 | 0.00 | 0.00 | 0 | 0 | 0 |
| ZM_S22 | female | 16 | 6 | 0 | 0 | 37.50 | 0.00 | 0.00 | 1 | 0 | 0 |
| 321298 | male | 0 | 0 | 0 | 0 | 0.00 | 0.00 | 0.00 | 0 | 0 | 0 |
| ZM_S22 | female | 39 | 26 | 4 | 4 | 66.67 | 10.26 | 10.26 | 10 | 4 | 4 |
| 321299 | male | 13 | 4 | 0 | 0 | 30.77 | 0.00 | 0.00 | 1 | 0 | 0 |
| ZM_S22 | female | 162 | 100 | 25 | 25 | 61.73 | 15.43 | 15.43 | 20 | 16 | 16 |
| 321304 | male | 38 | 7 | 0 | 0 | 18.42 | 0.00 | 0.00 | 2 | 0 | 0 |
| ZM_S22 | female | 72 | 29 | 2 | 2 | 40.28 | 2.78 | 2.78 | 4 | 2 | 2 |
| 321307 | male | 27 | 2 | 0 | 0 | 7.41 | 0.00 | 0.00 | 1 | 0 | 0 |
| ZM_S22 | female | 182 | 114 | 24 | 24 | 62.64 | 13.19 | 13.19 | 22 | 15 | 15 |
| 321323 | male | 70 | 36 | 6 | 6 | 51.43 | 8.57 | 8.57 | 6 | 1 | 1 |
| ZM_S22 | female | 92 | 63 | 17 | 17 | 68.48 | 18.48 | 18.48 | 19 | 14 | 14 |

TABLE 17-continued

ZmES4::LbCas12a editing summary in F1s by event.

| Event | Event parent | Total Samples (Cas12a+) | Total samples with new** edits* | Total samples with new** edits | Total samples with new heritable edits$ | % samples with edits | % samples with new edits | % samples with new heritable edits | Different edits& in total edited samples | Different new edits | Different heritable edits |
|---|---|---|---|---|---|---|---|---|---|---|---|
| 321324 | male | 4 | 0 | 0 | 0 | 0.00 | 0.00 | 0.00 | 0 | 0 | 0 |
| ZM_S22 | female | 34 | 2 | 2 | 2 | 5.88 | 5.88 | 5.88 | 2 | 2 | 2 |
| 321326 | male | 30 | 0 | 0 | 0 | 0.00 | 0.00 | 0.00 | 0 | 0 | 0 |

*Total samples with edits includes samples with both new edits and edits that were inherited.

Example 7. Expression of Cas12a in Corn Egg Cells, Meiotic Cells or Embryos to Enable Editing from a Haploid Induction Line to a Target Genome Vectors are generated to preferentially express Cas12a in zygote, embryo, egg and/or meiotic cells of a haploid induction (HI) line, which generates haploids when crossed to another line. Non-limiting examples of promoters and regulatory sequences useful to drive expression embryo, egg and/or meiotic cells are provided in Table 1. An expression cassette is provided in which a plant codon optimized LbCas12a sequence is flanked by NLS sequences at the 5' and 3' ends and operably linked to a promoter as described in Table 1. Each vector may also contain an expression cassette encoding one or more Cas12a gRNAs targeting unique corn genomic target sites; and, optionally, an expression cassette encoding a selectable marker conferring resistance to the herbicide glyphosate. The vector may either be transformed directly into the haploid induction line, or events containing the vector may be generated in a different germplasm, which is then crossed into the haploid induction line. The resulting "editing inducer" will contain the haploid induction trait as well as the expression cassette encoding Cas12a and, optionally, a gRNA directed to the target site. In some embodiments, the gRNA could be delivered to the haploid induction line or WT germplasm separately from the cassette expressing Cas12a.

Editing induced by a DNA modification enzyme, such as a guided nuclease (e.g., a CRISPR/Cas system) expressed from the haploid inducer genome is limited by the efficiency of editing that can occur in the short period after fertilization but before elimination of the genome contributed by the haploid inducer. In systems where haploid induction is contributed by the female parent, having strong expression of the genome editing components from the maternal genome just before or shortly after fertilization is a desired characteristic. Thus, identifying and using promoters that express at high levels in the maternal tissue (e.g., in egg and embryo tissue), such as the ZmES4 promoter (see Example 6) is highly desired.

An inducer line carrying an event comprising the expression construct(s) described above (editing inducer) is crossed as a female to a male wild type germplasm. After pollen from the male wild type parent contacts the female haploid inducer parent, there will be a period of time (shortly before/during, and/or after fertilization) during which the editing machinery (e.g., a CRISPR/Cas system) expressed from the inducer parent will contact the genome inherited from the male parent, and induce a modification. In certain embodiments, genome editing occurs while the progeny of the induction cross is in the zygote phase of its life cycle. In certain embodiments, genome editing requires a longer period of time, potentially spanning several rounds of mitotic divisions in the tissues of the progeny plant.

Following the editing of the wild type genome, the inducer genome and the expression cassettes encoding the editing machinery (e.g., Cas12a and gRNA), will be lost from the cells in a certain frequency of progeny via one of the mechanisms of genome elimination that is characteristic of maternal haploid induction lines, thus yielding a corresponding frequency of haploid progeny plants containing edits in the male genome but no expression cassettes encoding the editing machinery. Haploid progeny can be identified using any method known in the art including sequencing of genomic DNA, genotyping with molecular markers, and phenotyping with plant or seed markers. The haploid progeny can be screened for editing at the target site(s) by any method known in the art, including sequencing of the target site. Edited haploids are selected and then doubled using any method known in the art, such as colchine treatment. The doubled haploid is homozygous for the edited allele and can be utilized in a breeding pipeline.

A single editing inducer line could be used to create a wide variety of unique edits across multiple germplasms, alleviating germplasm dependent transformation constraints. Further, an inducer line expressing the editing machinery (e.g., Cas12a and gRNA) in the egg, embryo, and/or meiotic tissue can produce a wide array of unique edits, eliminating the need to create multiple transgenic events to identify a particular edit or generate a range of edited alleles.

Example 8: TALE Activators Can Drive Robust LbCas12a Expression in Corn Protoplasts This example describes the use of TALEs to induce robust and specific expression of a transcribable polynucleotide in egg, embryo, and/or meiotic plant cells.

Figure 2:
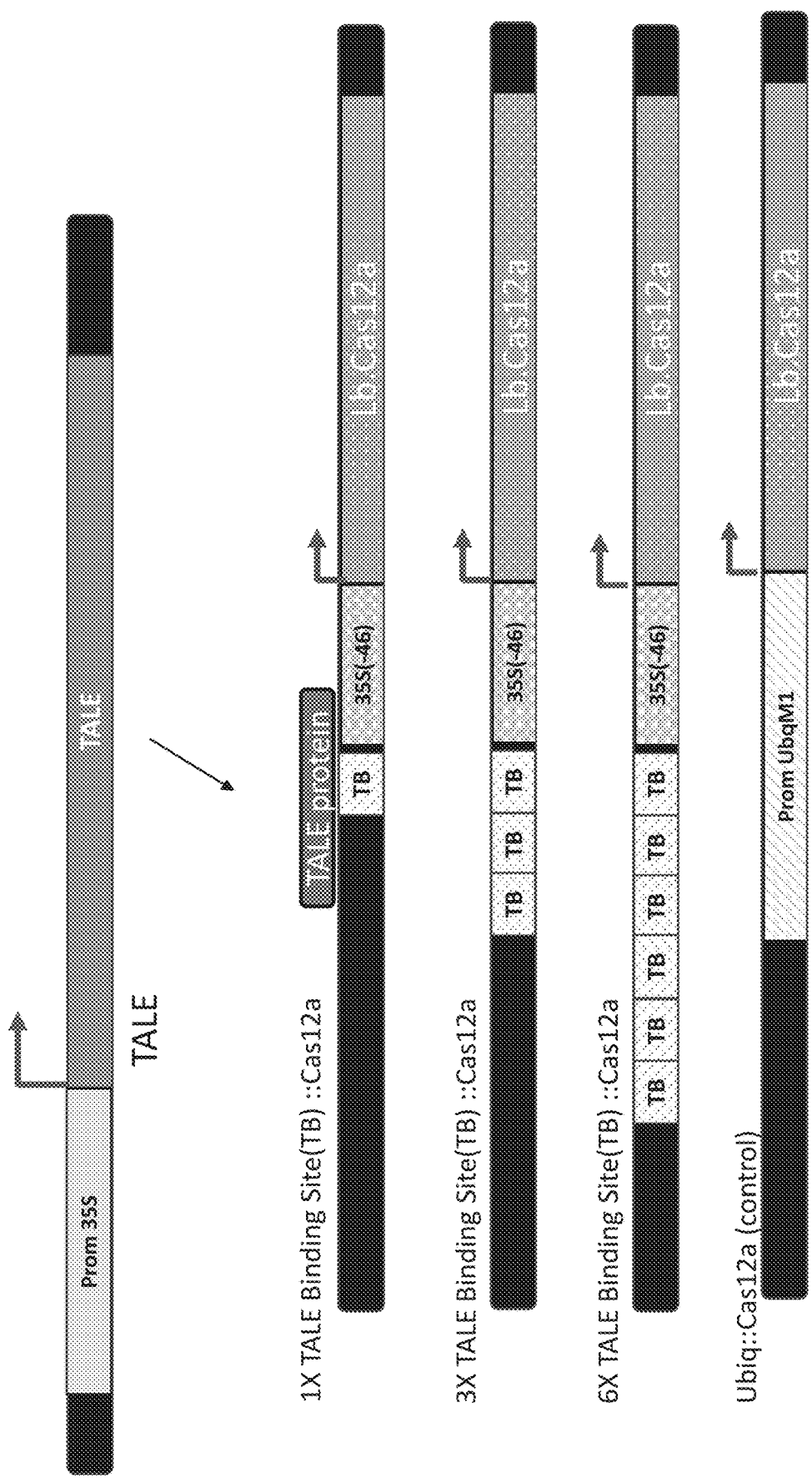
FIG. 2: Depicts a schematic illustrating vectors designed for TALE induced expression of LbCas12a. 35S(-46) is the 35S minimal promoter. TB indicates the TALE Binding site.

Transcription Activator-Like Effectors (TALEs) are transcription factors that comprise a C terminal activation domain and can activate/increase the expression of an operably linked transcribable polynucleotide once TALEs bind to the TALE binding site at or near the promoter. To test if a TALE could boost expression of Cas12a, several cassettes were designed that employed the minimal 35S(-46) promoter operably linked to a Zea mays DNAK intron and placed upstream of a polynucleotide sequence encoding Cas12a (See FIG. 2). The minimal 35S(-46) promoter has the TATA box, but lacks the transcription factor binding sites that will induce gene expression. Three expression constructs were generated, each comprising the 35S(-46): Lb.Cas12a cassette with one to six TALE protein binding sites (TB) (SEQ ID NO 15) placed upstream of the minimal 35S(-46) promoter (see Table 7). As a control, a polynucleotide sequence encoding LbCas12a was operably linked to the constitutive Ubiquitin promoter. Finally, a separate expression construct comprising a polynucleotide sequence (SEQ ID NO 16) encoding the TALE protein with the C terminal activation domain (SEQ ID NO 17) operably linked to the full 35S promoter was also generated.

TABLE 18

Cassettes designed to express Cas12a preferentially, or solely, in the presence of TALE activator protein. TB = Tale Binding site.

| Construct | Cassette | Details | Regulatory Seq |
|---|---|---|---|
| 28 | 1XTB:35S(−46): LbCas12a | At most one TALE protein will bind upstream of the 35S(−46): Lb.Cas12a | 12 |
| 29 | 3XTB:35S(−46): LbCas12a | At most three TALE proteins will bind upstream of the 35S(−46): Lb.Cas12a | 13 |
| 30 | 6XTB:35S(−46): LbCas12a | At most six TALE proteins will bind upstream of the 35S(−46): Lb.Cas12a | 14 |
| 31 (control) | Ubiquitin: LbCas12a | TALE proteins are not expected to bind/drive the expression of the Ubiquitin promoter | 11 |

The constructs described in Table 18 were transfected into corn leaf protoplasts with and without the TALE expressing construct. After 18-24 hours, RNA was isolated and the expression of Cas12a and TALE was quantified using TaqMan assays (See FIG. 3).

Figure 3:
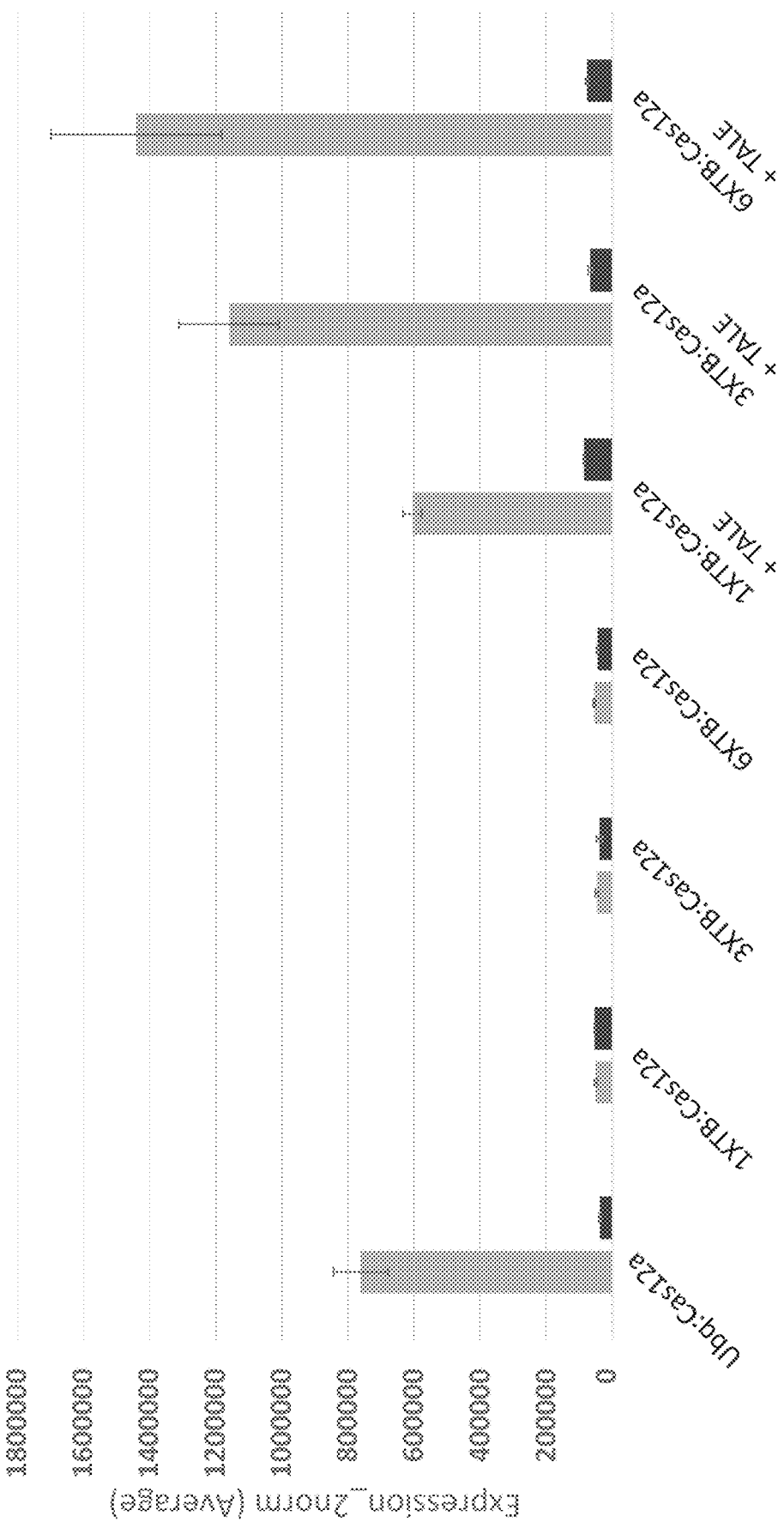
FIG. 3. RNA expression of Cas12a and TALE in corn leaf protoplasts.
Figure 4:
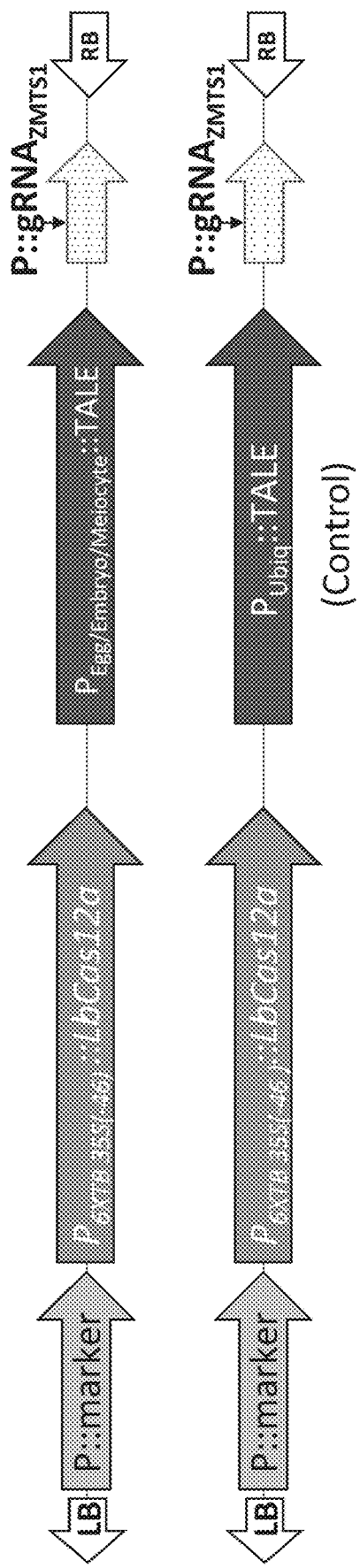
FIG. 4: Schematic illustration of T-DNA vectors designed for TALE-induced Meiocyte/Embryo/egg-cell preferred expression of LbCas12a in planta. LB indicates Left Border. RB indicates Right Border. P indicates promoter. 35S(-46) is the 35S minimal promoter. TB is the TALE Binding site.

The data showed that the 1XTB:Cas12a, 3XTB:Cas12a and 6XTB:Cas12a constructs did not express well as the Ubq:Cas12a control in the absence of TALE expression (see FIG. 3). However, in the presence of TALE expression, high expression of Cas12a was observed, and expression increased with the number of TALE binding sites. The 3XTB:Cas12a and 6XTB:Cas12a constructs showed higher Cas12a expression than the Ubq:Cas12a control (see FIG. 3). This data suggests that not only can a TALE protein induce high expression of a gene operably linked to a TALE binding site, but that expression can be modulated depending on how many of the TALE binding sites are included.

Example 9: TALE Induced Meiocyte/Embryo/Egg-Cell Preferred Expression of LbCas12a A potential downside of tissue/cell preferred promoters is that they tend to not be robustly expressed. This example describes constructs that have been generated to overcome this limitation and induce robust expression of a transcribable polynucleotide, such as Cas12a, in a tissue/cell preferred manner.

Several constructs are generated for robust, TALE-induced Cas12a expression preferentially in egg, embryo and/or meiotic cells. Constructs are generated comprising a plant codon optimized LbCas12a coding sequence flanked by NLS sequences at the 5' and 3' ends and operably linked to the OsLTP transcription terminator sequence and the minimal 35S(-46) promoter with 1, 3, or 6 TALE binding sites. Expression constructs are also generated comprising a TALE coding sequence (SEQ ID NO 16) operably linked to a promoter that preferentially or solely expresses in egg, embryo and/or meiotic cells. Non-limiting examples of promoters and regulatory sequences to drive preferential egg, embryo and/or meiotic cell expression are provided in Table 1. An expression cassette comprising a TALE coding sequence operably linked to a constitutive Ubiquitin promoter is generated as a control. Corn 01DKD2 cultivar embryos are transformed with a vector(s) comprising the expression cassettes as described above and an expression cassette encoding a Cas12a gRNA complementary to a unique corn genomic target site (ZmTS1) under the control of a plant Pol III promoter and an expression cassette for a selectable marker conferring resistance to the herbicide glyphosate by *agrobacterium*-mediated transformation and R0 plants are generated from the transformed corn cells. Several R0 lines from each transformed construct are grown to maturity and at least one ear from each transformed corn plant are pollinated. Several R1 lines are selected, seedlings are germinated and screened for LbCas12a induced edits in the target site and the editing rates are calculated. It is anticipated that when plants comprising the Cas12a, gRNA and TALE expression vectors described above reach the reproductive stage, TALE expressed preferentially in the meiocytes, egg cells, and/or embryo cells will bind to TALE protein binding sites upstream of the 35S(-46):Lb.Cas12a and induce robust expression preferentially in meiocytes, egg cells, and/or embryo cells. The R1 plants generated from the transformed R0 lines are expected to exhibit a significant number of unique mutations at the ZmTS1 target site.

Example 10: Tissue Preferred High Expression of CRISPR/Cas12a Editing System Components This example describes the design of a vector to enable Meiocyte/Embryo/egg-cell preferred expression of Cas12a that is driven by a strong constitutive promoter.

Figure 5:
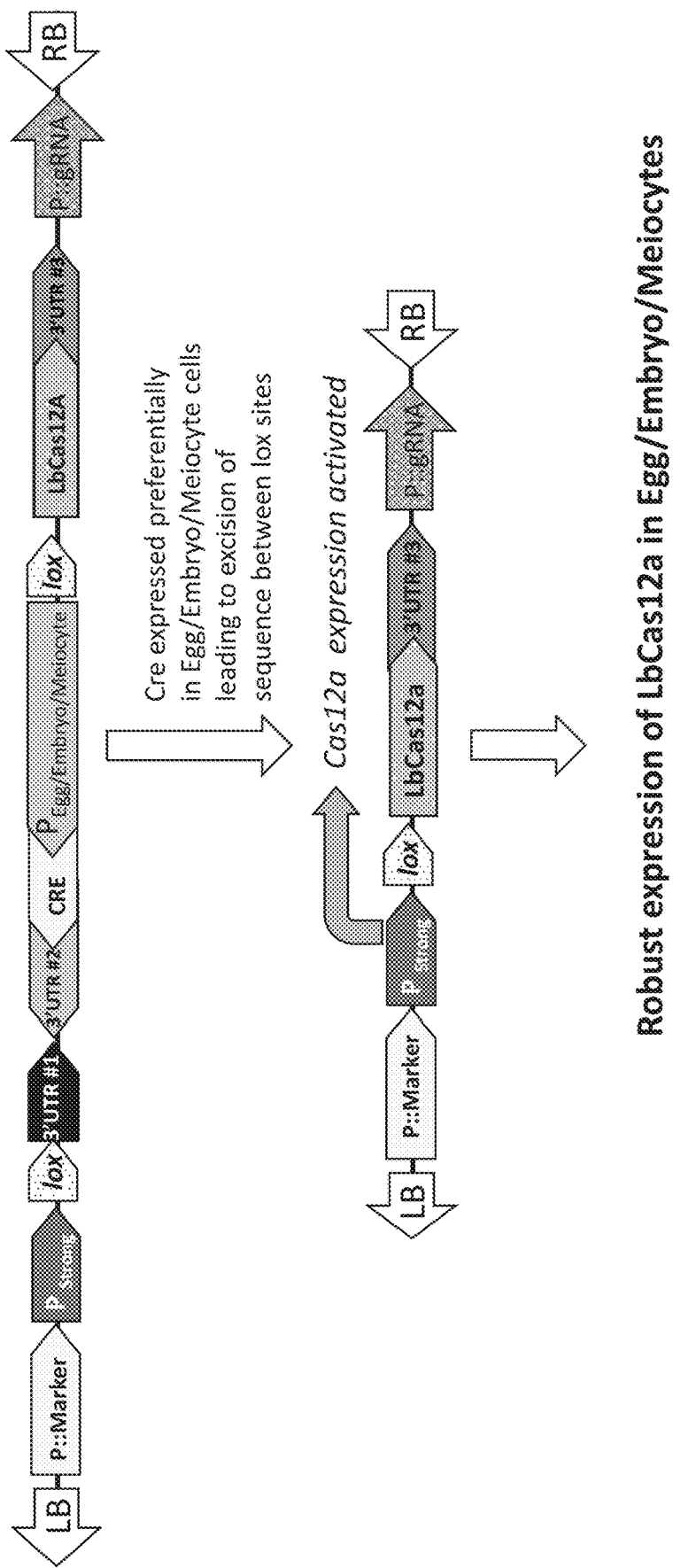
FIG. 5: Schematic illustration of T-DNA vectors designed for Meiocyte/Embryo/egg-cell preferred expression of Cas12a driven by a strong constitutive promoter. P indicates Promoter. Cre is for Cre recombinase. Arrowheads represent directionality.

A recombinant *Agrobacterium* T-DNA construct is produced that comprises in 5' to 3' order, a left Border (LB) sequence; a selectable marker cassette in forward orientation; a sequence encoding a strong expression promoter in forward orientation; a first lox site, a first 3'UTR (UnTranslated Region) in forward orientation; a CRE recombinase cassette comprising a second 3'UTR in reverse orientation, a sequence encoding the CRE recombinase in reverse orientation operably linked to a promoter that preferentially or solely expresses in meiocytes, egg cells, and/or embryo cells; a second lox site in the same orientation as the first; a sequence encoding a plant codon optimized LbCas12a nuclease in forward orientation and operably linked to a third 3'UTR also in the forward orientation; and optionally an LbCas12a guide RNA expression cassette. The recombinant T-DNA construct is illustrated in FIG. 5. Non limiting examples of a strong promoters include: the 35S promoter from Cauliflower mosaic virus (SEQ ID NO:18), a promoter from Citrus Yellow mosaic virus (SEQ ID NO:19), Ubiquitin promoter from *Sorghum bicolor* (SEQ ID NO 20), and *Zea mays* Ubiquitin promoter (SEQ ID NO:11).

The vector described above comprises an expression cassette comprising a sequence encoding CRISPR/Cas editing system components and a constitutive, strong/high-expressing promoter that is interrupted by an expression cassette that preferentially expresses Cre recombinase in egg cells and/or embryo cells and/or cells undergoing meiosis. The Cre expression cassette is flanked by lox sites in the same orientation, such that preferential expression of Cre in egg, embryo and/or meiotic cells will cause excision of the sequence between the lox sites and operably linking the sequence encoding CRISPR/Cas editing system components with the constitutive, strong/high-expressing promoter. The excised sequence includes the Cre expression cassette and the first 3'UTR sequence that is intended to terminate any unintended transcription that might be initiated by the constitutive, strong/high-expressing promoter.

The vector is introduced to plant cells via *Agrobacterium*-mediated transformation. Once Cre recombinase is expressed in egg, embryo and/or meiotic cells, it mediates the excision of the sequence between the lox sites enabling high expression of Cas12a only in the tissue where Cre is expressed.

The invention claimed is:

1. A method of editing a genome of a plant comprising:
(a) introducing to a plant cell:
(i) a first nucleic acid sequence encoding a CRISPR effector protein operably linked to a heterologous first promoter, wherein the heterologous first promoter is an ES4 promoter, wherein the ES4 promoter comprises a nucleic acid sequence that is at least 90% identical to SEQ ID NO: 3 or a functional fragment thereof that drives expression in at least one egg cell or at least one embryonic cell of the plant; and
(ii) a second nucleic acid sequence encoding at least one guide nucleic acid operably linked to a heterologous second promoter, wherein the at least one guide nucleic acid is capable of hybridizing to a target sequence within the genome; and (b) regenerating at least one plant from the plant cell of step (a), wherein the CRISPR effector protein and at least one guide nucleic acid form a ribonucleoprotein within the at least one egg cell or the at least one embryonic cell of the plant, and wherein the ribonucleoprotein generates at least one modification within the target sequence in the at least one egg cell or the at least one embryonic cell.

2. The method of claim 1, wherein the CRISPR effector protein is selected from the group consisting of Cas9, Cas12a, Cas12b and CasX.

3. The method of claim 1, further comprising outcrossing the plant to produce a progeny plant.

4. The method of claim 3, wherein the plant is a haploid inducer and the progeny plant is haploid.

5. The method of claim 4, further comprising treating cells of the progeny plant with colchicine to generate a double haploid plant.

6. The method of claim 1, the method further comprising the steps of:
   c. pollinating the at least one plant of step (b);
   d. germinating two or more seeds produced from step (c) to produce two or more progeny plants with unique edits.

7. The method of claim 3, wherein the progeny plant is a female plant.

* * * * *